US012049471B2

(12) United States Patent
Sands et al.

(10) Patent No.: US 12,049,471 B2
(45) Date of Patent: Jul. 30, 2024

(54) CYANO CYCLOBUTYL COMPOUNDS FOR CBL-B INHIBITION AND USES THEREOF

(71) Applicant: Nurix Therapeutics, Inc., San Francisco, CA (US)

(72) Inventors: Arthur T. Sands, San Francisco, CA (US); Neil F. Bence, San Francisco, CA (US); Christoph W. Zapf, San Francisco, CA (US); Frederick Cohen, San Francisco, CA (US); Chenbo Wang, San Francisco, CA (US); Thomas Cummins, San Francisco, CA (US); Hiroko Tanaka, San Francisco, CA (US); Hunter Shunatona, Oakland, CA (US); Mario Cardozo, San Francisco, CA (US); Dahlia Weiss, San Mateo, CA (US); Jennifa Gosling, San Francisco, CA (US)

(73) Assignee: NURIX THERAPEUTICS, INC., San Francisco, CA (US)

( * ) Notice: Subject to any disclaimer, the term of this patent is extended or adjusted under 35 U.S.C. 154(b) by 0 days.

(21) Appl. No.: 18/068,195

(22) Filed: Dec. 19, 2022

(65) Prior Publication Data

US 2023/0212186 A1    Jul. 6, 2023

Related U.S. Application Data

(63) Continuation of application No. 16/875,917, filed on May 15, 2020, now Pat. No. 11,530,229.

(60) Provisional application No. 62/888,870, filed on Aug. 19, 2019, provisional application No. 62/888,845, filed on Aug. 19, 2019, provisional application No. 62/880,437, filed on Jul. 30, 2019, provisional application No. 62/849,722, filed on May 17, 2019.

(51) Int. Cl.
| | | |
|---|---|---|
| *C07D 498/08* | (2006.01) | |
| *C07D 401/14* | (2006.01) | |
| *C07D 403/12* | (2006.01) | |
| *C07D 403/14* | (2006.01) | |
| *C07D 405/14* | (2006.01) | |
| *C07D 413/14* | (2006.01) | |
| *C07D 471/04* | (2006.01) | |
| *C07D 491/08* | (2006.01) | |

(52) U.S. Cl.
CPC ......... *C07D 498/08* (2013.01); *C07D 401/14* (2013.01); *C07D 403/12* (2013.01); *C07D 403/14* (2013.01); *C07D 405/14* (2013.01); *C07D 413/14* (2013.01); *C07D 471/04* (2013.01); *C07D 491/08* (2013.01)

(58) Field of Classification Search
CPC .. C07D 401/12; C07D 403/12; C07D 403/14; C07D 413/14; C07D 471/04; C07D 498/08; A61K 31/454
See application file for complete search history.

(56) References Cited

U.S. PATENT DOCUMENTS

| | | |
|---|---|---|
| 5,273,986 A | 12/1993 | Holland et al. |
| 11,401,267 B2 | 8/2022 | Sands et al. |
| 11,464,802 B2 | 10/2022 | Sands et al. |
| 11,530,229 B2 * | 12/2022 | Sands ............... C07D 403/14 |
| 2007/0054355 A1 | 3/2007 | Reiss et al. |
| 2014/0010781 A1 | 1/2014 | Lametschwandtner et al. |
| 2017/0015655 A1 | 1/2017 | Kaieda et al. |
| 2020/0323904 A1 | 10/2020 | Sands et al. |
| 2021/0053961 A1 | 2/2021 | Sands et al. |
| 2021/0053986 A1 | 2/2021 | Sands et al. |
| 2021/0085717 A1 | 3/2021 | Gosling et al. |
| 2021/0087259 A1 | 3/2021 | Gosling et al. |
| 2021/0198280 A1 | 7/2021 | Kelly et al. |
| 2022/0324835 A1 | 10/2022 | Barsanti et al. |
| 2022/0339152 A1 | 10/2022 | Guiducci et al. |
| 2022/0378839 A1 | 12/2022 | Sands et al. |
| 2022/0387395 A1 | 12/2022 | Sands et al. |
| 2023/0086137 A1 | 3/2023 | Somanath et al. |

FOREIGN PATENT DOCUMENTS

| | | |
|---|---|---|
| CN | 101918544 A | 12/2010 |
| CN | 103898051 A | 7/2014 |
| EP | 1 364 949 A1 | 11/2003 |
| EP | 3 254 701 A1 | 12/2017 |

(Continued)

OTHER PUBLICATIONS

International Search Report and Written Opinion for International Patent Application PCT/US2019/015250, 10 pages, Jun. 11, 2019.
International Search Report and Written Opinion for International Patent Application PCT/US2019/056112, 8 pages, Dec. 6, 2019.
International Search Report and Written Opinion for International Patent Application PCT/US2020/016489, 8 pages, May 27, 2020.
International Search Report and Written Opinion for International Patent Application PCT/US2020/027492, 21 pages, Aug. 11, 2020.
International Search Report and Written Opinion for International Patent Application PCT/US2020/039957, 16 pages, Oct. 5, 2020.

(Continued)

*Primary Examiner* — Deepak R Rao
(74) *Attorney, Agent, or Firm* — Squire Patton Boggs (US) LLP

(57) ABSTRACT

Compounds, compositions, and methods for use in inhibiting the E3 enzyme Cbl-b in the ubiquitin proteasome pathway are disclosed. The compounds, compositions, and methods can be used to modulate the immune system, to treat diseases amenable to immune system modulation, and for treatment of cells in vivo, in vitro, or ex vivo. Also disclosed are pharmaceutical compositions comprising a Cbl-b inhibitor and a cancer vaccine, as well as methods for treating cancer using a Cbl-b inhibitor and a cancer vaccine; and pharmaceutical compositions comprising a Cbl-b inhibitor and an oncolytic virus, as well as methods for treating cancer using a Cbl-b inhibitor and an oncolytic virus.

16 Claims, No Drawings

Specification includes a Sequence Listing.

(56) References Cited

FOREIGN PATENT DOCUMENTS

| | | |
|---|---|---|
| WO | WO 2005/021532 A1 | 3/2005 |
| WO | WO 2007/072225 A2 | 6/2007 |
| WO | WO 2008/033403 A2 | 3/2008 |
| WO | WO 2009/073905 A2 | 6/2009 |
| WO | WO 2009/098144 A1 | 8/2009 |
| WO | WO 2011/076725 A1 | 6/2011 |
| WO | WO 2011/140488 A1 | 11/2011 |
| WO | WO 2012/020008 A1 | 2/2012 |
| WO | WO 2012/089736 A1 | 7/2012 |
| WO | WO 2012/175513 A1 | 12/2012 |
| WO | WO 2013/067264 A1 | 5/2013 |
| WO | WO 2013/067274 A1 | 5/2013 |
| WO | WO 2013/106643 A2 | 7/2013 |
| WO | WO 2014/040965 A1 | 3/2014 |
| WO | WO 2015/084998 A1 | 6/2015 |
| WO | WO 2016/196776 A2 | 12/2016 |
| WO | WO 2018/098275 A1 | 5/2018 |
| WO | WO 2019/063748 A1 * | 4/2019 |
| WO | WO 2019/148005 A1 | 8/2019 |
| WO | WO 2020/081450 A1 | 4/2020 |
| WO | WO 2020/167518 A1 | 8/2020 |
| WO | WO 2020/210508 A1 | 10/2020 |
| WO | WO 2020/236654 A1 | 11/2020 |
| WO | WO 2020/264398 A1 | 12/2020 |
| WO | WO 2021/021761 A1 | 2/2021 |
| WO | WO 2021/061853 A1 | 4/2021 |
| WO | WO 2021/091575 A1 | 5/2021 |
| WO | WO 2021/113557 A1 | 6/2021 |
| WO | WO 2022/217123 A1 | 10/2022 |

OTHER PUBLICATIONS

International Search Report and Written Opinion for International Patent Application PCT/US2020/033274, 19 pages, Oct. 23, 2020.
International Search Report and Written Opinion for International Patent Application PCT/US2019/043788, 13 pages, Oct. 23, 2020.
International Search Report and Written Opinion for International Patent Application PCT/US2020/052335, 12 pages, Apr. 1, 2021.
International Search Report and Written Opinion for International Patent Application PCT/US2019/060584, pages, May 14, 2021.
Extended European Search Report for European Patent Application No. 19744118.1, 12 pages dated Sep. 22, 2021.
International Search Report and Written Opinion for International Patent Application PCT/US2020/024119, 19 19 pages, Jan. 5, 2023.
International Search Report and Written Opinion for International Patent Application PCT/US2022/049171, 14 pages, Mar. 16, 2023.
Riling, C. et al. "Abstract A206: Small-molecule Cbl-b inhibitors as novel intracellular checkpoint inhibitors for cancer immunotherapy | Molecular Cancer Therapeutics," Jan. 1, 2018 (Jan. 1, 2018), XP055700949, Retrieved from the Internet:URL:https:// mct.aacrjournals.org/content/17/1_Supplement/A206 [retrieved on Jun. 4, 2020].
Acute Leukemia, Merck Manual (Online Edition) 6 pages, pp. 1-6 (2013).
Gosling, J. et al., "Abstract 2696: Genetic and pharmacologic evaluation of the ubiquitin ligase CBL-B as a small-molecule, tumor immunotherapy target | Cancer Research," Apr. 3, 2019 (Apr. 3, 2019), XP055701108, Retrieved from the Internet:U RL:https://cancerres.aacrjournals.org/content/79/13_Supplement/2696 [retrieved on Jun. 4, 2020].
Gura, T. "Systems for Identifying New Drugs Are Often Faulty," Cancer Models, Science, vol. 278, No. 5340, pp. 1041-1042, Nov. 1997.
Marelli, U. K. et al., "Tumor targeting via integrin ligands," Frontiers in Oncology, vol. 3, Article 222, pp. 1-12, 2013.
Jack, J. et al., "Gene Expression and Linkage Analysis Implicate CBLB as a mediator of rituximab reistsance," The Pharmacogenomics Journal (2018) 18: 467-473.
Wang, Z. et al., "Mathematical modeling in cancer drug discovery," Drug Discovery Today, vol. 19, No. 2, pp. 145-150, 2014.
Pearce et al., "Failure modes in anticancer drug discovery and development," Cancer Drug Design and Discovery Edited by Stephen Neidle, Chapter 18, pp. 424-435 (2008).
Johnson, J. I. et al., "Relationships between drug activity in NCI preclinical in vitro and in vivo models and early clinical trials," British Journal of Cancer (2001) 64(10): 1424-1431.
Ray, A. et al., "A novel TLR-9 agonist C792 inhibits plasmacytoid dendritic cell-induced myeloma cell growth and enhance cytotoxicity of bortexomib," Leukemia, Nature Publishing Group UK, London, vol. 28, No. 8 Jan. 30, 2014, pp. 1716-1724. DOI:10.1038/LEU.2014.46.
Simone, Oncology: Introduction, Cecil Textbook of Medicine, 20th Edition, vol. 1, pp. 1004-1010, 1996.
Sitaram, P. et al., "Beyond the Cell Surface: Targeting Intracellular Negative Regulators to Enhance T cell Anti-Tumor Activity," International Journal of Molecular Sciences, 20, 5821, 28 pages (2019).
Tigno-Aranjuez, J. T. et al., "Inhibition of RIP2's tyrosine kinase activity limits NOD2-driven cytokine responses," Genes & Development, 2010, 24:2666-2677; http://www.genesdev.org/cgi/doi/10.1101/gad.964410.
Bachmaier K et al.: "Negative regulation of lymphocyte activation and autoimmunity by the molecular adaptor Cbl-b", Nature, Nature Publishing Group UK, London, vol. 403, No. 6766, Jan. 13, 2000 (Jan. 13, 2000), pp. 211-216, XP002575145, ISSN: 0028-0836, DOI: 10.1038/35003228 the whole document abstract.
Chimera L. et al.: "c-Cbl: An Important Regulator and a Target in Angiogenesis and Tumorigenesis", Cells, vol. 8, No. 5, May 23, 2019 (May 23, 2019), p. 498, XP93071522, DOI: 10.3390/cells8050498 the whole document figure 3.
Lupher et al.:"Cbl-mediated negative regulation of the Syk tyrosine kinase. A critical role for Cbl phosphotyrosine-binding domain binding to Syk phosphotyrosine 323", The Journal of Biological Chemistry, Dec. 25, 1998 (Dec. 25, 1998), pp. 35273-35281, XP93071643, United States DOI:10.1074/jbc.273.52.35273.
Ota Y et al.: "The Product of the Proto-Oncogene c-cbl: A Negative Regulator of the Syk Tyrosine Kinase", Science Apr. 18, 1997;276(5311):418-20, Jan. 1, 1997 (Jan. 1, 1997), XP93071617, Retrieved from the Internet: URL:https://www.science.org/doi/pdf/10.112 6/science.276.5311.418 [retrieved on Aug. 8, 2023] the whole document, p. 419,col. 2.
Ota Y et al.: "Characterization of Cbl tyrosine phosphorylation and a Cbl-Syk complex in RBL-2H3 cells.", Journal of Experimental Medicine, vol. 184, No. 5, Nov. 1, 1996 (Nov. 1, 1996), pp. 1713-1723, XP93071596 ISSN: 0022-1007, DOI 10.1084/Jem.184.5.1713.

* cited by examiner

CYANO CYCLOBUTYL COMPOUNDS FOR CBL-B INHIBITION AND USES THEREOF

CROSS-REFERENCE TO RELATED APPLICATIONS

This application is a continuation application of U.S. patent application Ser. No. 16/875,917, filed May 15, 2020, which claims the benefit under 35 U.S.C. § 119 of U.S. provisional application numbers: 62/849,722, filed May 17, 2019; 62/880,437, filed Jul. 30, 2019; 62/888,845, filed Aug. 19, 2019; and 62/888,870, filed Aug. 19, 2019, wherein the contents of each are incorporated herein by reference in their entirety. This patent application contains a Sequence Listing which has been submitted electronically in .XML format and is hereby incorporated by reference in its entirety. The .XML copy, created on Nov. 14, 2022, is named "121843.00191.xml" and is 6,173 bytes in size. The sequence listing contained in this .XML file is part of the specification and is hereby incorporated by reference herein in its entirety.

FIELD

Provided herein are compounds and compositions for inhibition of the Cbl-b enzyme and methods of use thereof in modulating the immune system, treatment of diseases, and treatment of cells in vivo, in vitro, or ex vivo. Also provided herein are pharmaceutical compositions, kits, and methods of treating cancer comprising a combination of an inhibitor of the Cbl-b enzyme and a cancer vaccine; and pharmaceutical compositions, kits, and methods of treating cancer comprising a combination of an inhibitor of the Cbl-b enzyme and an oncolytic virus.

BACKGROUND

The ubiquitin proteasome pathway is a complex system involved in the regulation of protein function and catabolism. Proteins in eukaryotic cells are conjugated with ubiquitin, a 76 amino acid, 8.5 kilodalton protein. This conjugation, known as ubiquitination, results in altered function or degradation of the target protein. Ubiquitination of the target protein occurs via a coupled series of reactions involving ubiquitin and a set of enzymes known as E1, E2, and E3 enzymes. Ubiquitin is activated by the ubiquitin-activating enzyme, or E1 enzyme. Ubiquitin is then transferred to a ubiquitin-conjugating enzyme, or E2 enzyme. Finally, a ubiquitin ligase, or E3 enzyme, promotes the transfer of ubiquitin from the E2 enzyme to the target protein. Polyubiquitination of the target protein predominantly serves as a signal leading to degradation of the ubiquitin-conjugated protein by the proteasome, where it undergoes proteolysis. Ubiquitination by E3 ligases can also result in altered protein activity, interactions, or localization. Ubiquitination regulates diverse biology including cell division, DNA repair, and cellular signaling.

The synthesis and degradation of proteins in the cell is critical for cell cycle regulation, cell proliferation, apoptosis, and many other cellular processes. Thus, the ability to modulate the ubiquitin proteasome pathway offers a wealth of opportunities to intervene in disease processes. Mechanisms for intervention can include enhanced degradation of oncogene products, reduced degradation of tumor-suppressor proteins, modulation of immune cell response, and modulation of anti-tumor immune responses.

Therapeutic cancer vaccines have been evaluated in numerous clinical trials. However, only two therapeutic cancer vaccines have been licensed for use in the United States. In particular, the *Bacillus* of Calmette and Guerin strain of *Mycobacterium bovis* has been approved for treatment of bladder cancer, and an ex vivo-activated, autologous cell vaccine has been approved for treatment of prostate cancer. Even so, the response rates and overall survival of patients treated with cancer vaccines are considerably lower than desirable. Thus, what is needed in the art are methods of improving the efficacy of cancer vaccines.

Although numerous clinical trials employing an oncolytic virus to treat cancer have been conducted, only one oncolytic virus has been licensed for use in the United States and Europe. In particular, talimogene laherparepvec is a genetically modified herpes simplex virus approved for treatment of melanoma. However, even talimogene laherparepvec has not been shown to improve overall survival or to benefit patients with visceral metastases. Thus, what is needed in the art are methods of improving the efficacy of oncolytic virus therapy.

Approximately 35 E2 enzymes and over 500 E3 enzymes are encoded in the human genome. Casitas B-lineage lymphoma proto-oncogene-b (Cbl-b) is an E3 ubiquitin ligase that negatively regulates T-cell activation (Wallner et al., Clin Dev Immunol, 2012: 692639). Discovery of agents that modulate E2 or E3 enzymes accordingly provides the potential for therapies directed against disease processes involving a particular E2 or E3 enzyme. The present patent application is directed to agents that inhibit one such E3 enzyme, Casitas B-lineage lymphoma proto-oncogene-b (Cbl-b); agents that inhibit Cbl-b, for use in combination with cancer vaccines, and to pharmaceutical compositions comprising Cbl-b inhibitors and cancer vaccines; and agents that inhibit Cbl-b, for use in combination with oncolytic viruses, and to pharmaceutical compositions comprising Cbl-b inhibitors and oncolytic viruses.

SUMMARY

Disclosed herein are compounds and compositions for inhibition of the Cbl-b enzyme and methods of use thereof in modulating the immune system, treatment of diseases, and treatment of cells in vivo, in vitro, or ex vivo. Also disclosed herein are methods for use of a Cbl-b inhibitor in treating cancer. In brief, the Cbl-b inhibitor may be administered to an individual with cancer, either alone or as part of a combination therapy, with one or more of an immune checkpoint inhibitor, an anti-neoplastic agent, and radiation therapy. Additionally, cells treated in vivo and/or in vitro with a compound or composition as disclosed herein may be used in adoptive cell therapy for treating cancer.

Provided herein are compounds of Formula (I)

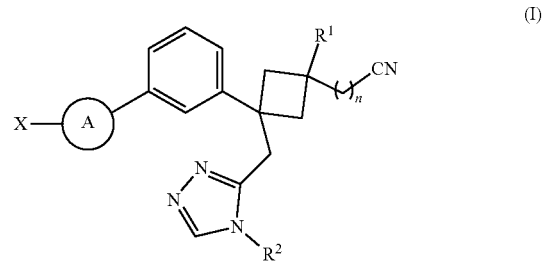

or a tautomer thereof, stereoisomer thereof, or a pharmaceutically acceptable salt thereof, wherein

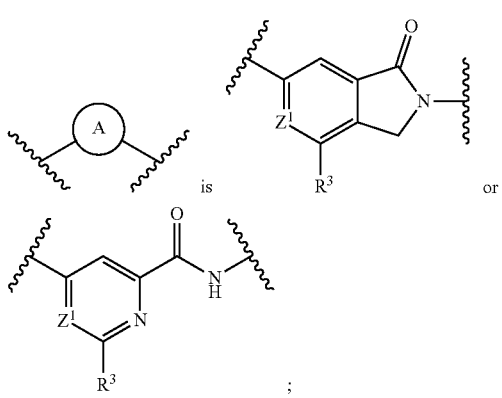

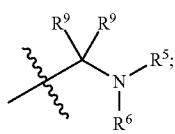

$Z^1$ is CH or nitrogen;
$Z^2$ is CH or nitrogen;
$R^1$ is hydrogen, $C_1$-$C_6$ alkyl, or $C_1$-$C_6$ haloalkyl;
$R^2$ is hydrogen, $C_1$-$C_6$ alkyl, $C_1$-$C_6$ haloalkyl, or $C_3$-$C_6$ cycloalkyl;
$R^3$ is —$CF_3$ or cyclopropyl;
$R^4$ is —$CF_3$ or cyclopropyl;
X is hydrogen, $C_1$-$C_6$ alkyl, $C_1$-$C_6$ haloalkyl, or $R^6$;

$R^5$ is hydrogen, $C_1$-$C_6$ alkyl, $C_1$-$C_6$ haloalkyl, $C_1$-$C_6$ alkyl-OH, or $C_1$-$C_6$ alkyl-CN;
$R^6$ is monocyclic $C_3$-$C_6$ cycloalkyl, fused bicyclic $C_4$-$C_8$ cycloalkyl, bridged bicyclic $C_4$-$C_8$ cycloalkyl, spiro bicyclic $C_5$-$C_8$ cycloalkyl, or 5- to 6-membered heterocyclyl, each of which is optionally substituted by one to five $R^7$ groups;
or $R^5$ and $R^6$ are taken together with the nitrogen atom to which they are attached to form a 5- to 10-membered monocyclic, fused bicyclic, or bridged heterocyclyl, or a 5- to 10-membered monocyclic or bicyclic heteroaryl, each of which heterocyclyl or heteroaryl optionally contains one to two additional heteroatoms selected from the group consisting of nitrogen and oxygen, and each of which heterocyclyl or heteroaryl is optionally substituted by one to five $R^8$ groups; each $R^7$ is independently halo, $C_1$-$C_6$ alkyl, $C_1$-$C_6$ haloalkyl, $C_1$-$C_6$ alkyl-OH, or $C_1$-$C_6$ alkyl-CN; each $R^8$ is independently $C_1$-$C_6$ alkyl, $C_1$-$C_6$ haloalkyl, $C_1$-$C_6$ alkyl-OH, —CN, $C_1$-$C_6$ alkyl-CN, —($C_1$-$C_6$ alkylene)-O—($C_1$-$C_6$ alkyl), hydroxy, or halo,
or two $R^8$ groups attached to the same carbon atom are taken together with the carbon atom to which they are attached to form a spiro $C_3$-$C_6$ cycloalkyl or a spiro 5- to 6-membered heterocyclyl;
each $R^9$ is independently hydrogen, $C_1$-$C_6$ alkyl, $C_1$-$C_6$ haloalkyl, or $C_1$-$C_6$ alkyl-OH; and
n is zero or one.

In some embodiments,

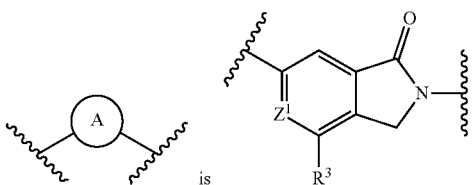

In some embodiments, $Z^1$ is CH. In some embodiments, $Z^1$ is N.

In some embodiments,

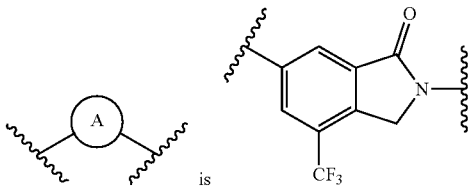

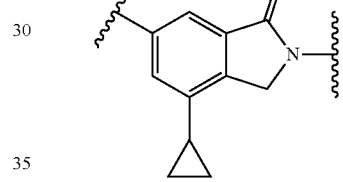

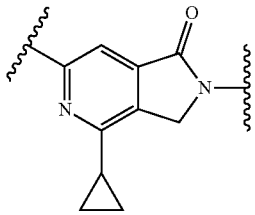

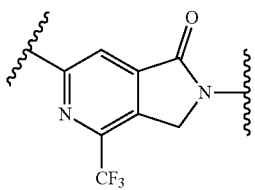

In some embodiments,

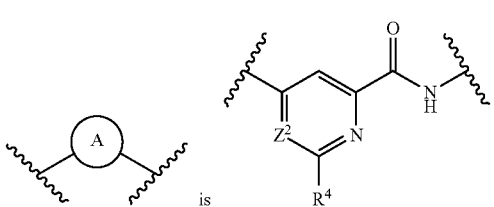

In some embodiments, $Z^2$ is CH. In some embodiments, $Z^2$ is N.

In some embodiments,

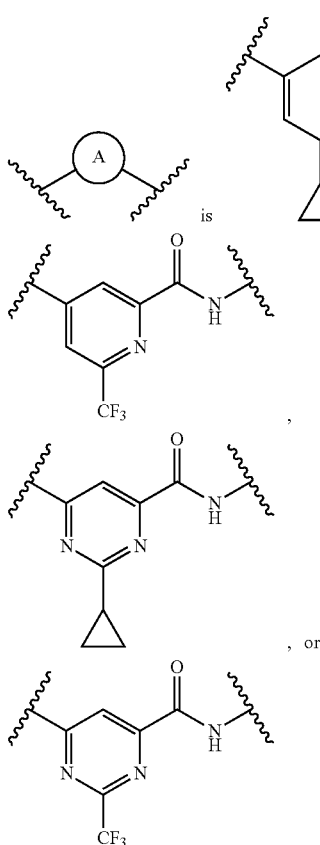

is

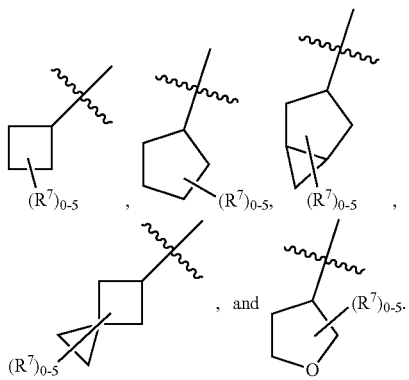

In some embodiments, each $R^7$, where present, is independently halo, $C_1$-$C_3$ alkyl, $C_1$-$C_3$ haloalkyl, $C_1$-$C_3$ alkyl-OH, or $C_1$-$C_3$ alkyl-CN. In some embodiments, each $R^7$, where present, is independently fluoro, —$CH_3$, —$CF_3$, —$CH_2OH$, or —$CH_2CN$.

In some embodiments, $R^5$ and $R^6$ are taken together with the nitrogen atom to which they are attached to form a 5- to 10-membered monocyclic, fused bicyclic, or bridged heterocyclyl, or a 5- to 10-membered monocyclic or bicyclic heteroaryl, each of which heterocyclyl or heteroaryl optionally contains 1-2 additional heteroatoms selected from the group consisting of N and O, and each of which heterocyclyl or heteroaryl is optionally substituted by 1-5 $R^8$ groups. In some embodiments, $R^5$ and $R^6$ are taken together with the nitrogen atom to which they are attached to form a moiety which is selected from the group consisting of

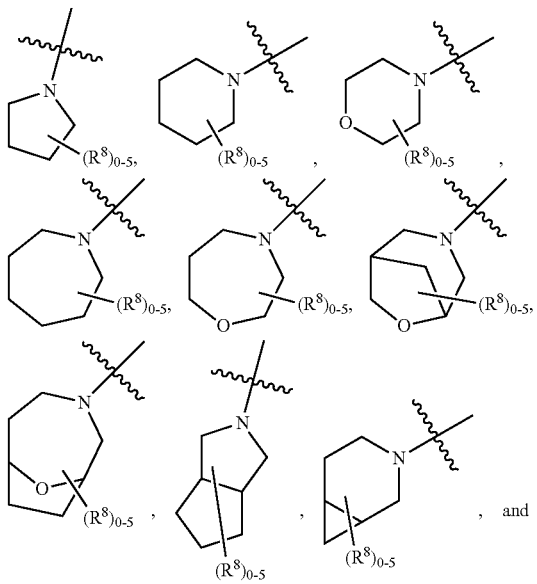

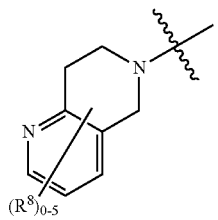

.

In some embodiments, R is H, $C_1$-$C_3$ alkyl, or $C_1$-$C_3$ haloalkyl. In some embodiments, $R^1$ is H, —$CH_3$, or —$CF_3$.

In some embodiments, $R^2$ is H, $C_1$-$C_3$ alkyl, $C_1$-$C_3$ haloalkyl, or $C_3$-$C_4$ cycloalkyl. In some embodiments, $R^2$ is H, —$CH_3$, —$CF_3$, —$CHF_2$, —$CH_2F$, or cyclopropyl.

In some embodiments, n is 0. In some embodiments, n is 1.

In some embodiments, X is H. In some embodiments, X is $C_1$-$C_3$ alkyl or $C_1$-$C_3$ haloalkyl. In some embodiments, X is —$CH_3$ or —$CF_3$.

In some embodiments, X is

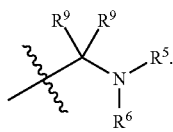

In some embodiments, $R^5$ is H, $C_1$-$C_3$ alkyl, or $C_1$-$C_3$ haloalkyl. In some embodiments, $R^5$ is H, —$CH_3$, —$CF_3$, —$CH_2CN$, or —$CH_2OH$.

In some embodiments, $R^6$ is monocyclic $C_3$-$C_6$ cycloalkyl, fused bicyclic $C_4$-$C_8$ cycloalkyl, bridged bicyclic $C_4$-$C_8$ cycloalkyl, spiro bicyclic $C_5$-$C_8$ cycloalkyl, or 5- to 6-membered heterocyclyl, each of which is optionally substituted by 1-5 $R^7$ groups. In some embodiments, $R^6$ is selected from the group consisting of In some embodiments, each $R^8$, where present, is independently $C_1$-$C_3$ alkyl, $C_1$-$C_3$ haloalkyl, $C_1$-$C_3$ alkyl-OH, —CN, $C_1$-$C_3$ alkyl-CN, —($C_1$-$C_3$ alkylene)-O—($C_1$-$C_3$ alkyl), hydroxy, or halo, or two $R^8$ groups attached to the same carbon atom are taken together with the carbon atom to which they are attached to form a spiro $C_3$-$C_4$ cycloalkyl or a spiro 5- to 6-membered heterocyclyl. In some embodiments, each $R^8$, where present, is independently —$CH_3$, —$CH_2CH_3$, —$CF_3$, —$CH_2OH$, —CN, —$CH_2CN$, —$CH_2$—O—$CH_3$, hydroxy, or F, or two $R^8$ groups attached to the same carbon atom are taken together with the carbon atom to which they are attached to form a spiro cyclopropyl.

In some embodiments, each $R^9$ is independently H, $C_1$-$C_3$ alkyl, $C_1$-$C_3$ haloalkyl, or $C_1$-$C_3$ alkyl-OH. In some embodiments, each $R^9$ is independently H, —$CH_3$, —$CF_3$, or —$CH_2OH$.

Also disclosed herein is a compound selected from the compounds in Table 1, or a tautomer thereof, or a pharmaceutically acceptable salt thereof. Also disclosed herein is a compound selected from any compound disclosed above or herein, or a tautomer thereof, or a pharmaceutically acceptable salt thereof, and a pharmaceutically acceptable excipient.

Also disclosed herein is a method of modulating activity of an immune cell, the method comprising contacting the immune cell with an effective amount of any compound disclosed above or herein, or a tautomer thereof, or a pharmaceutically acceptable salt thereof.

Also disclosed herein is a method of treating a cancer responsive to inhibition of Cbl-b activity in an individual in need thereof, the method comprising administering an effective amount of any compound disclosed above or herein, or a tautomer thereof, or a pharmaceutically acceptable salt thereof, to the individual.

Also disclosed herein is a method of inhibiting Cbl-b activity in an individual in need thereof, the method comprising administering an effective amount of any compound disclosed above or herein, or a tautomer thereof, or a pharmaceutically acceptable salt thereof, to the individual.

Also disclosed herein is a method for treating or preventing a disease or condition associated with Cbl-b activity in an individual in need thereof, the method comprising administering any compound disclosed above or herein, or a tautomer thereof, or a pharmaceutically acceptable salt thereof, to the individual.

Also disclosed herein is a method of producing a modified immune cell, the method comprising culturing a cell population containing an immune cell in the presence of an effective amount of any compound disclosed above or herein, or a tautomer thereof, or a pharmaceutically acceptable salt thereof.

Also disclosed herein is a modified immune cell comprising a Cbl-b inhibitor, wherein the Cbl-b inhibitor is any compound disclosed above or herein, or a tautomer thereof, or a pharmaceutically acceptable salt thereof.

Also disclosed herein is an isolated modified immune cell, wherein the immune cell has been contacted or is in contact with any compound disclosed above or herein, or a tautomer thereof, or a pharmaceutically acceptable salt thereof.

Also disclosed herein is a composition comprising a cell population containing an isolated modified immune cell, wherein the immune cell has been contacted or is in contact with any compound disclosed above or herein, or a tautomer thereof, or a pharmaceutically acceptable salt thereof.

Also disclosed herein is a method of inhibiting abnormal cell proliferation, the method comprising administering an effective amount of an isolated modified immune cell, wherein the immune cell has been contacted or is in contact with any compound disclosed above or herein, or a tautomer thereof, or a pharmaceutically acceptable salt thereof, to an individual in need thereof.

Also disclosed herein is a method of inhibiting abnormal cell proliferation, the method comprising administering a composition comprising a cell population containing an isolated modified immune cell, wherein the immune cell has been contacted or is in contact with any compound disclosed above or herein, or a tautomer thereof, or a pharmaceutically acceptable salt thereof, to an individual in need thereof.

Also disclosed herein is a method of inhibiting abnormal cell proliferation, the method comprising administering an effective amount of any compound disclosed above or herein, or a tautomer thereof, or a pharmaceutically acceptable salt thereof.

Also disclosed herein is a cell culture composition comprising a cell population containing an immune cell and a Cbl-b inhibitor, wherein the Cbl-b inhibitor is any compound disclosed above or herein, or a tautomer thereof, or a pharmaceutically acceptable salt thereof.

Also disclosed herein is a pharmaceutical composition comprising a Cbl-b inhibitor and one or both of an adjuvant and an antigen, wherein the Cbl-b inhibitor is any compound disclosed above or herein, or a tautomer thereof, or a pharmaceutically acceptable salt thereof.

Also disclosed herein is an article of manufacture comprising any modified immune cell as disclosed herein, any composition comprising a cell population as disclosed herein, any cell culture composition as disclosed herein, or any pharmaceutical composition as disclosed herein.

Also disclosed herein is a kit comprising any modified immune cell as disclosed herein or any composition comprising a cell population as disclosed herein.

Also disclosed herein is the use of a Cbl-b inhibitor in the manufacture of a medicament for treating or preventing a disease or condition associated with Cbl-b activity, wherein the Cbl-b inhibitor is any compound disclosed above or herein, or a tautomer thereof, or a pharmaceutically acceptable salt thereof.

In any of the embodiments disclosed herein, the Cbl-b protein can be a mammalian Cbl-b, or a human Cbl-b.

Also, disclosed herein are Cbl-b inhibitor compounds, vaccines, and compositions comprising Cbl-b inhibitors and vaccines, as well as methods of use thereof in treating cancer. The Cbl-b inhibitor and the cancer vaccine may be administered to an individual with cancer.

Also, disclosed herein are Cbl-b inhibitor compounds, oncolytic viruses, and compositions comprising Cbl-b inhibitors and oncolytic viruses, as well as methods of use thereof in treating cancer. The Cbl-b inhibitor and the oncolytic virus may be administered to an individual with cancer.

Provided herein is a method of immunizing, the method comprising administering to an individual in need thereof an effective amount of a small molecule Cbl-b inhibitor, and administering to the individual an effective amount of a vaccine.

Provided herein is a method of treating cancer, the method comprising administering to an individual with cancer an effective amount of a small molecule Cbl-b inhibitor, and administering to the individual an effective amount of an oncolytic virus.

Provided herein is a method of treating cancer, the method comprising administering to an individual with cancer an effective amount of an agent capable of lowering activation threshold of an immune cell, and administering to the individual an effective amount of a therapeutic cancer vaccine; or administering to the individual an effective amount of an oncolytic virus.

Provided herein is a pharmaceutical composition comprising a cancer vaccine and a small molecule Cbl-b inhibitor, optionally wherein the composition further comprises a pharmaceutically acceptable excipient.

Provided herein is a kit for treating cancer, the kit comprising (a) a small molecule Cbl-b inhibitor; (b) a therapeutic cancer vaccine; and (c) instructions for administration of an effective amount of the Cbl-b inhibitor and the therapeutic cancer vaccine to treat cancer in an individual.

Provided herein is a kit for treating cancer, the kit comprising (a) a pharmaceutical composition comprising a small molecule Cbl-b inhibitor and a therapeutic cancer vaccine; and (b) instructions for administration of an effective amount of the pharmaceutical composition comprising the Cbl-b inhibitor and the therapeutic cancer vaccine to treat cancer in an individual.

Provided herein is a pharmaceutical composition comprising an oncolytic virus and a small molecule Cbl-b inhibitor, optionally wherein the composition further comprises a pharmaceutically acceptable excipient.

Provided herein is a kit for treating cancer, the kit comprising (a) a small molecule Cbl-b inhibitor; (b) an oncolytic virus; and (c) instructions for administration of an effective amount of the Cbl-b inhibitor and the oncolytic virus to treat cancer in an individual.

And, provided herein is a kit for treating cancer, the kit comprising (a) a pharmaceutical composition comprising a small molecule Cbl-b inhibitor and an oncolytic virus; and (b) instructions for administration of an effective amount of the pharmaceutical composition comprising the small molecule Cbl-b inhibitor and the oncolytic virus to treat cancer in an individual.

DETAILED DESCRIPTION

Provided herein are compounds and pharmaceutical compositions that inhibit the Cbl-b enzyme, as well as methods of treatment using such compounds and pharmaceutical compositions. The compounds and compositions can be used in methods of modulating the immune system, for treatment of diseases, and for treatment of cells in vivo, in vitro, or ex vivo. Also, provided herein are pharmaceutical compositions comprising cancer vaccines and compounds that inhibit the Cbl-b enzyme, as well as methods of treatment using such compounds, cancer vaccines, and pharmaceutical compositions. Also provided herein are pharmaceutical compositions comprising oncolytic viruses and compounds that inhibit the Cbl-b enzyme, as well as methods of treatment using such compounds, oncolytic viruses, and pharmaceutical compositions.

T-cell activation and T-cell tolerance are tightly controlled processes regulating the immune response to tumors while preventing autoimmunity. Tolerance prevents the immune system from attacking cells expressing "self" antigens. During peripheral tolerance, T-cells that recognize "self" antigens (i.e., self-reactive T-cells) become functionally unresponsive or are deleted after encountering "self" antigens outside of the thymus. Peripheral tolerance processes therefore are important for preventing autoimmune diseases. Normally, cancer cells are removed by activated T-cells that recognize tumor antigens expressed on the surface of the cancer cells. However, in cancer, the tumor microenvironment can support T-cell tolerance to cancer cells, which allows cancer cells to avoid recognition and removal by the immune system. The ability of cancer cells to avoid tumor immunosurveillance can contribute to uncontrolled tumor growth. Therefore, T-cell tolerance can be a form of T-cell dysfunction. General principles of T-cell dysfunction are well known in the art (see Schietinger et al., Trends Immunol., 35: 51-60, 2014). Additional types of T-cell dysfunction that can contribute to uncontrolled tumor growth include T-cell exhaustion, T-cell senescence, and/or T-cell anergy. Therefore, treating T-cell dysfunction, for example, by increasing T-cell activation, increasing T-cell proliferation, decreasing T-cell tolerance, and/or decreasing T-cell exhaustion, is beneficial for preventing or treating cancer. Additional cells of the immune system are important for recognition and removal of cancer cells during immune surveillance. For example, Natural Killer (NK) cells are lymphocytes of the innate immune system that are able to identify and kill cancer cells (see Martinez-Losato et al., Clin Cancer Res., 21: 5048-5056, 2015). Recent studies have also shown that B-cell subsets with distinct phenotypes and functions exhibit diverse roles in the anti-tumor response (see Saravaria et al., Cell Mol Immunol., 14: 662-674, 2017). Due to their role in tumor surveillance, NK-cells and B-cells may also be amenable as therapeutic targets for the prevention or treatment of cancer.

Cbl-b is a RING-type E3 ligase that plays an important role in the immune system due to its function as a negative regulator of immune activation. Cbl-b has an essential role in decreasing the activation of T-cells, thereby enhancing T-cell tolerance. Studies have found that cbl-b-deficient T-cells display lower thresholds for activation by antigen recognition receptors and co-stimulatory molecules (e.g., CD28). For example, loss of Cbl-b in T-cells uncouples the requirement for CD28 costimulation during T-cell activation and proliferation (see Bachmaier et al., Nature, 403: 211-216, 2000). Such cbl-b-/- T-cells are largely resistant to T-cell anergy, a tolerance mechanism in which T-cells are functionally inactivated and T-cell proliferation is greatly impaired (see Jeon et al., Immunity, 21: 167-177, 2004; and Schwartz et al., Annu Rev Immunol., 21: 305-34, 2003). In support of this, loss of Cbl-b in cbl-b knockout mice resulted in impaired induction of T-cell tolerance and exacerbated autoimmunity (see Jeon et al., Immunity, 21: 167-177, 2004). Importantly, loss of Cbl-b in mice also resulted in a robust anti-tumor response that depends primarily on cytotoxic T-cells. One study showed that cbl-b-/- CD8+ T-cells are resistant to T regulatory cell-mediated suppression and exhibit enhanced activation and tumor infiltration. Therapeutic transfer of naive cbl-b-/- CD8+ T-cells was sufficient to mediate rejection of established tumors (see Loeser et al., J Exp Med., 204: 879-891, 2007). Recent studies have shown that Cbl-b also plays a role in NK-cell activation. Genetic deletion of Cbl-b or targeted inactivation of its E3 ligase activity allowed NK-cells to spontaneously reject metastatic tumors in a mouse model (see Paolino et al., Nature, 507: 508-512, 2014).

Provided herein are compounds and compositions that are potent inhibitors of Cbl-b and can be used in novel approaches to treat diseases such as cancer. In some embodiments, the compounds and compositions provided herein can be used in methods of modulating the immune system, such as increasing activation of T-cells, NK-cells, and B-cells, as well as in the treatment of such cells in vivo, in vitro, or ex vivo.

I. Definitions

An "effective amount" of an agent disclosed herein is an amount sufficient to carry out a specifically stated purpose.

An "effective amount" may be determined empirically and in a routine manner, in relation to the stated purpose. An "effective amount" or an "amount sufficient" of an agent is that amount adequate to produce a desired biological effect, such as a beneficial result, including a beneficial clinical result. In some embodiments, the term "effective amount" refers to an amount of an agent effective to "treat" a disease or disorder in an individual (e.g., a mammal such as a human).

The term "Cbl-b" as used herein refers to a Cbl-b protein. The term also includes naturally occurring variants of Cbl-b, including splice variants or allelic variants. The term also includes non-naturally occurring variants of Cbl-b, such as a recombinant Cbl-b protein or truncated variants thereof, which generally preserve the binding ability of naturally occurring Cbl-b or naturally occurring variants of Cbl-b (e.g., the ability to bind to an E2 enzyme).

The terms "pharmaceutical formulation" and "pharmaceutical composition" refer to preparations that are in such form as to permit the biological activity of the active ingredient to be effective, and that contain no additional components that are unacceptably toxic to an individual to which the formulation or composition would be administered. Such formulations or compositions may be sterile. Such formulations or compositions may be sterile, with the exception of the inclusion of an oncolytic virus.

"Excipients" as used herein include pharmaceutically acceptable excipients, carriers, vehicles, or stabilizers that are nontoxic to the cell or mammal being exposed thereto at the dosages and concentrations employed. Often the physiologically acceptable excipient is an aqueous pH buffered solution.

Reference to a compound as described in a pharmaceutical composition, or to a compound as described in a claim to a pharmaceutical composition, refers to the compound described by the formula recited in the pharmaceutical composition, without the other elements of the pharmaceutical composition, that is, without carriers, excipients, etc.

The terms "treating" or "treatment" of a disease refer to executing a protocol, which may include administering one or more therapeutic agent to an individual (human or otherwise), in an effort to obtain beneficial or desired results in the individual, including clinical results. Beneficial or desired clinical results include, but are not limited to, alleviation or amelioration of one or more symptoms, diminishment of extent of disease, stabilized (i.e., not worsening) state of disease, preventing spread of disease, delay or slowing of disease progression, amelioration or palliation of the disease state, and remission (whether partial or total). "Treatment" also can mean prolonging survival as compared to expected survival of an individual not receiving treatment. Further, "treating" and "treatment" may occur by administration of one dose of a therapeutic agent or therapeutic agents, or may occur upon administration of a series of doses of a therapeutic agent or therapeutic agents. "Treating" or "treatment" does not require complete alleviation of signs or symptoms, and does not require a cure. "Treatment" also can refer to clinical intervention, such as administering one or more therapeutic agents to an individual, designed to alter the natural course of the individual or cell being treated (i.e., to alter the course of the individual or cell that would occur in the absence of the clinical intervention). The term "therapeutic agent" can refer to a Cbl-b inhibitor, a modified immune cell or compositions thereof.

As used herein, an "individual" or a "subject" is a mammal. A "mammal" for purposes of treatment includes humans; non-human primates; domestic and farm animals; and zoo, sports, or pet animals, such as dogs, horses, rabbits, cattle, pigs, hamsters, gerbils, mice, ferrets, rats, cats, etc. In some embodiments, the individual or subject is human.

As used herein, the term "T-cell dysfunction" refers to a state of reduced immune responsiveness to antigenic stimulation. The term "T-cell dysfunction" includes common elements of both T-cell exhaustion and/or T-cell anergy in which antigen recognition may occur, but the ensuing immune response is ineffective to control tumor growth. The term "T-cell dysfunction" also includes being refractory or unresponsive to antigen recognition, such as, impaired capacity to translate antigen recognition to downstream T-cell effector functions, such as proliferation, cytokine production, and/or target cell killing.

The term "T-cell anergy" refers to the state of unresponsiveness to antigen stimulation resulting from incomplete or insufficient signals delivered through the T-cell receptor. "T-cell anergy" can also result upon stimulation with antigen in the absence of co-stimulation, resulting in the cell becoming refractory to subsequent activation by the antigen even in the context of co-stimulation.

The term "T-cell exhaustion" refers to a state of T-cell dysfunction that arises from sustained TCR signaling that can occur during cancer. It is distinguished from anergy in that it arises not through incomplete or deficient signaling, but from sustained signaling. It is defined by poor effector function, sustained expression of inhibitory receptors, and a transcriptional state distinct from that of functional effector or memory T-cell.

A "T-cell dysfunction disorder" is a disorder or condition characterized by decreased responsiveness of T-cells to antigenic stimulation. Decreased responsiveness may result in ineffective control of a tumor. In some embodiments, the term "T-cell dysfunction disorder" encompasses cancer such as a hematologic cancer or a non-hematologic cancer. In some embodiments, a "T-cell dysfunctional disorder" is one in which T-cells are anergic or have decreased ability to secrete cytokines, proliferate, or execute cytolytic activity.

"Enhancing T-cell function" means to induce, cause, or stimulate a T-cell to have a sustained or amplified biological function, or renew or reactivate exhausted or inactive T-cells. Examples of enhanced T-cell function include increased T-cell activation (e.g., increased cytokine production, increased expression of T-cell activation markers, etc.), increased T-cell proliferation, decreased T-cell exhaustion, and/or decreased T-cell tolerance relative to the state of the T-cells before treatment with a Cbl-b inhibitor. Methods of measuring enhancement of T-cell function are known in the art.

"Proliferation" is used herein to refer to the proliferation of a cell. Increased proliferation encompasses the production of a greater number of cells relative to a baseline value. Decreased proliferation encompasses the production of a reduced number of cells relative to a baseline value. In some embodiments, the cell is an immune cell such as a T-cell and increased proliferation is desired. In some embodiments, the cell is a cancer cell and reduced proliferation is desired.

"Alkyl" as used herein refers to a saturated linear (i.e., unbranched) or branched univalent hydrocarbon chain or combination thereof. Particular alkyl groups are those having a designated number of carbon atoms, for example, an alkyl group having 1 to 20 carbon atoms (a "$C_1$-$C_{20}$ alkyl"), having 1 to 10 carbon atoms (a "$C_1$-$C_{10}$" alkyl), having 1 to 8 carbon atoms (a "$C_1$-$C_8$ alkyl"), having 1 to 6 carbon atoms (a "$C_1$-$C_6$ alkyl"), having 2 to 6 carbon atoms (a "$C_2$-$C_6$ alkyl"), or having 1 to 4 carbon atoms (a "$C_1$-$C_4$ alkyl"). Examples of alkyl groups include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like.

"Alkenyl" as used herein refers to an unsaturated linear (i.e., unbranched) or branched univalent hydrocarbon chain or combination thereof, having at least one site of olefinic unsaturation (i.e., having at least one moiety of the formula C═C). Particular alkenyl groups are those having a designated number of carbon atoms, for example, an alkenyl group having 2 to 20 carbon atoms (a "$C_2$-$C_{20}$ alkenyl"), having 2 to 10 carbon atoms (a "$C_2$-$C_{10}$" alkenyl), having 2 to 8 carbon atoms (a "$C_2$-$C_8$ alkenyl"), having 2 to 6 carbon atoms (a "$C_2$-$C_6$ alkenyl"), or having 2 to 4 carbon atoms (a "$C_2$-$C_4$ alkenyl"). The alkenyl group may be in "cis" or "trans" configurations or, alternatively, in "E" or "Z" configurations. Examples of alkenyl groups include, but are not limited to, groups such as ethenyl (or vinyl), prop-1-enyl, prop-2-enyl (or allyl), 2-methylprop-1-enyl, but-1-enyl, but-2-enyl, but-3-enyl, buta-1,3-dienyl, 2-methylbuta-1,3-dienyl, homologs, and isomers thereof, and the like.

"Alkynyl" as used herein refers to an unsaturated linear (i.e., unbranched) or branched univalent hydrocarbon chain or combination thereof, having at least one site of acetylenic unsaturation (i.e., having at least one moiety of the formula C≡C). Particular alkynyl groups are those having a designated number of carbon atoms, for example, an alkynyl group having 2 to 20 carbon atoms (a "$C_2$-$C_{20}$ alkynyl"), having 2 to 10 carbon atoms (a "$C_2$-$C_{10}$ alkynyl"), having 2 to 8 carbon atoms (a "$C_2$-$C_8$ alkynyl"), having 2 to 6 carbon atoms (a "$C_2$-$C_6$ alkynyl"), or having 2 to 4 carbon atoms (a "$C_2$-$C_4$ alkynyl"). Examples of alkynyl groups include, but are not limited to, groups such as ethynyl (or acetylenyl), prop-1-ynyl, prop-2-ynyl (or propargyl), but-1-ynyl, but-2-ynyl, but-3-ynyl, homologs, and isomers thereof, and the like.

"Alkylene" as used herein refers to the same residues as alkyl, but having bivalency. Particular alkylene groups are those having 1 to 6 carbon atoms (a "$C_1$-$C_6$ alkylene"), 1 to 5 carbon atoms (a "$C_1$-$C_5$ alkylene"), 1 to 4 carbon atoms (a "$C_1$-$C_4$ alkylene"), or 1 to 3 carbon atoms (a "$C_1$-$C_3$ alkylene"). Examples of alkylene groups include, but are not limited to, groups such as methylene (—$CH_2$—), ethylene (—$CH_2CH_2$—), propylene (—$CH_2CH_2CH_2$—), butylene (—$CH_2CH_2CH_2CH_2$—), and the like.

"Cycloalkyl" as used herein refers to non-aromatic, saturated or unsaturated, cyclic univalent hydrocarbon structures. Particular cycloalkyl groups are those having a designated number of annular (i.e., ring) carbon atoms, for example, a cycloalkyl group having from 3 to 12 annular carbon atoms (a "$C_3$-$C_{12}$ cycloalkyl"). A particular cycloalkyl is a cyclic hydrocarbon having from 3 to 8 annular carbon atoms (a "$C_3$-$C_8$ cycloalkyl"), or having 3 to 6 annular carbon atoms (a "$C_3$-$C_6$ cycloalkyl"). Cycloalkyl can consist of one ring, such as cyclohexyl, or multiple rings, such as adamantyl, but excludes aromatic (e.g., aryl) groups. A cycloalkyl comprising more than one ring may be fused, spiro, or bridged, or combinations thereof. Examples of cycloalkyl groups include, but are not limited to, cyclopropyl

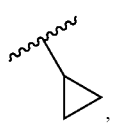 [SMILES: *C1CC1]

cyclobutyl,

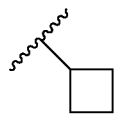 [SMILES: *C1CCC1]

cyclopentyl

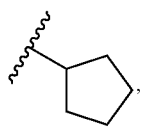 [SMILES: *C1CCCC1]

cyclohexyl

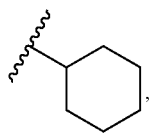

1-cyclohexenyl, 3-cyclohexenyl, cycloheptyl

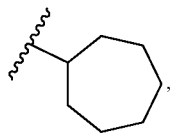 [SMILES: *C1CCCCCC1]

norbornyl, and the like.

"Cycloalkylene" as used herein refers to the same residues as cycloalkyl, but having bivalency (i.e., in contrast to being univalent). Particular cycloalkylene groups are those having 3 to 12 annular carbon atoms (a "$C_3$-$C_{12}$ cycloalkylene"), having from 3 to 8 annular carbon atoms (a "$C_3$-$C_8$ cycloalkylene"), or having 3 to 6 annular carbon atoms (a "$C_3$-$C_6$ cycloalkylene"). Examples of cycloalkylene groups include, but are not limited to, cyclopropylene

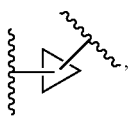

cyclobutylene

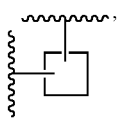

cyclopentylene

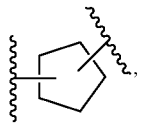

cyclohexylene

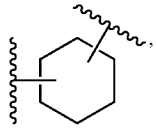

1,2-cyclohexenylene, 1,3-cyclohexenylene, 1,4-cyclohexenylene, cycloheptylene

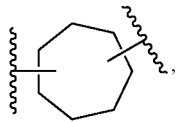

norbornylene, and the like.

"Aryl" as used herein refers to an aromatic carbocyclic group having a single ring (e.g., phenyl), or multiple condensed rings (e.g., naphthyl or anthryl) where one or more of the condensed rings may not be aromatic. Particular aryl groups are those having from 6 to 14 annular (i.e., ring) carbon atoms (a "$C_6$-$C_{14}$ aryl"). An aryl group having more than one ring where at least one ring is non-aromatic may be connected to the parent structure at either an aromatic ring position or at a non-aromatic ring position. In one variation, an aryl group having more than one ring where at least one ring is non-aromatic is connected to the parent structure at an aromatic ring position. Examples of aryls include, but are not limited to, groups such as phenyl, naphthyl, 1-naphthyl, 2-naphthyl, 1,2,3,4-tetrahydronaphthalen-6-yl

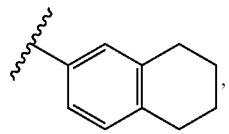 [SMILES: *c1ccc2c(c1)CCCC2]

and the like.

"Carbocyclyl" or "carbocyclic" refers to an aromatic or non-aromatic univalent cyclic group in which all of the ring members are carbon atoms, such as cyclohexyl, phenyl, 1,2-dihydronaphthyl, etc.

"Arylene" as used herein refers to the same residues as aryl, but having bivalency. Particular arylene groups are those having from 6 to 14 annular carbon atoms (a "$C_6$-$C_{14}$ arylene"). Examples of arylene include, but are not limited to, groups such as phenylene, o-phenylene (i.e., 1,2-phenylene), m-phenylene (i.e., 1,3-phenylene), p-phenylene (i.e., 1,4-phenylene), naphthylene, 1,2-naphthylene, 1,3-naphthylene, 1,4-naphthylene, 2,7-naphthylene, 2,6-naphthylene, and the like.

"Heteroaryl" as used herein refers to an unsaturated aromatic cyclic group having from 1 to 14 annular carbon atoms and at least one annular heteroatom, including, but not limited to, heteroatoms such as nitrogen, oxygen, and sulfur. A heteroaryl group may have a single ring (e.g., pyridyl or imidazolyl) or multiple condensed rings (e.g., indolizinyl, indolyl, or quinolinyl) where at least one of the condensed rings is aromatic. Particular heteroaryl groups are 5- to 14-membered rings having 1 to 12 annular carbon atoms and 1 to 6 annular heteroatoms independently selected from the group consisting of nitrogen (N), oxygen (O), and sulfur (S) (a "5- to 14-membered heteroaryl"); 5- to 10-membered rings having 1 to 8 annular carbon atoms and 1 to 4 annular heteroatoms independently selected from the group consisting of nitrogen, oxygen, and sulfur (a "5- to 10-membered heteroaryl"); or 5-, 6-, or 7-membered rings having 1 to 5 annular carbon atoms and 1 to 4 annular heteroatoms independently selected from the group consisting of nitrogen, oxygen, and sulfur (a "5- to 7-membered heteroaryl"). In one variation, heteroaryl includes monocyclic aromatic 5-, 6-, or 7-membered rings having from 1 to 6 annular carbon atoms and 1 to 4 annular heteroatoms independently selected from the group consisting of nitrogen, oxygen, and sulfur. In another variation, heteroaryl includes polycyclic aromatic rings having from 1 to 12 annular carbon atoms and 1 to 6 annular heteroatoms independently selected from the group consisting of nitrogen, oxygen, and sulfur. A heteroaryl group having more than one ring where at least one ring is non-aromatic may be connected to the parent structure at either an aromatic ring position or at a non-aromatic ring position. Examples of heteroaryl include, but are not limited to, groups such as pyridyl, benzimidazolyl, benzotriazolyl, benzo[b]thienyl, quinolinyl, indolyl, benzothiazolyl, and the like. "Heteroaryl" also includes moieties such as

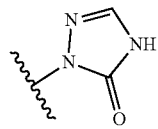 [SMILES: *n1nc[nH]c1=O]

(2,4-dihydro-3H-1,2,4-triazol-3-one-2-yl), which has the aromatic tautomeric structure

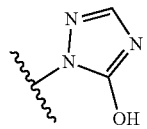 [SMILES: *n1ncnc1O]

(1H-1,2,4-triazol-5-ol-1-yl).

"Heterocyclyl" and "heterocyclic groups" as used herein refer to non-aromatic saturated or partially unsaturated cyclic groups having the number of atoms and heteroatoms as specified, or if no number of atoms or heteroatoms is specified, having at least three annular atoms, from 1 to 14 annular carbon atoms, and at least one annular heteroatom, including, but not limited to, heteroatoms such as nitrogen, oxygen, and sulfur. A heterocyclic group may have a single ring (e.g., tetrahydrothiophenyl, oxazolidinyl) or multiple condensed rings (e.g., decahydroquinolinyl, octahydrobenzo[d]oxazolyl). Multiple condensed rings include, but are not limited to, bicyclic, tricyclic, and quadracyclic rings, as well as bridged or spirocyclic ring systems. Examples of heterocyclic groups include, but are not limited to, aziridinyl, azetidinyl, pyrrolidinyl, piperidinyl, oxiranyl, oxetanyl, tetrahydrofuranyl, tetrahydropyranyl, oxazolidinyl, piperazinyl, morpholinyl, dioxanyl, 3,6-dihydro-2H-pyranyl, 2,3-dihydro-1H-imidazolyl, and the like.

"Heteroarylene" as used herein refers to the same residues as heteroaryl, but having bivalency. Particular heteroarylene groups are 5- to 14-membered rings having 1 to 12 annular carbon atoms and 1 to 6 annular heteroatoms independently selected from the group consisting of nitrogen, oxygen, and sulfur (a "5- to 14-membered heteroarylene"); 5- to 10-membered rings having 1 to 8 annular carbon atoms and 1 to 4 annular heteroatoms independently selected from the group consisting of nitrogen, oxygen, and sulfur (a "5- to 10-membered heteroarylene"); or 5-, 6-, or 7-membered rings having 1 to 5 annular carbon atoms and 1 to 4 annular heteroatoms independently selected from the group consisting of nitrogen, oxygen, and sulfur (a "5- to 7-membered heteroarylene"). Examples of heteroarylene include, but are not limited to, groups such as pyridylene, benzimidazolylene, benzotriazolylene, benzo[b]thienylene, quinolinylene, indolylene, benzothiazolylene, and the like.

"Halo" or "halogen" refers to elements of the Group 17 series having atomic number 9 to 85. Halo groups include fluoro (F), chloro (Cl), bromo (Br), and iodo (I).

"Haloalkyl," "haloalkylene," "haloaryl," "haloarylene," "haloheteroaryl," and similar terms refer to a moiety substituted with at least one halo group. Where a haloalkyl moiety or other halo-substituted moiety is substituted with more than one halogen, it may be referred to by using a prefix corresponding to the number of halogen moieties attached. For example, dihaloaryl, dihaloalkyl, trihaloaryl, trihaloalkyl, etc., refer to aryl and alkyl substituted with two ("di") or three ("tri") halo groups, which may be, but are not necessarily, the same halo; thus, for example, the haloaryl group 4-chloro-3-fluorophenyl is within the scope of dihaloaryl. The subset of haloalkyl groups in which each hydrogen (H) of an alkyl group is replaced with a halo group is referred to as a "perhaloalkyl." A particular perhaloalkyl group is trifluoroalkyl (—$CF_3$). Similarly, "perhaloalkoxy" refers to an alkoxy group in which a halogen takes the place of each hydrogen (H) in the hydrocarbon making up the alkyl moiety of the alkoxy group. An example of a perhaloalkoxy group is trifluoromethoxy (—$OCF_3$). "Haloalkyl" includes monohaloalkyl, dihaloalkyl, trihaloalkyl, perhaloalkyl, and any other number of halo substituents possible on an alkyl group; and similarly for other groups such as haloalkylene, haloaryl, haloarylene, haloheteroaryl, etc.

"Amino" refers to the group —$NH_2$.

"Oxo" refers to the group =O, that is, an oxygen atom doubly bonded to carbon or another chemical element.

"Optionally substituted," unless otherwise specified, means that a group is unsubstituted or substituted by one or more (e.g., 1, 2, 3, 4, or 5) of the substituents listed for that group, in which the substituents may be the same or different. In one embodiment, an optionally substituted group is unsubstituted. In one embodiment, an optionally substituted group has one substituent. In another embodiment, an optionally substituted group has two substituents. In another embodiment, an optionally substituted group has three substituents. In another embodiment, an optionally substituted group has four substituents. In some embodiments, an optionally substituted group has 1 to 2, 1 to 3, 1 to 4, or 1 to 5 substituents. When multiple substituents are present, each substituent is independently chosen unless indicated otherwise. For example, each ($C_1$-$C_4$ alkyl) substituent on the group —$N(C_1$-$C_4$ alkyl)($C_1$-$C_4$ alkyl) can be selected independently from the other, so as to generate groups such as —$N(CH_3)(CH_2CH_3)$, etc.

In addition to the disclosure herein, the term "substituted," when used to modify a specified group or radical, can also mean that one or more hydrogen atoms (H) of the specified group or radical are each, independently of one another, replaced with the same or different substituent groups as defined herein. In some embodiments, a group that is substituted has 1, 2, 3, or 4 substituents, 1, 2, or 3 substituents, 1 or 2 substituents, or 1 substituent.

Substituents can be attached to any chemically possible location on the specified group or radical, unless indicated otherwise. Thus, for example, in one embodiment, —$C_1$-$C_8$ alkyl-OH includes, for example, —$CH_2CH_2OH$ and —CH(OH)—$CH_3$, and —$CH_2C(OH)(CH_3)_2$, and the like. By way of further example, in one embodiment, —$C_1$-$C_6$ alkyl-OH includes, for example, —$CH_2CH_2OH$ and —CH(OH)—$CH_3$, and —$CH_2C(OH)(CH_3)_2$, and the like. By way of further example, in one embodiment, —$C_1$-$C_6$ alkyl-CN includes, for example, —$CH_2CH_2CN$ and —CH(CN)—$CH_3$, and —$CH_2C(CN)(CH_3)_2$, and the like.

Unless a specific isotope of an element is indicated in a formula, the disclosure includes all isotopologues of the compounds disclosed herein, such as, for example, deuterated derivatives of the compounds (where H can be 2H, i.e., deuterium (D)). Deuterated compounds may provide favorable changes in pharmacokinetic (ADME) properties. Isotopologues can have isotopic replacements at any or at all locations in a structure, or can have atoms present in natural abundance at any or all locations in a structure.

A "small molecule" as used herein refers to a compound of 1,000 daltons or less in molecular weight.

Hydrogen atoms can also be replaced with close bioisosteres, such as fluorine, provided that such replacements result in stable compounds.

The disclosure also includes any or all of the stereochemical forms, including any enantiomeric or diastereomeric forms of the compounds described herein, and cis/trans or E/Z isomers. Unless stereochemistry is explicitly indicated in a chemical structure or name, the structure or name is intended to embrace all possible stereoisomers of a compound depicted. In addition, where a specific stereochemical form is depicted, it is understood that all other stereochemical forms are also described and embraced by the disclosure, as well as the general non-stereospecific form and mixtures of the disclosed compounds in any ratio, including mixtures of two or more stereochemical forms of a disclosed compound in any ratio, such that racemic, non-racemic, enantioenriched, and scalemic mixtures of a compound are embraced. Compositions comprising a disclosed compound also are intended, such as a composition of substantially pure compound, including a specific stereochemical form thereof. Compositions comprising a mixture of disclosed compounds in any ratio also are embraced by the disclosure, including compositions comprising mixtures of two or more stereochemical forms of a disclosed compound in any ratio, such that racemic, non-racemic, enantioenriched, and scalemic mixtures of a compound are embraced by the disclosure. If stereochemistry is explicitly indicated for one portion or portions of a molecule, but not for another portion or portions of a molecule, the structure is intended to embrace all possible stereoisomers for the portion or portions where stereochemistry is not explicitly indicated. The disclosure also embraces any and all tautomeric forms of the compounds described herein.

The disclosure is intended to embrace all salts of the compounds described herein, as well as methods of using such salts of the compounds. In one embodiment, the salts of the compounds comprise pharmaceutically acceptable salts. Pharmaceutically acceptable salts are those salts that can be administered as drugs or pharmaceuticals to humans and/or animals and that, upon administration, retain at least some of the biological activity of the free compound (neutral compound or non-salt compound). The desired salt of a basic compound may be prepared by methods known to those of skill in the art by treating the compound with an acid. Examples of inorganic acids include, but are not limited to, hydrochloric acid, hydrobromic acid, sulfuric acid, nitric acid, and phosphoric acid. Examples of organic acids include, but are not limited to, formic acid, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, sulfonic acids, and salicylic acid. Salts of basic compounds with amino acids, such as aspartate salts and glutamate salts, also can be prepared. The desired salt of an acidic compound can be prepared by methods known to those of skill in the art by treating the compound with a base. Examples of inorganic salts of acid compounds include, but are not limited to, alkali metal and alkaline earth salts, such as sodium salts, potassium salts, magnesium salts, and calcium salts; ammonium salts; and aluminum salts. Examples of organic salts of acid compounds include, but are not limited to, procaine, dibenzylamine, N-ethylpiperidine, N,N'-dibenzylethylenediamine, and triethylamine salts. Salts of acidic compounds with amino acids, such as lysine salts, also can be prepared. For lists of pharmaceutically acceptable salts, see, for example, P. H. Stahl and C. G. Wermuth (eds.) "Handbook of Pharmaceutical Salts, Properties, Selection and Use" Wiley-VCH, 2011 (ISBN: 978-3-90639-051-2). Several pharmaceutically acceptable salts are also disclosed in Berge, J. Pharm. Sci. 66:1 (1977).

As described in Biological Example 1, 8, and/or 12, the Cbl-b activity assay (Cbl-b inhibition assay) used to measure the $IC_{50}$ values for Cbl-b inhibition uses a mixture comprising an N-terminal biotinylated Avi-tagged Cbl-b, a fluorescently-labeled inhibitor probe tagged with BODIPY FL (Example 59), and assay buffer. In one embodiment, the Cbl-b activity assay (Cbl-b inhibition assay) used to measure $IC_{50}$ for inhibition of Cbl-b uses the conditions described in Biological Example 1, 8, and/or 12, with 0.5 nM Cbl-b ("High" final concentration). In another embodiment, the Cbl-b activity assay (Cbl-b inhibition assay) used to measure $IC_{50}$ for inhibition of Cbl-b uses the conditions described in Biological Example 1, 8, and/or 12, with 0.125 nM Cbl-b ("Low" final concentration).

It is appreciated that certain features disclosed herein, which are, for clarity, described in the context of separate embodiments, also may be provided in combination in a single embodiment. Conversely, various features disclosed herein, which are, for brevity, described in the context of a single embodiment, also may be provided separately or in any suitable subcombination. All combinations of the embodiments pertaining to the chemical groups represented by the variables are specifically embraced by the present disclosure and are disclosed herein just as if each and every combination was individually and explicitly disclosed, to the extent that such combinations embrace compounds that are stable compounds (i.e., compounds that can be isolated, characterized, and tested for biological activity). In addition, all subcombinations of the chemical groups listed in the embodiments describing such variables also are specifically embraced by the present disclosure and are disclosed herein just as if each and every such subcombination of chemical groups was individually and explicitly disclosed herein.

It is understood that aspects and embodiments described herein as "comprising" include "consisting of" and "consisting essentially of" embodiments.

As used herein and in the appended claims, the singular forms "a," "an," and "the" include plural referents unless otherwise indicated or clear from context. For example, "an" excipient includes one or more excipients.

Reference to "about" a value, encompasses from 90% to 110% of that value. For instance, about 50 billion cells refers to 45 to 55 billion cells, and includes 50 billion cells. For instance, a temperature of "about 100 degrees" refers to a temperature of about 90 degrees to about 110 degrees.

When numerical ranges of compounds are given, all compounds within those numerical limits, including any designated "a" and "b," are included, unless expressly excluded. For example, reference to compounds 41-43 refers to compounds 41, 42, and 43.

II. Compounds

In one aspect, provided is a compound of Formula (I)

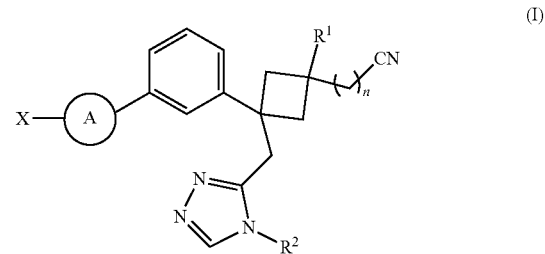

or a tautomer thereof, stereisomer thereof, or a pharmaceutically acceptable salt thereof, wherein.

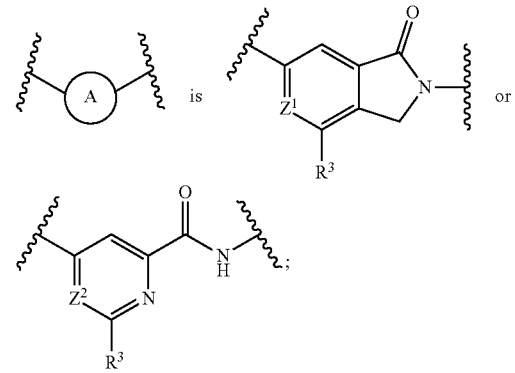

$Z^1$ is CH or N;
$Z^2$ is CH or N;
$R^1$ is H, $C_1$-$C_6$ alkyl, or $C_1$-$C_6$ haloalkyl;
$R^2$ is H, $C_1$-$C_6$ alkyl, $C_1$-$C_6$ haloalkyl, or $C_3$-$C_6$ cycloalkyl;
$R^3$ is —$CF_3$ or cyclopropyl;
$R^4$ is —$CF_3$ or cyclopropyl;
n is 0 or 1;
X is H, $C_1$-$C_6$ alkyl, $C_1$-$C_6$ haloalkyl, or

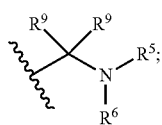

$R^5$ is H, $C_1$-$C_6$ alkyl, $C_1$-$C_6$ haloalkyl, $C_1$-$C_6$ alkyl-OH, or $C_1$-$C_6$ alkyl-CN;

$R^6$ is monocyclic $C_3$-$C_6$ cycloalkyl, fused bicyclic $C_4$-$C_8$ cycloalkyl, bridged bicyclic $C_4$-$C_8$ cycloalkyl, spiro bicyclic $C_5$-$C_8$ cycloalkyl, or 5- to 6-membered heterocyclyl, each of which is optionally substituted by 1-5 $R^7$ groups;

or $R^5$ and $R^6$ are taken together with the nitrogen atom to which they are attached to form a 5- to 10-membered monocyclic, fused bicyclic, or bridged heterocyclyl, or a 5- to 10-membered monocyclic or bicyclic heteroaryl, each of which heterocyclyl or heteroaryl optionally contains 1-2 additional heteroatoms selected from the group consisting of N and O, and each of which heterocyclyl or heteroaryl is optionally substituted by 1-5 $R^1$ groups;

each $R^7$ is independently halo, $C_1$-$C_6$ alkyl, $C_1$-$C_6$ haloalkyl, $C_1$-$C_6$ alkyl-OH, or $C_1$-$C_6$ alkyl-CN;

each $R^8$ is independently $C_1$-$C_6$ alkyl, $C_1$-$C_6$ haloalkyl, $C_1$-$C_6$ alkyl-OH, —CN, $C_1$-$C_6$ alkyl-CN, —($C_1$-$C_6$ alkylene)-O—($C_1$-$C_6$ alkyl), hydroxy, or halo, or two $R^8$ groups attached to the same carbon atom are taken together with the carbon atom to which they are attached to form a spiro $C_3$-$C_6$ cycloalkyl or a spiro 5- to 6-membered heterocyclyl; and each $R^9$ is independently H, $C_1$-$C_6$ alkyl, $C_1$-$C_6$ haloalkyl, or $C_1$-$C_6$ alkyl-OH.

In some embodiments,

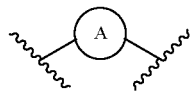

(i.e., the Ring A moiety), is

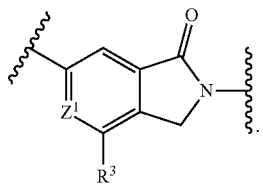

In some embodiments, $Z^1$ is CH. In other embodiments, $Z^1$ is N. In some embodiments, $R^3$ is —$CF_3$. In other embodiments, $R^3$ is cyclopropyl. In some embodiments, the Ring A moiety is

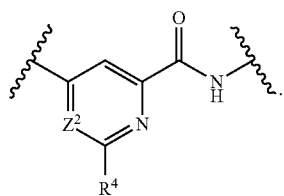

In some embodiments, $Z^2$ is CH. In other embodiments, $Z^2$ is N. In some embodiments, $R^4$ is —$CF_3$. In other embodiments, $R^4$ is cyclopropyl. In some embodiments, the Ring A moiety is selected from the group consisting of

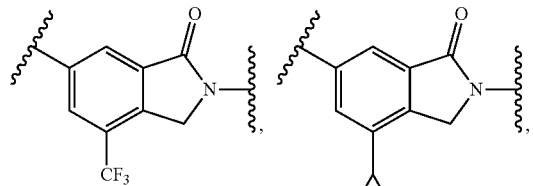

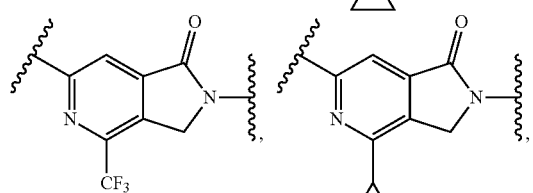

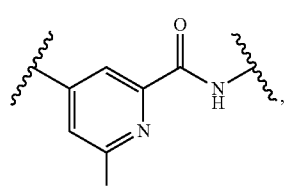

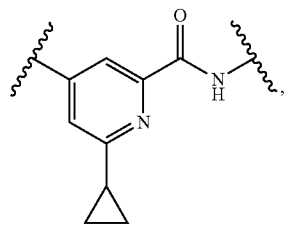

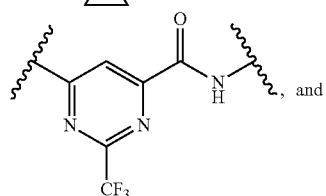, and

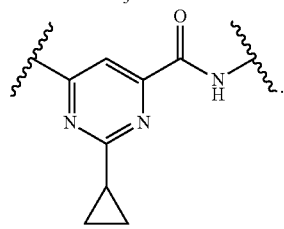

In some embodiments, the Ring A moiety is

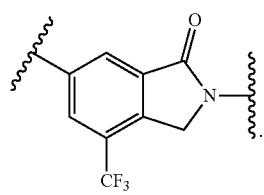 [SMILES: *c1cc2c(c(C(F)(F)F)c1)CN(*)C2=O]

In some embodiments, the Ring A moiety is

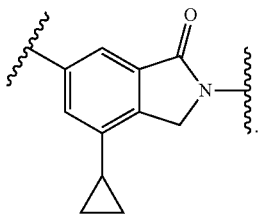 [SMILES: *c1cc2c(c(C3CC3)c1)CN(*)C2=O]

In some embodiments, the Ring A moiety is

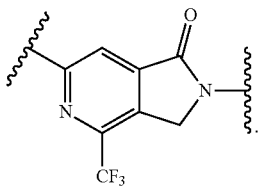 [SMILES: *c1cc2c(c(C(F)(F)F)n1)CN(*)C2=O]

In some embodiments, the Ring A moiety is

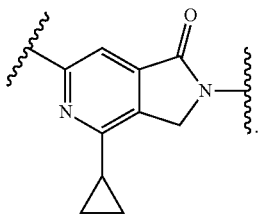 [SMILES: *c1cc2c(c(C3CC3)n1)CN(*)C2=O]

In some embodiments, the Ring A moiety is

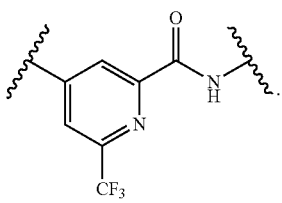

In some embodiments, the Ring A moiety is

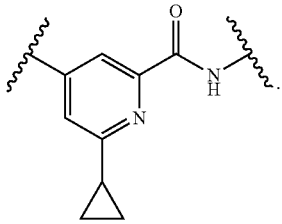 [SMILES: *NC(=O)c1cc(*)cc(C2CC2)n1]

In some embodiments, the Ring A moiety is

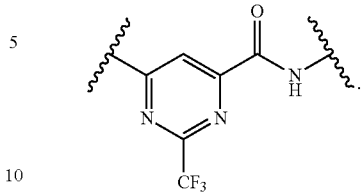

In some embodiments, the Ring A moiety is

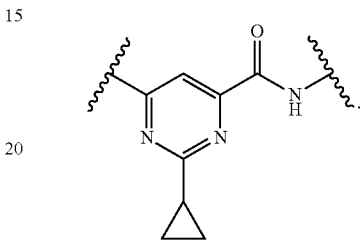

In some embodiments, $R^1$ is H, $C_1$-$C_6$ alkyl, or $C_1$-$C_6$ haloalkyl. In some embodiments, $R^1$ is H, $C_1$-$C_3$ alkyl, or $C_1$-$C_3$ haloalkyl. In some embodiments, $R^1$ is H, —$CH_3$, or —$CF_3$. In some embodiments, $R^1$ is H.

In some embodiments, $R^1$ is $C_1$-$C_6$ alkyl. In some embodiments, R is $C_1$-$C_3$ alkyl. In some embodiments, $R^1$ is methyl, ethyl, n-propyl, or isopropyl. In some embodiments, $R^1$ is —$CH_3$.

In some embodiments, $R^1$ is $C_1$-$C_6$ haloalkyl. In some embodiments, $R^1$ is $C_1$-$C_6$ haloalkyl containing 1-13 halogen atoms. In some embodiments, $R^1$ is $C_1$-$C_6$ haloalkyl containing 1-7 halogen atoms. In some embodiments, $R^1$ is $C_1$-$C_3$ haloalkyl. In some embodiments, $R^1$ is $C_1$-$C_3$ haloalkyl containing 1-7 halogen atoms. In some embodiments, $R^1$ is $C_1$-$C_2$ haloalkyl containing 1-5 halogen atoms. In some embodiments, the halogen atoms are independently selected from the group consisting of chloro, bromo, and fluoro atoms. In some embodiments, the halogen atoms are independently selected from the group consisting of chloro and fluoro atoms. In some embodiments, the halogen atoms are all fluoro atoms. In some embodiments, the halogen atoms are a combination of chloro and fluoro atoms. In some embodiments, $R^1$ is —$CF_3$, —$CCl_3$, —$CF_2Cl$, —$CFCl_2$, —$CHF_2$, —$CH_2F$, —$CHCl_2$, —$CH_2F$, or —$CHFCl$. In some embodiments, $R^1$ is —$CF_3$.

In some embodiments, $R^2$ is H, $C_1$-$C_6$ alkyl, $C_1$-$C_6$ haloalkyl, or $C_3$-$C_6$ cycloalkyl. In some embodiments, $R^2$ is H, $C_1$-$C_3$ alkyl, $C_1$-$C_3$ haloalkyl, or $C_3$-$C_4$ cycloalkyl. In some embodiments, $R^2$ is H, —$CH_3$, —$CF_3$, —$CHF_2$, —$CH_2F$, or cyclopropyl.

In some embodiments, $R^2$ is H.

In some embodiments, $R^2$ is $C_1$-$C_6$ alkyl. In some embodiments, $R^2$ is $C_1$-$C_3$ alkyl. In some embodiments, $R^2$ is methyl, ethyl, n-propyl, or isopropyl. In some embodiments, $R^2$ is —$CH_3$.

In some embodiments, $R^2$ is $C_1$-$C_6$ haloalkyl. In some embodiments, $R^2$ is $C_1$-$C_6$ haloalkyl containing 1-7 halogen atoms. In some embodiments, $R^2$ is $C_1$-$C_3$ haloalkyl. In some embodiments, $R^2$ is $C_1$-$C_3$ haloalkyl containing 1-7 halogen atoms. In some embodiments, $R^2$ is $C_1$-$C_2$ haloalkyl containing 1-5 halogen atoms. In some embodiments, the halogen atoms are independently selected from the group consisting of chloro, bromo, and fluoro atoms. In some embodiments, the halogen atoms are independently selected from the group consisting of chloro and fluoro atoms. In some embodiments, the halogen atoms are all fluoro atoms. In some embodiments, the halogen atoms are a combination of chloro and fluoro atoms. In some embodiments, $R^2$ is —$CF_3$, —$CCl_3$, —$CF_2C_1$, —$CFCl_2$, —$CHF_2$, —$CH_2F$, —$CHCl_2$, —$CH_2F$, or —$CHFCl$. In some embodiments, $R^2$ is —$CF_3$, —$CHF_2$, or —$CH_2F$.

In some embodiments, $R^2$ is $C_3$-$C_6$ cycloalkyl. In some embodiments, $R^2$ is $C_3$-$C_5$ cycloalkyl. In some embodiments, $R^2$ is $C_3$-$C_4$ cycloalkyl. In some embodiments, $R^2$ is cyclopropyl, cyclobutyl, or cyclopentyl. In some embodiments, $R^2$ is cyclopropyl.

In some embodiments, n is 1. In some embodiments, n is 0.

In some embodiments, X is H, $C_1$-$C_6$ alkyl, $C_1$-$C_6$ haloalkyl, or

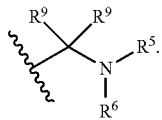

In some embodiments, X is H. In some embodiments, X is $C_1$-$C_3$ alkyl or $C_1$-$C_3$ haloalkyl. In some embodiments, X is —$CH_3$ or —$CF_3$.

In some embodiments, X is $C_1$-$C_6$ alkyl. In some embodiments, X is $C_1$-$C_3$ alkyl. In some embodiments, X is methyl, ethyl, n-propyl, or isopropyl. In some embodiments, X is —$CH_3$.

In some embodiments, X is $C_1$-$C_6$ haloalkyl. In some embodiments, X is $C_1$-$C_6$ haloalkyl containing 1-7 halogen atoms. In some embodiments, X is $C_1$-$C_3$ haloalkyl. In some embodiments, X is $C_1$-$C_3$ haloalkyl containing 1-7 halogen atoms. In some embodiments, X is $C_1$-$C_2$ haloalkyl containing 1-5 halogen atoms. In some embodiments, the halogen atoms are independently selected from the group consisting of chloro, bromo, and fluoro atoms. In some embodiments, the halogen atoms are independently selected from the group consisting of chloro and fluoro atoms. In some embodiments, the halogen atoms are all fluoro atoms. In some embodiments, the halogen atoms are a combination of chloro and fluoro atoms. In some embodiments, X is —$CF_3$, —$CCl_3$, —$CF_2C_1$, —$CFCl_2$, —$CHF_2$, —$CH_2F$, —$CHCl_2$, —$CH_2F$, or —$CHFCl$. In some embodiments, X is —$CF_3$.

In some embodiments, X is

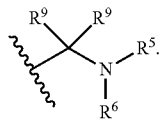

In some embodiments, $R^5$ is H, $C_1$-$C_6$ alkyl, $C_1$-$C_6$ haloalkyl, $C_1$-$C_6$ alkyl-OH, or $C_1$-$C_6$ alkyl-CN. In some embodiments, $R^5$ is H, $C_1$-$C_3$ alkyl, or $C_1$-$C_3$ haloalkyl. In some embodiments, $R^5$ is H, —$CH_3$, —$CF_3$, —$CH_2CN$, or —$CH_2OH$. In some embodiments, $R^5$ is H.

In some embodiments, $R^5$ is $C_1$-$C_6$ alkyl. In some embodiments, $R^5$ is $C_1$-$C_3$ alkyl. In some embodiments, $R^5$ is methyl, ethyl, n-propyl, or isopropyl. In some embodiments, $R^5$ is —$CH_3$.

In some embodiments, $R^5$ is $C_1$-$C_6$ haloalkyl. In some embodiments, $R^5$ is $C_1$-$C_6$ haloalkyl containing 1-7 halogen atoms. In some embodiments, $R^5$ is $C_1$-$C_3$ haloalkyl. In some embodiments, $R^5$ is $C_1$-$C_3$ haloalkyl containing 1-7 halogen atoms. In some embodiments, $R^5$ is $C_1$-$C_2$ haloalkyl containing 1-5 halogen atoms. In some embodiments, the halogen atoms are independently selected from the group consisting of chloro, bromo, and fluoro atoms. In some embodiments, the halogen atoms are independently selected from the group consisting of chloro and fluoro atoms. In some embodiments, the halogen atoms are all fluoro atoms. In some embodiments, the halogen atoms are a combination of chloro and fluoro atoms. In some embodiments, $R^5$ is —$CF_3$, —$CCl_3$, —$CF_2C_1$, —$CFCl_2$, —$CHF_2$, —$CH_2F$, —$CHCl_2$, —$CH_2F$, or —$CHFCl$. In some embodiments, $R^5$ is —$CF_3$.

In some embodiments, $R^5$ is $C_1$-$C_6$ alkyl-OH. In some embodiments, $R^5$ is $C_1$-$C_3$ alkyl-OH. In some embodiments, $R^5$ is —$CH_2OH$, —$CH_2CH_2$—OH, —$CH_2CH_2CH_2$—OH, or —$C(CH_3)_2$—OH. In some embodiments, $R^5$ is —$CH_2OH$.

In some embodiments, $R^5$ is $C_1$-$C_6$ alkyl-CN. In some embodiments, $R^5$ is $C_1$-$C_3$ alkyl-CN. In some embodiments, $R^5$ is —$CH_2CN$, —$CH_2CH_2$—CN, —$CH_2CH_2CH_2$—CN, or —$C(CH_3)_2$—CN. In some embodiments, $R^5$ is —$CH_2CN$.

In some embodiments, $R^6$ is monocyclic $C_3$-$C_6$ cycloalkyl, fused bicyclic $C_4$-$C_8$ cycloalkyl, bridged bicyclic $C_4$-$C_8$ cycloalkyl, spiro bicyclic $C_5$-$C_8$ cycloalkyl, or 5- to 6-membered heterocyclyl, each of which is optionally substituted by 1-5 $R^7$ groups.

In some embodiments, $R^6$ is monocyclic $C_3$-$C_6$ cycloalkyl optionally substituted by 1-5 $R^7$ groups. In some embodiments, $R^6$ is monocyclic $C_3$-$C_5$ cycloalkyl optionally substituted by 1-5 $R^7$ groups. In some embodiments, $R^6$ is monocyclic $C_4$-$C_5$ cycloalkyl optionally substituted by 1-5 $R^7$ groups. In some embodiments, $R^6$ is cyclopropyl, cyclobutyl, or cyclopentyl, each of which is optionally substituted by 1-5 $R^7$ groups. In some embodiments, $R^6$ is cyclobutyl or cyclopentyl, each of which is optionally substituted by 1-5 $R^7$ groups. In some embodiments, $R^6$ is monocyclic $C_3$-$C_6$ cycloalkyl substituted by 1-5 $R^7$ groups. In some embodiments, $R^6$ is monocyclic $C_3$-$C_6$ cycloalkyl substituted by one $R^7$ group. In some embodiments, $R^6$ is monocyclic $C_3$-$C_6$ cycloalkyl substituted by 2 $R^7$ groups. In some embodiments, $R^6$ is monocyclic $C_3$-$C_6$ cycloalkyl substituted by 3 $R^7$ groups. In some embodiments, $R^6$ is monocyclic $C_3$-$C_6$ cycloalkyl substituted by 4 $R^7$ groups. In some embodiments, $R^6$ is monocyclic $C_3$-$C_6$ cycloalkyl substituted by 5 $R^7$ groups. In some embodiments, $R^6$ is unsubstituted monocyclic $C_3$-$C_6$ cycloalkyl.

In some embodiments, $R^6$ is fused bicyclic $C_4$-$C_8$ cycloalkyl optionally substituted by 1-5 $R^7$ groups. In some embodiments, $R^6$ is fused bicyclic $C_4$-$C_7$ cycloalkyl optionally substituted by 1-5 $R^7$ groups. In some embodiments, $R^6$ is fused bicyclic $C_5$-$C_8$ cycloalkyl optionally substituted by 1-5 $R^7$ groups. In some embodiments, $R^6$ is fused bicyclic $C_4$-$C_8$ cycloalkyl substituted by 1-5 $R^7$ groups. In some embodiments, $R^6$ is fused bicyclic $C_4$-$C_8$ cycloalkyl substituted by one $R^7$ group. In some embodiments, $R^6$ is fused bicyclic $C_4$-$C_8$ cycloalkyl substituted by 2 $R^7$ groups. In some embodiments, $R^6$ is fused bicyclic $C_4$-$C_8$ cycloalkyl substituted by 3 $R^7$ groups. In some embodiments, $R^6$ is fused bicyclic $C_4$-$C_8$ cycloalkyl substituted by 4 $R^7$ groups. In some embodiments, $R^6$ is fused bicyclic $C_4$-$C_8$ cycloalkyl substituted by 5 $R^7$ groups. In some embodiments, $R^6$ is unsubstituted fused bicyclic $C_4$-$C_8$ cycloalkyl. In some embodiments, $R^6$ is

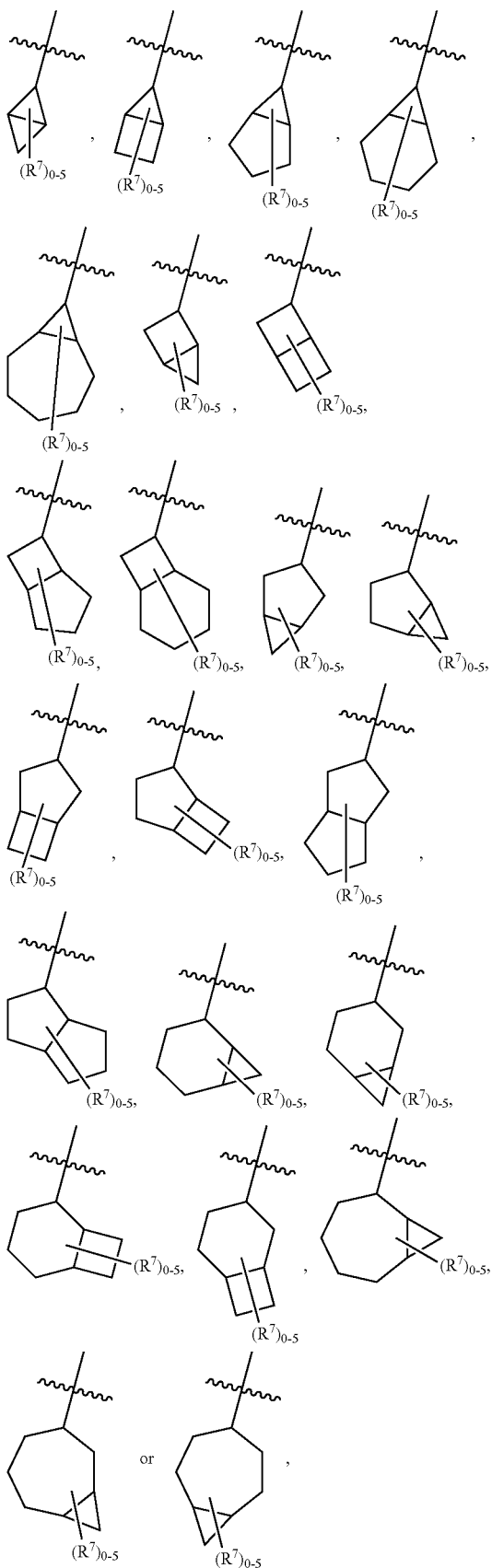

wherein —$(R^7)_{0-5}$ represents optional substitution of either of the two rings which make up the fused bicyclic ring system. In some embodiments, both rings of the fused bicyclic ring system are substituted. In some embodiments, one of the two rings of the fused bicyclic ring system is substituted and the other ring is unsubstituted. In some embodiments, both rings of the fused bicyclic ring system are unsubstituted.

In some embodiments, $R^6$ is bridged bicyclic $C_4$-$C_8$ cycloalkyl optionally substituted by 1-5 $R^7$ groups. In some embodiments, $R^6$ is bridged bicyclic $C_5$-$C_8$ cycloalkyl optionally substituted by 1-5 $R^7$ groups. In some embodiments, $R^6$ is bridged bicyclic $C_4$-$C_8$ cycloalkyl substituted by 1-5 $R^7$ groups. In some embodiments, $R^6$ is bridged bicyclic $C_4$-$C_8$ cycloalkyl substituted by one $R^7$ group. In some embodiments, $R^6$ is bridged bicyclic $C_4$-$C_8$ cycloalkyl substituted by 2 $R^7$ groups. In some embodiments, $R^6$ is bridged bicyclic $C_4$-$C_8$ cycloalkyl substituted by 3 $R^7$ groups. In some embodiments, $R^6$ is bridged bicyclic $C_4$-$C_8$ cycloalkyl substituted by 4 $R^7$ groups. In some embodiments, $R^6$ is bridged bicyclic $C_4$-$C_8$ cycloalkyl substituted by 5 $R^7$ groups. In some embodiments, $R^6$ is unsubstituted bridged bicyclic $C_4$-$C_8$ cycloalkyl. In some embodiments, $R^6$ is

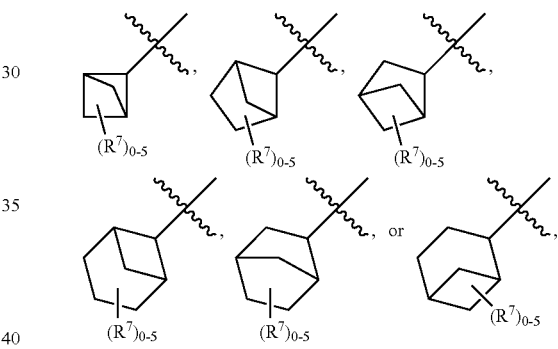

wherein —$(R^7)_{0-5}$ represents optional substitution at any of the carbon atoms which make up the bridged bicyclic ring system. In some embodiments, the bridging moiety of the bridged bicyclic $C_4$-$C_8$ cycloalkyl is $C_1$-$C_3$ alkylene. In some embodiments, the bridging moiety of the bridged bicyclic $C_4$-$C_8$ cycloalkyl is —$CH_2$— or —$CH_2CH_2$—. In some embodiments, the bridging moiety of the bridged bicyclic $C_4$-$C_8$ cycloalkyl is —$CH_2$—.

In some embodiments, $R^6$ is spiro bicyclic $C_5$-$C_8$ cycloalkyl optionally substituted by 1-5 $R^7$ groups. In some embodiments, $R^6$ is spiro bicyclic $C_6$-$C_8$ cycloalkyl optionally substituted by 1-5 $R^7$ groups. In some embodiments, $R^6$ is spiro bicyclic $C_5$-$C_7$ cycloalkyl optionally substituted by 1-5 $R^7$ groups. In some embodiments, $R^6$ is spiro bicyclic $C_5$-$C_8$ cycloalkyl substituted by 1-5 $R^7$ groups. In some embodiments, $R^6$ is spiro bicyclic $C_5$-$C_8$ cycloalkyl substituted by one $R^7$ group. In some embodiments, $R^6$ is spiro bicyclic $C_5$-$C_8$ cycloalkyl substituted by 2 $R^7$ groups. In some embodiments, $R^6$ is spiro bicyclic $C_5$-$C_8$ cycloalkyl substituted by 3 $R^7$ groups. In some embodiments, $R^6$ is spiro bicyclic $C_5$-$C_8$ cycloalkyl substituted by 4 $R^7$ groups. In some embodiments, $R^6$ is spiro bicyclic $C_5$-$C_8$ cycloalkyl substituted by 5 $R^7$ groups. In some embodiments, $R^6$ is unsubstituted spiro bicyclic $C_5$-$C_8$ cycloalkyl. In some embodiments, $R^6$ is

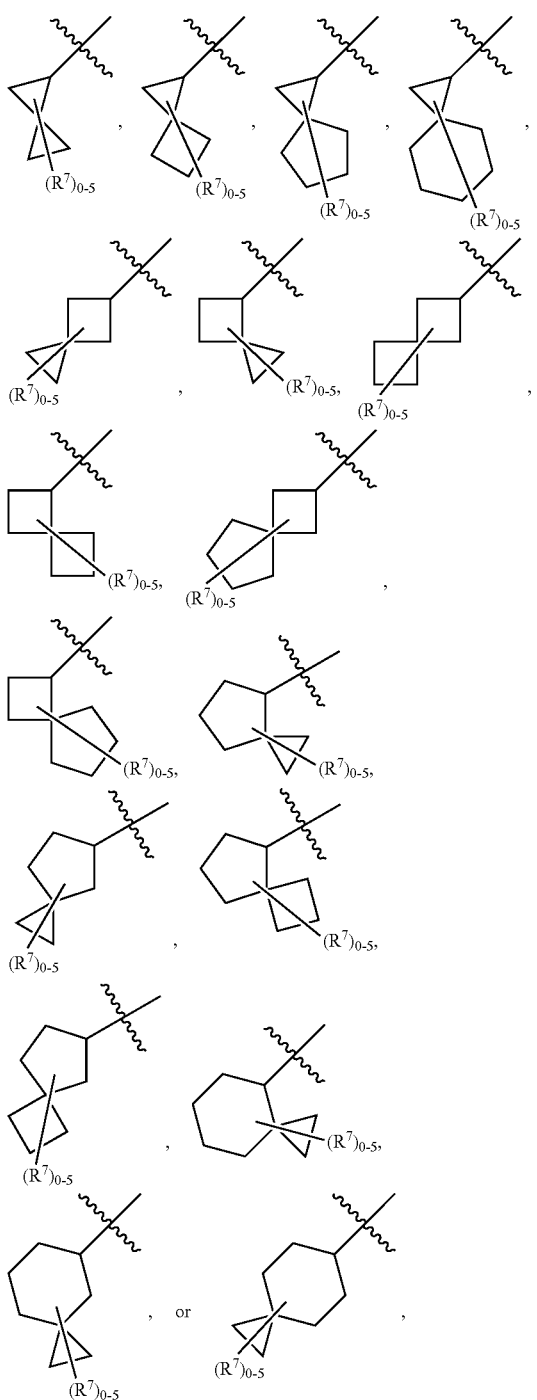

wherein —(R$^7$)$_{0-5}$ represents optional substitution of either of the two rings which make up the spiro bicyclic ring system. In some embodiments, both rings of the spiro bicyclic ring system are substituted. In some embodiments, one of the two rings of the spiro bicyclic ring system is substituted and the other ring is unsubstituted. In some embodiments, both rings of the spiro bicyclic ring system are unsubstituted.

In some embodiments, R$^6$ is 5- to 6-membered heterocyclyl optionally substituted by 1-5 R$^7$ groups. In some embodiments, R$^6$ is 5- to 6-membered heterocyclyl substituted by 1-5 R$^7$ groups. In some embodiments, R$^6$ is 5- to 6-membered heterocyclyl substituted by one R$^7$ group. In some embodiments, R$^6$ is 5- to 6-membered heterocyclyl substituted by 2 R$^7$ groups. In some embodiments, R$^6$ is 5- to 6-membered heterocyclyl substituted by 3 R$^7$ groups. In some embodiments, R$^6$ is 5- to 6-membered heterocyclyl substituted by 4 R$^7$ groups. In some embodiments, R$^6$ is 5- to 6-membered heterocyclyl substituted by 5 R$^7$ groups. In some embodiments, R$^6$ is unsubstituted 5- to 6-membered heterocyclyl. In some embodiments, the 5- to 6-membered heterocyclyl contains 1-3 heteroatoms selected from the group consisting of nitrogen, oxygen, and sulfur. In some embodiments, the 5- to 6-membered heterocyclyl contains one nitrogen atom. In some embodiments, the 5- to 6-membered heterocyclyl contains two nitrogen atoms. In some embodiments, the 5- to 6-membered heterocyclyl contains one oxygen atom. In some embodiments, the 5- to 6-membered heterocyclyl contains two oxygen atoms. In some embodiments, the 5- to 6-membered heterocyclyl contains one oxygen atom and one nitrogen atom. In some embodiments, the 5- to 6-membered heterocyclyl contains one sulfur atom. In some embodiments, the 5- to 6-membered heterocyclyl contains one nitrogen atom and one sulfur atom. In some embodiments, R$^6$ is tetrahydrofuranyl, dioxolanyl, pyrrolidinyl, pyrazolidinyl, piperidinyl, isoxazolidinyl, or tetrahydropyranyl, each of which is optionally substituted by 1-5 R$^7$ groups. In some embodiments, R$^6$ is

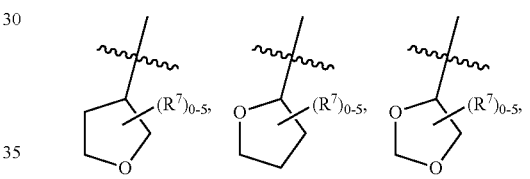

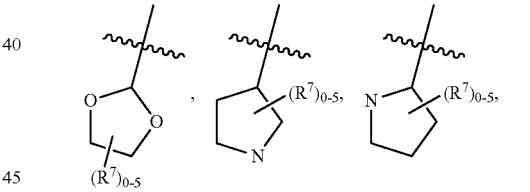

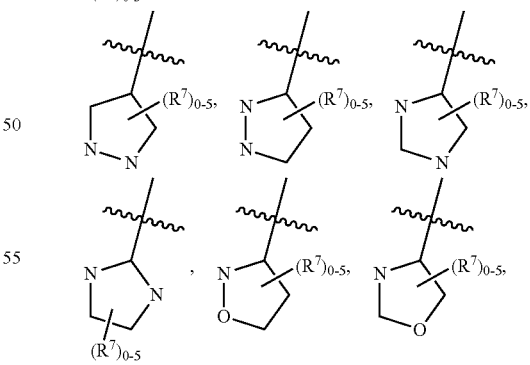

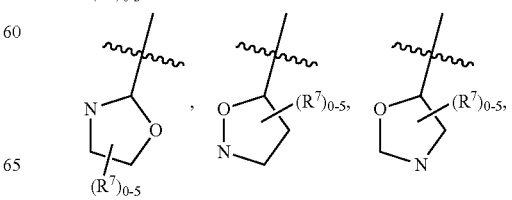

-continued
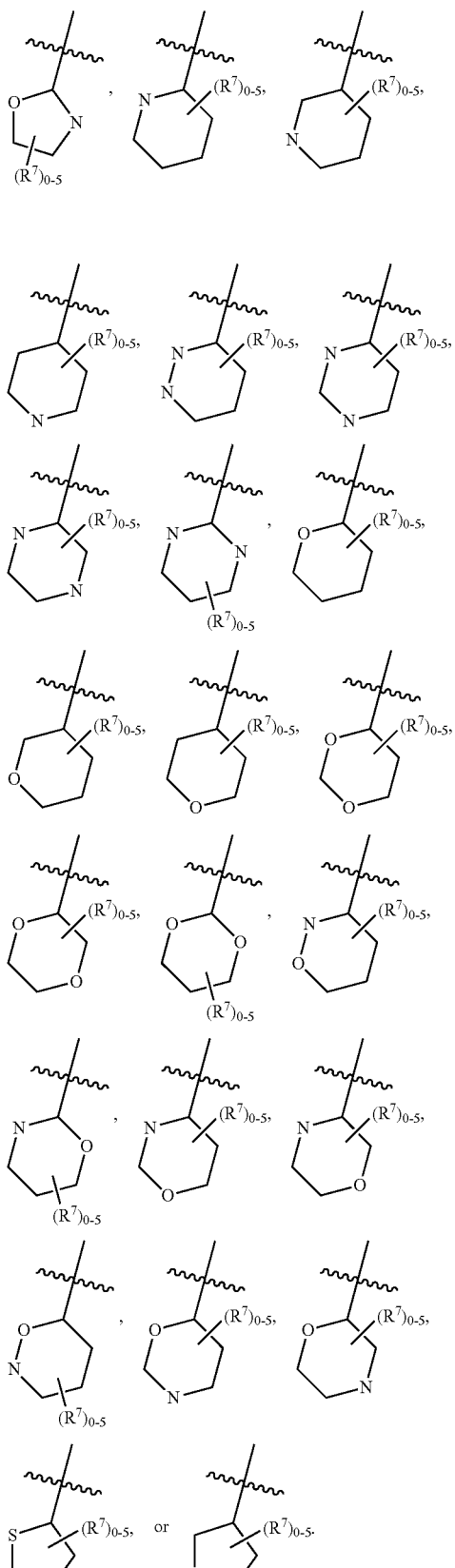
In some embodiments, $R^6$ is selected from the group consisting of
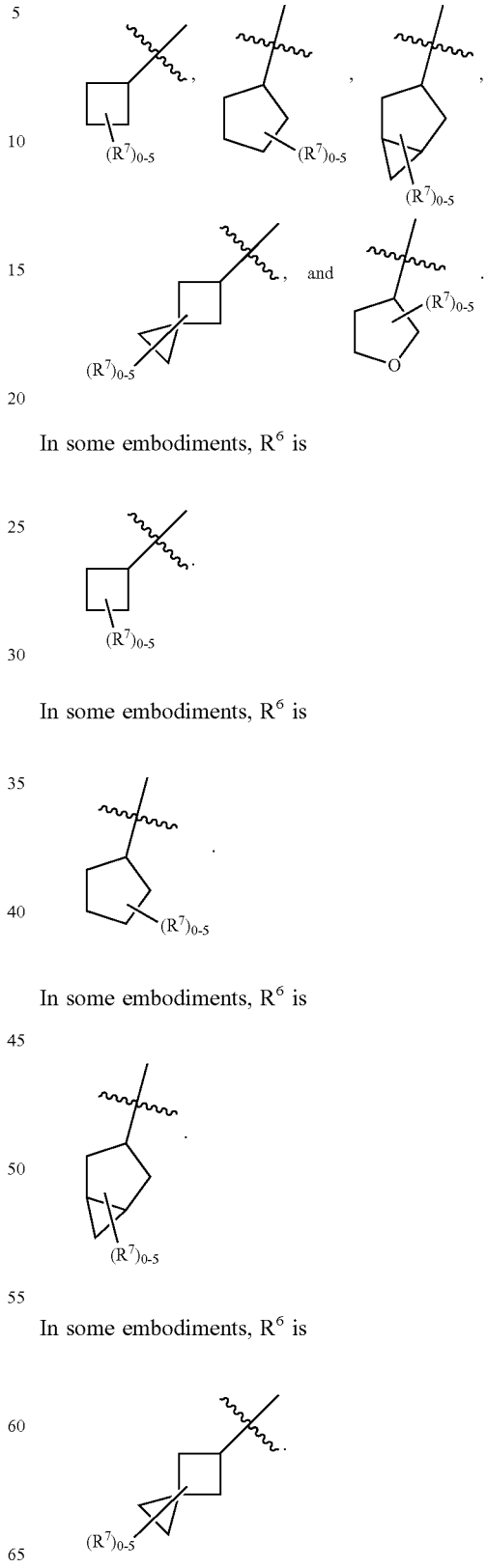
In some embodiments, $R^6$ is
In some embodiments, $R^6$ is
In some embodiments, $R^6$ is
In some embodiments, $R^6$ is In some embodiments, $R^6$ is

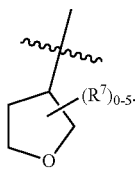

In some embodiments, each $R^7$ is independently halo, $C_1$-$C_6$ alkyl, $C_1$-$C_6$ haloalkyl, $C_1$-$C_6$ alkyl-OH, or $C_1$-$C_6$ alkyl-CN. In some embodiments, each $R^7$ is independently halo, $C_1$-$C_3$ alkyl, $C_1$-$C_3$ haloalkyl, $C_1$-$C_3$ alkyl-OH, or $C_1$-$C_3$ alkyl-CN. In some embodiments, each $R^7$ is independently fluoro, —$CH_3$, —$CF_3$, —$CH_2OH$, or —$CH_2CN$.

In some embodiments, $R^7$ is halo. In some embodiments, $R^7$ is chloro, fluoro, or bromo. In some embodiments, $R^7$ is chloro or fluoro. In some embodiments, $R^7$ is fluoro.

In some embodiments, $R^7$ is $C_1$-$C_6$ alkyl. In some embodiments, $R^7$ is $C_1$-$C_3$ alkyl. In some embodiments, $R^7$ is methyl, ethyl, n-propyl, or isopropyl. In some embodiments, $R^7$ is —$CH_3$.

In some embodiments, $R^7$ is $C_1$-$C_6$ haloalkyl. In some embodiments, $R^7$ is $C_1$-$C_6$ haloalkyl containing 1-7 halogen atoms. In some embodiments, $R^7$ is $C_1$-$C_3$ haloalkyl. In some embodiments, $R^7$ is $C_1$-$C_3$ haloalkyl containing 1-7 halogen atoms. In some embodiments, $R^7$ is $C_1$-$C_2$ haloalkyl containing 1-5 halogen atoms. In some embodiments, the halogen atoms are independently selected from the group consisting of chloro, bromo, and fluoro atoms. In some embodiments, the halogen atoms are independently selected from the group consisting of chloro and fluoro atoms. In some embodiments, the halogen atoms are all fluoro atoms. In some embodiments, the halogen atoms are a combination of chloro and fluoro atoms. In some embodiments, $R^7$ is —$CF_3$, —$CCl_3$, —$CF_2Cl$, —$CFCl_2$, —$CHF_2$, —$CH_2F$, —$CHCl_2$, —$CH_2F$, or —$CHFCl$. In some embodiments, $R^7$ is —$CF_3$.

In some embodiments, $R^7$ is $C_1$-$C_6$ alkyl-OH. In some embodiments, $R^7$ is $C_1$-$C_3$ alkyl-OH. In some embodiments, $R^7$ is —$CH_2OH$, —$CH_2CH_2$—OH, —$CH_2CH_2CH_2$—OH, or —$C(CH_3)_2$—OH. In some embodiments, $R^7$ is —$CH_2OH$.

In some embodiments, $R^7$ is $C_1$-$C_6$ alkyl-CN. In some embodiments, $R^7$ is $C_1$-$C_3$ alkyl-CN. In some embodiments, $R^7$ is —$CH_2CN$, —$CH_2CH_2$—CN, —$CH_2CH_2CH_2$—CN, or —$C(CH_3)_2$—CN. In some embodiments, $R^7$ is —$CH_2CN$.

In some embodiments, $R^5$ and $R^6$ are taken together with the nitrogen atom to which they are attached to form a 5- to 10-membered monocyclic, fused bicyclic, or bridged heterocyclyl, or a 5- to 10-membered monocyclic or bicyclic heteroaryl, each of which heterocyclyl or heteroaryl optionally contains 1-2 additional heteroatoms selected from the group consisting of N and O, and each of which heterocyclyl or heteroaryl is optionally substituted by 1-5 $R^8$ groups.

In some embodiments, $R^5$ and $R^6$ are taken together with the nitrogen atom to which they are attached to form a 5- to 10-membered monocyclic heterocyclyl optionally substituted by 1-5 $R^8$ groups. In some embodiments, $R^5$ and $R^6$ are taken together with the nitrogen atom to which they are attached to form a 5- to 8-membered monocyclic heterocyclyl optionally substituted by 1-5 $R^8$ groups. In some embodiments, $R^5$ and $R^6$ are taken together with the nitrogen atom to which they are attached to form a 5- to 7-membered monocyclic heterocyclyl optionally substituted by 1-5 $R^8$ groups. In some embodiments, the 5- to 10-membered monocyclic heterocyclyl is substituted by 1-5 $R^8$ groups. In some embodiments, the 5- to 10-membered monocyclic heterocyclyl is substituted by one $R^8$ group. In some embodiments, the 5- to 10-membered monocyclic heterocyclyl is substituted by 2 $R^8$ groups. In some embodiments, the 5- to 10-membered monocyclic heterocyclyl is substituted by 3 $R^8$ groups. In some embodiments, the 5- to 10-membered monocyclic heterocyclyl is substituted by 4 $R^8$ groups. In some embodiments, the 5- to 10-membered monocyclic heterocyclyl is substituted by 5 $R^8$ groups. In some embodiments, the 5- to 10-membered monocyclic heterocyclyl is unsubstituted. In some embodiments, the 5- to 10-membered monocyclic heterocyclyl optionally contains 1-2 additional heteroatoms selected from the group consisting of N and O. In some embodiments, the 5- to 10-membered monocyclic heterocyclyl contains one nitrogen atom. In some embodiments, the 5- to 10-membered monocyclic heterocyclyl contains one nitrogen atom and one oxygen atom. In some embodiments, the 5- to 10-membered monocyclic heterocyclyl contains 2 nitrogen atoms.

In some embodiments, $R^5$ and $R^6$ are taken together with the nitrogen atom to which they are attached to form a 5- to 10-membered fused bicyclic heterocyclyl optionally substituted by 1-5 $R^1$ groups. In some embodiments, $R^5$ and $R^6$ are taken together with the nitrogen atom to which they are attached to form a 7- to 10-membered fused bicyclic heterocyclyl optionally substituted by 1-5 $R^8$ groups. In some embodiments, the 5- to 10-membered fused bicyclic heterocyclyl is substituted by 1-5 $R^8$ groups. In some embodiments, the 5- to 10-membered fused bicylic heterocyclyl is substituted by one $R^8$ group. In some embodiments, the 5- to 10-membered fused bicylic heterocyclyl is substituted by 2 $R^8$ groups. In some embodiments, the 5- to 10-membered fused bicylic heterocyclyl is substituted by 3 $R^8$ groups. In some embodiments, the 5- to 10-membered fused bicylic heterocyclyl is substituted by 4 $R^8$ groups. In some embodiments, the 5- to 10-membered fused bicylic heterocyclyl is substituted by 5 $R^8$ groups. In some embodiments, the 5- to 10-membered fused bicylic heterocyclyl is unsubstituted. In some embodiments, the 5- to 10-membered fused bicylic heterocyclyl optionally contains 1-2 additional heteroatoms selected from the group consisting of N and O. In some embodiments, the 5- to 10-membered fused bicylic heterocyclyl contains one nitrogen atom. In some embodiments, the 5- to 10-membered fused bicylic heterocyclyl contains one nitrogen atom and one oxygen atom. In some embodiments, the 5- to 10-membered fused bicylic heterocyclyl contains 2 nitrogen atoms. In some embodiments, the 5- to 10-membered fused bicylic heterocyclyl contains one saturated ring fused to a partially unsaturated ring. In some embodiments, the 5- to 10-membered fused bicylic heterocyclyl contains one saturated ring fused to a second saturated ring. In some embodiments, the 5- to 10-membered fused bicylic heterocyclyl contains one partially unsaturated ring fused to a second partially unsaturated ring.

In some embodiments, $R^5$ and $R^6$ are taken together with the nitrogen atom to which they are attached to form a 5- to 10-membered bridged heterocyclyl optionally substituted by 1-5 $R^8$ groups. In some embodiments, $R^5$ and $R^6$ are taken together with the nitrogen atom to which they are attached to form a 6- to 10-membered bridged heterocyclyl optionally substituted by 1-5 $R^8$ groups. In some embodiments, $R^5$ and $R^6$ are taken together with the nitrogen atom to which they are attached to form a 6- to 9-membered bridged heterocyclyl optionally substituted by 1-5 $R^8$ groups. In some embodiments, the 5- to 10-membered bridged heterocyclyl is substituted by 1-5 $R^8$ groups. In some embodiments, the 5- to 10-membered bridged heterocyclyl is substituted by one $R^8$ group. In some embodiments, the 5- to 10-membered bridged heterocyclyl is substituted by 2 $R^8$ groups. In some embodiments, the 5- to 10-membered bridged heterocyclyl is substituted by 3 $R^8$ groups. In some embodiments, the 5- to 10-membered bridged heterocyclyl is substituted by 4 $R^8$ groups. In some embodiments, the 5- to 10-membered bridged heterocyclyl is substituted by 5 $R^8$ groups. In some embodiments, the 5- to 10-membered bridged heterocyclyl is unsubstituted. In some embodiments, the 5- to 10-membered bridged heterocyclyl optionally contains 1-2 additional heteroatoms selected from the group consisting of N and O. In some embodiments, the 5- to 10-membered bridged heterocyclyl contains one nitrogen atom. In some embodiments, the 5- to 10-membered bridged heterocyclyl contains one nitrogen atom and one oxygen atom. In some embodiments, the 5- to 10-membered bridged heterocyclyl contains 2 nitrogen atoms. In some embodiments, the bridging moiety of the 5- to 10-membered bridged heterocyclyl is $C_1$-$C_3$ alkylene. In some embodiments, the bridging moiety of the 5- to 10-membered bridged heterocyclyl is —$CH_2$—. In some embodiments, the bridging moiety of the 5- to 10-membered bridged heterocyclyl is —$CH_2CH_2$—.

In some embodiments, $R^5$ and $R^6$ are taken together with the nitrogen atom to which they are attached to form a 5- to 10-membered monocyclic heteroaryl optionally substituted by 1-5 $R^8$ groups. In some embodiments, $R^5$ and $R^6$ are taken together with the nitrogen atom to which they are attached to form a 5- to 8-membered monocyclic heteroaryl optionally substituted by 1-5 $R^8$ groups. In some embodiments, $R^5$ and $R^6$ are taken together with the nitrogen atom to which they are attached to form a 5- to 6-membered monocyclic heteroaryl optionally substituted by 1-5 $R^8$ groups. In some embodiments, the 5- to 10-membered monocyclic heteroaryl is substituted by 1-5 $R^8$ groups. In some embodiments, the 5- to 10-membered monocyclic heteroaryl is substituted by one $R^8$ group. In some embodiments, the 5- to 10-membered monocyclic heteroaryl is substituted by 2 $R^8$ groups. In some embodiments, the 5- to 10-membered monocyclic heteroaryl is substituted by 3 $R^8$ groups. In some embodiments, the 5- to 10-membered monocyclic heteroaryl is substituted by 4 $R^8$ groups. In some embodiments, the 5- to 10-membered monocyclic heteroaryl is substituted by 5 $R^8$ groups. In some embodiments, the 5- to 10-membered monocyclic heteroaryl is unsubstituted. In some embodiments, the 5- to 10-membered monocyclic heteroaryl optionally contains 1-2 additional heteroatoms selected from the group consisting of N and O. In some embodiments, the 5- to 10-membered monocyclic heteroaryl contains one nitrogen atom. In some embodiments, the 5- to 10-membered monocyclic heteroaryl contains one nitrogen atom and one oxygen atom. In some embodiments, the 5- to 10-membered monocyclic heteroaryl contains 2 nitrogen atoms.

In some embodiments, $R^5$ and $R^6$ are taken together with the nitrogen atom to which they are attached to form a 5- to 10-membered bicylic heteroaryl optionally substituted by 1-5 $R^8$-groups. In some embodiments, $R^5$ and $R^6$ are taken together with the nitrogen atom to which they are attached to form a 6- to 10-membered bicyclic heteroaryl optionally substituted by 1-5 $R^8$ groups. In some embodiments, the 5- to 10-membered bicyclic heteroaryl is substituted by 1-5 $R^8$ groups. In some embodiments, the 5- to 10-membered bicyclic heteroaryl is substituted by one $R^8$ group. In some embodiments, the 5- to 10-membered bicyclic heteroaryl is substituted by 2 $R^8$ groups. In some embodiments, the 5- to 10-membered bicyclic heteroaryl is substituted by 3 $R^8$ groups. In some embodiments, the 5- to 10-membered bicyclic heteroaryl is substituted by 4 $R^8$ groups. In some embodiments, the 5- to 10-membered bicyclic heteroaryl is substituted by 5 R groups. In some embodiments, the 5- to 10-membered bicyclic heteroaryl is unsubstituted. In some embodiments, the 5- to 10-membered bicyclic heteroaryl optionally contains 1-2 additional heteroatoms selected from the group consisting of N and O. In some embodiments, the 5- to 10-membered bicyclic heteroaryl contains one nitrogen atom. In some embodiments, the 5- to 10-membered bicyclic heteroaryl contains one nitrogen atom and one oxygen atom. In some embodiments, the 5- to 10-membered bicyclic heteroaryl contains 2 nitrogen atoms. In some embodiments, the 5- to 10-membered bicyclic heteroaryl contains one aromatic ring fused to a saturated ring. In some embodiments, the 5- to 10-membered bicyclic heteroaryl contains one aromatic ring fused to a second aromatic ring. In some embodiments, the 5- to 10-membered bicyclic heteroaryl contains one aromatic ring fused to a partially unsaturated ring.

In some embodiments, $R^5$ and $R^6$ are taken together with the nitrogen atom to which they are attached to form a moiety selected from the group consisting of

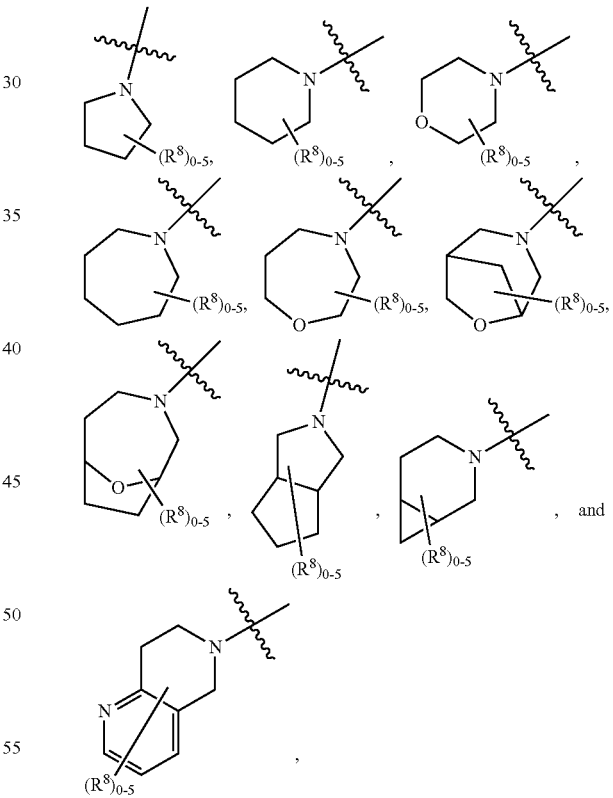

wherein —$(R^8)_{0-5}$ represents optional substitution of either of the two rings which make up the fused or bridged bicyclic ring system, or any carbon atom of the monocyclic ring system. In some embodiments, both rings of the fused or bridged bicyclic ring system are substituted. In some embodiments, one of the two rings of the fused or bridged bicyclic ring system is substituted and the other ring is unsubstituted. In some embodiments, both rings of the fused or bridged bicyclic ring system are unsubstituted.

In some embodiments, $R^5$ and $R^6$ are taken together with the nitrogen atom to which they are attached to form

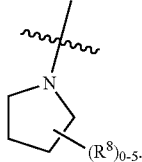

In some embodiments, $R^5$ and $R^6$ are taken together with the nitrogen atom to which they are attached to form

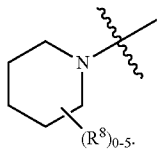

In some embodiments, $R^5$ and $R^6$ are taken together with the nitrogen atom to which they are attached to form

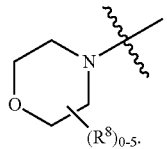

In some embodiments, $R^5$ and $R^6$ are taken together with the nitrogen atom to which they are attached to form

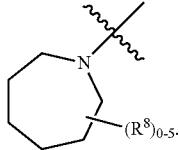

In some embodiments, $R^5$ and $R^6$ are taken together with the nitrogen atom to which they are attached to form

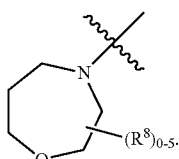

In some embodiments, $R^5$ and $R^6$ are taken together with the nitrogen atom to which they are attached to form

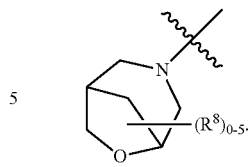

In some embodiments, $R^5$ and $R^6$ are taken together with the nitrogen atom to which they are attached to form

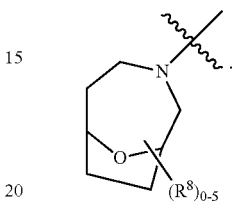

In some embodiments, $R^5$ and $R^6$ are taken together with the nitrogen atom to which they are attached to form

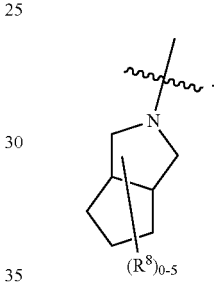

In some embodiments, $R^5$ and $R^6$ are taken together with the nitrogen atom to which they are attached to form

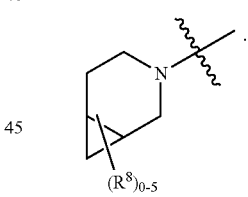

In some embodiments, $R^5$ and $R^6$ are taken together with the nitrogen atom to which they are attached to form

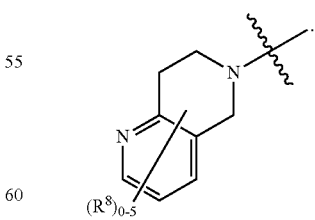

In some embodiments, each $R^8$ is independently $C_1$-$C_6$ alkyl, $C_1$-$C_6$ haloalkyl, $C_1$-$C_6$ alkyl-OH, —CN, $C_1$-$C_6$ alkyl-CN, —($C_1$-$C_6$ alkylene)-O—($C_1$-$C_6$ alkyl), hydroxy, or halo. In some embodiments, each $R^8$ is independently $C_1$-$C_3$ alkyl, $C_1$-$C_3$ haloalkyl, $C_1$-$C_3$ alkyl-OH, —CN, $C_1$-$C_3$ alkyl- CN, —($C_1$-$C_3$ alkylene)-O—($C_1$-$C_3$ alkyl), hydroxy, or halo. In some embodiments, each $R^8$ is independently —$CH_3$, —$CH_2CH_3$, —$CF_3$, —$CH_2OH$, —CN, —$CH_2CN$, —$CH_2$—O—$CH_3$, hydroxy, or F.

In some embodiments, $R^8$ is $C_1$-$C_6$ alkyl. In some embodiments, $R^8$ is $C_1$-$C_3$ alkyl. In some embodiments, $R^8$ is methyl, ethyl, n-propyl, or isopropyl. In some embodiments, $R^8$ is —$CH_3$ or —$CH_2CH_3$.

In some embodiments, $R^8$ is $C_1$-$C_6$ haloalkyl. In some embodiments, $R^8$ is $C_1$-$C_6$ haloalkyl containing 1-7 halogen atoms. In some embodiments, $R^8$ is $C_1$-$C_3$ haloalkyl. In some embodiments, $R^8$ is $C_1$-$C_3$ haloalkyl containing 1-7 halogen atoms. In some embodiments, $R^8$ is $C_1$-$C_2$ haloalkyl containing 1-5 halogen atoms. In some embodiments, the halogen atoms are independently selected from the group consisting of chloro, bromo, and fluoro atoms. In some embodiments, the halogen atoms are independently selected from the group consisting of chloro and fluoro atoms. In some embodiments, the halogen atoms are all fluoro atoms. In some embodiments, the halogen atoms are a combination of chloro and fluoro atoms. In some embodiments, $R^8$ is —$CF_3$, —$CCl_3$, —$CF_2Cl$, —$CFCl_2$, —$CHF_2$, —$CH_2F$, —$CHCl_2$, —$CH_2F$, or —$CHFCl$. In some embodiments, $R^8$ is —$CF_3$.

In some embodiments, $R^8$ is $C_1$-$C_6$ alkyl-OH. In some embodiments, $R^8$ is $C_1$-$C_3$ alkyl-OH. In some embodiments, $R^8$ is —$CH_2OH$, —$CH_2CH_2$—OH, —$CH_2CH_2CH_2$—OH, or —$C(CH_3)_2$—OH. In some embodiments, $R^8$ is —$CH_2OH$.

In some embodiments, $R^8$ is —CN. In some embodiments, $R^8$ is $C_1$-$C_6$ alkyl-CN. In some embodiments, $R^8$ is $C_1$-$C_3$ alkyl-CN. In some embodiments, $R^8$ is —$CH_2CN$, —$CH_2CH_2$—CN, —$CH_2CH_2CH_2$—CN, or —$C(CH_3)_2$—CN. In some embodiments, $R^8$ is —$CH_2CN$.

In some embodiments, $R^8$ is —($C_1$-$C_6$ alkylene)-O—($C_1$-$C_6$ alkyl). In some embodiments, $R^8$ is —($C_1$-$C_3$ alkylene)-O—($C_1$-$C_3$ alkyl). In some embodiments, $R^8$ is —($C_1$-$C_2$ alkylene)-O—($C_1$-$C_2$ alkyl). In some embodiments, $R^8$ is —$CH_2$—O—$CH_3$, —$CH_2$—O—$CH_2CH_3$, —$CH_2CH_2$—O—$CH_2CH_3$, or —$CH_2CH_2$—O—$CH_3$. In some embodiments, $R^8$ is —$CH_2$—O—$CH_3$.

In some embodiments, $R^8$ is hydroxy.

In some embodiments, $R^8$ is halo. In some embodiments, $R^8$ is chloro, fluoro, or bromo. In some embodiments, $R^8$ is chloro or fluoro. In some embodiments, $R^8$ is fluoro.

In some embodiments, two $R^8$ groups attached to the same carbon atom are taken together with the carbon atom to which they are attached to form a spiro $C_3$-$C_6$ cycloalkyl or a spiro 5- to 6-membered heterocyclyl. In some embodiments, two $R^8$ groups attached to the same carbon atom are taken together with the carbon atom to which they are attached to form a spiro $C_3$-$C_4$ cycloalkyl or a spiro 5- to 6-membered heterocyclyl. In some embodiments, two $R^8$ groups attached to the same carbon atom are taken together with the carbon atom to which they are attached to form a spiro cyclopropyl.

In some embodiments, two $R^8$ groups attached to the same carbon atom are taken together with the carbon atom to which they are attached to form a spiro $C_3$-$C_6$ cycloalkyl. In some embodiments, two $R^8$ groups attached to the same carbon atom are taken together with the carbon atom to which they are attached to form a spiro $C_3$-$C_5$ cycloalkyl. In some embodiments, two $R^8$ groups attached to the same carbon atom are taken together with the carbon atom to which they are attached to form a spiro cyclopropyl, cyclobutyl, or cyclopentyl. In some embodiments, two $R^8$ groups attached to the same carbon atom are taken together with the carbon atom to which they are attached to form a spiro cyclopropyl.

In some embodiments, two $R^8$ groups attached to the same carbon atom are taken together with the carbon atom to which they are attached to form a spiro 5- to 6-membered heterocyclyl. In some embodiments, the spiro 5- to 6-membered heterocyclyl contains 1-3 heteroatoms selected from the group consisting of nitrogen, oxygen, and sulfur. In some embodiments, the spiro 5- to 6-membered heterocyclyl contains one nitrogen atom. In some embodiments, the spiro 5- to 6-membered heterocyclyl contains two nitrogen atoms. In some embodiments, the spiro 5- to 6-membered heterocyclyl contains one oxygen atom. In some embodiments, the spiro 5- to 6-membered heterocyclyl contains two oxygen atoms. In some embodiments, the spiro 5- to 6-membered heterocyclyl contains one nitrogen atom and one oxygen atom. In some embodiments, the spiro 5- to 6-membered heterocyclyl is pyrrolidinyl, tetrahydrofuranyl, piperdinyl, tetrahydropyranyl, or thiolanyl.

In some embodiments, each $R^9$ is independently H, $C_1$-$C_6$ alkyl, $C_1$-$C_6$ haloalkyl, or $C_1$-$C_6$ alkyl-OH. In some embodiments, each $R^9$ is independently H, $C_1$-$C_3$ alkyl, $C_1$-$C_3$ haloalkyl, or $C_1$-$C_3$ alkyl-OH. In some embodiments, each $R^9$ is independently H, —$CH_3$, —$CF_3$, or —$CH_2OH$.

In some embodiments, $R^9$ is H. In some embodiments, at least one $R^9$ is H. In some embodiments, one $R^9$ is H, and the other $R^9$ is $C_1$-$C_6$ alkyl, $C_1$-$C_6$ haloalkyl, or $C_1$-$C_6$ alkyl-OH. In some embodiments, one $R^9$ is H, and the other $R^9$ is $C_1$-$C_6$ alkyl. In some embodiments, one $R^9$ is H, and the other $R^9$ is $C_1$-$C_6$ alkyl. In some embodiments, one $R^9$ is H, and the other $R^9$ is —$CH_3$. In some embodiments, both $R^9$ groups are H.

In some embodiments, $R^9$ is $C_1$-$C_6$ alkyl. In some embodiments, $R^9$ is $C_1$-$C_3$ alkyl. In some embodiments, $R^9$ is methyl, ethyl, n-propyl, or isopropyl. In some embodiments, $R^9$ is —$CH_3$. In some embodiments, both $R^9$ groups are independently $C_1$-$C_6$ alkyl. In some embodiments, both $R^9$ groups are independently $C_1$-$C_3$ alkyl. In some embodiments, both $R^9$ groups are —$CH_3$.

In some embodiments, $R^9$ is $C_1$-$C_6$ haloalkyl. In some embodiments, $R^9$ is $C_1$-$C_6$ haloalkyl containing 1-7 halogen atoms. In some embodiments, $R^9$ is $C_1$-$C_3$ haloalkyl. In some embodiments, $R^9$ is $C_1$-$C_3$ haloalkyl containing 1-7 halogen atoms. In some embodiments, $R^9$ is $C_1$-$C_2$ haloalkyl containing 1-5 halogen atoms. In some embodiments, the halogen atoms are independently selected from the group consisting of chloro, bromo, and fluoro atoms. In some embodiments, the halogen atoms are independently selected from the group consisting of chloro and fluoro atoms. In some embodiments, the halogen atoms are all fluoro atoms. In some embodiments, the halogen atoms are a combination of chloro and fluoro atoms. In some embodiments, $R^9$ is —$CF_3$, —$CCl_3$, —$CF_2Cl$, —$CFCl_2$, —$CHF_2$, —$CH_2F$, —$CHCl_2$, —$CH_2F$, or —$CHFCl$. In some embodiments, $R^9$ is —$CF_3$.

In some embodiments, $R^9$ is $C_1$-$C_6$ alkyl-OH. In some embodiments, $R^9$ is $C_1$-$C_3$ alkyl-OH. In some embodiments, $R^9$ is —$CH_2OH$, —$CH_2CH_2$—OH, —$CH_2CH_2CH_2$—OH, or —$C(CH_3)_2$—OH. In some embodiments, $R^9$ is —$CH_2OH$.

In some embodiments, the compound of Formula (I), or any variation or aspect thereof, has the stereochemistry shown for Formula (I-a):

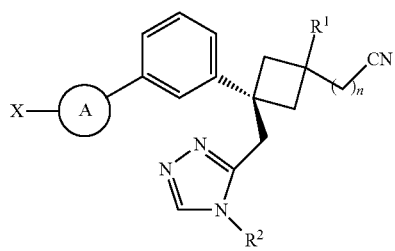
(I-a)
wherein R¹, R², n, X, and the ring A moiety are as described for the compound of Formula (I).
In some embodiments, the compound is of Formula (I-A) or (I-B):
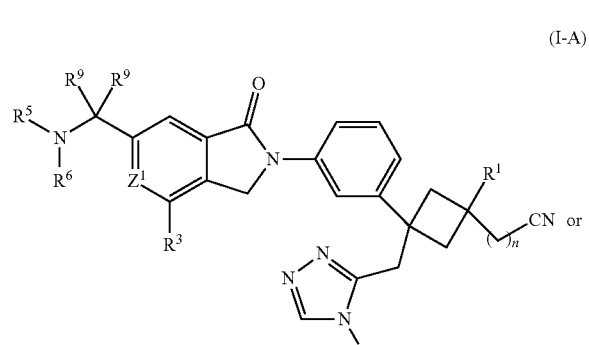
(I-A)
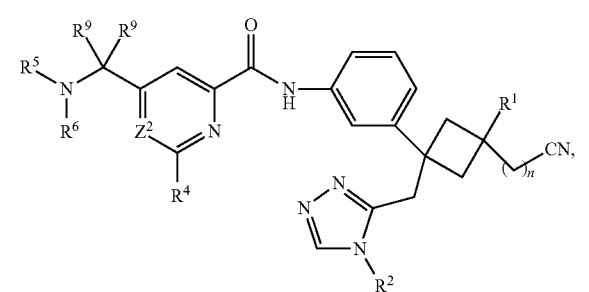
(I-B)
wherein R¹, R², R³, R⁴, R⁵, R⁶, R⁹, Z¹, Z², and n are as described for the compound of Formula (I).
In some embodiments, the compound is of Formula (I-C), (I-D), (I-E), (I-F), (I-G), (I-H), (I-I), or (I-J):
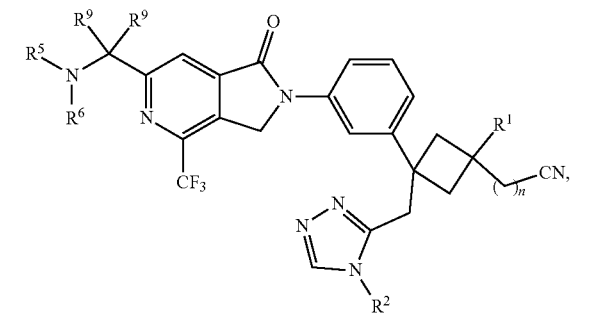
(I-C)
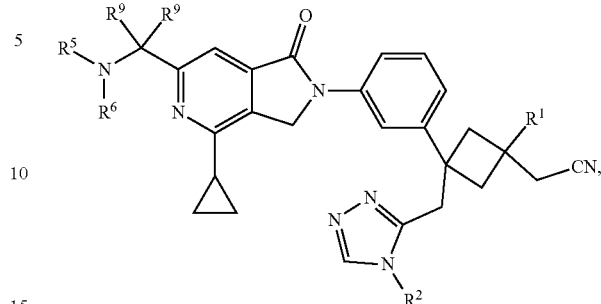
(I-D)
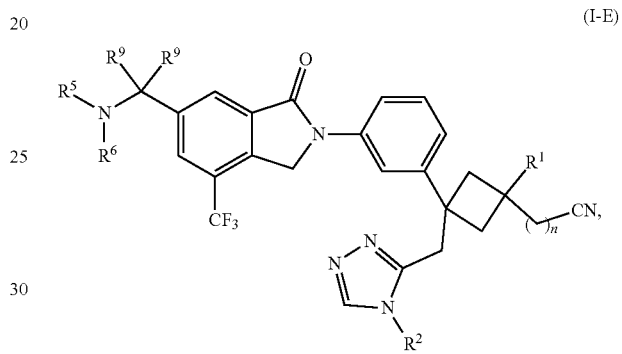
(I-E)
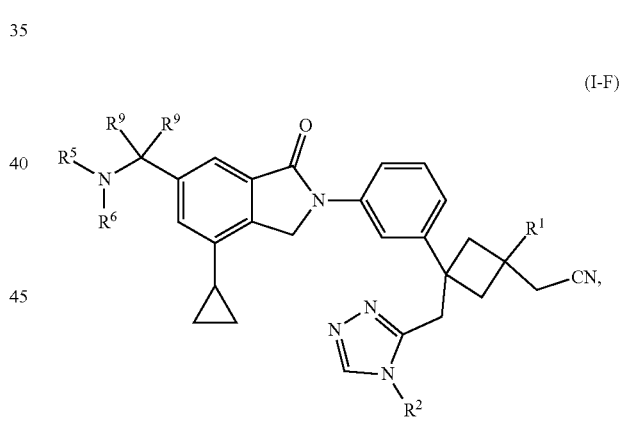
(I-F)
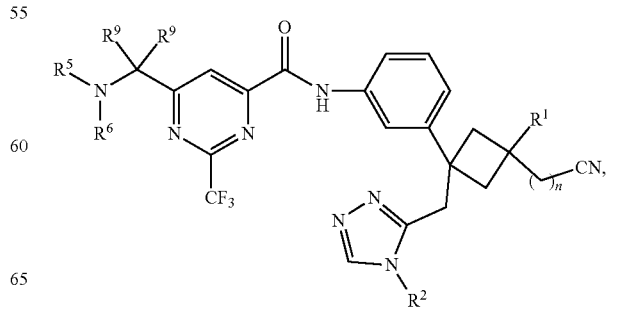
(I-G)

(I-H)
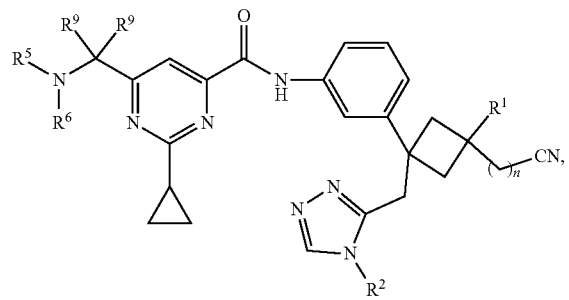
(I-I)
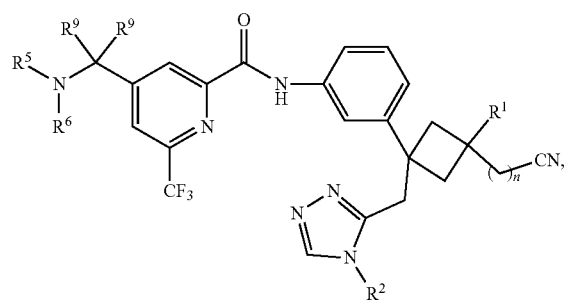
or
(I-J)
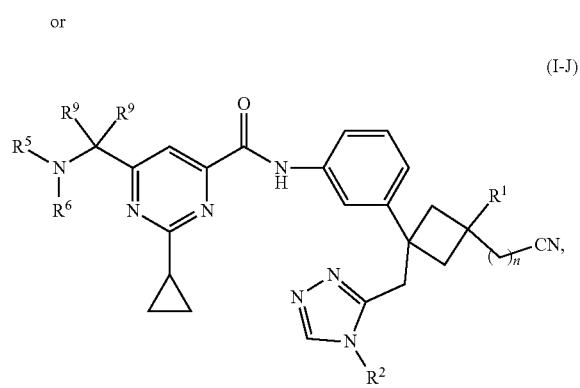
wherein $R^1$, $R^2$, $R^3$, $R^6$, $R^9$, and n are as described for the compound of Formula (I).
In some embodiments, the compound is of Formula (II-A), (II-B), (II-C), (II-D), (II-E), (II-F), (II-G), or (II-H).
(II-A)
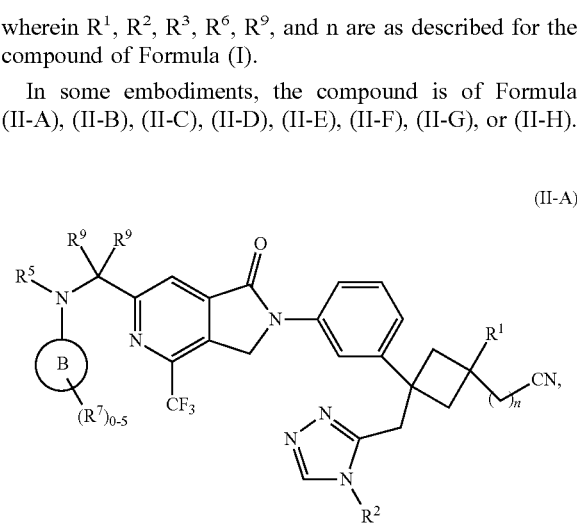
(II-B)
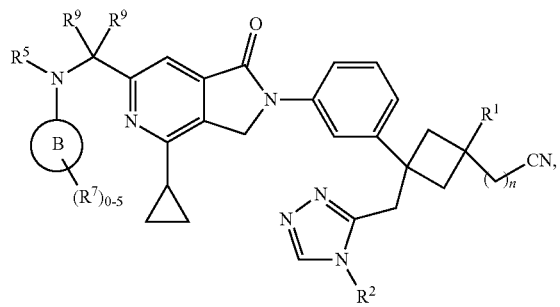
(II-C)
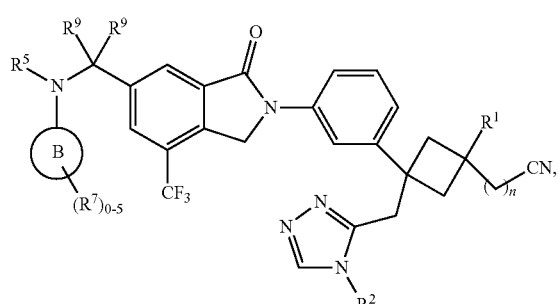
(II-D)
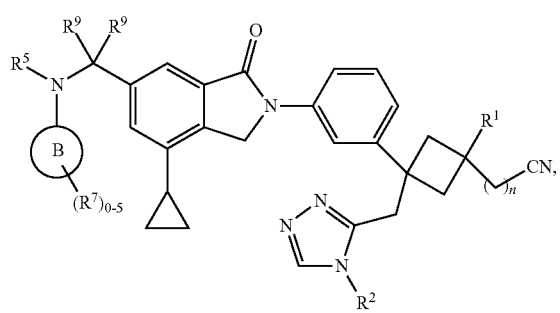
(II-E)
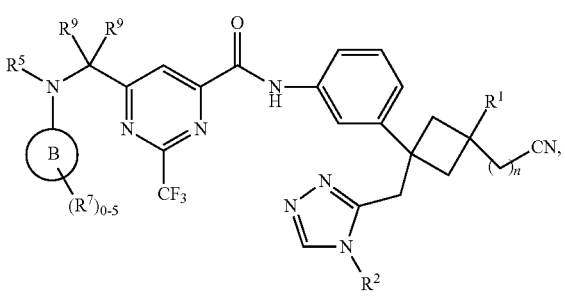
(II-F)
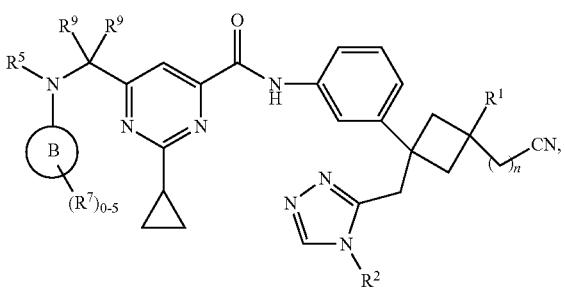

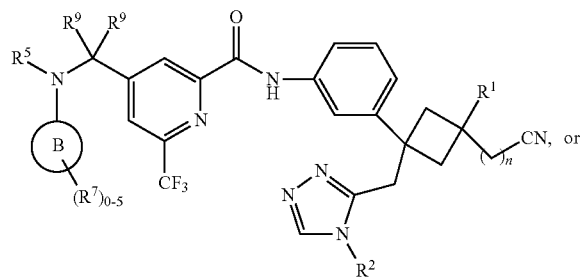
(II-G)
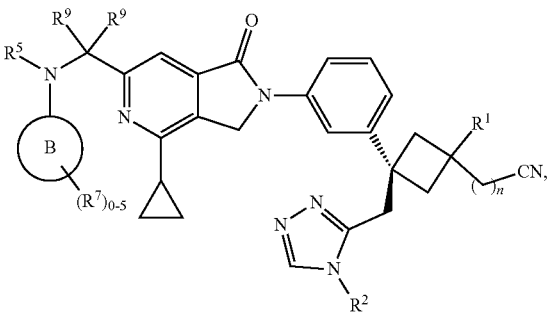
(II-B-1)
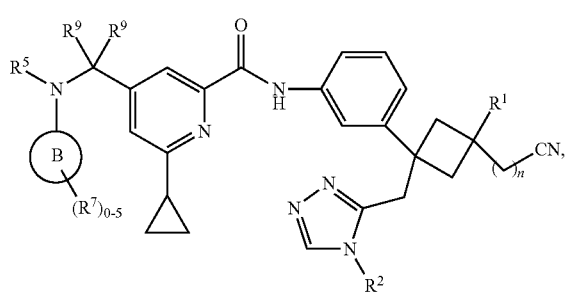
(II-H)
wherein R¹, R², R⁵, R⁷, R⁹, and n are as described for the compound of Formula (I), and
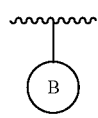
is a monocyclic $C_3$-$C_6$ cycloalkyl, fused bicyclic $C_4$-$C_8$ cycloalkyl, bridged bicyclic $C_4$-$C_8$ cycloalkyl, spiro bicyclic $C_5$-$C_8$ cycloalkyl, or 5- to 6-membered heterocyclyl.
In some embodiments, the compound is of Formula (II-A-1), (II-B-1), (II-C-1), (II-D-1), (II-E-1), (II-F-1), (II-G-1), or (II-H-1).
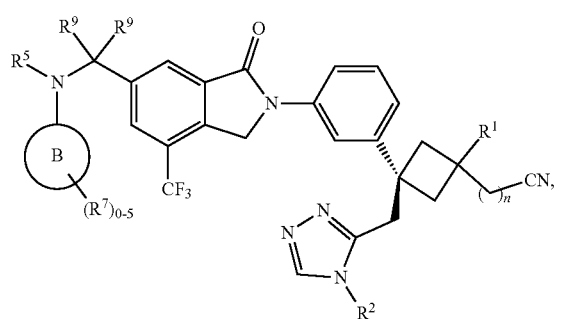
(II-C-1)
(II-D-1)
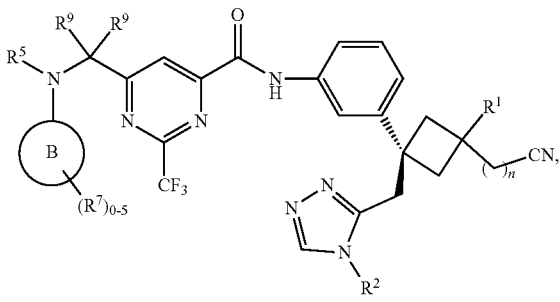
(II-E-1)
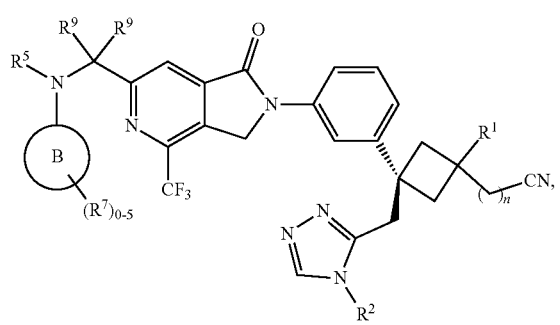
(II-A-1)
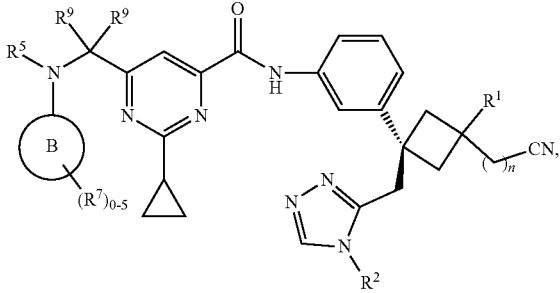
(II-F-1)

(II-G-1)

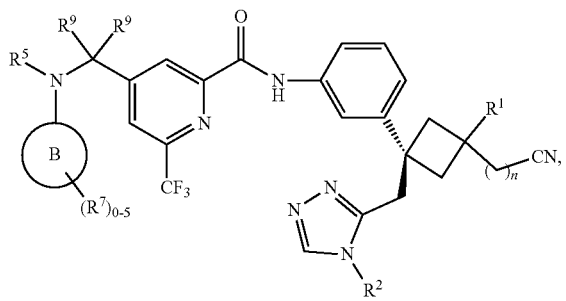

or (II-H-1)

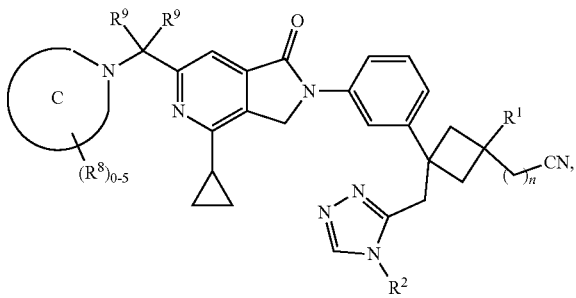

wherein R¹, R², R⁵, R⁷, R⁹, and n are as described for the compound of Formula (I), and

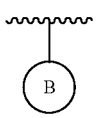

is a monocyclic $C_3$-$C_6$ cycloalkyl, fused bicyclic $C_4$-$C_8$ cycloalkyl, bridged bicyclic $C_4$-$C_8$ cycloalkyl, spiro bicyclic $C_5$-$C_8$ cycloalkyl, or 5- to 6-membered heterocyclyl.

In some embodiments, the compound is of Formula (III-A), (III-B), (III-C), (III-D), (III-E), (III-F), (III-G), or (III-H).

(III-A)

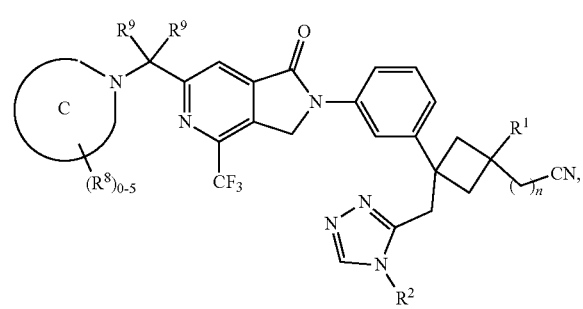

(III-B), (III-C), (III-D), (III-E), (III-F)

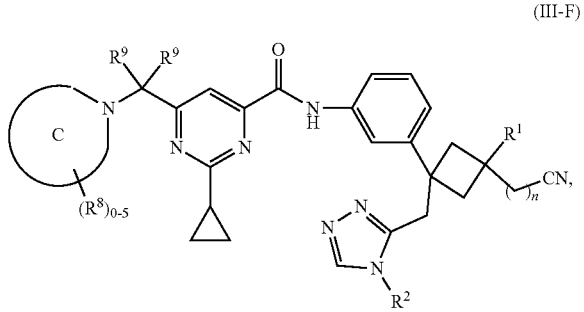

(III-G)

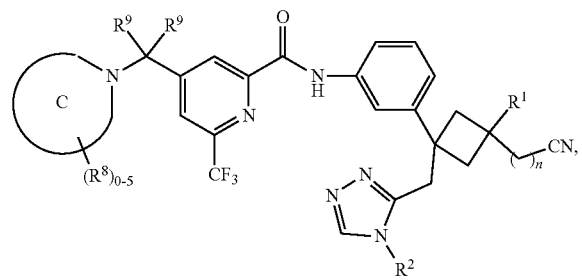

or (III-H)

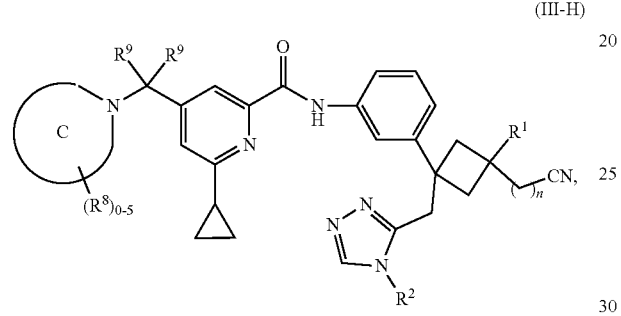

wherein R¹, R², R⁸, R⁹, and n are as described for the compound of Formula (I), and

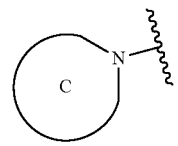

is a 5- to 10-membered monocyclic, fused bicyclic, or bridged heterocyclyl, or a 5- to 10-membered monocyclic or bicyclic heteroaryl, each of which heterocyclyl or heteroaryl optionally contains 1-2 additional heteroatoms selected from the group consisting of N and O.

In some embodiments, the compound is of Formula (III-A-1), (III-B-1), (III-C-1), (III-D-1), (III-E-1), (III-F-1), (III-G-1), or (III-H-1).

(III-A-1)

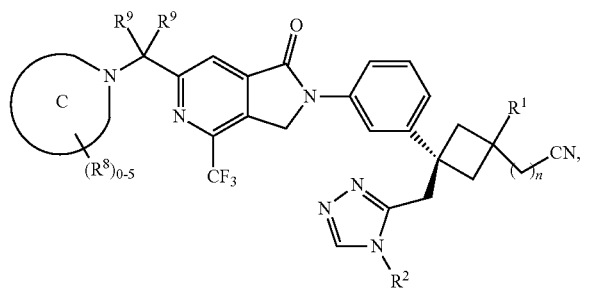

(III-B-1)

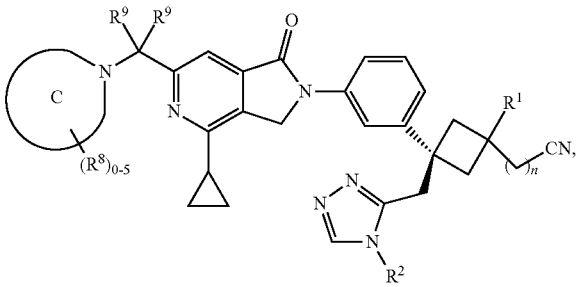

(III-C-1)

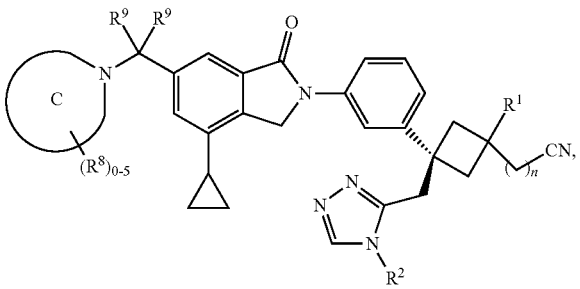

(III-D-1)

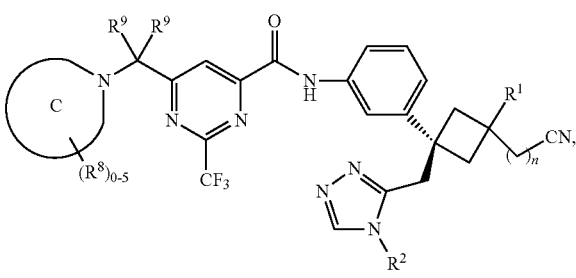

(III-E-1)

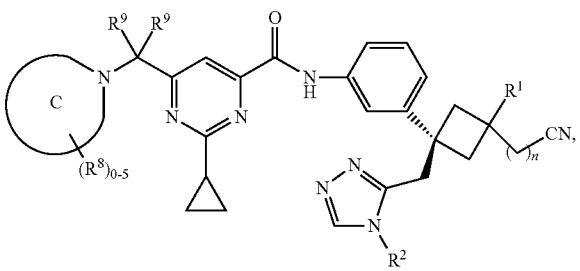

(III-F-1)

-continued (III-G-1)

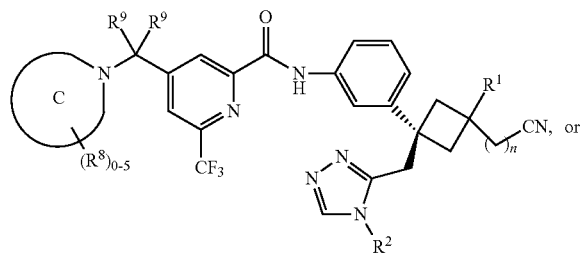

(III-H-1)

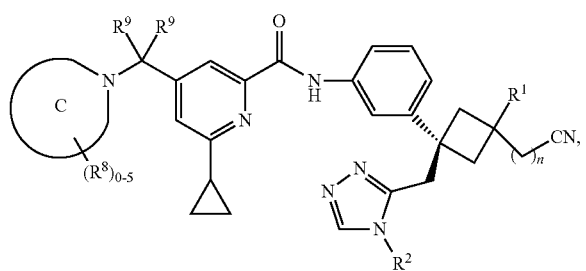

wherein $R^1$, $R^2$, $R^8$, $R^9$, and n are as described for the compound of Formula (I), and

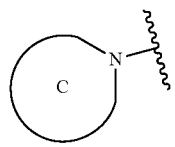

is a 5- to 10-membered monocyclic, fused bicyclic, or bridged heterocyclyl, or a 5- to 10-membered monocyclic or bicyclic heteroaryl, each of which heterocyclyl or heteroaryl optionally contains 1-2 additional heteroatoms selected from the group consisting of N and O.

In some embodiments, the compound is of Formula (IV-A) or (IV-B):

(IV-A)

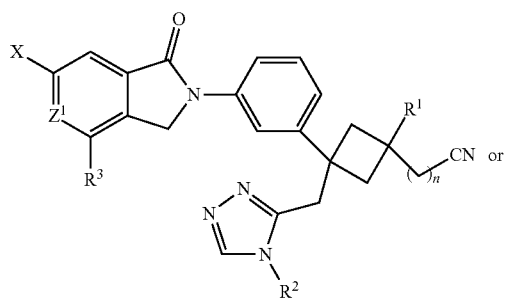

(IV-B)

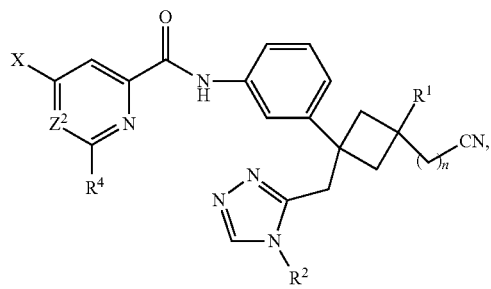

wherein $R^1$, $R^2$, $R^3$, $R^4$, $Z^1$, $Z^2$, and n are as described for the compound of Formula (I), and X is H, $C_1$-$C_6$ alkyl, or $C_1$-$C_6$ haloalkyl. In some embodiments, X is H. In some embodiments, X is $C_1$-$C_6$ alkyl. In some embodiments, X is $C_1$-$C_6$ haloalkyl.

In some embodiments, the compound is of Formula (IV-C), (IV-D), (IV-E), (IV-F), (IV-G), (IV-H), (IV-I), or (IV-J):

(IV-C)

(IV-D)

(IV-E)

(IV-F)
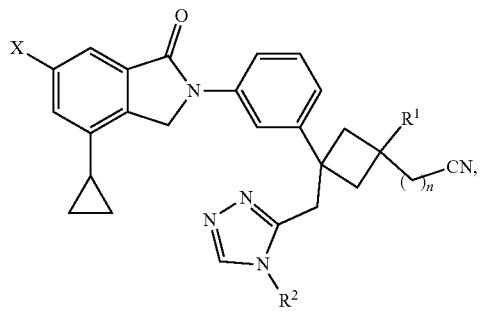
(IV-G)
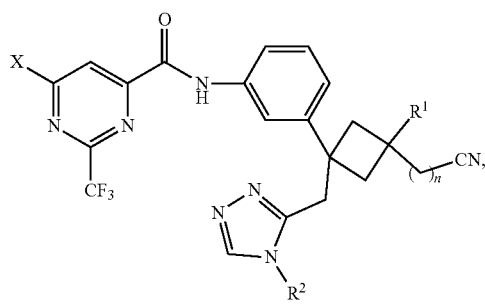
(IV-H)
(IV-I)
or
(IV-J)
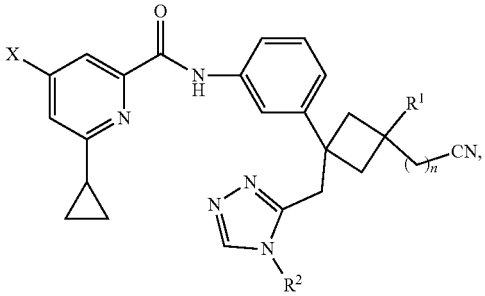
wherein $R^1$, $R^2$, and n are as described for the compound of Formula (I), and X is H, $C_1$-$C_6$ alkyl, or $C_1$-$C_6$ haloalkyl. In some embodiments, X is H. In some embodiments, X is $C_1$-$C_6$ alkyl. In some embodiments, X is $C_1$-$C_6$ haloalkyl.
In some embodiments, the compound is of Formula (IV-C-1), (IV-D-1), (IV-E-1), (IV-F-1), (IV-G-1), (IV-H-1), (IV-I-1), or (IV-J-1).
(IV-C-1)
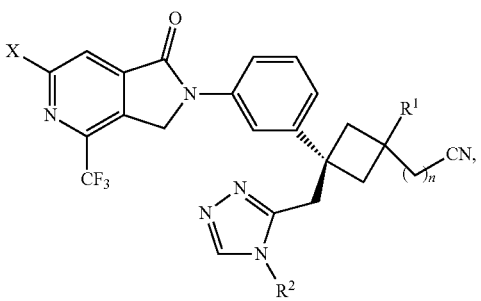
(IV-D-1)
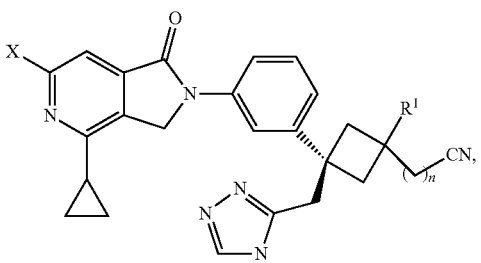
(IV-E-1)
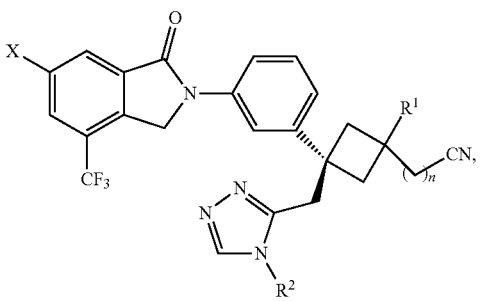

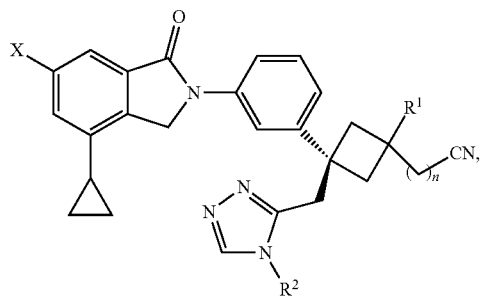
(IV-F-1)

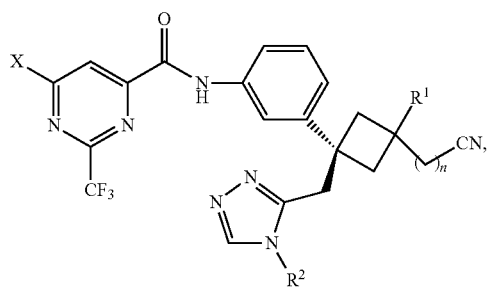
(IV-G-1)

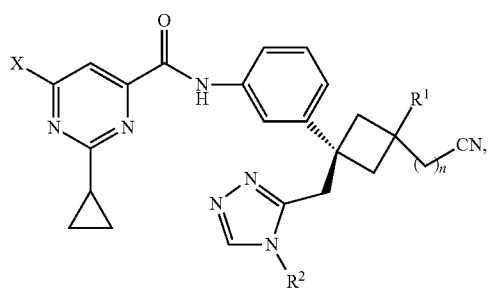
(IV-H-1)

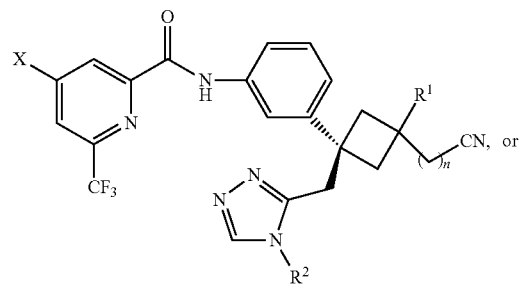
(IV-I-1)

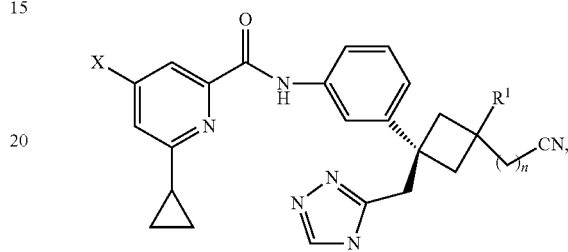
(IV-J-1)

wherein $R^1$, $R^2$, and n are as described for the compound of Formula (I), and X is H, $C_1$-$C_6$ alkyl, or $C_1$-$C_6$ haloalkyl. In some embodiments, X is H. In some embodiments, X is $C_1$-$C_6$ alkyl. In some embodiments, X is $C_1$-$C_6$ haloalkyl.

In any of the embodiments of Formula (I), (I-a), (I-A)-(I-J), (II-A)-(II-H), (II-A-1)-(II-H-1), (III-A)-(III-H), (III-A-1)-(III-H-1), (IV-A)-(IV-J), or (IV-C-1)-(IV-J-1), the absolute stereochemistry at the cyclobutyl carbon at which the cyano group is attached can be (R)-(using the Cahn-Ingold-Prelog rules). In any of the embodiments of Formula (I), (I-a), (I-A)-(I-J), (II-1), the absolute stereochemistry at the cyclobutyl carbon at which the cyano group is attached can be (S)-.

TABLE 1

Representative Compounds of the Present Disclosure

| Example No. | Structure |
|---|---|
| 1 | 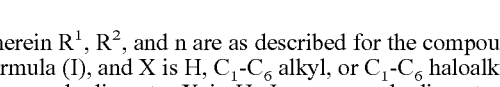 |
| 2 | 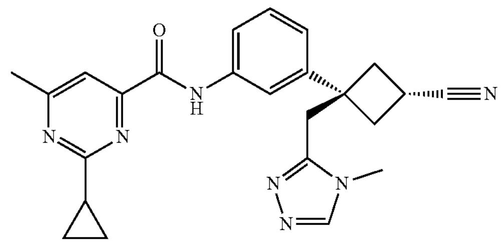 [SMILES: Cc1cc(C(=O)Nc2cccc([C@]3(Cc4nncn4C)C[C@H](C#N)C3)c2)nc(C2CC2)n1] |

TABLE 1-continued

Representative Compounds of the Present Disclosure

| Example No. | Structure |
|---|---|
| 3 | 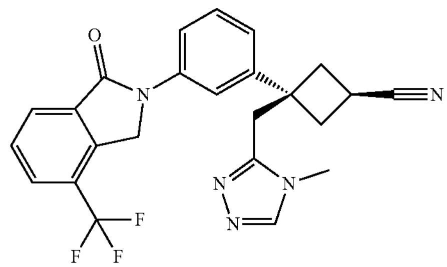 [SMILES: Cn1cnnc1C[C@]1(c2cccc(N3Cc4c(cccc4C(F)(F)F)C3=O)c2)C[C@H](C#N)C1] |
| 4 | 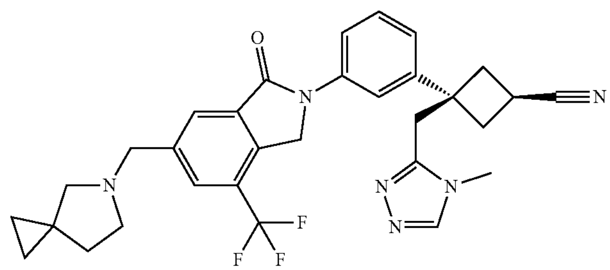 [SMILES: Cn1cnnc1C[C@]1(c2cccc(N3Cc4c(cc(CN5CCC6(CC6)C5)cc4C(F)(F)F)C3=O)c2)C[C@H](C#N)C1] |
| 5 | 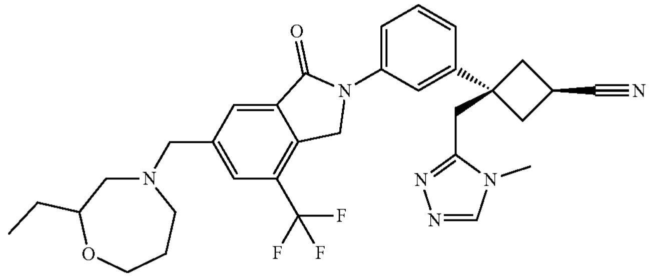 [SMILES: CCC1CN(Cc2cc3c(c(C(F)(F)F)c2)CN(c2cccc([C@]4(Cc5nncn5C)C[C@@H](C#N)C4)c2)C3=O)CCCO1] |
| 6 | 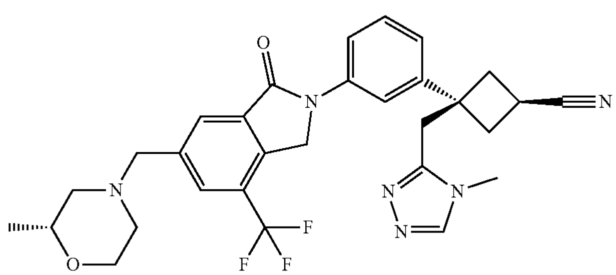 [SMILES: C[C@@H]1CN(Cc2cc3c(c(C(F)(F)F)c2)CN(c2cccc([C@]4(Cc5nncn5C)C[C@@H](C#N)C4)c2)C3=O)CCO1] |
| 7 | 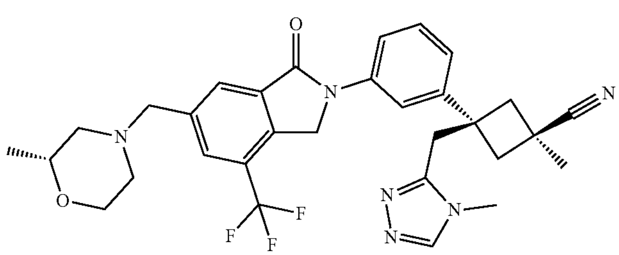 [SMILES: C[C@@H]1CN(Cc2cc3c(c(C(F)(F)F)c2)CN(c2cccc([C@]4(Cc5nncn5C)C[C@@](C)(C#N)C4)c2)C3=O)CCO1] |

TABLE 1-continued

Representative Compounds of the Present Disclosure

| Example No. | Structure |
|---|---|
| 8 | 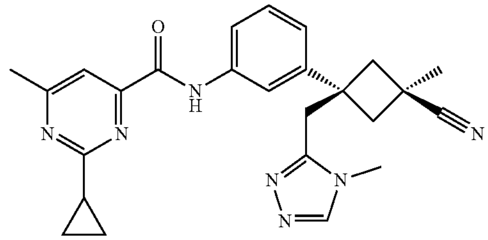 [SMILES: Cc1cc(C(=O)Nc2cccc([C@]3(Cc4nncn4C)C[C@@](C)(C#N)C3)c2)nc(C2CC2)n1] |
| 9 | 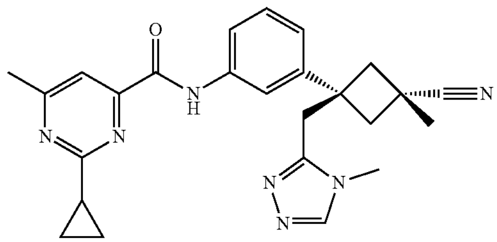 [SMILES: Cc1cc(C(=O)Nc2cccc([C@]3(Cc4nncn4C)C[C@](C)(C#N)C3)c2)nc(C2CC2)n1] |
| 10 | 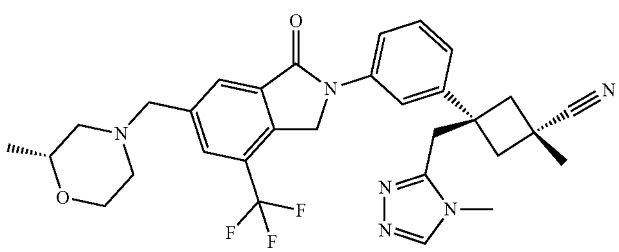 [SMILES: C[C@@H]1CN(Cc2cc3c(c(C(F)(F)F)c2)CN(c2cccc([C@]4(Cc5nncn5C)C[C@](C)(C#N)C4)c2)C3=O)CCO1] |
| 11 | 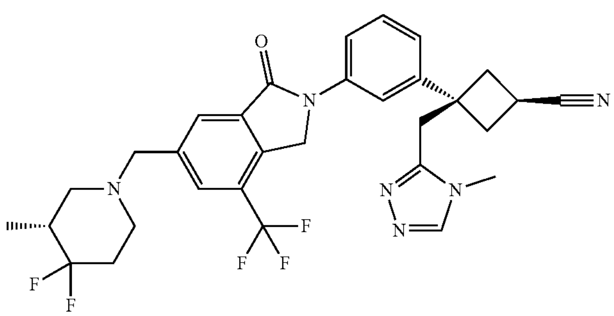 [SMILES: C[C@@H]1CN(Cc2cc3c(c(C(F)(F)F)c2)CN(c2cccc([C@]4(Cc5nncn5C)C[C@@H](C#N)C4)c2)C3=O)CCC1(F)F] |
| 12 | 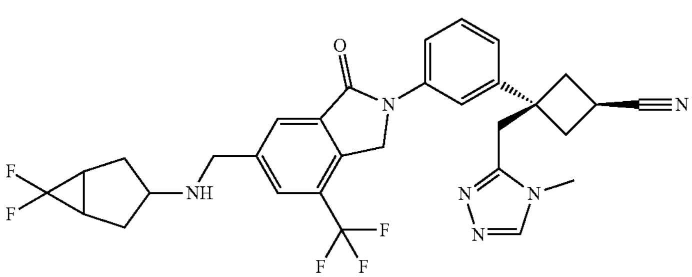 [SMILES: Cn1cnnc1C[C@]1(c2cccc(N3Cc4c(cc(CNC5CC6C(C5)C6(F)F)cc4C(F)(F)F)C3=O)c2)C[C@H](C#N)C1] |

TABLE 1-continued

Representative Compounds of the Present Disclosure

| Example No. | Structure |
|---|---|
| 13 | 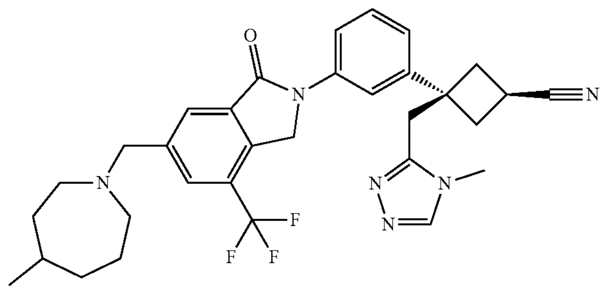 [SMILES: CC1CCCN(Cc2cc3c(c(C(F)(F)F)c2)CN(c2cccc([C@]4(Cc5nncn5C)C[C@@H](C#N)C4)c2)C3=O)CC1] |
| 14 | 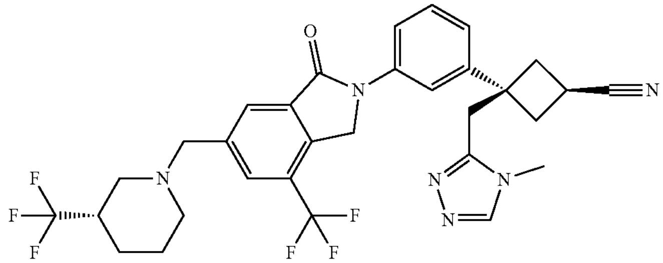 |
| 15 | 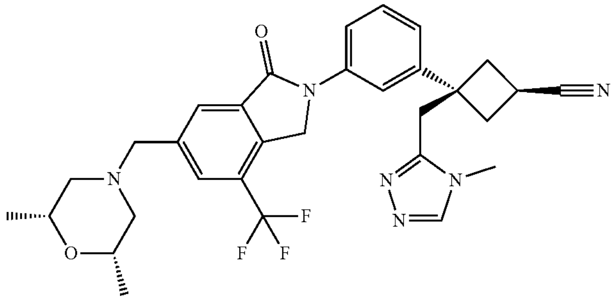 [SMILES: C[C@@H]1CN(Cc2cc3c(c(C(F)(F)F)c2)CN(c2cccc([C@]4(Cc5nncn5C)C[C@@H](C#N)C4)c2)C3=O)C[C@H](C)O1] |
| 16 | 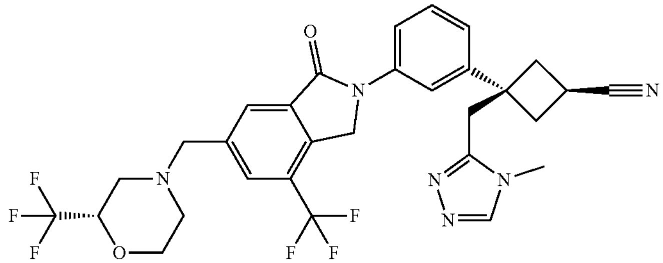 [SMILES: Cn1cnnc1C[C@]1(c2cccc(N3Cc4c(cc(CN5CCO[C@H](C(F)(F)F)C5)cc4C(F)(F)F)C3=O)c2)C[C@H](C#N)C1] |
| 17 | 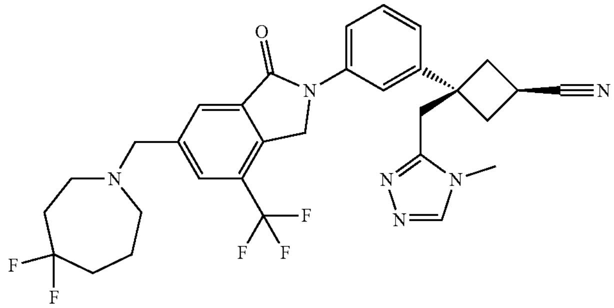 [SMILES: Cn1cnnc1C[C@]1(c2cccc(N3Cc4c(cc(CN5CCCC(F)(F)CC5)cc4C(F)(F)F)C3=O)c2)C[C@H](C#N)C1] |

TABLE 1-continued

Representative Compounds of the Present Disclosure

| Example No. | Structure |
|---|---|
| 18 | 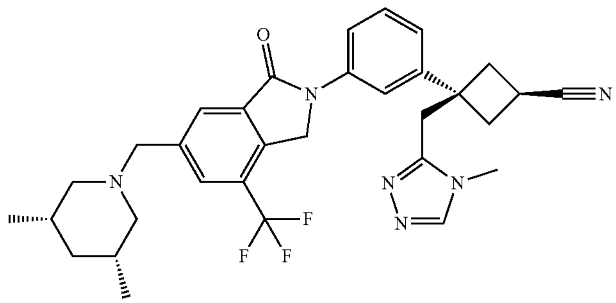 [SMILES: C[C@@H]1C[C@H](C)CN(Cc2cc3c(c(C(F)(F)F)c2)CN(c2cccc([C@]4(Cc5nncn5C)C[C@@H](C#N)C4)c2)C3=O)C1] |
| 19 | 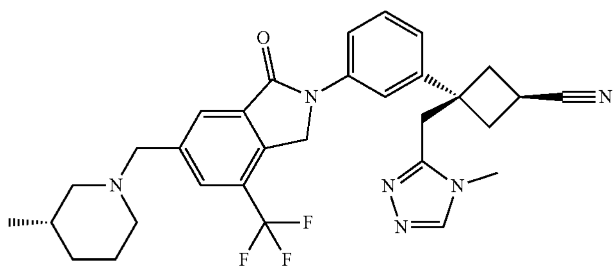 [SMILES: C[C@H]1CCCN(Cc2cc3c(c(C(F)(F)F)c2)CN(c2cccc([C@]4(Cc5nncn5C)C[C@@H](C#N)C4)c2)C3=O)C1] |
| 20 | 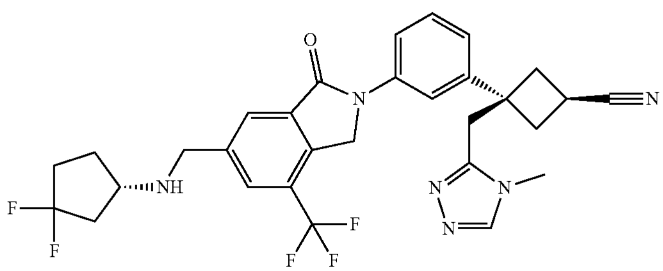 [SMILES: Cn1cnnc1C[C@]1(c2cccc(N3Cc4c(cc(CN[C@H]5CCC(F)(F)C5)cc4C(F)(F)F)C3=O)c2)C[C@H](C#N)C1] |
| 21 | 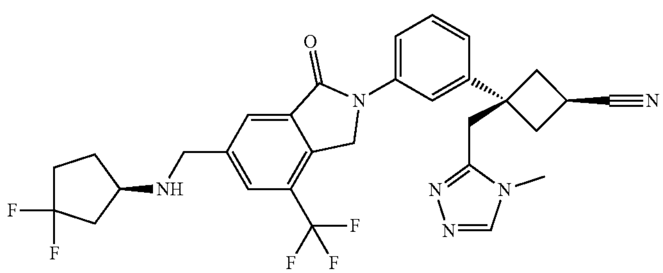 [SMILES: Cn1cnnc1C[C@]1(c2cccc(N3Cc4c(cc(CN[C@@H]5CCC(F)(F)C5)cc4C(F)(F)F)C3=O)c2)C[C@H](C#N)C1] |
| 22 | 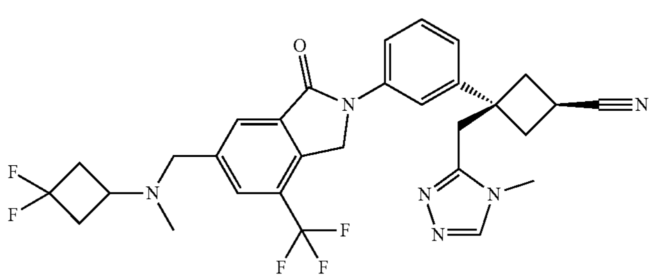 [SMILES: CN(Cc1cc2c(c(C(F)(F)F)c1)CN(c1cccc([C@]3(Cc4nncn4C)C[C@@H](C#N)C3)c1)C2=O)C1CC(F)(F)C1] |

TABLE 1-continued

Representative Compounds of the Present Disclosure

| Example No. | Structure |
|---|---|
| 23 | 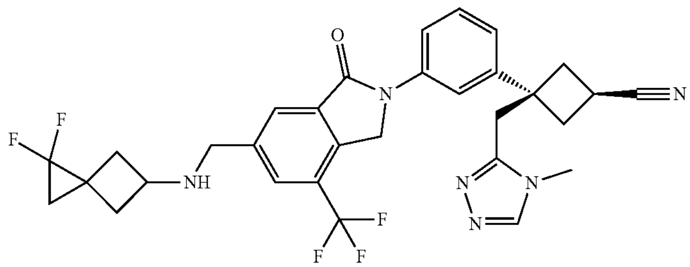 [SMILES: Cn1cnnc1C[C@]1(c2cccc(N3Cc4c(cc(CNC5CC6(C5)CC6(F)F)cc4C(F)(F)F)C3=O)c2)C[C@H](C#N)C1] |
| 24 | 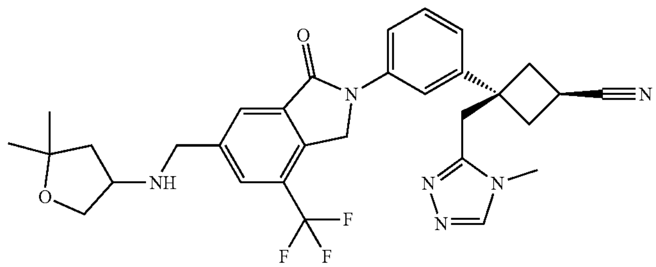 [SMILES: Cn1cnnc1C[C@]1(c2cccc(N3Cc4c(cc(CNC5COC(C)(C)C5)cc4C(F)(F)F)C3=O)c2)C[C@H](C#N)C1] |
| 25 | 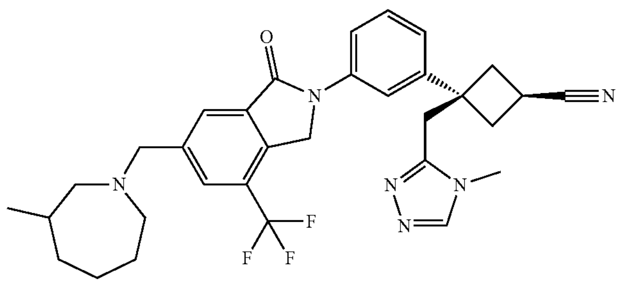 [SMILES: CC1CCCCN(Cc2cc3c(c(C(F)(F)F)c2)CN(c2cccc([C@]4(Cc5nncn5C)C[C@@H](C#N)C4)c2)C3=O)C1] |
| 26 | 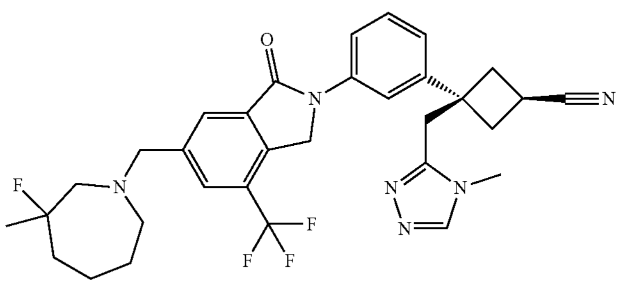 [SMILES: Cn1cnnc1C[C@]1(c2cccc(N3Cc4c(cc(CN5CCCCC(C)(F)C5)cc4C(F)(F)F)C3=O)c2)C[C@H](C#N)C1] |
| 27 | 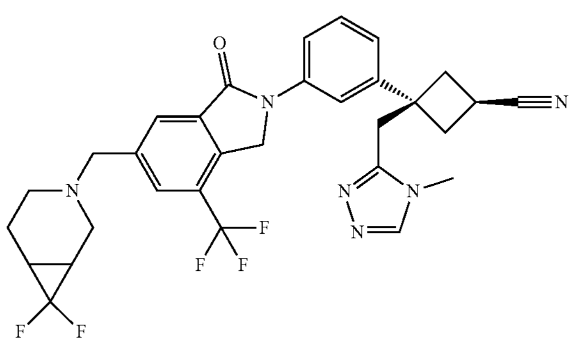 [SMILES: Cn1cnnc1C[C@]1(c2cccc(N3Cc4c(cc(CN5CCC6C(C5)C6(F)F)cc4C(F)(F)F)C3=O)c2)C[C@H](C#N)C1] |

TABLE 1-continued

Representative Compounds of the Present Disclosure

| Example No. | Structure |
|---|---|
| 28 | 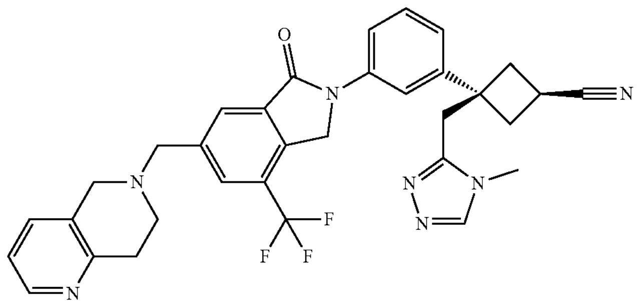 [SMILES: Cn1cnnc1C[C@]1(c2cccc(N3Cc4c(cc(CN5CCc6ncccc6C5)cc4C(F)(F)F)C3=O)c2)C[C@H](C#N)C1] |
| 29 | 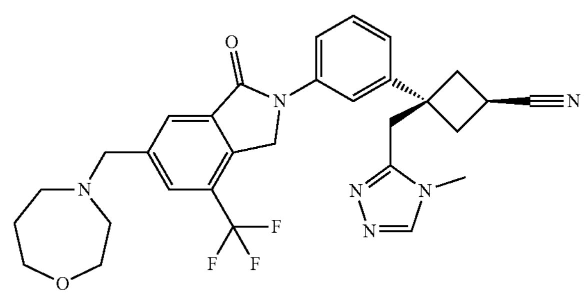 [SMILES: Cn1cnnc1C[C@]1(c2cccc(N3Cc4c(cc(CN5CCCOCC5)cc4C(F)(F)F)C3=O)c2)C[C@H](C#N)C1] |
| 30 | 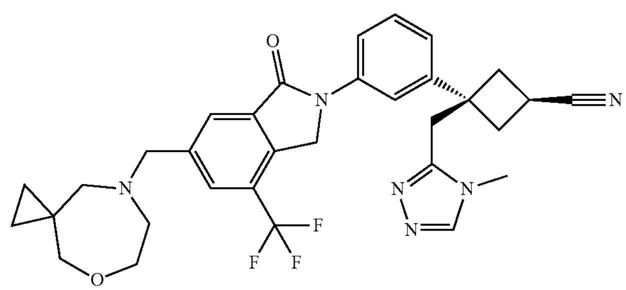 [SMILES: Cn1cnnc1C[C@]1(c2cccc(N3Cc4c(cc(CN5CCOCC6(CC6)C5)cc4C(F)(F)F)C3=O)c2)C[C@H](C#N)C1] |
| 31 | 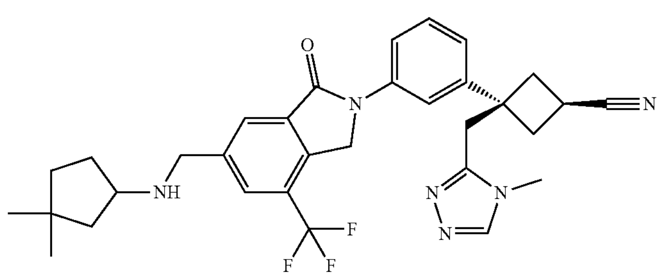 [SMILES: Cn1cnnc1C[C@]1(c2cccc(N3Cc4c(cc(CNC5CCC(C)(C)C5)cc4C(F)(F)F)C3=O)c2)C[C@H](C#N)C1] |
| 32 | 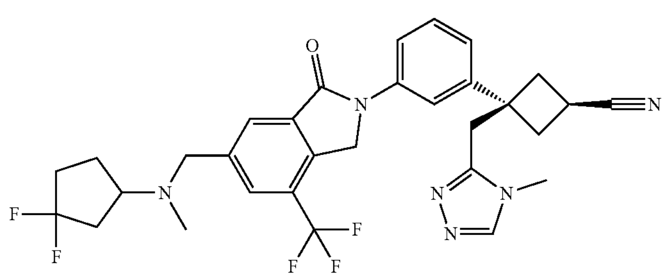 [SMILES: CN(Cc1cc2c(c(C(F)(F)F)c1)CN(c1cccc([C@]3(Cc4nncn4C)C[C@@H](C#N)C3)c1)C2=O)C1CCC(F)(F)C1] |

TABLE 1-continued
Representative Compounds of the Present Disclosure
| Example No. | Structure |
|---|---|
| 33 | 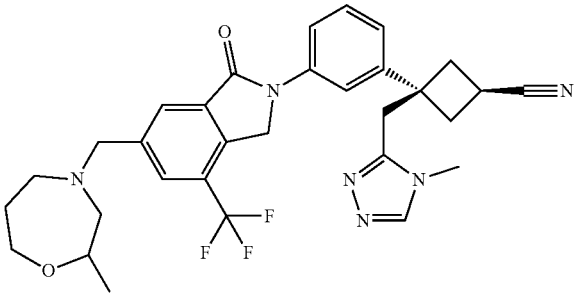 [SMILES: CC1CN(Cc2cc3c(c(C(F)(F)F)c2)CN(c2cccc([C@]4(Cc5nncn5C)C[C@@H](C#N)C4)c2)C3=O)CCCO1] |
| 34 | 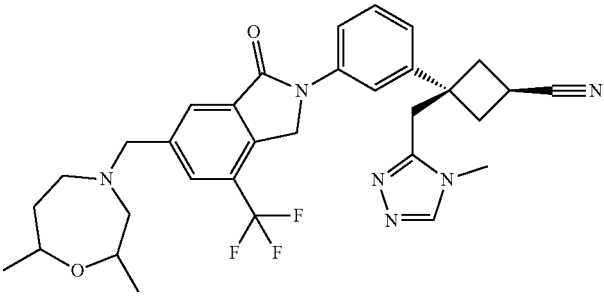 [SMILES: CC1CCN(Cc2cc3c(c(C(F)(F)F)c2)CN(c2cccc([C@]4(Cc5nncn5C)C[C@@H](C#N)C4)c2)C3=O)CC(C)O1] |
| 35 | 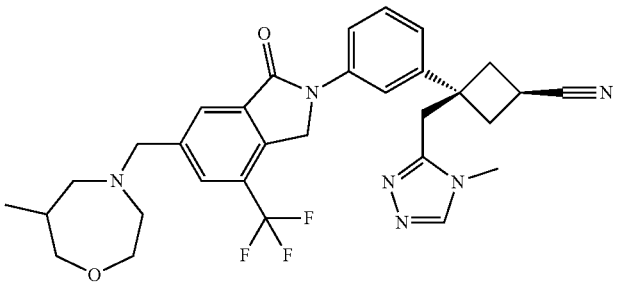 [SMILES: CC1COCCN(Cc2cc3c(c(C(F)(F)F)c2)CN(c2cccc([C@]4(Cc5nncn5C)C[C@@H](C#N)C4)c2)C3=O)C1] |
| 36 | 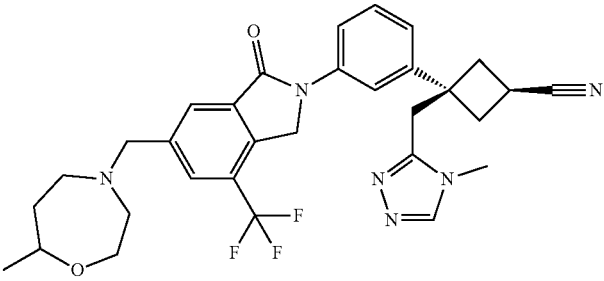 [SMILES: CC1CCN(Cc2cc3c(c(C(F)(F)F)c2)CN(c2cccc([C@]4(Cc5nncn5C)C[C@@H](C#N)C4)c2)C3=O)CCO1] |
| 37 | 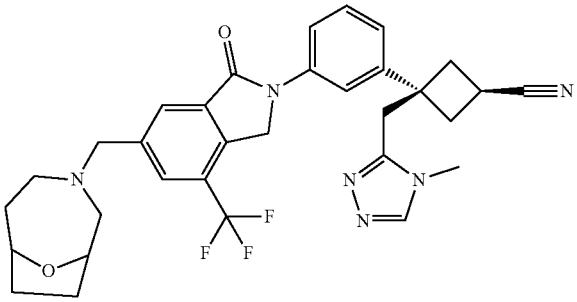 [SMILES: Cn1cnnc1C[C@]1(c2cccc(N3Cc4c(cc(CN5CCC6CCC(C5)O6)cc4C(F)(F)F)C3=O)c2)C[C@H](C#N)C1] |

TABLE 1-continued
Representative Compounds of the Present Disclosure
| Example No. | Structure |
|---|---|
| 38 | 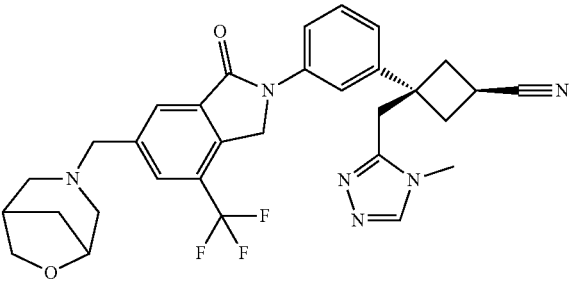 [SMILES: Cn1cnnc1C[C@]1(c2cccc(N3Cc4c(cc(CN5CC6COC(C6)C5)cc4C(F)(F)F)C3=O)c2)C[C@H](C#N)C1] |
| 39 | 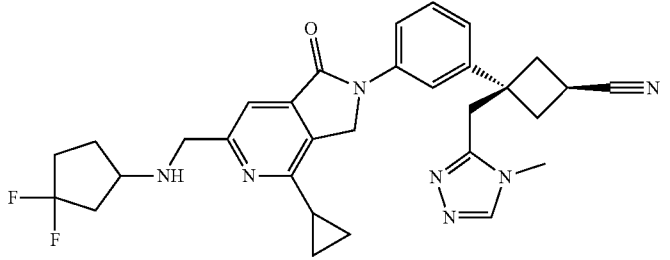 [SMILES: Cn1cnnc1C[C@]1(c2cccc(N3Cc4c(cc(CNC5CCC(F)(F)C5)nc4C4CC4)C3=O)c2)C[C@H](C#N)C1] |
| 40 | 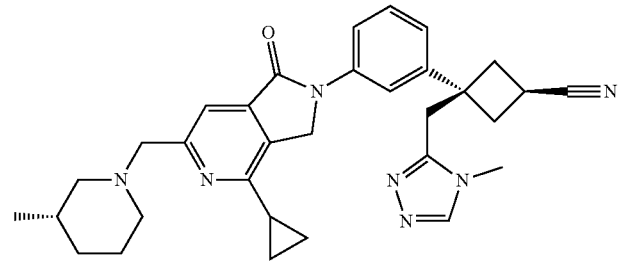 [SMILES: C[C@H]1CCCN(Cc2cc3c(c(C4CC4)n2)CN(c2cccc([C@]4(Cc5nncn5C)C[C@@H](C#N)C4)c2)C3=O)C1] |
| 41 | 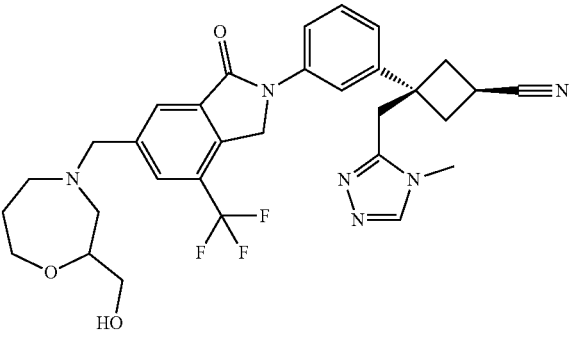 [SMILES: Cn1cnnc1C[C@]1(c2cccc(N3Cc4c(cc(CN5CCCOC(CO)C5)cc4C(F)(F)F)C3=O)c2)C[C@H](C#N)C1] |
| 42 | 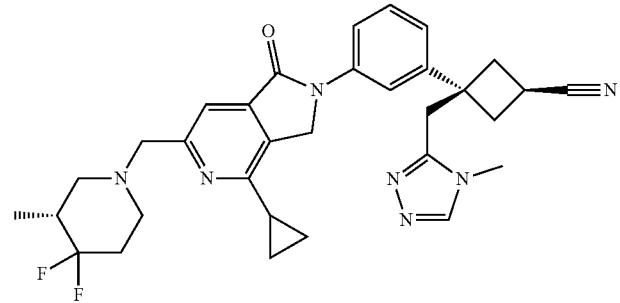 [SMILES: C[C@@H]1CN(Cc2cc3c(c(C4CC4)n2)CN(c2cccc([C@]4(Cc5nncn5C)C[C@@H](C#N)C4)c2)C3=O)CCC1(F)F] |

TABLE 1-continued

Representative Compounds of the Present Disclosure

| Example No. | Structure |
|---|---|
| 43 | 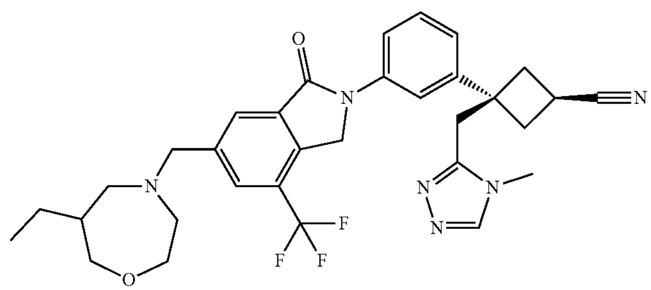 [SMILES: CCC1COCCN(Cc2cc3c(c(C(F)(F)F)c2)CN(c2cccc([C@]4(Cc5nncn5C)C[C@@H](C#N)C4)c2)C3=O)C1] |
| 44 | 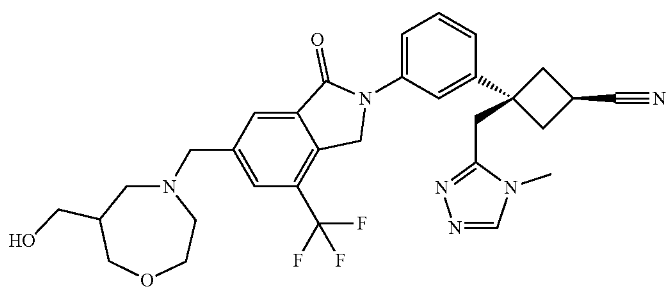 [SMILES: Cn1cnnc1C[C@]1(c2cccc(N3Cc4c(cc(CN5CCOCC(CO)C5)cc4C(F)(F)F)C3=O)c2)C[C@H](C#N)C1] |
| 45 | 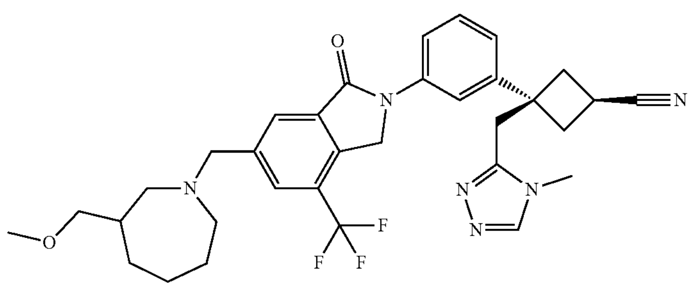 [SMILES: COCC1CCCCN(Cc2cc3c(c(C(F)(F)F)c2)CN(c2cccc([C@]4(Cc5nncn5C)C[C@@H](C#N)C4)c2)C3=O)C1] |
| 46 | 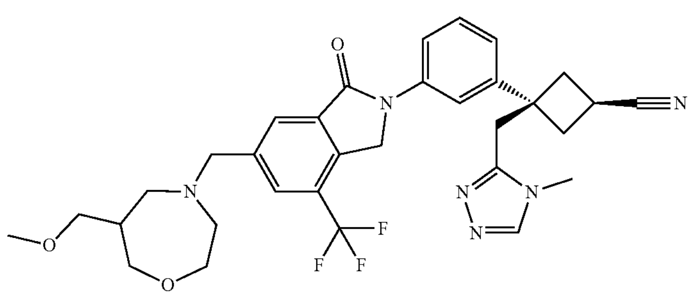 [SMILES: COCC1COCCN(Cc2cc3c(c(C(F)(F)F)c2)CN(c2cccc([C@]4(Cc5nncn5C)C[C@@H](C#N)C4)c2)C3=O)C1] |
| 47 | 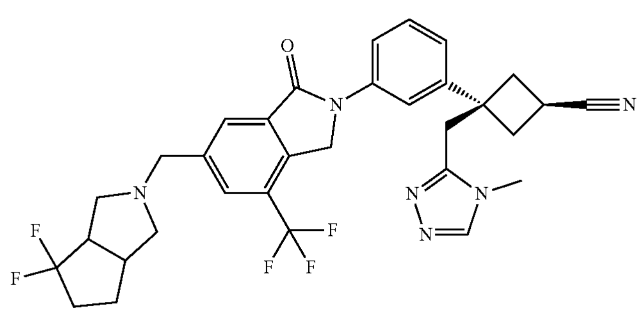 [SMILES: Cn1cnnc1C[C@]1(c2cccc(N3Cc4c(cc(CN5CC6CCC(F)(F)C6C5)cc4C(F)(F)F)C3=O)c2)C[C@H](C#N)C1] |

TABLE 1-continued

Representative Compounds of the Present Disclosure

| Example No. | Structure |
|---|---|
| 48 | 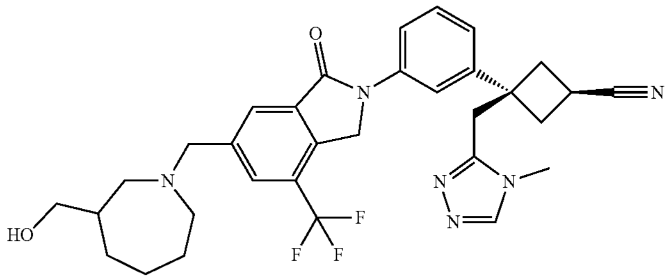 [SMILES: Cn1cnnc1C[C@]1(c2cccc(N3Cc4c(cc(CN5CCCCC(CO)C5)cc4C(F)(F)F)C3=O)c2)C[C@H](C#N)C1] |
| 49 | 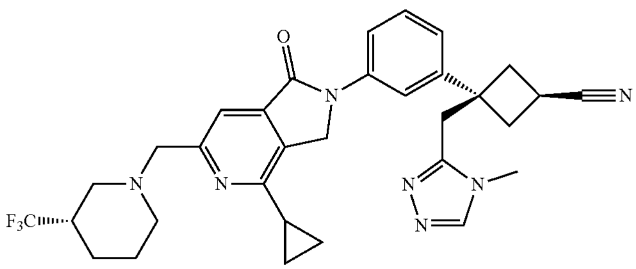 [SMILES: Cn1cnnc1C[C@]1(c2cccc(N3Cc4c(cc(CN5CCC[C@H](C(F)(F)F)C5)nc4C4CC4)C3=O)c2)C[C@H](C#N)C1] |
| 50 | 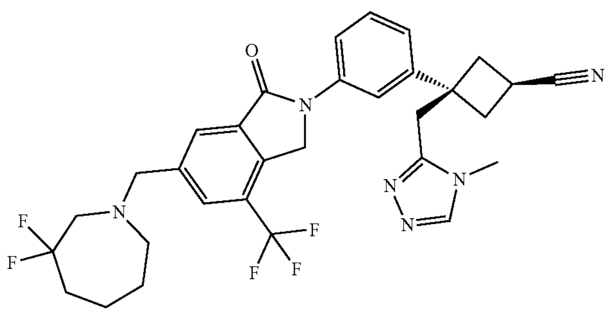 [SMILES: Cn1cnnc1C[C@]1(c2cccc(N3Cc4c(cc(CN5CCCCC(F)(F)C5)cc4C(F)(F)F)C3=O)c2)C[C@H](C#N)C1] |
| 51 | 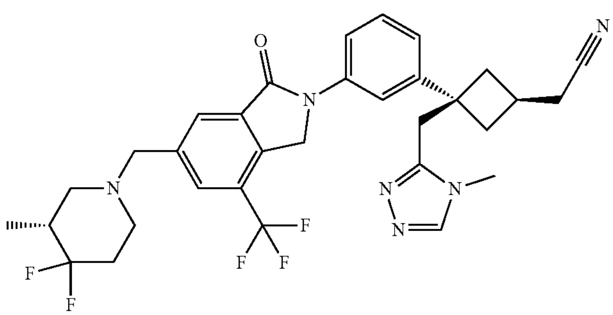 [SMILES: C[C@@H]1CN(Cc2cc3c(c(C(F)(F)F)c2)CN(c2cccc([C@]4(Cc5nncn5C)C[C@@H](CC#N)C4)c2)C3=O)CCC1(F)F] |
| 52 | 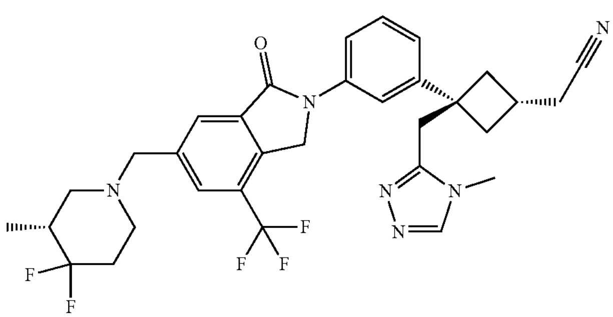 [SMILES: C[C@@H]1CN(Cc2cc3c(c(C(F)(F)F)c2)CN(c2cccc([C@]4(Cc5nncn5C)C[C@H](CC#N)C4)c2)C3=O)CCC1(F)F] |

TABLE 1-continued

Representative Compounds of the Present Disclosure

| Example No. | Structure |
|---|---|
| 53 | 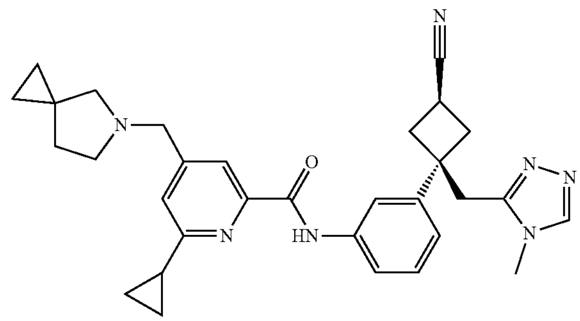 [SMILES: Cn1cnnc1C[C@]1(c2cccc(NC(=O)c3cc(CN4CCC5(CC5)C4)cc(C4CC4)n3)c2)C[C@H](C#N)C1] |
| 54 | 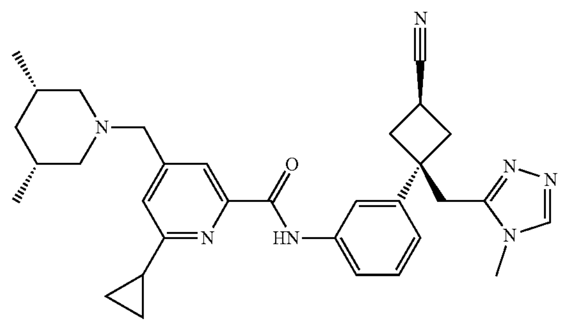 [SMILES: C[C@@H]1C[C@H](C)CN(Cc2cc(C(=O)Nc3cccc([C@]4(Cc5nncn5C)C[C@@H](C#N)C4)c3)nc(C3CC3)c2)C1] |
| 55 | 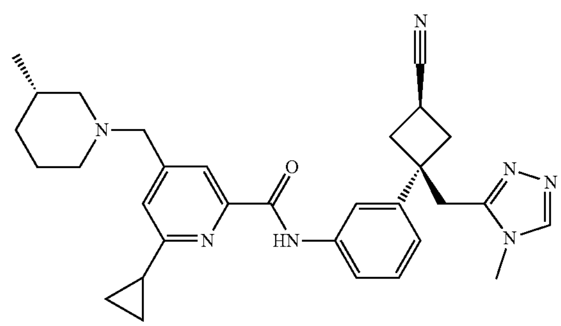 [SMILES: C[C@H]1CCCN(Cc2cc(C(=O)Nc3cccc([C@]4(Cc5nncn5C)C[C@@H](C#N)C4)c3)nc(C3CC3)c2)C1] |
| 56 | 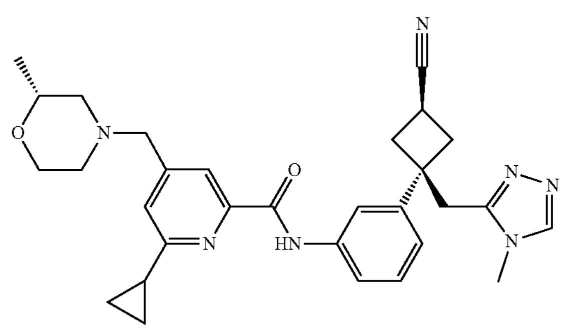 [SMILES: C[C@@H]1CN(Cc2cc(C(=O)Nc3cccc([C@]4(Cc5nncn5C)C[C@@H](C#N)C4)c3)nc(C3CC3)c2)CCO1] |

TABLE 1-continued

Representative Compounds of the Present Disclosure

| Example No. | Structure |
|---|---|
| 57 | [chemical structure] |
| 58 | [chemical structure] |
| 59 | Inhibitor Probe |
| 60 | [chemical structure] |

In some embodiments, provided is a compound selected from Compounds Nos. 1-58 in Table 1, or a tautomer thereof, stereoisomer thereof, or a pharmaceutically acceptable salt thereof.

In one aspect, provided herein are methods of preparing the compounds of Formula (I) described herein. In another aspect, provided herein are intermediate compounds for preparing the compounds of Formula (I). Also provided herein are compounds which are assay probes, and which are optionally tagged with, for example, a fluorescent label. In a further aspect, provided herein is a method for assaying inhibition of Cbl-b. In one variation, provided herein is a method for assaying inhibition of Cbl-b comprising pre-incubating Cbl-b with an assay probe, such as an assay probe tagged with a fluorescent label, followed by exposing the Cbl-b/assay probe mixture to a candidate compound, and then determining whether and to what extent the assay probe is displaced by the candidate compound using, for example, FRET signal detection.

In any of the pharmaceutical compositions, methods, or kits described herein, the Cbl-b inhibitor can be selected from one or more Cbl-b inhibitors disclosed in the following patent application: compounds 1-719 (including "a" and "b" variants thereof) of International Patent Appl. WO 2019/148005 or a compound of any of Formula (I-A), Formula (I), Formula (II-A), Formula (II), Formula (III-A), Formula (III), or Formula (IV) therein. The contents of International Patent Appl. WO 2019/148005 is incorporated by reference herein in its entirety.

In some embodiments, provided for use in the compositions and methods described herein is Compound 60 and/or Compound 56 in Table 1, or a tautomer thereof, stereoisomer thereof, or a pharmaceutically acceptable salt thereof.

In one embodiment, the small molecule Cbl-b inhibitors for the methods, pharmaceutical compositions, and kits disclosed herein have a molecular weight of 1,000 daltons or less, or about 1,000 daltons or less. In another embodiment, the small molecule Cbl-b inhibitors have a molecular weight of 900 daltons or less, or about 900 daltons or less. In another embodiment, the small molecule Cbl-b inhibitors have a molecular weight of 800 daltons or less, or about 800 daltons or less. In another embodiment, the small molecule Cbl-b inhibitors have a molecular weight of 750 daltons or less, or about 750 daltons or less. In another embodiment, the small molecule Cbl-b inhibitors have a molecular weight of 700 daltons or less, or about 700 daltons or less. In another embodiment, the small molecule Cbl-b inhibitors have a molecular weight of 650 daltons or less, or about 650 daltons or less. In another embodiment, the small molecule Cbl-b inhibitors have a molecular weight of 600 daltons or less, or about 600 daltons or less. For any of the foregoing embodiments, the lower limit for the molecular weight of the small molecule Cbl-b inhibitors can be 100 daltons, 200 daltons, or 300 daltons, or about 100 daltons, about 200 daltons, or about 300 daltons.

The schemes below describe methods of synthesizing the compounds disclosed herein. Mixtures of stereoisomers produced during synthesis, such as racemic mixtures of final compounds, can be separated into the respective enantiomers using common chromatography methods such as supercritical fluid chromatography in combination with chiral stationary phases, chiral column chromatography, or other methods known in the art.

Scheme I.

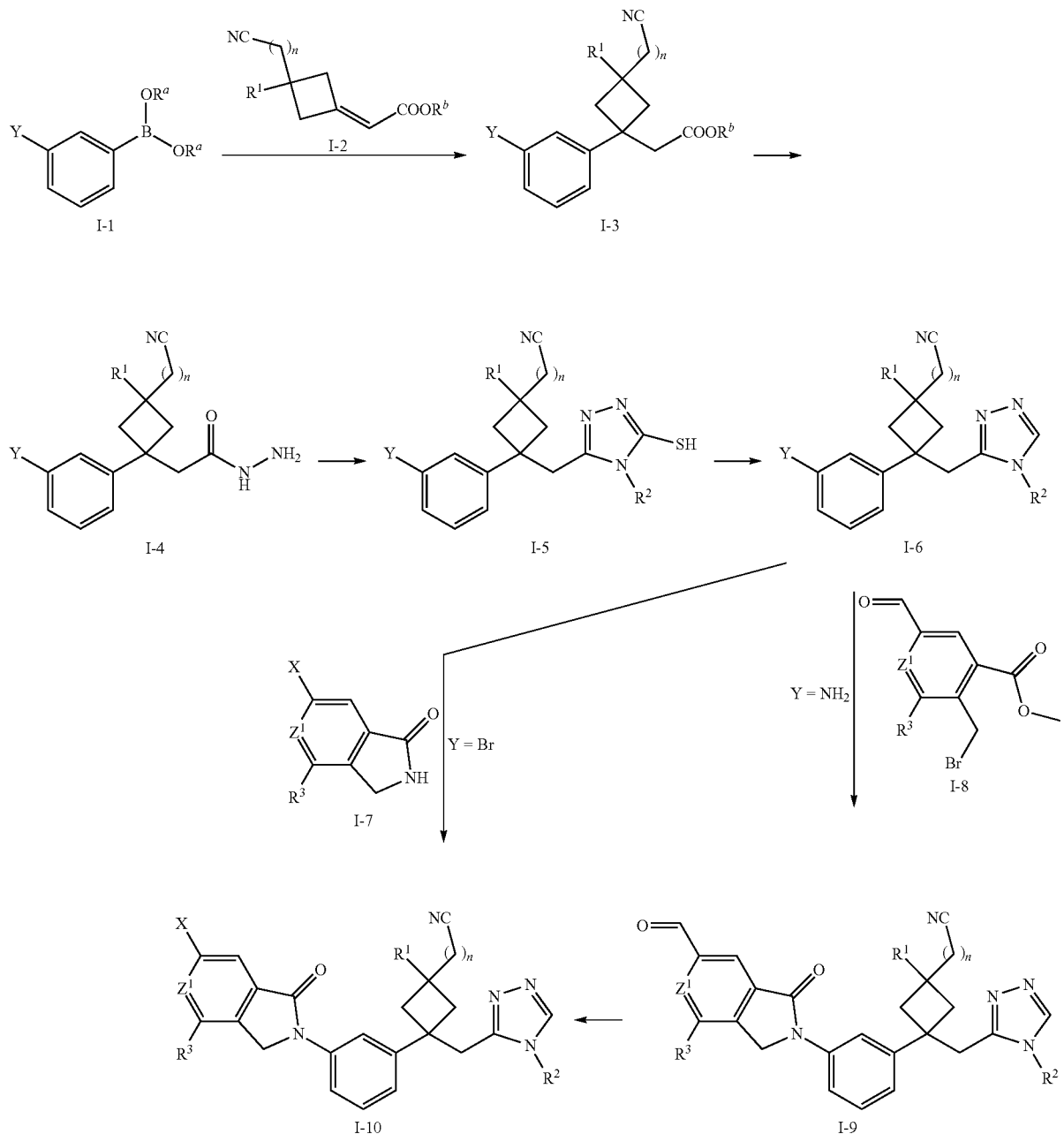

wherein $R^1$, $R^2$, $R^3$, X, $Z^1$, and n are as defined for the compound of Formula (I); Y is Br or $NH_2$; and $R^a$ and $R^b$ are suitable protecting groups.

Compounds of the general formula I-9 were synthesized as outlined in Scheme I. Coupling of boronic esters I-1 with alkenes I-2 under rhodium catalysis afforded esters I-3. A triazole was assembled by hydrazide formation (I-4), cyclization, and desulphurization to provide compounds I-6. Compounds I-6, wherein Y is $NH_2$, were treated with bromoesters I-8 to provide compounds I-9, which were subsequently converted to compounds I-10 by reductive amination with a substituted piperidine. Compounds I-6, wherein Y is Br, were treated with piperidine derivatives I-7 under palladium catalysis to directly provide compounds I-10.

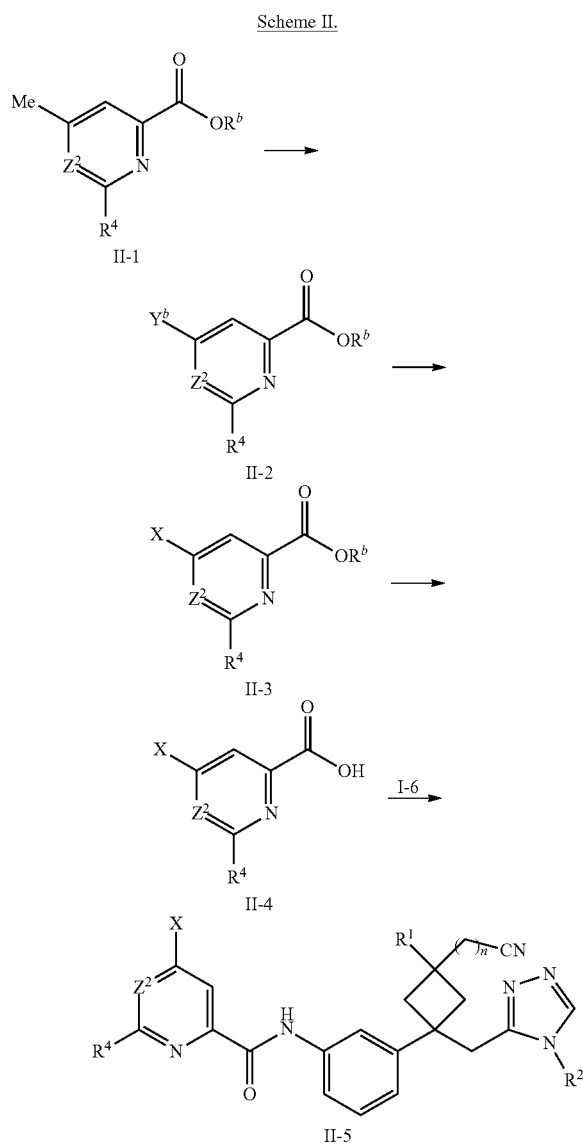

Scheme II.

wherein $R^1$, $R^2$, $R^4$, X, $Z^2$, and n are as defined for the compound of Formula (I); $R^b$ is a suitable protecting group; and $Y^b$ is an aldehyde or bromomethyl.

Scheme II outlines a synthesis of compounds of general formula II-5. Methyl pyridines or pyrimidines II-1 were oxidized to provide an aldehyde or bromomethyl of formula II-2. Amino groups X were then installed by reductive amination or displacement with a substituted amine to provide compounds II-3, followed by ester hydrolysis under basic conditions to afford compounds II-4. Carboxylic acids II-4 were then coupled to amines I-6 with a coupling reagent such as HATU or T3P to afford amides II-5.

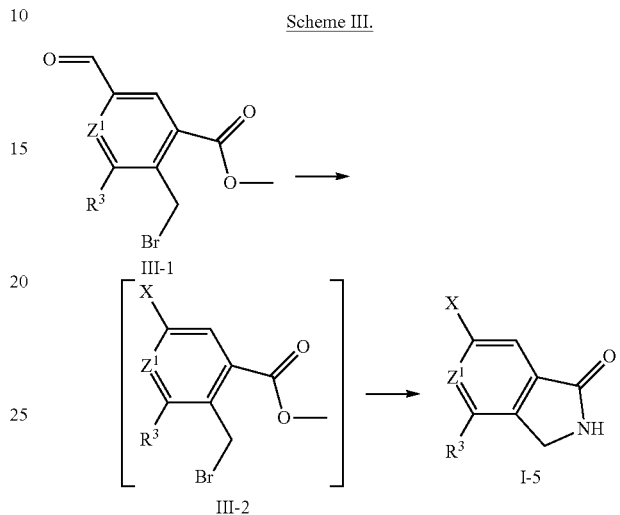

Scheme III.

wherein X, $R^3$, and $Z^1$ are as defined for the compound of Formula (I).

Intermediate compounds of general formula I-5, employed in the general synthesis outlined in Scheme I, were synthesized according to Scheme III. Aldehydes III-1 were coupled with substituted amines via reductive amination to provide intermediates III-2, which were treated with ammonia to provide compounds of formula I-5.

Compounds 12, 18-21, 25, 31, 49, and 53-57 display $IC_{50}$ values of less than 1 nM in the Cbl-b inhibition assay of Biological Example 1, and in one embodiment are used for the pharmaceutical compositions and in the methods as disclosed herein. Compounds 4, 11, 16, 17, 23, 39, 40, 44, and 48 display $IC_{50}$ values between 1 nM and less than 2 nM in the Cbl-b inhibition assay of Biological Example 1, and in one embodiment are used for the pharmaceutical compositions and in the methods as disclosed herein. Compounds 1, 2, 5, 6, 13-15, 22, 24, 26-30, 32-37, 41-43, 45, 47, 50, and 58 display $IC_{50}$ values between 2 and less than 5 nM in the Cbl-b inhibition assay of Biological Example 1, and in one embodiment are used for the pharmaceutical compositions and in the methods as disclosed herein. Compounds 7, 9, 38, 46, and 52 display $IC_{50}$ values between 5 and less than 20 nM in the Cbl-b inhibition assay of Biological Example 1, and in one embodiment are used for the pharmaceutical compositions and in the methods as disclosed herein. Compounds 3, 8, 10, and 51 display $IC_{50}$ values of 20 nM or greater in the Cbl-b inhibition assay of Biological Example 1, and in one embodiment are used for the pharmaceutical compositions and in the methods as disclosed herein.

In various embodiments, and as further described herein, compounds as provided herein (as well as compositions comprising the compounds described herein, and methods using the compounds or compositions described herein) have $IC_{50}$ values of less than 1 nM, between 1 nM and less than 2 nM, between 2 nM and less than 5 nM, between 5 nM and less than 20 nM, or 20 nM and greater, as determined by the Cbl-b inhibition assay of Biological Example 1. In a further embodiment, and as further described herein, compounds as provided herein (as well as compositions comprising the compounds described herein, and methods using the compounds or compositions described herein) have $IC_{50}$ values of less than 1 nM, as determined by the Cbl-b inhibition assay of Biological Example 1. In a further embodiment, and as further described herein, compounds as provided herein (as well as compositions comprising the compounds described herein, and methods using the compounds or compositions described herein) have $IC_{50}$ values of between 1 nM and less than 2 nM, as determined by the Cbl-b inhibition assay of Biological Example 1. In a further embodiment, and as further described herein, compounds as provided herein (as well as compositions comprising the compounds described herein, and methods using the compounds or compositions described herein) have $IC_{50}$ values of between 2 nM and less than 5 nM, as determined by the Cbl-b inhibition assay of Biological Example 1. In a further embodiment, and as further described herein, compounds as provided herein (as well as compositions comprising the compounds described herein, and methods using the compounds or compositions described herein) have $IC_{50}$ values of between 5 nM and less than 20 nM, as determined by the Cbl-b inhibition assay of Biological Example 1. In a further embodiment, and as further described herein, compounds as provided herein (as well as compositions comprising the compounds described herein, and methods using the compounds or compositions described herein) have $IC_{50}$ values 20 nM and greater, as determined by the Cbl-b inhibition assay of Biological Example 1.

For IL-2 secretion from an immune cell (e.g., T-cell) co-stimulated with an anti-CD3 antibody and an anti-CD28 antibody, compounds as provided herein (as well as compositions comprising the compounds described herein) induce ≤15 fold, between 15-20 fold, or greater than 20 fold change over baseline, at inhibitor concentrations of 1 micromolar or 0.3 micromolar.

For IL-2 secretion from an immune cell (e.g., T-cell) stimulated with an anti-CD3 antibody, compounds as provided herein (as well as compositions comprising the compounds described herein) induce less than 0.40 fold, between 0.40-0.85 fold, or greater than 0.85 fold change over baseline, at inhibitor concentrations of 3 micromolar or 1 micromolar.

For CD25 staining on the cell surface of an immune cell (e.g., T-cell) co-stimulated with an anti-CD3 antibody and an anti-CD28 antibody, compounds as provided herein (as well as compositions comprising the compounds described herein) induce ≤1.24 fold, between 1.24-1.39 fold, or greater than 1.39 fold change over baseline, at inhibitor concentrations 1 micromolar or 0.3 micromolar.

For CD25 staining on the cell surface of an immune cell (e.g., T-cell) stimulated with an anti-CD3 antibody, compounds as provided herein (as well as compositions comprising the compounds described herein) induce ≤1.00 fold, between 1.05-1.15 fold, or greater than 1.15 fold change over baseline, at inhibitor concentrations of 3 micromolar or 1 micromolar.

III. Methods, Medicaments, and Uses

Provided herein are methods for modulating activity of an immune cell (e.g., a T-cell, a B-cell, or a NK-cell) such as by contacting the immune cell with an effective amount of a Cbl-b inhibitor described herein or a composition thereof. Also provided are in vitro methods of producing said immune cells with modulated activity, referred to herein as "modified immune cells," wherein said modified immune cells can be administered to an individual in need thereof (e.g., an individual having cancer) by ex vivo methods. Further provided are in vivo methods of modulating a response in an individual in need thereof (e.g., an individual with cancer), wherein the method comprises administration of an effective amount of a Cbl-b inhibitor described herein or a composition thereof. Moreover, the present disclosure provides in vitro methods of producing an expanded population of lymphocytes after in vivo lympho-conditioning in an individual, wherein the lympho-conditioning occurs as a result of administration of an effective amount of a Cbl-b inhibitor described herein or a composition thereof to the individual. The expanded population of lymphocytes can then be administered to the individual. The expanded population of lymphocytes can then be administered to the individual with cancer. In some embodiments, the modified immune cells or the expanded population of lymphocytes are produced from a biological sample comprising immune cells obtained from the individual, such as a blood sample comprising peripheral blood mononuclear cells or a tumor biopsy comprising tumor infiltrating lymphocytes (TILs).

Additionally, provided are Cbl-b inhibitors for use as therapeutic active substances. A Cbl-b inhibitor for use in treating or preventing a disease or condition associated with Cbl-b activity is provided. Also, a Cbl-b inhibitor for use in treating cancer is provided. Further provided is the use of a Cbl-b inhibitor in the manufacture of a medicament for treating or preventing a disease or condition associated with Cbl-b activity. Also provided is the use of a Cbl-b inhibitor in the manufacture of a medicament for treating cancer. Moreover, the present disclosure provides treatment methods, medicaments, and uses comprising a Cbl-b inhibitor as part of a combination therapy for treating cancer involving one or more of an immune checkpoint inhibitor, an antineoplastic agent, and radiation therapy.

In some embodiments of the treatment methods, medicaments, and uses of the present disclosure, the cancer is a hematologic cancer such as lymphoma, a leukemia, or a myeloma. In other embodiments of the treatment methods, medicaments, and uses of the present disclosure, the cancer is a non-hematologic cancer such as a sarcoma, a carcinoma, or a melanoma.

Hematologic cancers include, but are not limited to, one or more leukemias such as B-cell acute lymphoid leukemia ("BALL"), T-cell acute lymphoid leukemia ("TALL"), acute lymphoid leukemia (ALL); one or more chronic leukemias including, but not limited to, chronic myelogenous leukemia (CML) and chronic lymphocytic leukemia (CLL); additional hematologic cancers or hematologic conditions including, but not limited to, B-cell prolymphocytic leukemia, blastic plasmacytoid dendritic cell neoplasm, Burkitt's lymphoma, diffuse large B-cell lymphoma, follicular lymphoma, hairy cell leukemia, small cell- or a large cell-follicular lymphoma, malignant lymphoproliferative conditions, MALT lymphoma, mantle cell lymphoma, Marginal zone lymphoma, multiple myeloma, myelodysplasia and myelodysplastic syndrome, non-Hodgkin's lymphoma, plasmablastic lymphoma, plasmacytoid dendritic cell neoplasm, Waldenstrom macroglobulinemia, and "preleukemia," which are a diverse collection of hematological conditions united by ineffective production (or dysplasia) of myeloid blood cells.

Non-hematologic cancers include but are not limited to, a neuroblastoma, renal cell carcinoma, colon cancer, colorectal cancer, breast cancer, epithelial squamous cell cancer, melanoma, stomach cancer, brain cancer, lung cancer (e.g., NSCLC), pancreatic cancer, cervical cancer, ovarian cancer, liver cancer, bladder cancer, prostate cancer, testicular cancer, thyroid cancer, uterine cancer, adrenal cancer, and head and neck cancer.

In some aspects, the effectiveness of administration of a Cbl-b inhibitor in the treatment of a disease or disorder such as cancer is measured by assessing clinical outcome, such as reduction in tumor size or number of tumors, and/or survival. In some embodiments, "treating cancer" comprises assessing a patient's response to the treatment regimen according to the Response Evaluation Criteria in Solid Tumors (RECIST version 1.1) as described (see, e.g., Eisenhauer et al., Eur J Cancer, 45:228-247, 2009; and Nishino et al., Am J Roentgenol, 195: 281-289, 2010). Response criteria to determine objective anti-tumor responses per RECIST 1.1 include complete response (CR); partial response (PR); progressive disease (PD); and stable disease (SD).

A. Isolation and Processing of Cells

Provided are methods for the preparation and processing of immune cells produced (e.g., modified immune cells) and used in the methods herein. As used herein, the term "modified immune cells" refers to immune cells or a cell population comprising the immune cells which have been cultured, incubated, and/or have been contacted with an effective amount of a Cbl-b inhibitor to modulate the activity of said immune cells. In some embodiments, the modified immune cells can be used for immunotherapy, such as in connection with adoptive immunotherapy methods.

1. Samples

In some embodiments, the immune cells to be modified or cell populations comprising the immune cells to be modified are isolated from a sample, such as a biological sample, e.g., one obtained from or derived from an individual (e.g., a human). In some embodiments, the individual from which the immune cell is isolated is one having a particular disease or condition (e.g., cancer) or in need of a cell therapy or to which cell therapy will be administered. The individual in some embodiments is a human in need of a particular therapeutic intervention, such as the adoptive cell therapy for which immune cells are being isolated, processed, and/or modified. Accordingly, the cells isolated from the individual in some embodiments are primary cells (e.g., primary human cells). As used herein, the term "primary cells" refers to cells isolated directly from mammalian biological fluid or tissue (e.g., human biological fluid or tissue).

In some embodiments, the immune cells to be modified are hematopoietic cells, multipotent stem cells, myeloid progenitor cells, lymphoid progenitor cells, T-cells, B-cells, and/or NK-cells. As used herein, the term "hematopoietic cells" includes hematopoietic stem cells and hematopoietic progenitor cells. In some embodiments, the immune cells to be modified are present in a heterogeneous cell population or a composition comprising a heterogeneous cell population. For example, the immune cells to be modified may be hematopoietic cells present in a heterogeneous cell population comprising cells such as differentiated cells derived from a tissue or organ. In some embodiments, the immune cells to be modified are present in a homogenous cell population or a composition comprising a homogenous cell population. For example, the immune cells to be modified may be hematopoietic cells present in a homogenous cell population comprising only hematopoietic cells. In some embodiments, the immune cells to be modified or cell populations comprising the immune cells to be modified include one or more subsets of immune cells. For example, one or more subsets of immune cells may be CD4+ cells, CD8+ cells and subpopulations thereof, such as those defined by function, activation state, maturity, potential for differentiation, expansion, localization, persistence capacities, surface marker profile, cytokine secretion profile, and/or degree of differentiation.

In some embodiments, biological samples described herein include tissue, fluid, and other samples taken directly from the individual, as well as samples resulting from one or more processing steps, such as separation, centrifugation, genetic engineering (e.g., transduction with a viral vector encoding a recombinant chimeric receptor), washing, and/or incubation. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples (e.g., sample from a tissue or organ containing a tumor), including processed samples derived therefrom. In some embodiments, the biological sample is a biological fluid sample or a biological tissue sample. In some embodiments, the biological sample is a biological tissue sample. In some aspects, the biological sample from which the immune cells are derived or isolated is blood or a blood-derived sample, or is derived from an apheresis or leukapheresis product.

Exemplary biological samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Biological samples include, in the context of cell therapy (e.g., adoptive cell therapy) samples from autologous sources (i.e., obtained from or derived from the individual in need of cell therapy) and allogeneic sources (i.e., obtained from or derived from an individual or source other than the individual in need of cell therapy).

In some embodiments, the immune cells to be modified or a cell population comprising the immune cells to be modified are derived from a cell line (e.g., a T-cell line, a B-cell line, a NK-cell line, etc.). In some embodiments, the immune cells to be modified or a cell population comprising the immune cells to be modified are obtained from a xenogeneic source, such as from mouse, rat, non-human primate, or pig.

2. Cell Processing and Separation

In some embodiments, isolation of the immune cells to be modified includes one or more preparation and/or cell separation steps. The one or more cell separation steps can be non-affinity based separation or affinity based separation. As an example, non-affinity based separation can be centrifugation of a composition comprising the immune cells to be modified. In some embodiments, the non-affinity based separation methods include density-based cell separation methods, such as the preparation of white blood cells from peripheral blood by lysing the red blood cells and centrifugation through a Percoll or Ficoll gradient. Affinity-based separation methods can include contacting a composition comprising the immune cells to be modified with antibody coated beads. Antibody-coated beads contemplated herein include, but are not limited to, magnetic beads (e.g., Dynabeads® marketed by Life Technologies, Carlsbad, CA, MACS® microbeads marketed by Miltenyi Biotec Inc., Auburn, CA; or EasySep™ Direct RapidSpheres™ marketed by Stemcell Technologies, Vancouver, BC, Canada)

coated with an antibody that binds to a marker expressed on the surface of the immune cell to be modified. In some embodiments, specific subpopulations of T-cells, such as cells positive for or otherwise expressing high levels of one or more surface markers, e.g., CD4+, CD8+, etc., are isolated by positive or negative selection techniques. Positive selection can be based on a technique in which the target cells (e.g., immune cells to be modified) have bound to a reagent and are retained for further use. For example, T-cells that are CD3+ can be positively selected using magnetic beads conjugated to anti-CD3 antibodies (e.g., MACS® CD3 human microbeads). Negative selection can be based on a technique in which the targets cells (e.g., immune cells to be modified) that have not bound to a reagent are retained. For example, total human primary T-cells can be isolated from peripheral blood mononuclear cells (PMBCs) utilizing negative selection, wherein a cocktail of antibodies against surface markers CD14, CD15, CD16, CD19, CD34, CD36, CD56, CD123, and CD235a are incubated in a sample comprising the PBMCs before passing the sample by magnetic beads for removal of cells expressing those surface markers and retaining the remaining cells in the sample for subsequent processing. In some embodiments, the immune cells or a cell population comprising the immune cells to be modified are washed, centrifuged, and/or incubated in the presence of one or more reagents, for example, to remove unwanted components, enrich for desired components, lyse or remove cells sensitive to particular reagents. In some examples, the immune cells are separated based on one or more property, such as density, adherent properties, size, sensitivity, and/or resistance to particular components. Cell separation steps do not require 100% enrichment or removal of particular cells. In some embodiments, positive selection of or enrichment for immune cells of a particular type (e.g., CD4+ T-cells) refers to increasing the number or percentage of such cells. In some embodiments, removal, or depletion of cells of a particular type that are not of interest such as by negative selection, refers to decreasing the number or percentage of such cells.

In some embodiments, immune cells or a cell population comprising the immune cells are obtained from the circulating blood of an individual, e.g., by apheresis or leukapheresis. In some aspects, a sample comprising the immune cells to be modified contains lymphocytes, including T-cells, B-cells, and NK-cells, as well as monocytes, granulocytes, red blood cells, and/or platelets, and in some aspects contains cells other than red blood cells and platelets.

In some embodiments, the blood cells collected from the individual are washed such as to remove the plasma fraction and to place the cell population comprising the immune cells to be modified in an appropriate buffer or media for subsequent processing steps. In some embodiments, the cell population comprising the immune cells to be modified is washed with phosphate-buffered saline. In some embodiments, the wash solution lacks calcium and/or magnesium. In some aspects, a washing step is accomplished by a semi-automated "flow-through" centrifuge. In some aspects, a washing step is accomplished by tangential flow filtration. In some embodiments, the immune cells to be modified or cell population containing the immune cells to be modified are resuspended in a variety of suitable buffers after washing, such as, for example, calcium and/or magnesium-free phosphate-buffered saline. In some embodiments, components of a blood cell sample are removed and the immune cells to be modified or a cell population comprising the immune cells to be modified are directly resuspended in a suitable cell culture medium.

Representative methods for processing and/or separating immune cells, such as hematopoietic cells from samples containing a cell population containing said hematopoietic cells (e.g., samples comprising PBMCs), are described in Biological Example 2 and Biological Example 3 herein. Methods and techniques for processing and/or separating immune cells such as hematopoietic cells, multipotent stem cells, myeloid progenitor cells, lymphoid progenitor cells, T-cells, B-cells, and/or NK-cells are well known in the art. See for example, U.S. Patent Application No. 2017/0037369; U.S. Patent Application No. 2012/0148553; U.S. Pat. Nos. 6,461,645; 6,352,694; and 7,776,562.

3. Incubation and Treatment

Provided herein are methods for modulating the activity of an immune cell, such as the processed and/or separated immune cells described above, by contacting the immune cell with an effective amount of a Cbl-b inhibitor described herein. Also provided herein are modified immune cells produced by any of the methods described herein such as by culturing a cell population containing an immune cell (e.g., the processed and/or separated immune cells described above) in the presence of an effective amount of a Cbl-b inhibitor to modulate the activity of the immune cell and thereby produce the modified immune cell.

In some embodiments, the immune cells to be modified (e.g., the processed and/or separated immune cells described above) are incubated and/or cultured in a suitable culture medium prior to contacting said immune cells with a Cbl-b inhibitor provided herein. In some embodiments, the immune cells to be modified are incubated and/or cultured in a suitable culture medium simultaneously to contacting said immune cells with a Cbl-b inhibitor provided herein.

The processed and/or separated immune cells to be modified or cell population comprising the immune cells to be modified can be differentiated and/or expanded in vitro. In some embodiments, the immune cells to be modified are hematopoietic cells, multipotent stem cells, myeloid progenitor cells, lymphoid progenitor cells, T-cells, B-cells, and/or NK-cells. In some embodiments, the immune cell to be modified is incubated in a suitable cell culture medium comprising a Cbl-b inhibitor described herein before differentiation and/or expansion of the immune cell. In some embodiments, the immune cell to be modified is incubated in a suitable cell culture medium comprising a Cbl-b inhibitor described herein after differentiation and/or expansion of the immune cell. The immune cells become modified (i.e., modified immune cells) upon contact with a Cbl-b inhibitor provided herein in an effective amount to modulate the activity of said immune cells. In some embodiments, the immune cell to be modified is not differentiated and/or expanded in vitro and is therefore the same cell type as the modified immune cell that has been contacted with a Cbl-b inhibitor. For example, a T-cell can be incubated in a suitable medium comprising a Cbl-b inhibitor without differentiation of the T-cell. In other embodiments, the immune cell to be modified is differentiated and/or expanded in vitro and is therefore a different cell type than the modified immune cell that has been contacted with a Cbl-b inhibitor. For example, a hematopoietic cell can be incubated in a suitable medium comprising a Cbl-b inhibitor as well as other agents that drive differentiation of the hematopoietic cell into a mature hematopoietic cell. Accordingly, in some aspects of the embodiments herein, the modified immune cells are hematopoietic cells, multipotent stem cells, myeloid progenitor cells, lymphoid progenitor cells, T-cells, B-cells, and/or NK-cells. Methods for expansion and/or differentiation of immune cells are well known in the art. See, for example, International Patent Application No. WO 2017/037083.

An effective amount of a Cbl-b inhibitor is the amount or concentration of the Cbl-b inhibitor that is sufficient to modulate the activity of the immune cell as compared to a reference sample. The reference sample may be immune cells that have not been contacted with the Cbl-b inhibitor. In some embodiments, the concentration of a Cbl-b inhibitor added to a composition (e.g., cell culture medium) comprising the immune cells to be modified is from about 1 pM to about 100 µM, about 5 µM to about 100 µM, about 10 pM to about 100 µM, about 20 pM to about 100 µM, about 40 pM to about 100 µM, about 60 pM to about 100 µM, about 80 pM to about 100 µM, about 1 nM to about 100 µM, about 3 nM to about 100 µM, about 10 nM to about 100 µM, about 15 nM to about 100 µM, about 20 nM to about 100 µM, about 40 nM to about 100 µM, about 60 nM to about 100 µM, about 80 nM to about 100 µM, about 0.1 µM to about 100 µM, about 0.1 µM to about 90 µM, about 0.1 µM to about 80 µM, about 0.1 µM to about 70 µM, about 0.1 µM to about 60 µM, about 0.1 µM to about 50 µM, about 0.1 µM to about 40 µM, about 0.1 µM to about 30 µM, about 0.1 µM to about 20 µM, about 0.1 µM to about 10 µM, about 0.2 µM to about 10 µM, or about 0.3 µM to about 8 µM. In some embodiments, the concentration of a Cbl-b inhibitor added to a composition (e.g., cell culture medium) comprising the immune cells to be modified is about 1 µM, about 2 µM, about 3 µM, about 4 µM, about 5 µM, about 10 µM, about 20 µM, about 30 µM, about 40 µM, about 50 µM, about 60 µM, about 70 µM, about 80 µM, about 90 µM, about 1 nM, about 3 nM, about 5 nM, about 10 nM, about 20 nM, about 40 nM, about 50 nM, about 80 nM, about 0.1 µM, about 0.2 µM, about 0.3 µM, about 0.4 µM, about 0.5 µM, about 1 µM, about 5 µM, about 10 µM, about 15 µM, about 20 µM, about 25 µM, about 30 µM, about 40 µM, about 50 µM, about 60 µM, about 70 µM, about 80 µM, about 90 µM, or about 100 µM. In some embodiments, the concentration of a Cbl-b inhibitor added to a composition (e.g., cell culture medium) comprising the immune cells to be modified is about 0.3 µM, about 1 µM, or about 4 µM. In some embodiments, the concentration of a Cbl-b inhibitor added to a composition (e.g., cell culture medium) comprising the immune cells to be modified is about 1 µM or about 8 µM.

The effective amount of a Cbl-b inhibitor is in contact with the immune cells for a sufficient time to modulate the activity of the immune cell as compared to a reference sample. The reference sample may be immune cells that have not been contacted with the Cbl-b inhibitor but are incubated for the same length of time as the composition (e.g., cell culture medium) comprising the immune cells and the Cbl-b inhibitor. In some embodiments, the Cbl-b inhibitor is in contact and/or is incubated with the immune cells from about 1 minute to about 1 hour, about 5 minutes to about 1 hour, about 10 minutes to about 1 hour, about 15 minutes to about 1 hour, about 20 minutes to about 1 hour, about 30 minutes to about 1 hour, about 45 minutes to about 1 hour, about 1 hour to about 2 hours, about 1 hour to about 4 hours, about 1 hour to about 6 hours, about 1 hour to about 8 hours, about 1 hour to about 12 hours, about 1 hour to about 24 hours, about 2 hours to about 24 hours, about 6 hours to about 7 hours, about 6 hours to about 24 hours, about 8 hours to about 24 hours, about 10 hours to about 24 hours, about 15 hours to about 24 hours, about 20 hours to about 24 hours, about 12 hours to about 48 hours, about 24 hours to about 48 hours, or about 36 hours to about 48 hours. In some embodiments, the Cbl-b inhibitor is in contact and/or is incubated with the immune cells for about 1 minute, about 5 minutes, about 10 minutes, about 15 minutes, about 20 minutes, about 30 minutes, about 40 minutes, about 50 minutes, about 1 hour, about 2 hours, about 3 hours, about 4 hours, about 5 hours, about 6 hours, about 7 hours, about 8 hours, about 9 hours, about 10 hours, about 12 hours, about 14 hours, about 16 hours, about 18 hours, about 20 hours, about 22 hours, or about 24 hours. In some embodiments, the Cbl-b inhibitor is in contact and/or is incubated with the immune cells from about 1 day to about 7 days, about 2 days to about 7 days, about 3 days to about 7 days, about 4 days to about 7 days, about 5 days to about 7 days, or about 6 days to about 7 days. In some embodiments, the Cbl-b inhibitor is in contact and/or is incubated with the immune cells from about 7 days to about 14 days, about 14 days to about 21 days, or about 21 days to about 28 days. In some embodiments, the Cbl-b inhibitor is in contact and/or is incubated with the immune cells for about 1 day, about 2 days, about 3 days, about 4 days, about 5 days, about 6 days, about 7 days, about 8 days, about 9 days, about 10 days, about 11 days, about 12 days, about 13 days, or about 14 days.

In some embodiments, the immune cells or a cell population comprising the immune cells are incubated under a suitable condition to induce proliferation, expansion, activation, and/or survival of the immune cells. Suitable conditions during incubation include, but are not limited to, use of one or more of cell culture medium, temperature, incubation time, the presence of a stimulating agent (e.g., anti-CD3 and/or anti-CD28 antibody), and the presence of any other beneficial agents, such as growth factors, cytokines, chemokines, and/or recombinant soluble receptors.

In some embodiments, a suitable condition to induce proliferation, expansion, activation, and/or survival of the immune cells includes the provision of stimulating conditions comprising agents that are capable of activating the immune cell (e.g., NK-cell). For example, a suitable condition to induce proliferation, expansion, activation, and/or survival of a T-cell includes the provision of stimulating conditions comprising agents that are capable of activating intracellular signaling in the T-cell. Full activation of T-cells generally requires the recognition of antigen by the T-cell receptor, referred to herein as "TCR" (signal one) as well as recognition of costimulators such as CD28 (signal two). In some aspects, one or more agents turn on or initiate a TCR complex-mediated intracellular signaling cascade in a T-cell. For example, a first agent can bind to a component of the TCR complex in order to activate the T-cell and a second agent can bind to a costimulatory molecule on the surface of the T-cell to thereby stimulate the activated T-cell. In some embodiments, the first agent stimulated a TCR/CD3 complex-associated signal in the T-cell by specifically binding to CD3 (e.g., an anti-CD3 antibody). In a further embodiment, the co-stimulatory molecule on the surface of the T-cell may be CD28 and the second agent specifically binds to CD28 (e.g., anti-CD28 antibody). Such agents include, but are not limited to, antibodies, divalent antibody fragments, and binding molecules such as those specific for a TCR complex component (e.g., anti-CD3 antibody) and/or those specific for costimulatory receptor (e.g., anti-CD28 antibody). In some embodiments, an agent that specifically binds to CD3 is an anti-CD3 antibody, a divalent antibody fragment of an anti-CD3 antibody (e.g., (Fab)$_2$' fragment or a divalent scFv fragment), a monovalent antibody fragment of an anti-CD3 antibody (e.g., a Fab fragment, a Fv fragment, or a scFv fragment), or a CD3 binding molecule (e.g., an aptamer). In some embodiments, an agent that specifically binds to CD28 is an anti-CD28 antibody, a divalent antibody fragment of an anti-CD28 antibody (e.g., (Fab)₂' fragment or a divalent scFv fragment), a monovalent antibody fragment of an anti-CD28 antibody (e.g., a Fab fragment, a Fv fragment, or a scFv fragment), and a CD28 binding molecule (e.g., an aptamer). The one or more agents provided herein (e.g., anti-CD3 antibody and anti-CD28 antibody) for example, can be bound to a solid support such as a bead, or crosslinked with an anti-Fc antibody. In some embodiments, the expansion method step may further comprise the step of adding anti-CD3 antibody and/or anti-CD28 antibody to the culture medium. In some embodiments, the stimulating agents added to the cell culture medium include one or more cytokines such as, but not limited to one or more of IL-2, IL-7, IL-15, and IL-21. For example, IL-2 can be added at a concentration of at least about 10 units/mL to a cell culture medium comprising the immune cells and agents such as anti-CD3 antibodies and/or anti-CD28 antibodies.

In some embodiments, a suitable condition to induce proliferation, expansion, activation, and/or survival of a T-cell includes the provision of stimulating conditions or agents which are capable of activating intracellular signaling through the T-cell receptor (TCR) complex, and a Cbl-b inhibitor as described herein. In some embodiments, the immune cells or a cell population comprising the immune cells are incubated with a first agent that stimulates a TCR/CD3 complex-associated signal in the T-cell by specifically binding to CD3 (e.g., an anti-CD3 antibody). In a further embodiment, the immune cells or a cell population comprising the immune cells are incubated with a first agent that stimulates a TCR/CD3 complex-associated signal in the T-cell by specifically binding to CD3 (e.g., an anti-CD3 antibody), with a second agent that binds to the co-stimulatory molecule CD28 (e.g., an anti-CD28 antibody), and with a Cbl-b inhibitor at a concentration of about 1 µM to about 100 µM (e.g., about 0.3 µM, about 1 µM, or about 4 µM). In some embodiments, a suitable condition to induce proliferation, expansion, activation, and/or survival of a T-cell when in the presence of a Cbl-b inhibitor does not require stimulation through a co-stimulatory molecule (e.g., CD28). Contacting T-cells with a Cbl-b inhibitor or a composition thereof can bypass the need for co-stimulation required for T-cells to enter into an activated state. In certain embodiments, the immune cells or a cell population comprising the immune cells are incubated with a first agent that stimulates a TCR/CD3 complex-associated signal in the T-cell by specifically binding to CD3 (e.g., an anti-CD3 antibody) and with a Cbl-b inhibitor at a concentration of about 0.001 µM to about 1,000 µM, about 0.01 µM to about 100 µM, about 0.1 µM to about 10 µM, or about 0.1 µM to about 50 µM (e.g., about 1 µM or about 8 µM).

In some embodiments of the methods for modulating activity of an immune cell, the immune cell is a T-cell and modulating activity of the T-cell comprises increased T-cell activation and/or increased T-cell proliferation. T-cells contemplated in embodiments herein may be in a tolerant state even in the presence of an activating agent that binds to a component of the TCR complex, such as an anti-CD3 antibody, as well as in the presence of a stimulating agent that binds a co-stimulatory molecule, such as an anti-CD28 antibody. In some embodiments, the method of modulating activity of a T-cell comprises contacting the T-cell with an effective amount of a Cbl-b inhibitor or a composition thereof in the presence of an anti-CD3 antibody in combination with an anti-CD28 antibody. In some embodiments, the method of modulating activity of a T-cell comprises contacting the T-cell with an effective amount of a Cbl-b inhibitor or a composition thereof, wherein the T-cell previously has been in contact with an anti-CD3 antibody in combination with an anti-CD28 antibody. In some embodiments, stimulation via the co-stimulatory CD28 molecule is not required for modulating the activity of the T-cell (e.g., increasing T-cell activation and/or increasing T-cell proliferation). In some embodiments, the method of modulating activity of a T-cell comprises contacting the T-cell with an effective amount of a Cbl-b inhibitor or a composition thereof in the presence of an anti-CD3 antibody alone. In some embodiments, the method of modulating activity of a T-cell comprises contacting the T-cell with an effective amount of a Cbl-b inhibitor or a composition thereof, wherein the T-cell has previously been in contact with one or more agents that activate the T-cell (e.g., an anti-CD3 antibody), wherein said agents do not include an agent that stimulates the CD28 co-stimulatory molecule (e.g., an anti-CD28 antibody).

In some embodiments, the immune cell is a T-cell, and modulating activity of the T-cell comprises enhanced T-cell activation and/or enhanced T-cell proliferation. For example, T-cells contemplated in embodiments herein may be in an activated state such as when in the presence of agents that activate the T-cells (e.g., anti-CD3 antibody), and in some further embodiments, in the presence of agents that stimulate the T-cells (e.g., anti-CD28 antibody). Contacting T-cells with a Cbl-b inhibitor or composition thereof can lower the threshold required for activation and therefore enhance activation and/or proliferation of T-cells that are in the presence of an activating agent (e.g., an anti-CD3 antibody) and in some further embodiments, a stimulating agent (e.g., an anti-CD28 antibody). In some embodiments, the method of modulating activity of a T-cell comprises contacting the T-cell with an effective amount of a Cbl-b inhibitor or a composition thereof in the presence of an anti-CD3 antibody in combination with an anti-CD28 antibody. In some embodiments, the method of modulating activity of a T-cell comprises contacting the T-cell with an effective amount of a Cbl-b inhibitor or a composition thereof, wherein the T-cell has previously been in contact with an anti-CD3 antibody in combination with an anti-CD28 antibody. In some embodiments, stimulation via the co-stimulatory CD28 molecule is not required for modulating the activity of the T-cell (e.g., enhancing T-cell activation and/or enhancing T-cell proliferation). In some embodiments, the method of modulating activity of a T-cell comprises contacting the T-cell with an effective amount of a Cbl-b inhibitor or a composition thereof in the presence of an anti-CD3 antibody alone. In some embodiments, the method of modulating activity of a T-cell comprises contacting the T-cell with an effective amount of a Cbl-b inhibitor or a composition thereof, wherein the T-cell has previously been in contact with one or more agents that activate the T-cell (e.g., anti-CD3 antibody).

In some embodiments, the immune cell is a T-cell and modulating activity of the T-cell comprises decreased T-cell dysfunction including decreased T-cell exhaustion, decreased T-cell tolerance, and/or decreased T-cell anergy. General principles of T-cell dysfunction are well known in the art (see e.g., Schietinger et al., Trends Immunol., 35: 51-60, 2014). Immune tolerance is a process that is part of the normal function of the immune system. Antigen-specific immune tolerance is characterized by a decrease in responsiveness to an antigen, which is induced by previous exposure to that antigen. When specific lymphocytes (e.g., T-cells) encounter antigens, the lymphocytes may be activated, leading to an antigen-specific immune response, or the lymphocytes (e.g., T-cells) may be inactivated or eliminated, leading instead to antigen-specific immune tolerance. In some aspects, tolerance can be caused by clonal anergy, peripheral clonal deletion, suppression of T-cells, and/or other forms of antigen-specific tolerance. In some embodiments, tolerance may result from or be characterized by the induction of anergy. In some aspects, anergy can result from exposure of T-cells to an antigen in the absence of costimulation. Prolonged antigen recognition by the TCR alone, in the absence of the co-stimulatory signal, may lead to anergy (i.e., functional unresponsiveness). Anergic T-cells may be refractory to subsequent antigenic challenge and may be capable of suppressing other immune responses. Generally, in the natural setting, tolerance is involved in non-reactivity or nonproductive reactivity to self-antigens. In some cases, however, tolerance to a "non-self" antigen can be induced. Thus, in some aspects, the same mechanisms by which mature T-cells that recognize self-antigens in peripheral tissues become incapable of subsequently responding to these antigens also may regulate unresponsiveness to foreign or "non-self" antigens such as those expressed by cancer cells. Accordingly, T-cells contemplated in embodiments herein may be in a tolerant state even in the presence of stimulatory agents such as agents that bind to a co-stimulatory molecule such as CD28. Contacting T-cells with a Cbl-b inhibitor provided herein or a composition thereof can bypass aspects of T-cell dysfunction such as T-cell tolerance, T-cell anergy, and/or T-cell exhaustion. In some embodiments, the method of modulating activity of a T-cell (e.g., decreasing T-cell tolerance, decreasing T-cell anergy, and/or decreasing T-cell exhaustion) comprises contacting the T-cell with an effective amount of a Cbl-b inhibitor or a composition thereof. In some embodiments of the methods herein, modulating activity of a T-cell (e.g., decreasing T-cell tolerance, decreasing T-cell anergy, and/or decreasing T-cell exhaustion) comprises contacting the T-cell with an effective amount of a Cbl-b inhibitor or a composition thereof in the presence of an anti-CD3 antibody in combination with an anti-CD28 antibody. In some embodiments of the methods herein, the method of modulating activity of a T-cell (e.g., decreasing T-cell tolerance, decreasing T-cell anergy, and/or decreasing T-cell exhaustion) comprises contacting the T-cell with an effective amount of a Cbl-b inhibitor or a composition thereof, wherein the T-cell previously has been in contact with an anti-CD3 antibody in combination with an anti-CD28 antibody. In some embodiments, stimulation via the co-stimulatory CD28 molecule is not required for modulating the activity of the T-cell (e.g., decreasing T-cell tolerance, decreasing T-cell anergy, and/or decreasing T-cell exhaustion). In some embodiments of the methods herein, the method of modulating activity of a T-cell (e.g., decreasing T-cell tolerance, decreasing T-cell anergy, and/or decreasing T-cell exhaustion) comprises contacting the T-cell with an effective amount of a Cbl-b inhibitor or a composition thereof in the presence of an anti-CD3 antibody alone. In some embodiments, the method of modulating activity of a T-cell (e.g., decreasing T-cell tolerance, decreasing T-cell anergy, and/or decreasing T-cell exhaustion) comprises contacting the T-cell with an effective amount of a Cbl-b inhibitor or a composition thereof, wherein the T-cell has previously been in contact with one or more agents that activate the T-cell, such as an anti-CD3 antibody alone.

T-cell activation and T-cell tolerance are tightly controlled processes regulating the immune response. Accordingly, provided herein are methods of modulating activity of the T-cell, wherein modulating activity of the T-cell comprises increased T-cell activation, increased T-cell proliferation, decreased T-cell exhaustion, and/or decreased T-cell tolerance. In some embodiments, the method of modulating activity of a T-cell (e.g., increased T-cell activation, increased T-cell proliferation, decreased T-cell exhaustion, and/or decreased T-cell tolerance) comprises contacting the T-cell with an effective amount of a Cbl-b inhibitor or a composition thereof. In some embodiments of the methods herein, modulating activity of a T-cell (e.g., increasing T-cell activation, increasing T-cell proliferation, decreasing T-cell exhaustion, and/or decreasing T-cell tolerance) comprises contacting the T-cell with an effective amount of a Cbl-b inhibitor or a composition thereof in the presence of an anti-CD3 antibody in combination with an anti-CD28 antibody. In some embodiments of the methods herein, the method of modulating activity of a T-cell (e.g., increasing T-cell activation, increasing T-cell proliferation, decreasing T-cell exhaustion, and/or decreasing T-cell tolerance) comprises contacting the T-cell with an effective amount of a Cbl-b inhibitor or a composition thereof, wherein the T-cell previously has been in contact with an anti-CD3 antibody in combination with an anti-CD28 antibody. In some embodiments, stimulation via the co-stimulatory CD28 molecule is not required for modulating the activity of the T-cell (e.g., increasing T-cell activation, increasing T-cell proliferation, decreasing T-cell exhaustion, and/or decreasing T-cell tolerance). In some embodiments of the methods herein, the method of modulating activity of a T-cell (e.g., increasing T-cell activation, increasing T-cell proliferation, decreasing T-cell exhaustion, and/or decreasing T-cell tolerance) comprises contacting the T-cell with an effective amount of a Cbl-b inhibitor provided herein or a composition thereof in the presence of an anti-CD3 antibody alone. In some embodiments, the method of modulating activity of a T-cell (e.g., increasing T-cell activation, increasing T-cell proliferation, decreasing T-cell exhaustion, and/or decreasing T-cell tolerance) comprises contacting the T-cell with an effective amount of a Cbl-b inhibitor or a composition thereof, wherein the T-cell has previously been in contact with one or more agents that activate the T-cell (e.g., an anti-CD3 antibody).

In some embodiments of the methods herein, increased T-cell activation comprises increased production of one or more cytokines from T-cells or surrounding immune cells in the activated T-cell microenvironment (e.g., myeloid cells). In some embodiments, the one or more cytokines include, but are not limited to IFN-γ, IL-1β, IL-2, IL-4, IL-5, IL-6, IL-13, IL-18, TNFα, and GM-CSF. In some embodiments, the cytokine is one or more of IL-2, IFN-γ, TNFα, and GM-CSF. In some embodiments, the cytokine is a chemokine. In some embodiments, the one or more chemokines include, but are not limited to IP-10, Eotaxin, GRO alpha, RANTES, MIP-1α, MIP-1β, MIP-2, MCP-1, and MCP-3. Increased expression of cytokines can be measured by ELISA.

In some embodiments of the methods herein, increased T-cell activation comprises increased cell surface expression of one or more T-cell activation markers. In some embodiments, the one or more T-cell activation markers include, but are not limited to CD25, CD44, CD62L, CD69, CD152 (CTLA4), CD154, CD137, and CD279. In some embodiments, the T-cell activation marker is one or more of CD25, CD69, and CTLA4. Increased expression of cell surface markers can be measured by FACS.

Methods for experimentally determining increased T-cell activation, increased T-cell proliferation, decreased T-cell exhaustion, and/or decreased T-cell tolerance are well known in the art. In some embodiments, representative methods of determining T-cell activation can be found in Biological Example 2 provided herein. In some embodiments, representative in vitro and in vivo methods of determining increased T-cell activation, increased T-cell proliferation, decreased T-cell exhaustion, and/or decreased T-cell tolerance can be found in Biological Example 3 provided herein.

In some embodiments of the methods for modulating activity of an immune cell, the immune cell is a B-cell and modulating activity of the B-cell comprises increased B-cell activation. In some embodiments, increased B-cell activation comprises increased cell surface expression of one or more B-cell activation markers. In some embodiments, the one or more B-cell activation markers include, but are not limited to CD69, CD86, and MHIC class II (e.g., HLA-DR). In some embodiments, the B-cell activation marker is CD69. Increased expression of cell surface markers can be measured by FACS. In some embodiments, increased B-cell activation comprises increased activation of proteins in signaling pathways such as those mediated by ERK, INK, and Syk. Increased activation of said proteins can be detected by measurement of levels of phosphorylation on the proteins using reagents such as anti-phospho antibodies available in the art.

In some embodiments of the methods for modulating activity of an immune cell, the immune cell is a NK-cell and modulating activity of the NK-cell comprises increased NK-cell activation. In some embodiments, increased NK-cell activation comprises secretion of one or more cytokines. In some embodiments, the one or more cytokines include, but are not limited to IFN-7, TNFα, and MIP-1β. Increased expression of cytokines can be measured by ELISA. In some embodiments, increased NK-cell activation comprises increased cell surface expression of one or more NK-cell activation markers. In some embodiments, the one or more NK-cell activation markers include, but are not limited to CD69, and CD107a. Increased expression of cell surface markers can be measured by FACS. In some embodiments, increased NK-cell activation comprises increased killing of target cells such as tumor cells, including primary tumor cells, and cell line derived tumor cells such as the K562 cell line.

Methods for experimentally determining increased B-cell activation and NK-cell activation are well known in the art (see e.g., Fauriat et al., Blood. 115: 2167-76, 2010; Beano et al., J. Transl. Med., 6:25 2008; Claus et al., J. Immunol. Methods, 341: 154-64, 2009; and Fujisaki et al., Cancer Res. 69: 4010-4017, 2009). In some embodiments, representative methods of determining B-cell activation can be found in Biological Example 3 provided herein. In some embodiments, representative methods of determining NK-cell activation can be found in Biological Example 3 provided herein.

Modulation of activity of an immune cell, such as a T-cell, a B-cell or a NK-cell can be measured by determining a baseline value for a parameter of interest (e.g., cytokine secretion). For example, T-cell activation, such as in a sample obtained from in vitro experiments of cells contacted with a Cbl-b inhibitor, can be measured before contacting or administering said Cbl-b inhibitor to determine a baseline value. A reference value then is obtained for T-cell activation after contacting or administering said Cbl-b inhibitor. The reference value is compared to the baseline value in order to determine the amount of T-cell activation due to contact or administration of the Cbl-b inhibitor or composition thereof.

For example, in some embodiments, immune cell (e.g., T-cell) activation is increased by at least 0.1-fold in a sample as compared to a baseline value, wherein the baseline value is obtained before contacting the immune cell (e.g., T-cell) with a Cbl-b inhibitor or a composition thereof. In some embodiments, immune cell (e.g., T-cell) activation is increased by at least about 0.1-fold, about 0.2-fold, about 0.3-fold, about 0.4-fold, about 0.5-fold, about 0.6-fold, about 0.7-fold, about 0.8-fold, about 0.9-fold, about 1-fold, about 2-fold, about 4-fold, about 6-fold, about 8-fold, about 10-fold, about 20-fold, about 30-fold, about 40-fold, about 50-fold, about 75-fold, or about 100-fold over a baseline value (e.g., about 0.1-fold to about 100-fold, or about 1-fold to about 100-fold). Immune cell activation can be assessed by measuring biological markers of activation such as increased cytokine secretion, increased cell surface expression of activation markers (e.g., cell surface markers), or increased phosphorylation of proteins in a downstream signaling pathway. The fold over baseline value that indicates immune cell activation can be determined for the parameter being tested and the conditions under which the immune cells are treated. For example, for measuring T-cell activation, a baseline value can be obtained from T-cells stimulated with anti-CD3 antibody in combination with anti-CD28 antibody, wherein the cells are not incubated with a Cbl-b inhibitor. A reference value is then obtained from T-cells stimulated with anti-CD3 antibody in combination with anti-CD28 antibody, wherein the T-cells have been or are in contact with a Cbl-b inhibitor. A positive response for immune cell activation can then be determined by the obtained reference value. Similar reference value measurements can be obtained and compared to a baseline value for assessing T-cell activation, T-cell proliferation, T-cell exhaustion, T-cell tolerance, B-cell activation and/or NK-cell activation. Measurements for these parameters can be obtained utilizing techniques well known in the art, as well as the techniques provided in Biological Examples 2 and 3.

The terms "baseline" or "baseline value" as used herein can refer to a measurement or characterization before administration of a therapeutic agent as disclosed herein (e.g., a composition comprising a Cbl-b inhibitor as described herein) or at the beginning of administration of the therapeutic agent. The baseline value can be compared to a reference value in order to determine the increase or decrease of an immune cell function (e.g., increasing T-cell activation, increasing T-cell proliferation, decreasing T-cell exhaustion, and/or decreasing T-cell tolerance). The terms "reference" or "reference value" as used herein can refer to a measurement or characterization after administration of the therapeutic agent as disclosed herein (e.g., a composition comprising a Cbl-b inhibitor as described herein). The reference value can be measured one or more times during an experimental time course, dosage regimen, or treatment cycle, or at the completion of the experimental time course, dosage regimen, or treatment cycle. A "reference value" can be an absolute value, a relative value, a value that has an upper and/or lower limit, a range of values, an average value, a median value, a mean value, or a value as compared to a baseline value. Similarly, a "baseline value" can be an absolute value, a relative value, a value that has an upper and/or lower limit, a range of values, an average value, a median value, a mean value, or a value as compared to a reference value. The reference value and/or baseline value can be obtained from one sample (e.g., one sample obtained from an individual), from two different samples (e.g., a sample obtained from two different individuals) or from a group of samples (e.g., samples obtained from a group of two, three, four, five, or more individuals).

In some embodiments, a positive response for T-cell activation as measured by cytokine secretion (e.g., IL-2 secretion) by T-cells stimulated with anti-CD3 antibody in combination with anti-CD28 antibody in the presence of a Cbl-b inhibitor is at least 2.5-fold over the baseline value for cytokine secretion (e.g., IL-2 secretion) obtained from T-cells stimulated with anti-CD3 antibody in combination with anti-CD28 antibody in the absence of a Cbl-b inhibitor. In some embodiments, a positive response for T-cell activation as measured by surface marker expression (e.g., CD25 surface marker staining) by T-cells stimulated with anti-CD3 antibody in combination with anti-CD28 antibody in the presence of a Cbl-b inhibitor is at least 1.3-fold over the baseline value for surface marker expression (e.g., CD25 surface marker staining) obtained from T-cells stimulated with anti-CD3 antibody in combination with anti-CD28 antibody in the absence of a Cbl-b inhibitor. In some embodiments, a baseline value can be obtained from T-cells stimulated with anti-CD3 antibody alone, wherein the cells are not incubated with a Cbl-b inhibitor. In some embodiments, a positive response for T-cell activation as measured by cytokine secretion (e.g., IL-2 secretion) by T-cells stimulated with anti-CD3 antibody alone in the presence of a Cbl-b inhibitor is at least 0.1-fold over the baseline value for cytokine secretion (e.g., IL-2 secretion) obtained from T-cells stimulated with anti-CD3 antibody alone in the absence of a Cbl-b inhibitor. In some embodiments, a positive response for T-cell activation as measured by surface marker expression (e.g., CD25 surface marker staining) by T-cells stimulated with anti-CD3 antibody alone in the presence of a Cbl-b inhibitor is at least 0.6-fold over the baseline value for surface marker expression (e.g., CD25 surface marker staining) obtained from T-cells stimulated with anti-CD3 antibody alone in the absence of a Cbl-b inhibitor.

In some aspects, provided herein are methods of producing a modified immune cell, comprising culturing a cell population containing an immune cell in the presence of an effective amount of a Cbl-b inhibitor provided herein or a composition thereof to modulate the activity of the immune cell, thereby producing the modified immune cell. In some embodiments, the immune cell is a T-cell, a B-cell, or a natural killer (NK) cell.

In some embodiments of the methods for producing a modified immune cell, the immune cell that is to be modified is a cell selected from the group consisting of a hematopoietic cell, a multipotent stem cell, a myeloid progenitor cell, a lymphoid progenitor cell, a T-cell, a B-cell, and a NK-cell. In some embodiments, the method further comprises culturing the immune cell with stimulating agents such as cytokines or antibodies that bind to activating proteins expressed by the immune cell (e.g., an anti-CD3 antibody and/or an anti-CD28 antibody). In some embodiments, the immune cell that is to be modified is in a cell population containing the immune cell, wherein the cell population is obtained as a sample from an individual. In some embodiments, the immune cell that is to be modified is in a cell population containing the immune cell, wherein the cell population is obtained from culturing a biological sample (e.g., blood sample, bone marrow sample, etc.) from an individual. In some embodiments, the immune cell is modified by contacting the cell population containing the immune cell with a Cbl-b inhibitor or composition thereof thereby producing a modified immune cell. In some embodiments, the modified immune cell is a cell selected from the group consisting of a hematopoietic cell, a multipotent stem cell, a myeloid progenitor cell, a lymphoid progenitor cell, a T-cell, a B-cell, and a NK-cell. In some embodiments, the immune cell is the same cell type as the modified immune cell. For example, the immune cell can be an inactive T-cell and the modified immune cell can be an activated T-cell. In some embodiments, the immune cell is a different cell type than the modified immune cell. For example, the immune cell can be a hematopoietic stem cell and the modified immune cell can be an NK-cell that has differentiated from the hematopoietic stem cell. In some embodiments of the method of producing the modified immune cell, the method further comprises recovering the modified immune cell. In some embodiments, the cell population containing the immune cell, the immune cell or the modified immune cell is from an individual (e.g., a human). In some embodiments, the immune cell or modified immune cell is a human immune cell or human modified immune cell, respectively.

Further provided herein are modified immune cells produced by any of the methods described herein such as culturing a cell population containing an immune cell in the presence of an effective amount of a Cbl-b inhibitor to modulate the activity of the immune cell and thereby produce the modified immune cell.

In some embodiments, the Cbl-b inhibitors provided herein are cell membrane permeable. Accordingly, in some embodiments, a modified immune cell provided herein can comprise a Cbl-b inhibitor described herein such as in the cytoplasm of the modified immune cell.

In some aspects, provided herein is an isolated modified immune cell, wherein the modified immune cell has been contacted or is in contact with a Cbl-b inhibitor described herein or a composition thereof. In some embodiments, the modified immune cell is a T-cell, a B-cell, or a natural killer (NK) cell. In some embodiments, the modified immune cell is a hematopoietic cell, a multipotent stem cell, a myeloid progenitor cell, a lymphoid progenitor cell, a T-cell, a B-cell, or a NK-cell.

In some embodiments of the isolated modified immune cell, the modified immune cell is a T-cell, and the T-cell exhibits increased T-cell activation, increased T-cell proliferation, decreased T-cell exhaustion, and/or decreased T-cell tolerance. In some embodiments, increased T-cell activation comprises increased production of one or more cytokines from T-cells or surrounding immune cells in the activated T-cell microenvironment (e.g., myeloid cells). In some embodiments, the one or more cytokines include, but are not limited to IFN-γ, IL-1β, IL-2, IL-4, IL-5, IL-6, IL-13, IL-18, TNFα, and GM-CSF. In some embodiments, the one or more cytokines is one or more selected from the group consisting of IL-2, IFN-γ, TNFα, and GM-CSF. In some embodiments, the cytokine is a chemokine. In some embodiments, the one or more chemokines include, but are not limited to IP-10, Eotaxin, GRO alpha, RANTES, MIP-1α, MIP-1β, MIP-2, MCP-1, and MCP-3. In some embodiments, increased T-cell activation comprises increased cell surface expression of one or more T-cell activation markers. In some embodiments, the one or more T-cell activation markers include, but are not limited to CD25, CD44, CD62L, CD69, CD152 (CTLA4), CD154, CD137, and CD279. In some embodiments, the one or more T-cell activation markers include, but are not limited to CD25, CD69, and CTLA4. In some embodiments, the T-cell activation markers are CD25 and/or CD69. In some embodiments, the T-cell has been or is in contact with an anti-CD3 antibody. In some embodiments, the T-cell has been or is in contact with an anti-CD3 antibody in combination with an anti-CD28 antibody.

In some embodiments of the isolated modified immune cell, the modified immune cell is a NK-cell, and the NK-cell exhibits increased NK-cell activation. In some embodiments, increased NK-cell activation comprises increased secretion of one or more cytokines (e.g., IFN-γ, TNFα, and/or MIP-1β). In some embodiments, increased NK-cell activation comprises increased cell surface expression of one or more NK-cell activation markers (e.g., CD69 and/or CD107a).

In some embodiments of the isolated modified immune cell, the modified immune cell is a B-cell, and the B-cell exhibits increased B-cell activation. In some embodiments, increased B-cell activation comprises increased cell surface expression of one or more B-cell activation markers (e.g., CD69, CD86, and/or HLA-DR).

In some of any embodiments of the methods or modified immune cells provided herein, the immune cell or modified immune cell is a mammalian cell (e.g., human cell). In some embodiments, the immune cell or modified immune cell is a human cell.

In some aspects, incubation is carried out in accordance with techniques such as those described in U.S. Pat. No. 6,040,177; Klebanoff et al., J Immunother., 35: 651-660, 2012; Terakura et al., Blood, 119: 72-82, 2012; and Wang et al., J Immunother., 35:689-701, 2012.

The immune cells to be modified or modified immune cells provided herein can be engineered to express a recombinant chimeric receptor such as a chimeric antigen receptor (CAR). In some embodiments, the CAR comprises from its N terminus to C terminus: an extracellular ligand-binding domain, a transmembrane domain, an intracellular costimulatory domain, and an activating cytoplasmic signaling domain. In some embodiments, the CAR comprises from its N terminus to C terminus: an extracellular ligand-binding domain, a transmembrane domain, and an activating cytoplasmic signaling domain. The immune cells can be engineered to express the recombinant chimeric receptor (e.g., CAR) before, during, or after contact with a Cbl-b inhibitor provided herein. In some embodiments, an immune cell to be modified is a T-cell (e.g., a $CD4^+$ T-cell or a CD8+ T-cell). In a further embodiment, the T-cell comprises a recombinant chimeric receptor such as a CAR. In some embodiments, the modified immune cell is a modified T-cell (e.g., a CD4+ T-cell or a CD8+ T-cell). In a further embodiment, the modified T-cell comprises a recombinant chimeric receptor such as a CAR. Methods for producing immune cells expressing recombinant chimeric receptors are well known in the art such as by the introduction of a nucleic acid encoding the recombinant chimeric receptor (e.g., CAR) to an immune cell (e.g., T-cell) via a vector (e.g., viral vector). See, for example, see International Patent Application No. WO 2017/096329 and U.S. Publication No. US 2017/0204372.

In particular, the present disclosure provides methods of producing an expanded population of lymphocytes, the method comprising: (a) obtaining a biological sample comprising lymphocytes from an individual with cancer, wherein the individual has received or is receiving an effective amount of a Cbl-b inhibitor as a monotherapy or as part of a combination therapy, and (b) culturing the lymphocytes in cell culture medium comprising at least one T-cell growth factor to produce an expanded population of lymphocytes. In some embodiments, the lymphocytes are tumor infiltrating lymphocytes (TILs). In some embodiments, the lymphocytes are TILs that have been or are isolated from a tumor of a mammalian subject with cancer. In other embodiments, the lymphocytes are peripheral blood mononuclear cells (PBMCs). In some embodiments, the at least one T-cell growth factor comprises one or more of the group consisting of IL-2, IL-7, IL-15, and IL-21, optionally wherein the at least one T-cell growth factor comprises IL-2. In some embodiments, the cell culture medium further comprises an anti-CD3 antibody, or both an anti-CD3 antibody and an anti-CD28 antibody. In some embodiments, the cell culture medium further comprises the Cbl-b inhibitor. In some embodiments, the cell culture medium further comprises irradiated feeder cells. In some embodiments, the individual is a human patient. Also provided herein are compositions comprising the expanded population of TILs produced by the aforementioned methods, and a physiologically acceptable buffer.

In some embodiments, methods for isolation and processing of immune cells to be modified or which have been modified (i.e., modified immune cells) include steps for freezing (e.g., cryopreserving) the cells, either before or after isolation, incubation (e.g., incubation with a Cbl-b inhibitor), and/or engineering (e.g., introduction of a nucleic acid encoding a recombinant chimeric receptor to the immune cell). A variety of freezing solutions and parameters known in the art may be used.

B. Adoptive Cell Therapy

The modified immune cells, such as an expanded population of lymphocytes or compositions thereof produced by the methods described herein, can be used as a therapeutic agent in methods of treatment of an individual in need thereof, such as an individual having cancer. Such methods of treatment include adoptive cell therapy. In some embodiments, the method of treatment includes isolating cells from an individual, preparing, processing, culturing, and/or engineering them, as described herein, and re-introducing them into the same individual, before or after cryopreservation. In some embodiments, the method of treatment includes isolating cells from an individual, preparing, processing, culturing, and/or engineering them, as described herein, and re-introducing them into a different individual, before or after cryopreservation.

Accordingly, in some aspects, provided herein is a method of modulating the immune response in an individual, the method comprising administering an effective amount of a modified immune cell described herein or a composition thereof to an individual in need thereof (e.g., an individual with a T-cell dysfunction disorder). In some embodiments, the individual has a cancer. In some embodiments, provided herein is a method of treating a cancer responsive to inhibition of Cbl-b activity, the method comprising administering an effective amount of a modified immune cell described herein or a composition thereof to an individual having the cancer responsive to inhibition of Cbl-b activity. In some embodiments, provided herein is a method of inhibiting abnormal cell proliferation, the method comprising administering an effective amount of a modified immune cell described herein or a composition thereof to an individual in need thereof. The term "abnormal cell proliferation" as used herein includes hyperplasia or cancer cell proliferation. The cancer cell may be derived from a hematologic cancer, such as lymphoma, a leukemia, or a myeloma. In other embodiments, the cancer cell may be derived from a non-hematologic cancer, such as a sarcoma, a carcinoma, or a melanoma.

In certain embodiments, an individual in need of treatment, such as an individual having cancer or a T-cell dysfunction disorder, is administered a composition comprising the modified immune cells provided herein at a range of about one million to about 100 billion cells, such as, e.g., 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges.

The modified immune cells and compositions thereof are administered using standard administration techniques, formulations, and/or devices. Provided are formulations and devices, such as syringes and vials, for storage and administration of the compositions. Formulations or pharmaceutical compositions comprising the modified immune cells include those for intravenous, intraperitoneal, subcutaneous, or intramuscular administration. In some embodiments, the modified immune cells are administered parenterally. The term "parenteral," as used herein, includes but is not limited to intravenous, intramuscular, subcutaneous, and intraperitoneal administration. In some embodiments, the cell populations are administered to a subject using peripheral systemic delivery by intravenous, intraperitoneal, or subcutaneous injections. Compositions of the modified immune cells can be provided as sterile liquid preparations, e.g., isotonic aqueous solutions, suspensions, emulsions, dispersions, or viscous compositions, which may in some aspects be buffered to a selected pH. Viscous compositions can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, and liquid polyethylene glycol) and suitable mixtures thereof. Sterile injectable solutions can be prepared by incorporating the modified immune cells in a solvent, such as in admixture with a suitable carrier, diluent, or excipient such as sterile water, physiological saline, glucose, dextrose, or the like.

In some embodiments, the modified immune cells are co-administered with one or more additional therapeutic agents or in connection with another therapeutic intervention, either simultaneously or sequentially in any order. For instance, in some therapeutic regimens of the present disclosure, both the modified immune cells and a Cbl-b inhibitor are administered to a mammalian subject in need thereof, wherein the Cbl-b inhibitor is a compound of Formula (I), (I-a), (I-A)-(I-J), (II-A)-(II-H), (II-A-1)-(II-H-1), (III-A)-(III-H), (III-A-1)-(III-H-1), (IV-A)-(IV-J), or (IV-C-1)-(IV-J-1), or any variation thereof. Thus, in some embodiments the therapeutic regimens comprise both adoptive cell therapy and chemotherapy.

After the modified immune cells are administered to an individual (e.g., a human), the biological activity of the modified immune cell populations can be measured by methods known in the art. Parameters to assess include specific binding of modified immune cell or other immune cell to antigen, in vivo (e.g., by imaging) or ex vivo (e.g., by ELISA or flow cytometry). In some embodiments, the ability of modified immune cells to destroy target cells can be measured using a cytotoxicity assay (see, e.g., Kochenderfer et al., J. Immunotherapy, 32: 689-702, 2009; and Herman et al., J. Immunological Methods, 285: 25-40, 2004). In some embodiments, the biological activity of the modified immune cells also can be measured by assaying expression and/or secretion of certain cytokines, such as IL-2 and IFNγ.

C. Administration of Cbl-b Inhibitor

In some aspects, a Cbl-b inhibitor or composition thereof can be administered directly to an individual to modulate an immune response, treat a disease or condition (e.g., cancer and/or abnormal cell proliferation) and/or inhibit Cbl-b activity in the individual. The Cbl-b inhibitor may be a compound of Table 1, a tautomer thereof, stereoisomer thereof, or a pharmaceutically acceptable salt thereof.

In some embodiments, provided herein is a method of modulating the immune response, the method comprising administering an effective amount of a Cbl-b inhibitor provided herein or a composition thereof to an individual to modulate the immune response in the individual. In some embodiments, the individual has a cancer such as a hematologic cancer or non-hematological cancer described herein.

In some embodiments, provided herein is a method of treating cancer responsive to inhibition of Cbl-b activity, the method comprising administering an effective amount of a Cbl-b inhibitor provided herein or a composition thereof to an individual to treat the cancer responsive to inhibition of Cbl-b activity. In some embodiments, the cancer is a hematologic cancer or non-hematological cancer such as one described herein.

In some embodiments, provided herein is a method of inhibiting abnormal cell proliferation (e.g., hyperplasia), the method comprising administering an effective amount of a Cbl-b inhibitor provided herein or a composition thereof to an individual to inhibit abnormal cell proliferation in the individual.

In some embodiments, provided herein is a method of inhibiting Cbl-b activity, the method comprising administering an effective amount of a Cbl-b inhibitor provided herein or a composition thereof to an individual to inhibit Cbl-b activity in the individual.

In some embodiments, such as in the modulation of an immune response in an individual in need thereof (e.g., an individual with a T-cell dysfunction disorder), treatment of a disease or condition in an individual (e.g., an individual cancer and/or abnormal cell proliferation) and/or inhibition of Cbl-b activity in an individual, the appropriate dosage of an active agent, will depend on the type of condition, disease, or disorder to be treated, as defined above, the severity and course of the condition, disease, or disorder, whether the agent is administered for preventive or therapeutic purposes, previous therapy, the subject's clinical history and response to the Cbl-b inhibitor, and the discretion of the attending physician.

The Cbl-b inhibitor or composition thereof is suitably administered to the individual at one time or over a series of treatments. In some embodiments, the treatment includes multiple administrations of the Cbl-b inhibitor or composition thereof, wherein the interval between administrations may vary. For example, the interval between the first administration and the second administration is about one month, and the intervals between the subsequent administrations are about three months. In some embodiments, the Cbl-b inhibitor is administered at a flat dose. In some embodiments, the Cbl-b inhibitor is administered to an individual at a fixed dose based on the individual's weight (e.g., mg/kg).

In some aspects of the present disclosure, the cancer is a hematologic cancer. For example, the hematologic cancer may be a lymphoma, a leukemia, or a myeloma. In other aspects of the present disclosure, the cancer is a non-hematologic cancer. In particular, the non-hematologic cancer may be a carcinoma, a sarcoma, or a melanoma.

In some embodiments, the Cbl-b inhibitor is co-administered with one or more additional therapeutic agents or in connection with another therapeutic intervention, either simultaneously or sequentially in any order. For instance, in some therapeutic regimens of the present disclosure, both the Cbl-b inhibitor and modified immune cells are administered to a mammalian subject in need thereof, wherein the Cbl-b inhibitor is a compound of Formula (I), (I-a), (I-A)-(I-J), (II-A)-(II-H), (II-A-1)-(II-H-1), (III-A)-(III-H), (III-A-1)-(III-H-1), (IV-A)-(IV-J), or (IV-C-1)-(IV-J-1), or any variation thereof. The Cbl-b inhibitor may be a compound of Table 1, a tautomer thereof, stereoisomer thereof, or a pharmaceutically acceptable salt thereof. Thus, in some embodiments, the therapeutic regimens comprise both adoptive cell therapy and chemotherapy.

In some embodiments, the effectiveness of Cbl-b inhibitor administration in the methods herein (e.g., method of modulating an immune response in an individual) can be assessed by measuring the biological activity of immune cells present in a sample (e.g., blood sample) isolated from the treated individual. For example, the ability of immune cells isolated from the individual after treatment with a Cbl-b inhibitor to destroy target cells in a cytotoxicity assay may be measured to assess treatment efficacy. In some embodiments, the biological activity of immune cells present in a sample (e.g., blood sample) can be measured by assaying expression and/or secretion of certain cytokines, such as IL-2 and IFNγ.

The present disclosure provides methods of treating cancer, comprising: administering to an individual with cancer an effective amount of a Cbl-b inhibitor, and administering to the individual an effective amount of an additional therapeutic agent. Also provided are methods of treating an individual with cancer, comprising: administering to the individual an effective amount of a Cbl-b inhibitor; and administering to the individual an effective amount of an additional therapeutic agent. Additionally, the present disclosure provides methods of increasing an anti-cancer immune response, comprising: administering to an individual with cancer an effective amount of a Cbl-b inhibitor, and administering to the individual an effective amount of an additional therapeutic agent. Further provided are methods of treating cancer, comprising: administering to an individual with cancer an effective amount of a Cbl-b inhibitor, wherein the individual has received or is receiving an effective amount of an additional therapeutic agent.

In some embodiments of the methods of the preceding paragraph, the Cbl-b inhibitor and the additional therapeutic agent are administered consecutively in either order. As used herein, the terms "consecutively," "serially," and "sequentially" refer to administration of a Cbl-b inhibitor after an additional therapeutic agent, or administration of the additional therapeutic agent after the Cbl-b inhibitor. For instance, consecutive administration may involve administration of the Cbl-b inhibitor in the absence of the additional therapeutic agent during an induction phase (primary therapy), which is followed by a post-induction treatment phase comprising administration of the additional therapeutic agent. The methods may further comprise a maintenance phase comprising administration of the Cbl-b inhibitor or the additional therapeutic agent. Alternatively, consecutive administration may involve administration of the additional therapeutic agent in the absence of the Cbl-b inhibitor during an induction phase (primary therapy), which is followed by a post-induction treatment phase comprising administration of the Cbl-b inhibitor. The methods may further comprise a maintenance phase comprising administration of the Cbl-b inhibitor or the additional therapeutic agent.

In some embodiments of the combination therapy methods, the Cbl-b inhibitor and the additional therapeutic agent are administered concurrently. As used herein, the terms "concurrently," "simultaneously," and "in parallel" refer to administration of a Cbl-b inhibitor and an additional therapeutic agent during the same doctor visit or during the same phase of treatment. For instance, both the Cbl-b inhibitor and the additional therapeutic agent may be administered during one or more of an induction phase, a treatment phase, and a maintenance phase. However, concurrent administration does not require that the Cbl-b inhibitor and the additional therapeutic agent be present together in a single formulation or pharmaceutical composition, or that the Cbl-b inhibitor and the additional therapeutic agent be administered at precisely the same time.

1. Combination Therapy Comprising a Cbl-b Inhibitor and an Immune Checkpoint Inhibitor In some embodiments of the combination therapy methods of the present disclosure, the additional therapeutic agent comprises an immune checkpoint inhibitor. In some embodiments of the combination therapy methods of the present disclosure for treating cancer, the additional therapeutic agent comprises an immune checkpoint inhibitor. The term "immune checkpoint" refers to a signaling pathway that prevents activation of immune cells, while the term "immune checkpoint inhibitor" refers to a compound that impedes the immune checkpoint to remove the brake on activation of immune cells. In some embodiments, the immune checkpoint inhibitor is an antagonist of at least one inhibitory checkpoint molecule. In some embodiments, the inhibitory checkpoint molecule is selected from the group consisting of PD-1 (CD279), PD-L1 (CD274), CTLA-4 (CD125), LAG3 (CD223), PVR (CD155), PVRL2 (CD112), PVRL3 (CD113), TIGIT, TIM3 (CD366), and VISTA. In some embodiments, the immune checkpoint inhibitor is an antagonist of at least one inhibitory checkpoint molecule selected from the group consisting of PD-1 (CD279), PD-L1 (CD274), and CTLA-4 (CD152).

PD-1 refers to programmed cell death protein 1 (PD-1). PD-1 antagonists suitable for the treatment methods, medicaments, and uses of the present disclosure include any chemical compound or biological molecule that blocks binding of PD-L1 expressed on a cancer cell or antigen presenting cell to PD-1 expressed on a lymphocyte (T-cell, B-cell, and/or NK-cell). Alternative names or synonyms for PD-1 and its ligand include CD279, PDCD1, PD1, and SLEB2 for PD-1; and CD274, PDCDIL1, PDL1, B7H1, B7-4, and B7-H for programmed cell death 1 ligand 1 (PD-L1). In some embodiments in which a human subject is being treated, the PD-1 antagonist blocks binding of human PD-L1 to human PD-1. The amino acid sequence of the mature form of human PD-1 is set forth as residues 21-288 in NCBI Locus No. NP_005009. The amino acid sequence of the mature form of human PD-L1 is set forth as residues 19-290 in NCBI Locus No. NP_054862.

CTLA-4 refers to cytotoxic T-lymphocyte associated protein 4. CTLA-4 antagonists suitable for the treatment methods, medicaments, and uses of the present disclosure include any chemical compound or biological molecule that blocks binding of CTLA-4 expressed on a lymphocyte (T-cell, B-cell, and/or NK-cell) to a ligand (CD80 and/or CD86) expressed on an antigen presenting cell. Alternative names or synonyms for CTLA-4 include CD152, CTLA4, ALPS5, CELIAC3, GRD4, GSE, and IDDM12. In some embodiments in which a human subject is being treated, the CTLA-4 antagonist blocks binding of human CTLA-4 to a human ligand. The amino acid sequence of the mature form of human CTLA-4 is set forth as residues 36-223 in NCBI Locus No. NP_005205.

LAG3 refers to lymphocyte activating gene 3 protein. LAG3 antagonists suitable for the treatment methods, medicaments, and uses of the present disclosure include any chemical compound or biological molecule that blocks binding of LAG3 expressed on a lymphocyte (T-cell, B-cell, and/or NK-cell) to a ligand (MHC class II) expressed on an antigen presenting cell. LAG3 is also known as CD223. In some embodiments in which a human subject is being treated, the LAG3 antagonist blocks binding of human LAG3 to a human ligand. The amino acid sequence of the mature form of human LAG3 is set forth as residues 23-525 in NCBI Locus No. NP_002277.

PVR refers to poliovirus receptor. PVR antagonists suitable for the treatment methods, medicaments, and uses of the present disclosure include any chemical compound or biological molecule that blocks binding of PVR expressed on a cancer cell or an antigen presenting cell to TIGIT expressed on a lymphocyte (T-cell, B-cell, and/or NK-cell). Alternative names or synonyms for PVR include CD155, PVS, HVED, NECL5, nectin-like protein 5, and TAGE4. In some embodiments in which a human subject is being treated, the PVR antagonist blocks binding of human PVR to human TIGIT. There are multiple isoforms of human PVR. The amino acid sequence of alpha isoform of human PVR is set forth in NCBI Locus No. NP_006496. The amino acid sequence of beta isoform of human PVR is set forth in NCBI Locus No. NP_001129240. The amino acid sequence of gamma isoform of human PVR is set forth in NCBI Locus No. NP_001129241. The amino acid sequence of delta isoform of human PVR is set forth in NCBI Locus No. NP_001129242.

PVRL2 refers to poliovirus receptor related 2. PVRL2 antagonists suitable for the treatment methods, medicaments, and uses of the present disclosure include any chemical compound or biological molecule that blocks binding of PVRL2 expressed on a cancer cell or an antigen presenting cell to TIGIT expressed on a lymphocyte (T-cell, B-cell, and/or NK-cell). Alternative names or synonyms for PVRL2 include CD112, NECTIN2, HVEB, herpesvirus entry mediator B, PRR2, and PVRR2. In some embodiments in which a human subject is being treated, the PVRL2 antagonist blocks binding of human PVRL2 to human TIGIT. The amino acid sequence of the alpha isoform of human PVRL2 is set forth in NCBI Locus No. NP_002847. The amino acid sequence of the delta isoform of human PVRL2 is set forth in NCBI Locus No. NP_001036189.

PVRL3 refers to poliovirus receptor related 3. PVRL3 antagonists suitable for the treatment methods, medicaments, and uses of the present disclosure include any chemical compound or biological molecule that blocks binding of PVRL3 expressed on a cancer cell or an antigen presenting cell to TIGIT expressed on a lymphocyte (T-cell, B-cell, and/or NK-cell). Alternative names or synonyms for PVRL3 include CD113, NECTIN3, PRR3, and PVRR3. In some embodiments in which a human subject is being treated, the PVRL3 antagonist blocks binding of human PVRL3 to human TIGIT. The amino acid sequence of isoform 1 of human PVRL3 is set forth in NCBI Locus No. NP_056295. The amino acid sequence of isoform 2 of human PVRL3 is set forth in NCBI Locus No. NP_001230215. The amino acid sequence of isoform 3 of human PVRL3 is set forth in NCBI Locus No. NP_001230217.

TIGIT refers to T-cell immunoreceptor with Ig and ITIM domains protein. TIGIT antagonists suitable for the treatment methods, medicaments, and uses of the present disclosure include any chemical compound or biological molecule that blocks binding of TIGIT expressed on a lymphocyte (T-cell, B-cell, or NK-cell) to a ligand (CD112, CD113, and/or CD155) expressed on a cancer cell or an antigen presenting cell. Alternative names or synonyms for TIGIT include VSIG9, V-set and immunoglobulin domain containing 9, VSTM3, V-set and transmembrane domain containing 3, and Washington University cell adhesion molecule (WUCAM). In some embodiments in which a human subject is being treated, the TIGIT antagonist blocks binding of human TIGIT to a human ligand. The amino acid sequence of the mature form of human TIGIT is set forth as residues 22-244 in NCBI Locus No.: NP_776160.

TIM3 refers to T-cell immunoglobulin and mucin-domain containing-3 protein. TIM3 antagonists suitable for the treatment methods, medicaments, and uses of the present disclosure include any chemical compound or biological molecule that blocks binding of TIM3 expressed on a lymphocyte (T-cell, B-cell, or NK-cell) to a ligand (galectin-9 phosphatidylserine) expressed on an antigen presenting cell. Alternative names or synonyms for TIM3 include CD366, HAVCR2, hepatitis A virus cellular receptor 2, KIM3, and SPTCL. In some embodiments in which a human subject is being treated, the TIM3 antagonist blocks binding of human TIM3 to a human ligand. The amino acid sequence of the mature form of human TIM3 is set forth as residues 22-301 in NCBI Locus No. NP_116171.

VISTA refers to V-domain Ig suppressor of T-cell activation. VISTA antagonists suitable for the treatment methods, medicaments, and uses of the present disclosure include any chemical compound or biological molecule that blocks binding of VISTA expressed on a lymphocyte (T-cell, B-cell, and/or NK-cell) to a ligand expressed on a cancer cell or an antigen presenting cell. Alternative names or synonyms for VISTA include VSIR, V-set immunoregulatory receptor, PD-1H, B7H5, GI24, PP2135, SISP1, and Diesi. In some embodiments in which a human subject is being treated, the VISTA antagonist blocks binding of human VISTA to a human ligand. The amino acid sequence of the mature form of human VISTA is set forth as residues 33-311 in NCBI Locus No.: NP_071436.

The immune checkpoint inhibitor may be a biological molecule. For instance, the immune checkpoint inhibitor may comprise an antibody or antigen-binding fragment thereof. The antibody or fragment may be a monoclonal antibody (mAb), for example, a human antibody, a humanized antibody, or a chimeric antibody, and may include a human constant region. In some embodiments the human constant region is selected from the group consisting of IgG1, IgG2, IgG3, and IgG4 constant regions, and in certain embodiments, the human constant region is an IgG1 or IgG4 constant region. In some embodiments, the antibody or fragment is a bispecific antibody. In some embodiments, the antigen-binding fragment comprises one of the group consisting of Fab, Fab'-SH, F(ab')$_2$, scFv, and Fv fragments.

In some embodiments, the at least one inhibitory checkpoint molecule comprises PD-1. In some embodiments, the immune checkpoint inhibitor is selected from the group consisting of pembrolizumab, nivolumab, cemiplimab, and biosimilars thereof. In one embodiment, the anti-PD-1 antibody is pembrolizumab (MK-3475 marketed as KEYTRUDA® by Merck & Co.). In one embodiment, the anti-PD-1 antibody is nivolumab (BMS-936558 or MDX-1106, marketed as OPDIVO® by Bristol-Myers Squibb). In one embodiment, the anti-PD-1 antibody is cemiplimab (REGN2810, Regeneron). In some embodiments, the immune checkpoint inhibitor is a variant of pembrolizumab, nivolumab, or cemiplimab.

In some embodiments, the at least one inhibitory checkpoint molecule comprises PD-L1. In some embodiments, the immune checkpoint inhibitor is selected from the group consisting of atezolizumab, avelumab, durvalumab, and biosimilars thereof. In one embodiment, the anti-PD-L1 antibody is atezolizumab (marketed as TECENTRIQ® by Genentech, Inc.). In one embodiment, the anti-PD-L1 antibody is avelumab (marketed as BAVENCIO® by EMD Serono, Inc. and Pfizer, Inc.). In one embodiment, the anti-PD-L1 antibody is durvalumab (MEDI4736 marketed as IMFINZI® by AstraZeneca). In some embodiments, the immune checkpoint inhibitor is a variant of atezolizumab, avelumab, or durvalumab.

In some embodiments, the at least one inhibitory checkpoint molecule comprises CTLA-4. In some embodiments, the immune checkpoint inhibitor is selected from the group consisting of ipilimumab, tremelimumab, and biosimilars thereof. In one embodiment, the anti-CTLA4 antibody is ipilimumab (MDX-010 or BMS-734016, marketed as YERVOY® by Bristol-Myers Squibb). In one embodiment, the anti-CTLA4 antibody is tremelimumab (ticilimumab, CP-675,206, developed by AstraZeneca). In some embodiments, the immune checkpoint inhibitor is a variant of ipilimumab, or tremelimumab.

In some embodiments, the monoclonal antibody is a "variant" antibody which comprises heavy chain and light chain sequences that are identical to those in the "reference" antibody, except for having three, two, or one conservative amino acid substitutions at positions that are located outside of the light chain CDRs and/or six, five, four, three, two, or one conservative amino acid substitutions that are located outside of the heavy chain CDRs (e.g., the variant positions are located in the framework regions or the constant region). In other words, the reference antibody and the variant antibody comprise identical CDR sequences, but differ from each other due to having a conservative amino acid substitution at no more than three or six other positions in their full length light and heavy chain sequences, respectively. A variant antibody is substantially the same as a reference antibody with respect to the following properties: binding affinity to the inhibitory checkpoint molecule and ability to block the binding of the inhibitory checkpoint molecule to its ligand.

In other embodiments, the immune checkpoint inhibitor may comprise an immunoadhesin comprising the inhibitory checkpoint molecule binding domain of one of its ligands fused to a constant region such as an Fc region of an immunoglobulin molecule.

As used herein the term "biosimilar" refers to a biological product that is similar to but without clinically meaningful differences in safety and effectiveness from a Federal Drug Administration (FDA)-approved reference product. For instance, there may be differences between a biosimilar product and a reference product in clinically inactive components (e.g., differences in excipients of the formulations, minor differences in glycosylation, etc.). Clinically meaningful characteristics can be assessed through pharmacokinetic and pharmacodynamic studies. In some embodiments, the biosimilar product is an interchangeable product as determined by the FDA.

2. Combination Therapy Comprising a Cbl-b Inhibitor and an Antineoplastic Agent

In some embodiments of the combination therapy methods of the present disclosure, the additional therapeutic agent comprises an antineoplastic agent. In some embodiments of the combination therapy methods herein for treating cancer, the additional therapeutic agent comprises an antineoplastic agent. As used herein, the terms "anti-neoplastic agent" and "antineoplastic agent" refer to a therapeutic agent classified according to the Anatomical Therapeutic Chemical Classification System (ATC) code L01 developed by the World Health Organization. In some embodiments, the antineoplastic agent is classified as one of the group consisting of a cytotoxic antibiotic (ATC code L01D), a plant alkaloid (ATC code L01C), an antimetabolite (ATC code L01B), an alkylating agent (ATC code L01A), and other antineoplastic agent (ATC code L01X). In some embodiments, the antineoplastic agent is a small molecule drug (e.g., cancer chemotherapeutic agent) as opposed to a biological molecule.

A cytotoxic antibiotic is a suitable antineoplastic agent for the treatment methods, medicaments and uses of the present disclosure. In some embodiments, the cytotoxic antibiotic is selected from the group consisting of ixabepilone, mitomycin, plicamycin, bleomycin, pixantrone, amrubicin, valrubicin, pirarubicin, mitoxantrone, idarubicin, zorubicin, aclarubicin, epirubicin, daunorubicin, doxorubicin, and dactinomycin.

A plant alkaloid is a suitable antineoplastic agent for the treatment methods, medicaments, and uses of the present disclosure. In some embodiments, the plant alkaloid is selected from the group consisting of trabectedin, cabazitaxel, paclitaxel poliglumex, docetaxel, paclitaxel, demecolcine, teniposide, etoposide, vintafolide, vinflunine, vinorelbine, vindesine, vincristine, and vinblastine.

An antimetabolite is a suitable antineoplastic agent for the treatment methods, medicaments, and uses of the present disclosure. In some embodiments, the antimetabolite is a pyrimidine analog, a purine analog, or a folic acid analog. In some embodiments, the antimetabolite is selected from the group consisting of floxuridine, trifluridine, tegafur, fluorouracil, decitabine, azacitidine, capecitabine, gemcitabine, carmofur, tegafur, fluorouracil, cytarabine, nelarabine, clofarabine, fludarabine, cladribine, tioguanine, mercaptopurine, pralatrexate, pemetrexed, raltitrexed, and methotrexate.

An alkylating agent is a suitable antineoplastic agent for the treatment methods, medicaments, and uses of the present disclosure. In some embodiments, the alkylating agent is selected from the group consisting of dacarbazine, temozolomide, pipobroman, mitobronitol, etoglucid, uracil mustard, ranimustine, nimustine, fotemustine, streptozocin, semustine, lomustine, carmustine, carboquone, triaziquone, thiotepa, mannosulfan, treosulfan, busulfan, bendamustine, prednimustine, trofosfamide, ifosfamide, mechlorethamine, melphalan, chlorambucil, and cyclophosphamide.

In other embodiments, the antineoplastic agent comprises an other antineoplastic agent selected from the group consisting of a platinum compound (ATC Code L01XA), a methylhydrazine (ATC Code L01XB), a sensitizer (ATC Code L01XD), a protein kinase inhibitor (ATC Code L01XE), and an other agent (ATC Code L01XA).

A platinum compound is a suitable antineoplastic agent for the treatment methods, medicaments, and uses of the present disclosure. In some embodiments, the platinum compound is selected from the group consisting of cisplatin, carboplatin, oxaliplatin, satraplatin, and polyplatillen.

3. Combination Therapy Comprising a Cbl-b Inhibitor and Radiation Therapy

The present disclosure provides methods of treating cancer comprising: administering to an individual with cancer an effective amount of a Cbl-b inhibitor, and administering to the individual an effective amount of radiation therapy. Also provided are methods of treating an individual with cancer, comprising: administering to the individual an effective amount of a Cbl-b, and administering to the individual an effective amount of radiation therapy. Additionally, the present disclosure provides methods of increasing an anticancer immune response, comprising: administering to an individual with cancer an effective amount of a Cbl-b inhibitor, and administering to the individual an effective amount of radiation therapy. Further provided are methods of treating cancer, comprising: administering to an individual with cancer an effective amount of a Cbl-b inhibitor, wherein the individual has received or is receiving an effective amount of radiation therapy.

In some embodiments, the radiation therapy is external beam radiation therapy. In other embodiments, the radiation therapy is internal radiation therapy. In some embodiments, the radiation therapy is ablative radiation therapy.

In some embodiments, the combination therapy regimen of the present disclosure comprises administration of a Cbl-b inhibitor, radiation therapy, and one or both of an immune checkpoint inhibitor and an antineoplastic agent.

Provided herein are methods for treating cancer, comprising administering to an individual with cancer a combination therapy comprising an effective amount of a Cbl-b inhibitor, and an effective amount of a cancer vaccine. Also provided are medicaments comprising a Cbl-b inhibitor for use in combination with a cancer vaccine for treating cancer, and medicaments comprising both a Cbl-b inhibitor and a cancer vaccine for use in treating cancer. Further provided are uses of a Cbl-b inhibitor in the manufacture of a medicament for treating cancer in an individual when administered in combination with a cancer vaccine. Further provided are uses of a Cbl-b inhibitor and a cancer vaccine in the manufacture of a medicament(s) for treating cancer. In some embodiments, the Cbl-b inhibitor is a "small molecule."

Also provided herein are methods for treating cancer, comprising administering to an individual with cancer a combination therapy comprising an effective amount of a Cbl-b inhibitor, and an effective amount of an oncolytic virus. Also provided are medicaments comprising a Cbl-b inhibitor for use in combination with an oncolytic virus for treating cancer, and medicaments comprising both a Cbl-b inhibitor and an oncolytic virus for use in treating cancer. Further provided are uses of a Cbl-b inhibitor in the manufacture of a medicament for treating cancer in an individual when administered in combination with an oncolytic virus. Further provided are uses of a Cbl-b inhibitor and an oncolytic virus in the manufacture of a medicament(s) for treating cancer. In some embodiments, the Cbl-b inhibitor is a "small molecule."

In some embodiments of the treatment methods, medicaments and uses of the present disclosure, the cancer is a hematologic cancer such as lymphoma, a leukemia or a myeloma. In other embodiments of the treatment methods, medicaments and uses of the present disclosure, the cancer is a non-hematologic cancer such as a sarcoma, a carcinoma, or a melanoma.

Hematologic cancers include, but are not limited to, one or more leukemias such as B-cell acute lymphoid leukemia ("BALL"), T-cell acute lymphoid leukemia ("TALL"), acute lymphoid leukemia (ALL); one or more chronic leukemias including, but not limited to, chronic myelogenous leukemia (CML) and chronic lymphocytic leukemia (CLL); additional hematologic cancers or hematologic conditions including, but not limited to, B-cell prolymphocytic leukemia, blastic plasmacytoid dendritic cell neoplasm, Burkitt's lymphoma, diffuse large B-cell lymphoma, follicular lymphoma, hairy cell leukemia, small cell- or a large cell-follicular lymphoma, malignant lymphoproliferative conditions, MALT lymphoma, mantle cell lymphoma, Marginal zone lymphoma, multiple myeloma, myelodysplasia and myelodysplastic syndrome, non-Hodgkin's lymphoma, plasmablastic lymphoma, plasmacytoid dendritic cell neoplasm, Waldenstrom macroglobulinemia, and "preleukemia," which are a diverse collection of hematological conditions united by ineffective production (or dysplasia) of myeloid blood cells.

Non-hematologic cancers include but are not limited to, a neuroblastoma, renal cell carcinoma, colon cancer, colorectal cancer, breast cancer, epithelial squamous cell cancer, melanoma, stomach cancer, brain cancer, lung cancer (e.g., NSCLC), pancreatic cancer, cervical cancer, ovarian cancer, liver cancer, bladder cancer, prostate cancer, testicular cancer, thyroid cancer, uterine cancer, adrenal cancer, and head and neck cancer.

In some aspects, the effectiveness of administration an activation threshold reducer or a costimulation requirement reducer, such as a Cbl-b inhibitor, in the treatment of a cancer is measured by assessing clinical outcome, such as reduction in tumor size or number of tumors, and/or survival. In some embodiments, "treating cancer" comprises assessing a patient's response to the treatment regimen according to the Response Evaluation Criteria in Solid Tumors (RECIST version 1.1) as described (see, e.g., Eisenhauer et al., Eur J Cancer, 45:228-247, 2009; and Nishino et al., Am J Roentgenol, 195: 281-289, 2010). Response criteria to determine objective anti-tumor responses per RECIST 1.1 include complete response (CR); partial response (PR); progressive disease (PD); and stable disease (SD).

Also provided herein are methods for treating cancer, comprising administering to an individual with cancer a combination therapy comprising an effective amount of an agent that lowers activation threshold (activation threshold reducer) of an immune cell (e.g., T-cell, B-cell, and/or NK-cell), and an effective amount of a cancer vaccine. Also provided are medicaments comprising an activation threshold reducer for use in combination with a cancer vaccine for treating cancer, and medicaments comprising both an activation threshold reducer and a cancer vaccine for use in treating cancer. Further provided are uses of an activation threshold reducer in the manufacture of a medicament for treating cancer in an individual when administered in combination with a cancer vaccine. Further provided are uses of an activation threshold reducer and a cancer vaccine in the manufacture of a medicament(s) for treating cancer.

Also provided herein are methods for treating cancer, comprising administering to an individual with cancer a combination therapy comprising an effective amount of an agent that lowers activation threshold (activation threshold reducer) of an immune cell (e.g., T-cell, B-cell, and/or NK-cell), and an effective amount of an oncolytic virus. Also provided are medicaments comprising an activation threshold reducer for use in combination with an oncolytic virus for treating cancer, and medicaments comprising both an activation threshold reducer and an oncolytic virus for use in treating cancer. Further provided are uses of an activation threshold reducer in the manufacture of a medicament for treating cancer in an individual when administered in combination with an oncolytic virus. Further provided are uses of an activation threshold reducer and an oncolytic virus in the manufacture of a medicament(s) for treating cancer.

In some embodiments, the agent that lowers activation threshold (activation threshold reducer) is an agent that reduces costimulation requirement (costimulation requirement reducer) of an immune cell (e.g., T-cell, B-cell, and/or NK-cell). In some embodiments, the agent that lowers activation threshold (activation threshold reducer) is an agent that promotes tumor immune-surveillance. In some embodiments, the agent that lowers activation threshold (activation threshold reducer) is a Cbl-b inhibitor. In some embodiments, the agent that reduces costimulation requirement is a Cbl-b inhibitor. In some embodiments, the agent that promotes tumor immune-surveillance is a Cbl-b inhibitor.

In some embodiments, an activation threshold reducer, such as a Cbl-b inhibitor, is capable of increasing T-cell activation and/or T-cell proliferation. In some embodiments, an activation threshold reducer, such as a Cbl-b inhibitor, is capable of decreasing T-cell exhaustion, T-cell tolerance, and/or T-cell anergy.

In some embodiments, an activation threshold reducer, such as a Cbl-b inhibitor, is capable of increasing production of one or more cytokines by T-cells or surrounding immune cells in the activated T-cell microenvironment (e.g., myeloid cells). In some embodiments, the one or more cytokines include, but are not limited to IFN-γ, IL-1β, IL-2, IL-4, IL-5, IL-6, IL-13, IL-18, TNFα, and GM-CSF. In some embodiments, the cytokine is one or more of IL-2, IFN-γ, TNFα, and GM-CSF. In some embodiments, the cytokine is a chemokine. In some embodiments, the one or more chemokines include, but are not limited to IP-10, Eotaxin, GRO alpha, RANTES, MIP-1α, MIP-1β, MIP-2, MCP-1, and MCP-3. Increased expression of cytokines can be measured by ELISA.

In some embodiments, an activation threshold reducer, such as a Cbl-b inhibitor, is capable of increasing cell surface expression of one or more T-cell activation markers. In some embodiments, the one or more T-cell activation markers include, but are not limited to CD25, CD44, CD62L, CD69, CD152 (CTLA4), CD154, CD137, and CD279. In some embodiments, the T-cell activation marker is one or more of CD25, CD69, and CTLA4. Increased expression of cell surface markers can be measured by FACS.

Methods for experimentally determining increased T-cell activation, increased T-cell proliferation, decreased T-cell exhaustion, and/or decreased T-cell tolerance are well known in the art. In some embodiments, representative methods of determining T-cell activation can be found in Biological Example 9 and/or Biological Example 13 provided herein. In some embodiments, representative in vitro and in vivo methods of determining increased T-cell activation, increased T-cell proliferation, decreased T-cell exhaustion, and/or decreased T-cell tolerance can be found in Biological Example 10 and/or Biological Example 14.

In some embodiments, an activation threshold reducer, such as a Cbl-b inhibitor, is capable of increasing B-cell activation. In some embodiments, increased B-cell activation comprises increased cell surface expression of one or more B-cell activation markers. In some embodiments, the one or more B-cell activation markers include, but are not limited to CD69, CD86, and MHIC class II (e.g., HLA-DR). In some embodiments, the B-cell activation marker is CD69.

Increased expression of cell surface markers can be measured by FACS. In some embodiments, increased B-cell activation comprises increased activation of proteins in signaling pathways, such as those mediated by ERK, INK, and Syk. Increased activation of proteins can be detected by measurement of levels of phosphorylation on the proteins using reagents, such as anti-phospho antibodies available in the art.

In some embodiments, an activation threshold reducer, such as a Cbl-b inhibitor, is capable of increasing NK-cell activation. In some embodiments, increased NK-cell activation comprises secretion of one or more cytokines. In some embodiments, the one or more cytokines include, but are not limited to IFN-γ, TNFα, and MIP-1β. Increased expression of cytokines can be measured by ELISA. In some embodiments, increased NK-cell activation comprises increased cell surface expression of one or more NK-cell activation markers. In some embodiments, the one or more NK-cell activation markers include, but are not limited to CD69, and CD107a. Increased expression of cell surface markers can be measured by FACS. In some embodiments, increased NK-cell activation comprises increased killing of target cells such as tumor cells, including primary tumor cells, and cell line derived tumor cells, such as the K562 cell line.

Methods for experimentally determining increased B-cell activation and NK-cell activation are well known in the art. In some embodiments, representative methods of determining B-cell activation can be found in Biological Example 10 and/or Biological Example 14. In some embodiments, representative methods of determining NK-cell activation can be found in Biological Example 10 and/or Biological Example 14.

Modulation of activity of an immune cell, such as a T-cell, a B-cell, or a NK-cell can be measured by determining a baseline value for a parameter of interest (e.g., cytokine secretion). For example, T-cell activation, such as in a sample obtained from in vitro experiments of cells contacted with a Cbl-b inhibitor, can be measured before contacting or administering said Cbl-b inhibitor to determine a baseline value. A reference value then is obtained for T-cell activation after contacting or administering said Cbl-b inhibitor. The reference value is compared to the baseline value in order to determine the amount of T-cell activation due to contact or administration of the Cbl-b inhibitor or composition thereof. For example, in some embodiments, immune cell (e.g., T-cell) activation is increased by at least 0.1-fold in a sample as compared to a baseline value, wherein the baseline value is obtained before contacting the immune cell (e.g., T-cell) with a Cbl-b inhibitor or a composition thereof. In some embodiments, immune cell (e.g., T-cell) activation is increased by at least about 0.1-fold, about 0.2-fold, about 0.3-fold, about 0.4-fold, about 0.5-fold, about 0.6-fold, about 0.7-fold, about 0.8-fold, about 0.9-fold, about 1-fold, about 2-fold, about 4-fold, about 6-fold, about 8-fold, about 10-fold, about 20-fold, about 30-fold, but no more than about 50-fold over a baseline value. Immune cell activation can be assessed by measuring biological markers of activation such as increased cytokine secretion, increased cell surface expression of activation markers (e.g., cell surface markers), or increased phosphorylation of proteins in a downstream signaling pathway. The fold over baseline value that indicates immune cell activation can be determined for the parameter being tested and the conditions under which the immune cell were treated. For example, for measuring T-cell activation, a baseline value can be obtained from T-cells stimulated with anti-CD3 antibody in combination with anti-CD28 antibody, wherein the cells are not incubated with a Cbl-b inhibitor. A reference value is then obtained from T-cells stimulated with anti-CD3 antibody in combination with anti-CD28 antibody, wherein the T-cells have been or are in contact with a Cbl-b inhibitor. A positive response for immune cell activation can then be determined by the obtained reference value. Similar reference value measurements can be obtained and compared to a baseline value for assessing T-cell activation, T-cell proliferation, T-cell exhaustion, T-cell tolerance, B-cell activation and/or NK-cell activation. Measurements for these parameters can be obtained utilizing techniques well known in the art, as well as the techniques provided in Biological Examples 9, 10, 13, and 14.

The terms "baseline" or "baseline value" as used herein can refer to a measurement or characterization before administration of a therapeutic agent as disclosed herein (e.g., a composition comprising a Cbl-b inhibitor as described herein) or at the beginning of administration of the therapeutic agent. The baseline value can be compared to a reference value in order to determine the increase or decrease of an immune cell function (e.g., increasing T-cell activation, increasing T-cell proliferation, decreasing T-cell exhaustion, and/or decreasing T-cell tolerance). The terms "reference" or "reference value" as used herein can refer to a measurement or characterization after administration of the therapeutic agent as disclosed herein (e.g., a composition comprising a Cbl-b inhibitor as described herein). The reference value can be measured one or more times during an experimental time course, dosage regimen, or treatment cycle, or at the completion of the experimental time course, dosage regimen, or treatment cycle. A "reference value" can be an absolute value, a relative value, a value that has an upper and/or lower limit, a range of values, an average value, a median value, a mean value, or a value as compared to a baseline value. Similarly, a "baseline value" can be an absolute value, a relative value, a value that has an upper and/or lower limit, a range of values, an average value, a median value, a mean value, or a value as compared to a reference value. The reference value and/or baseline value can be obtained from one sample (e.g., one sample obtained from an individual), from two different samples (e.g., a sample obtained from two different individuals) or from a group of samples (e.g., samples obtained from a group of two, three, four, five or more individuals).

In some embodiments, a positive response for T-cell activation as measured by cytokine secretion (e.g., IL-2 secretion) by T-cells stimulated with anti-CD3 antibody in combination with anti-CD28 antibody in the presence of a Cbl-b inhibitor is at least 2.5-fold over the baseline value for cytokine secretion (e.g., IL-2 secretion) obtained from T-cells stimulated with anti-CD3 antibody in combination with anti-CD28 antibody in the absence of a Cbl-b inhibitor. In some embodiments, a positive response for T-cell activation as measured by surface marker expression (e.g., CD25 surface marker staining) by T-cells stimulated with anti-CD3 antibody in combination with anti-CD28 antibody in the presence of a Cbl-b inhibitor is at least 1.3-fold over the baseline value for surface marker expression (e.g., CD25 surface marker staining) obtained from T-cells stimulated with anti-CD3 antibody in combination with anti-CD28 antibody in the absence of a Cbl-b inhibitor. In some embodiments, a baseline value can be obtained from T-cells stimulated with anti-CD3 antibody alone, wherein the cells are not incubated with a Cbl-b inhibitor. In some embodiments, a positive response for T-cell activation as measured by cytokine secretion (e.g., IL-2 secretion) by T-cells stimulated with anti-CD3 antibody alone in the presence of a Cbl-b inhibitor is at least 0.1-fold over the baseline value for cytokine secretion (e.g., IL-2 secretion) obtained from T-cells stimulated with anti-CD3 antibody alone in the absence of a Cbl-b inhibitor. In some embodiments, a positive response for T-cell activation as measured by surface marker expression (e.g., CD25 surface marker staining) by T-cells stimulated with anti-CD3 antibody alone in the presence of a Cbl-b inhibitor is at least 0.6-fold over the baseline value for surface marker expression (e.g., CD25 surface marker staining) obtained from T-cells stimulated with anti-CD3 antibody alone in the absence of a Cbl-b inhibitor.

The present disclosure provides methods of treating cancer, comprising: administering to an individual with cancer an effective amount of a Cbl-b inhibitor, and administering to the individual an effective amount of a cancer vaccine. Also provided are methods of treating an individual with cancer, comprising: administering to the individual an effective amount of a Cbl-b inhibitor; and administering to the individual an effective amount of a cancer vaccine. Additionally, the present disclosure provides methods of increasing an anti-cancer immune response, comprising: administering to an individual with cancer an effective amount of a Cbl-b inhibitor, and administering to the individual an effective amount of a cancer vaccine. Further provided are methods of treating cancer, comprising: administering to an individual with cancer an effective amount of a Cbl-b inhibitor, wherein the individual has received or is receiving an effective amount of a cancer vaccine.

In addition, the present disclosure provides methods of treating cancer, comprising: administering to an individual with cancer an effective amount of a Cbl-b inhibitor, and administering to the individual an effective amount of an oncolytic virus. Also provided are methods of treating an individual with cancer, comprising: administering to the individual an effective amount of a Cbl-b inhibitor; and administering to the individual an effective amount of an oncolytic virus. Additionally, the present disclosure provides methods of increasing an anti-cancer immune response, comprising: administering to an individual with cancer an effective amount of a Cbl-b inhibitor, and administering to the individual an effective amount of an oncolytic virus. Further provided are methods of treating cancer, comprising: administering to an individual with cancer an effective amount of a Cbl-b inhibitor, wherein the individual has received or is receiving an effective amount of an oncolytic virus.

In some embodiments of the methods of the preceding paragraph, the Cbl-b inhibitor and the cancer vaccine are administered consecutively in either order. In certain embodiments, as used herein, the terms "consecutively", "serially", and "sequentially" refer to administration of a Cbl-b inhibitor after a cancer vaccine, or administration of the cancer vaccine after the Cbl-b inhibitor. For instance, consecutive administration may involve administration of the Cbl-b inhibitor in the absence of the cancer vaccine during an induction phase (primary therapy), which is followed by a post-induction treatment phase comprising administration of both the cancer vaccine and the Cbl-b inhibitor. The methods may further comprise a maintenance phase comprising administration of the Cbl-b inhibitor or administration of a further dose of the cancer vaccine. Alternatively, consecutive administration may involve administration of the cancer vaccine in the absence of the Cbl-b inhibitor during an induction phase (primary therapy), which is followed by a post-induction treatment phase comprising administration of the Cbl-b inhibitor. The methods may further comprise a maintenance phase comprising administration of the Cbl-b inhibitor or a further dose of the cancer vaccine.

In some embodiments of the methods of the preceding paragraph, the Cbl-b inhibitor and the oncolytic virus are administered consecutively in either order. In certain embodiments, as used herein, the terms "consecutively", "serially", and "sequentially" refer to administration of a Cbl-b inhibitor after an oncolytic virus, or administration of the oncolytic virus after the Cbl-b inhibitor. For instance, consecutive administration may involve administration of the Cbl-b inhibitor in the absence of the oncolytic virus during an induction phase (primary therapy), which is followed by a post-induction treatment phase comprising administration of both the oncolytic virus and the Cbl-b inhibitor. The methods may further comprise a maintenance phase comprising administration of the Cbl-b inhibitor or administration of a further dose of the oncolytic virus. Alternatively, consecutive administration may involve administration of the oncolytic virus in the absence of the Cbl-b inhibitor during an induction phase (primary therapy), which is followed by a post-induction treatment phase comprising administration of the Cbl-b inhibitor. The methods may further comprise a maintenance phase comprising administration of the Cbl-b inhibitor or a further dose of the oncolytic virus.

In some embodiments of the combination therapy methods, the Cbl-b inhibitor and the cancer vaccine are administered concurrently. In certain embodiments, as used herein, the terms "concurrently", "simultaneously", and "in parallel" refer to administration of a Cbl-b inhibitor and a cancer vaccine during the same doctor visit or during the same phase of treatment. For instance, both the Cbl-b inhibitor and the cancer vaccine may be administered during one or more of an induction phase, a treatment phase, and a maintenance phase. However, concurrent administration does not require that the Cbl-b inhibitor and the cancer vaccine be present together in a single formulation or pharmaceutical composition, or that the Cbl-b inhibitor and the cancer vaccine be administered at precisely the same time.

In some embodiments of the combination therapy methods, the Cbl-b inhibitor and the oncolytic virus are administered concurrently. In certain embodiment, as used herein, the terms "concurrently", "simultaneously", and "in parallel" refer to administration of a Cbl-b inhibitor and an oncolytic virus during the same doctor visit or during the same phase of treatment. For instance, both the Cbl-b inhibitor and the oncolytic virus may be administered during one or more of an induction phase, a treatment phase, and a maintenance phase. However, concurrent administration does not require that the Cbl-b inhibitor and the oncolytic virus be present together in a single formulation or pharmaceutical composition, or that the Cbl-b inhibitor and the oncolytic virus be administered at precisely the same time.

In some aspects, the treatment includes multiple administrations of the Cbl-b inhibitor or composition thereof, wherein the interval between administrations may vary. In some embodiments, the Cbl-b inhibitor is administered at a flat dose to an individual (e.g., mg/adult or mg/child). In some embodiments, the Cbl-b inhibitor is administered to an individual at a fixed dose based in the individual's weight (e.g., mg/kg).

In some embodiments, the effectiveness of the combination therapies disclosed herein can be assessed by measuring the biological activity of immune cells present in a sample isolated from the treated individual. For example, the ability of immune cells, which are isolated from the individual after treatment, to destroy target cells using a cytotoxicity assay can be used to assess treatment efficacy. In some embodiments, the biological activity of immune cells present in a sample can be measured by assaying expression and/or secretion of certain cytokines, such as IL-2 and IFNγ.

The term "cancer vaccine" as used herein, unless otherwise specified, refers to a "therapeutic cancer vaccine" to be administered to an individual with cancer for the purpose of treating cancer (and optionally preventing recurrence of the cancer). In contrast, a "preventative cancer vaccine" (prophylactic cancer vaccine) is to be administered to an individual without cancer for the purpose of preventing cancer or reducing the individual's risk of developing cancer. Examples of preventative cancer vaccines are human papillomavirus vaccines for prevention squamous cell carcinoma and hepatitis B virus vaccines for prevention of hepatocellular carcinoma. Cancer vaccines are immunogenic compositions comprising a pharmaceutically acceptable excipient and at least one tumor antigen, such as a tumor-specific antigen or a tumor-associated antigen.

As used herein, the terms "oncolytic virus" and "OV" refer to a virus that infects and kills cancer cells. Death of cancer cells is a result of both direct cytolysis and induction of anti-tumor immunity. In some embodiments, the "oncolytic virus" is a replication-competent virus, which selectively replicates in cancer cells. In other embodiments, the "oncolytic virus" is a replication-deficient virus, which does not replicate in cancer cells either as a consequence of genetic engineering or inactivation (e.g., UV-irradiation or heat) of the oncolytic virus.

In some embodiments, the tumor antigen comprises a "shared tumor antigen" that is common to many cancers of the same type. Non-limiting examples of shared tumor antigens are the breast cancer antigen HER2, the prostate cancer antigens PAP and PSA, and the melanoma antigens MART-1 and MAGE. In other embodiments, the tumor antigen comprises a "neoantigen" that arises as a result of a tumor-specific DNA alteration (e.g., somatic mutation). As such, neoantigens typically possess an amino acid sequence not present in a normal mammalian genome (Schumacher and Schreiber, Science, 348: 69-74, 2015). Non-limiting examples of neoantigens are BRAF V600E, KRAS G12D, KRAS G12V, PIK3CA H1047R, and PIC3CA E545K. A tumor-specific neoantigen database (TSNAdb) is now freely available (Wu et al., Genomics Proteomics Bioinformatics 16: 276-282, 2018).

A variety of techniques are suitable for identification of neoantigens for inclusion in a cancer vaccine as part of a combination therapy comprising an activation threshold reducer, such as a Cbl-b inhibitor. For instance, neoantigens can be identified with methods comprising isolating DNA from a tumor biopsy obtained from an individual, sequencing the DNA, and computational analysis of the sequence to identify one or more neoantigens (Aldous and Dong, Bioorg Med Chem, 26: 2842-2849, 2018). In some embodiments, the computational analysis involves identifying peptides of 8-11 amino acids in length that are predicted to bind to at least one HLA allele expressed by cells of the tumor and which comprise at least one missense mutation (Wu et al., Genomics Proteomics Bioinformatics 16: 276-282, 2018). Neoantigen inclusion in a cancer vaccine is thought to be advantageous for overcoming tolerance and reducing autoimmunity risk.

Cancer vaccine platforms suitable for use in the methods, medicaments, and uses of the present disclosure include, but are not limited to, synthetic peptides, recombinant proteins, nucleic acids (DNA or mRNA), microbial vectors, tumor cells, and antigen presenting cells (see, e.g., DeMaria and Bilusic, Hematol Oncol Cin North Am, 33: 199-214, 2019; and Maeng and Berzofsky, F1000Research 2019, 8(F1000 Faculty Rev): 654, 2019).

In some embodiments, the tumor antigen of the cancer vaccine comprises at least one synthetic peptide or recombinant protein. In some embodiments, the synthetic peptide is at least 8 amino acids in length, and in certain embodiments, less than 80 amino acids in length. In some embodiments, the tumor antigen comprises a plurality of synthetic peptides, or the tumor antigen comprises a synthetic peptide or a recombinant protein comprising the amino acid sequence of two, three, or more epitopes. An "epitope" is a portion of an antigen that is bound by an antibody or a B-cell receptor, or that is presented for binding by a T-cell receptor by a major histocompatibility complex molecule (MHC class I or class II) on the surface of a cell, such as a tumor cell or a dendritic cell. In some embodiments, the epitope is a "linear epitope" composed of contiguous amino acids of a tumor antigen sequence (primary structure). In some embodiments, the epitope is a "conformational epitope" composed of non-contiguous amino acids of a tumor antigen (tertiary structure). In some embodiments, the tumor antigen comprises a recombinant protein comprising both linear epitope(s) and conformational epitope(s).

In some embodiments, the tumor antigen is encoded by a DNA or an mRNA molecule. In some embodiments, the tumor antigen is encoded by a nucleic acid of a microbial vector, or said another way, the cancer vaccine comprises a microbial vector. In some embodiments, the microbial vector is a live, attenuated microbial vector. In one embodiment, the live, attenuated microbial vector is TICE® BCG, a live culture preparation of the *Bacillus* of Calmette and Guerin (BCG) strain of *Mycobacterium bovis*, marketed by Organon USA, Inc., (Roseland, NJ). TICE® BCG is Federal Drug Administration (FDA)-approved for intravesical use upon reconstitution with sterile saline (e.g., pharmaceutically acceptable excipient), and is indicated for the treatment and prophylaxis of carcinoma in situ of the urinary bladder, and for the prophylaxis of primary or recurrent stage Ta and/or T1 papillary tumors following transurethral resection.

In some embodiments, the microbial vector is a recombinant microbial vector, such as a recombinant viral vector or a recombinant bacterial vector. Recombinant viral vectors suitable for use in the combination therapies of the present disclosure include, but are not limited to, retroviruses, lentiviruses, adenoviruses, adeno-associated viruses, poxviruses, and herpesviruses (Chulpanova et al., Biomedicines, 6: 94, 2018). In some embodiments, the microbial vector is a recombinant bacterial vector. Recombinant bacterial vectors suitable for use in the combination therapies of the present disclosure include, but are not limited to, *Clostridium* (*C. novyi*), *Listeria* (e.g., *L. monocytogenes*), *Pseudomonas* (e.g., *P. aeruginosa*), and *Salmonella* (*S. typhimurium*) (Toussant et al., Expert Rev Vaccines, 12: 1139-1154, 2013).

In some embodiments, the cancer vaccine comprises an antigen presenting cell (APC), that has been contacted with a tumor antigen, such as a synthetic peptide or a recombinant protein. In some embodiments, the APC is transfected with a nucleic acid encoding a tumor antigen. In some embodiments, the APC is transfected with a nucleic acid encoding a cytokine. In some embodiments, the APCs comprises dendritic cells or mesenchymal stem cells. In one embodiment, the cancer vaccine is PROVENGE® (sipuleucel-T) marketed by Dendreon Corp. (Seattle, WA). PROVENGE® comprises Lactated Ringer's (e.g., pharmaceutically acceptable excipient) and peripheral blood mononuclear cells (PBMC) that have been activated with a PAP-GM-CSF fusion protein consisting of prostatic acid phosphatase linked to granulocyte-macrophage colony-stimulating factor. PROVENGE® is Federal Drug Administration (FDA)-approved for intravenous infusion for the treatment of asymptomatic or minimally symptomatic metastatic prostate cancer.

In some embodiments, the cancer vaccine comprises a killed tumor cell. In some embodiments, the cancer vaccine comprises a tumor cell lysate. In some embodiments, the cancer vaccine comprises an APC that has been contacted with a tumor cell lysate.

Adjuvants of the cancer vaccines suitable for use in the methods, medicaments and uses of the present disclosure include, but are not limited to, adjuvants of FDA-approved licensed products. In particular, adjuvants of current FDA-approved licensed products comprise aluminum salts, monophosphoryl lipid A, oil-in-water emulsions (e.g., squalene-in-water emulsions MF59 or AS03), saponins, and CpG oligodeoxynucleotides.

Oncolytic viruses suitable for use in the methods, medicaments, and uses of the present disclosure include, but are not limited to, adenovirus, coxsackievirus, echovirus, fowlpox virus, herpes simplex virus, maraba virus, measles virus, myxoma virus, Newcastle disease virus, parvovirus, poliovirus, retrovirus, reovirus, Seneca Valley virus, Semiliki Forest virus, vaccinia virus, and vesicular stomatitis virus (see, e.g., Russell and Peng, Chin Clin Oncol, 7: 16, 2018; and Sivanandam et al., Molecular Therapy Oncolytics, 13: 93-106).

In some embodiments, the oncolytic virus has not been genetically-engineered (non-recombinant virus). In some embodiments, the non-recombinant virus is an echovirus (e.g., Rigvir), a Newcastle disease virus, a parvovirus, a reovirus, or a Seneca Valley virus.

In some embodiments, the oncolytic virus is a recombinant virus that has been genetically engineered to include one or more gene deletions, one or more gene insertions, or one or more gene deletions and one or more gene insertions. In some embodiments, the recombinant virus has been genetically engineered to alter host cell specificity and/or tumor cell cytotoxicity. In some embodiments, the recombinant oncolytic virus has been genetically engineered by functional deletion of one or more viral genes encoding proteins that suppress a response (e.g., an anti-viral response) of a host cell, and/or by insertion of one or more transgenes encoding proteins that promote a response (e.g., an anti-tumor response) of a host cell (see, e.g., Guo et al., Frontiers in Immunology, 8: Article 555, 2017; and Lin et al., Oncology Letters, 15: 4053-4060, 2018). In some embodiments, the recombinant virus is further engineered by insertion of a transgene encoding a detectable marker, such as fluorescent protein. Desirable anti-tumor responses include one or both of innate immune response and adaptive immune response.

In some embodiments, the recombinant oncolytic virus is a recombinant herpes simplex virus (HSV), such as HSV type-1. In one embodiment, the recombinant oncolytic virus is IMYGIC®, also known as talimogene laherparepvec or T-VEC, marketed by Amgen Inc. (Thousand Oaks, CA). IMLYGIC® is a recombinant HSV-1 that includes functional deletions of ICP34.5 and ICP47 genes, and insertion of a nucleic acid encoding human granulocyte macrophage colony-stimulating factor (GM-CSF). ILYGIC® is Federal Drug Administration (FDA)-approved for local treatment by intralesional injection (intratumoral administration) of unresectable cutaneous, subcutaneous, and nodal lesions in patients with recurrent melanoma. In addition, IMLYGIC® is European Medicines Agency (EMA)-approved for treatment of adults with unresectable melanomas that is regionally or distantly metastatic (Stages IIIB, IIIC or IVM1a). In particular, the EMA-approved product is to be administered by intralesional injection (intratumoral administration) into cutaneous, subcutaneous, and/or nodal lesions that are visible, palpable or detectable by ultrasound guidance.

In some embodiments, the recombinant oncolytic virus is a recombinant adenovirus, such as a serotype 5 adenovirus. In one embodiment, the recombinant adenovirus is Oncorine (H101), formerly known as Onyx-015. Oncorine is a serotype 5 adenovirus engineered by inactivation (functional deletion) of viral E1B-55k and viral E3 genes. Oncorine is approved by the Chinese State Food and Drug Administration for treating head and neck cancer in combination with chemotherapy (anti-neoplastic agent therapy).

In some embodiments, the recombinant oncolytic virus is a recombinant pox virus. In some embodiments, the poxvirus is a vaccinia virus or a fowlpox virus. In some embodiments, the vaccinia virus is Modified Vaccinia Ankara. In some embodiments, the recombinant vaccinia virus has been genetically engineered by functional deletion of one or more viral genes encoding proteins that suppress a response (e.g., an anti-viral response) of a host cell, and/or by insertion of one or more transgenes encoding proteins that promote a response (e.g., an anti-tumor response) of a host cell (see, e.g., Guo et al., Journal of ImmunoTherapy of Cancer, 7: 6, 2019). In one embodiment, the recombinant vaccinia virus is Pexa-Vec, also known as pexastimogene devacirepvec and JX-594, which is a vaccinia virus engineered by inactivation (functional deletion) of the viral thymidine kinase gene, and by insertion of transgenes encoding human GM-CSF and beta-galactosidase (Heo et al., Nat Med, 19: 329-336, 2013). In another embodiment, the recombinant vaccinia virus comprises functional deletion of viral thymidine kinase and vaccinia growth factor genes, and insertion of a transgene encoding the chemokine, CXCL11 (see, e.g., Liu et al., OncoImmunology, 5: 3, e1091554, 2016; and Liu et al., Nature Communications, 8: 14754, 2017).

Further embodiments of the combination therapies of the present disclosure comprise at least one additional therapeutic agent. In some embodiments, the at least one additional therapeutic agent is selected from the group consisting of an immune checkpoint inhibitor, chemotherapy (antineoplastic agent), radiation therapy, and combinations thereof.

In some embodiments, the immune checkpoint inhibitor is an antagonist of at least one inhibitory immune checkpoint molecule. In some embodiments, the at least one inhibitory immune checkpoint molecule is selected from the group consisting PD-1 (CD279), PD-L1 (CD274), and CTLA4 (CD152). The immune checkpoint inhibitor may be a therapeutic biological product. For instance the immune checkpoint inhibitor may comprise an antibody or antigen-binding fragment thereof. The antibody or fragment may be a monoclonal antibody (mAb), a human antibody, a humanized antibody, or a chimeric antibody, and may include a human constant region. In some embodiments the human constant region is selected from the group consisting of IgG1, IgG2, IgG3, and IgG4 constant regions, and in certain embodiments, the human constant region is an IgG1 or IgG4 constant region. In some embodiments, the antibody or fragment is a bispecific antibody. In some embodiments, the antigen-binding fragment comprises one of the group consisting of Fab, Fab'-SH, F(ab')$_2$, scFv, and Fv fragments.

In some embodiments, the chemotherapy comprises at least one antineoplastic agent (i.e., WHO ATC code L01). In some embodiments, the at least one antineoplastic agent is selected from the group consisting of a cytotoxic antibiotic, a plant alkaloid, an antimetabolite, and alkylating agent, an other antineoplastic agent, and combinations thereof. As used in reference to chemotherapy, the antineoplastic agent is a "drug", as opposed to a "therapeutic biological product".

In some embodiments, the radiation therapy is external beam radiation therapy. In other embodiments, the radiation therapy is internal radiation therapy. In some embodiments, the radiation therapy is ablative radiation therapy.

As used herein the term "biosimilar" refers to a biological product that is similar to but without clinically meaningful differences in safety and effectiveness from a Federal Drug Administration (FDA)-approved reference product. For instance, there may be differences between a biosimilar product and a reference product in clinically inactive components (e.g., differences in excipients of the formulations, minor differences in glycosylation, etc.). Clinically meaningful characteristics can be assessed through pharmacokinetic and pharmacodynamic studies. In some embodiments, the biosimilar product is an interchangeable product as determined by the FDA. In some embodiments, the cancer vaccine is a biosimilar of an FDA-approved product.

IV. Compositions, Formulations and Routes of Administration

Pharmaceutical compositions of any of the compounds disclosed herein, or a salt thereof, or solvate thereof, are embraced by the present disclosure. Thus, the disclosure includes pharmaceutical compositions comprising a Cbl-b inhibitor, wherein the Cbl-B inhibitor is a compound of Formula (I), (I-a), (I-A)-(I-J), (II-A)-(II-H), (II-A-1)-(II-H-1), (III-A)-(III-H), (III-A-1)-(III-H-1), (IV-A)-(IV-J), or (IV-C-1)-(IV-J-1), or any variation thereof disclosed herein, or a pharmaceutically acceptable salt or solvate thereof, or tautomers thereof, or stereoisomers or mixtures of stereoisomers thereof, and a pharmaceutically acceptable excipient, such as a pharmaceutically acceptable vehicle or pharmaceutically acceptable carrier. In some embodiments, the compound is a compound selected from Compound Nos. 1-58 in Table 1, or a pharmaceutically acceptable salt or solvate thereof, or tautomers thereof, or stereoisomers or mixtures of stereoisomers thereof. In one aspect, the pharmaceutically acceptable salt is an acid addition salt, such as a salt formed with an inorganic or organic acid.

The compounds and compositions disclosed herein may be administered in any suitable form and by any suitable route that will provide sufficient levels of the compounds for treatment of the disease or disorder. In some embodiments, the Cbl-b inhibitor and/or the additional therapeutic agent are administered by enteral administration. In some embodiments, the enteral administration is oral administration. In other embodiments, the Cbl-b inhibitor and/or the additional therapeutic agent are administered by parenteral administration. In some embodiments, the parenteral administration is intratumoral injection. In some embodiments, the parenteral administration is by a route selected from the group consisting of intravenous, intraperitoneal, and subcutaneous.

Suitable routes of administration include oral administration, enteral administration, parenteral administration including subcutaneous injection, intravenous injection, intraarterial injection, intramuscular injection, intrasternal injection, intraperitoneal injection, intralesional injection, intraarticular injection, intratumoral injection, or infusion techniques. The compounds and compositions also can be administered sublingually, by mucosal administration, by buccal administration, subcutaneously, by spinal administration, by epidural administration, by administration to cerebral ventricles, by inhalation (e.g., as mists or sprays), nasal administration, vaginal administration, rectal administration, topical administration, or transdermal administration, or by sustained release or extended release mechanisms. The compounds and compositions can be administered in unit dosage formulations containing conventional pharmaceutically acceptable carriers, excipients, adjuvants, and vehicles as desired. The compounds and compositions may be administered directly to a specific or affected organ or tissue. The compounds can be mixed with pharmaceutically acceptable carriers, excipients, adjuvants, and vehicles to form compositions appropriate for the desired route of administration. In some embodiments, the compounds can be mixed with one or both of an antigen and an adjuvant. In some embodiments, the antigen is a cancer antigen.

In certain embodiments disclosed herein, especially those embodiments where a formulation is used for injection or other parenteral administration, including the routes listed herein, but also including any other route of administration described herein (such as oral, enteric, gastric, etc.), the formulations and preparations used in the methods are sterile. Sterile pharmaceutical formulations are compounded or manufactured according to pharmaceutical-grade sterilization standards (United States Pharmacopeia Chapters 797, 1072, and 1211; California Business & Professions Code 4127.7; 16 California Code of Regulations 1751, 21 Code of Federal Regulations 211) known to those of skill in the art. A "sterile" formulation is aseptic, or free or essentially free from all living microorganisms and their spores. Examples of methods of sterilization of pharmaceutical formulations include, but are not limited to, sterile filtration through sterile filtration membranes, exposure to radiation such as gamma radiation, and heat sterilization.

Oral administration is advantageous due to its ease of implementation and patient compliance. If a patient has difficulty swallowing, introduction of medicine via feeding tube, feeding syringe, or gastrostomy can be employed in order to accomplish enteric administration. The active compound, and, if present, other co-administered agents, can be enterally administered in any other pharmaceutically acceptable excipient suitable for formulation for administration via feeding tube, feeding syringe, or gastrostomy.

Intravenous administration also can be used advantageously, for delivery of the compounds or compositions to the bloodstream as quickly as possible and to circumvent the need for absorption from the gastrointestinal tract.

The compounds and compositions described for use herein can be administered in solid form, in liquid form, in aerosol form, or in the form of tablets, pills, caplets, capsules (such as hard gelatin capsules or soft elastic gelatin capsules), powder mixtures, granules, injectables, solutions, suppositories, enemas, colonic irrigations, emulsions, dispersions, food premixes, cachets, troches, lozenges, gums, ointments, cataplasms (poultices), pastes, powders, dressings, creams, patches, aerosols (e.g., nasal spray or inhalers), gels, suspensions (e.g., aqueous or non-aqueous liquid suspensions, oil-in-water emulsions or water-in-oil liquid emulsions), elixirs, or in other forms suitable for the route of administration. The compounds and compositions also can be administered in liposome formulations. The compounds also can be administered as prodrugs, where the prodrug undergoes transformation in the treated subject to a therapeutically effective form.

In addition, pharmaceutical formulations may contain preservatives, solubilizers, stabilizers, re-wetting agents, emulgators, sweeteners, dyes, adjusters, and salts for the adjustment of osmotic pressure, buffers, coating agents, or antioxidants. Formulations comprising the compound also may contain other substances that have valuable therapeutic properties. Pharmaceutical formulations may be prepared by known pharmaceutical methods. Additional formulations and methods of administration are known in the art. Suitable formulations can be found, e.g., in Remington: The Science and Practice of Pharmacy, Lippincott Williams & Wilkins, 21st ed. (2005), which is incorporated herein by reference.

Injectable preparations, for example, sterile injectable aqueous or oleaginous suspensions, may be formulated according to methods known in the art using suitable dispersing or wetting agents and suspending agents. The sterile injectable preparation also may be a sterile injectable solution or suspension in a parenterally acceptable diluent or solvent, for example, as a solution in propylene glycol. Among the acceptable vehicles and solvents that may be employed are water, saline, Ringer's solution, and isotonic sodium chloride solution. In addition, sterile, fixed oils are conventionally employed as a solvent or suspending medium. For this purpose, any bland fixed oil may be employed including synthetic mono or di-glycerides. In addition, fatty acids such as oleic acid may be used in the preparation of injectables.

Solid dosage forms for oral administration may include capsules, tablets, pills, powders, and granules. In such solid dosage forms, the active compound may be admixed with at least one inert diluent such as sucrose, lactose, talc, or starch. Such dosage forms also may comprise additional excipient substances other than inert diluents, e.g., lubricating agents such as magnesium stearate. In the case of capsules, tablets, and pills, the dosage forms also may comprise buffering agents. Tablets and pills additionally can be prepared with enteric coatings. Acceptable excipients for gel capsules with a soft shell are, for instance, plant oils, wax, fats, semisolid and liquid poly-ols, and so on.

Liquid dosage forms for oral administration may include pharmaceutically acceptable emulsions, solutions, suspensions, syrups, and elixirs containing inert diluents commonly used in the art, such as water. Such compositions also may comprise additional agents, such as wetting agents, emulsifying and suspending agents, cyclodextrins, and sweetening, flavoring, and perfuming agents. Alternatively, the compound also may be administered in neat form if suitable.

The compounds and compositions also can be administered in the form of liposomes. As is known in the art, liposomes are generally derived from phospholipids or other lipid substances. Liposomes are formed by mono or multilamellar hydrated liquid crystals that are dispersed in an aqueous medium. Any physiologically acceptable and metabolizable lipid capable of forming liposomes can be used. The present compositions in liposome form can contain stabilizers, preservatives, excipients, and the like, in addition to a compound as disclosed herein. Useful lipids include the phospholipids and phosphatidyl cholines (lecithins), both natural and synthetic. Methods to form liposomes are known in the art. See, for example, Gregoriadis, G. Ed., Liposome Technology, Third Edition: Liposome Technology: Liposome Preparation and Related Techniques, CRC Press, Boca Raton, Florida (2006); and Prescott, Ed., Methods in Cell Biology, Volume XIV, Academic Press, New York, N.W., p. 33 et seq (1976).

The amount of active ingredient that may be combined with the carrier materials to produce a single dosage form can vary depending upon the patient to whom the active ingredient is administered and the particular mode of administration. It will be understood, however, that the specific dose level for any particular patient will depend upon a variety of factors including the specific compound employed; the age, body weight, body area, body mass index (BMI), general health, sex, and diet of the patient; the time of administration and route of administration used; the rate of excretion; and the drug combination, if any, used. The compounds can be administered in a unit dosage formulation. The pharmaceutical unit dosage chosen is fabricated and administered to provide sufficient concentration of drug in the patient, subject, or individual.

Although the compounds for use as described herein can be administered as the sole active pharmaceutical agent, they also can be used in combination with one or more other agents. When additional active agents are used in combination with the compounds for use as described herein, the additional active agents may generally be employed in therapeutic amounts as indicated in the Physicians' Desk Reference (PDR) 71st Edition (2017), which is incorporated herein by reference, or such therapeutically useful amounts as would be known to one of ordinary skill in the art, or as are determined empirically for each patient.

Combinations of two or more of the compounds and compositions disclosed herein also can be used. The two or more compounds or compositions can be mixed together shortly before administration and administered together. The two or more compounds or compositions can be administered simultaneously, either by the same route of administration or by different routes of administration. The two or more compounds or compositions can be administered consecutively, either by the same route of administration or by different routes of administration. In one embodiment, a kit form can contain two or more compounds or compositions as individual compounds or compositions, with printed or electronic instructions for administration either as a mixture of compounds or compositions, as separate compounds or compositions administered simultaneously, or as separate compounds or compositions administered consecutively. Where three or more compounds or compositions are administered, they can be administered as a mixture of compounds or compositions, as separate compounds or compositions administered simultaneously, as separate compounds or compositions administered consecutively, as separate compounds or compositions where two or more may be administered simultaneously with the remainder administered consecutively before or after the simultaneous administration, or any other possible combination of mixed administration, simultaneous administration, and consecutive administration.

A compound as disclosed herein may in one aspect be in a purified form and compositions comprising a compound in purified forms are disclosed herein. Compositions comprising a compound as disclosed herein or a salt thereof are provided, such as compositions of substantially pure compounds. In some embodiments, a composition containing a compound as disclosed herein or a salt thereof is in substantially pure form. In one variation, "substantially pure" intends a composition that contains no more than 35% impurity, wherein the impurity denotes a compound other than the compound (or compounds, if combinations of compounds are used) to be administered in the composition, or a salt or solvate of the compound (or compounds, if combinations are used). The weight of any added vehicle, carrier, or excipient is excluded from such a calculation, and the added vehicle, carrier, or excipient is not considered as an impurity. For example, a composition of a substantially pure compound selected from a compound of Table 1 refers to a composition that contains no more than 35% impurity, wherein the impurity denotes a compound other than the compound or a salt or solvate thereof. In one variation, a composition of substantially pure compound or a salt or solvate thereof is provided wherein the composition contains no more than 25% impurity. In another variation, a composition of substantially pure compound or a salt or solvate thereof is provided wherein the composition contains no more than 20% impurity. In still another variation, a composition of substantially pure compound or a salt or solvate thereof is provided wherein the composition contains no more than 10% impurity. In a further variation, a composition of substantially pure compound or a salt or solvate thereof is provided wherein the composition contains no more than 5% impurity. In another variation, a composition of substantially pure compound or a salt or solvate thereof is provided wherein the composition contains no more than 3% impurity. In still another variation, a composition of substantially pure compound or a salt or solvate thereof is provided wherein the composition contains no more than 1% impurity. In a further variation, a composition of substantially pure compound or a salt or solvate thereof is provided wherein the composition contains no more than 0.5% impurity. In yet other variations, a composition of substantially pure compound means that the composition contains no more than 15%, no more than 10%, no more than 5%, no more than 3%, or no more than 1% impurity. An impurity may be the compound in a stereochemical form different from the desired stereochemical form. For instance, a composition of substantially pure (S)-compound means that the composition contains no more than 15%, no more than 10%, no more than 5%, no more than 3%, or no more than 1% of the (R)-form of the compound. Alternatively, as used herein, "enantiomeric excess (ee)" refers to a dimensionless mol ratio describing the purity of chiral substances that contain, for example, a single stereogenic center. For instance, an enantiomeric excess of zero would indicate a racemic (e.g., 50:50 mixture of enantiomers, or no excess of one enantiomer over the other). By way of further example, an enantiomeric excess of ninety-nine would indicate a nearly stereopure enantiomeric compound (i.e., large excess of one enantiomer over the other). The percentage enantiomeric excess, % ee=([(R)-compound]-[(S)-compound])/([(R)-compound]+[(S)-compound])×100, where the (R)-compound>(S)-compound; or % ee=([(S)-compound]-[(R)-compound])/([(S)-compound]+[(R)-compound])×100, where the (S)-compound>(R)-compound. Moreover, as used herein, "diastereomeric excess (de)" refers to a dimensionless mol ratio describing the purity of chiral substances that contain more than one stereogenic center. For example, a diastereomeric excess of zero would indicate an equimolar mixture of diastereoisomers. By way of further example, diastereomeric excess of ninety-nine would indicate a nearly stereopure diastereomeric compound (i.e., large excess of one diastereomer over the other). Diastereomeric excess may be calculated via a similar method to ee. As would be appreciated by a person of skill, de is usually reported as percent de (% de). % de may be calculated in a similar manner to % ee.

In some aspects, provided herein are compositions comprising a cell population containing a modified immune cell such as those described herein or produced by the methods disclosed herein. In some embodiments, the composition comprises a cell population containing a modified immune cell that has been in contact or is in contact with a Cbl-b inhibitor described herein or a composition thereof. In some embodiments, the modified immune cell has been or is in contact with an anti-CD3 antibody alone. In some embodiments, the modified immune cell has been or is in contact with an anti-CD3 antibody in combination with an anti-CD28 antibody. The provided compositions comprising a cell population containing a modified immune cell described herein may further comprise a pharmaceutical acceptable excipient.

In some aspects, also provided herein is a cell culture composition comprising a cell population containing an immune cell and a Cbl-b inhibitor described herein. In some embodiments, the immune cell is a human immune cell. In some embodiments, the immune cell is a cell selected from the group consisting of a hematopoietic cell, a multipotent stem cell, a myeloid progenitor cell, a lymphoid progenitor cell, a T-cell, a B-cell, and a NK-cell. In some embodiments, the cell culture composition further comprises an anti-CD3 antibody. In some embodiments, the cell culture composition further comprises an anti-CD3 antibody in combination with an anti-CD28 antibody. Methods for culturing cell compositions containing immune cells are well known in the art and are contemplated herein.

A modified immune cell or compositions as described herein, e.g., a composition comprising a cell population containing the modified immune cell or a pharmaceutical composition, can be provided in a suitable container. Suitable containers include, for example, bottles, vials (e.g., dual chamber vials), syringes (e.g., single or dual chamber syringes), bags (e.g., an intravenous bag), and tubes (e.g., test tubes). The container may be formed from a variety of materials such as glass or plastic.

In some embodiments, a composition comprising a cell population containing a modified immune cell as described herein (e.g., a cell culture composition) is provided in a culture vessel. A culture vessel as provided herein includes, but is not limited to, a tube (e.g., a test tube), a dish (e.g., a tissue culture dish), a bag, a multiwell plate (e.g., a 6-well tissue culture plate), and a flask (e.g., a cell culture flask).

Also provided are the compositions as described herein for any use described herein. In some embodiments, the compositions as described herein are for preparation of a medicament for treating or preventing a disease or condition associated with Cbl-b activity. In some embodiments, the compositions as described herein are for preparation of a medicament for treating cancer.

Pharmaceutical compositions of any of the compounds disclosed herein, or a salt or solvate thereof, for use in combination with a cancer vaccine are embraced by this disclosure. Thus, the disclosure includes pharmaceutical compositions comprising a Cbl-b inhibitor for use in combination with a cancer vaccine, wherein the Cbl-b inhibitor is a compound of 1-719 (including "a" and "b" variants thereof) of International Patent Appl. WO 2019/148005 or a compound of any of Formula (I-A), Formula (I), Formula (II-A), Formula (II), Formula (III-A), Formula (III), or Formula (IV), or any variation thereof disclosed therein, or a pharmaceutically acceptable salt or solvate thereof, or tautomers thereof, or stereoisomers or mixtures of stereoisomers thereof.

In addition, pharmaceutical compositions of any of the compounds disclosed herein, or a salt or solvate thereof, for use in combination with an oncolytic virus are embraced by this disclosure. Thus, the disclosure includes pharmaceutical compositions comprising a Cbl-b inhibitor for use in combination with an oncolytic virus, wherein the Cbl-b inhibitor is a compound of 1-719 (including "a" and "b" variants thereof) of International Patent Appl. WO 2019/148005 or a compound of any of Formula (I-A), Formula (I), Formula (II-A), Formula (II), Formula (III-A), Formula (III), or Formula (IV), or any variation thereof disclosed therein, or a pharmaceutically acceptable salt or solvate thereof, or tautomers thereof, or stereoisomers or mixtures of stereoisomers thereof. The compositions can further comprise a pharmaceutically acceptable excipient, such as a pharmaceutically acceptable vehicle or pharmaceutically acceptable carrier. In some embodiments, the pharmaceutical composition comprises both a small molecule Cbl-b inhibitor and a cancer vaccine. In some embodiments, the compound is a compound selected from Compound 60 and/or Compound 56 in Table 1, or a pharmaceutically acceptable salt or solvate thereof, or tautomers thereof, or stereoisomers or mixtures of stereoisomers thereof. In addition, in some embodiments, the pharmaceutical composition comprises both a small molecule Cbl-b inhibitor and an oncolytic virus. In some embodiments, the compound is a compound selected from Compound 60 and/or Compound 56 in Table 1, or a pharmaceutically acceptable salt or solvate thereof, or tautomers thereof, or stereoisomers or mixtures of stereoisomers thereof. In some embodiments, the compound is a compound selected from the Cbl-b inhibitors disclosed in the following patent applications: compounds 1-58 of U.S. Patent Appl. No. 62/849,722 or a compound of Formula (I) therein; compounds 1-58 of U.S. Patent Appl. No. 62/880, 437 or a compound of Formula (I) therein; or any variation thereof, or a pharmaceutically acceptable salt or solvate thereof, or tautomers thereof, or stereoisomers or mixtures of stereoisomers thereof.

In one aspect, the pharmaceutically acceptable salt is an acid addition salt, such as a salt formed with an inorganic acid or an organic acid.

The compounds, vaccines, and compositions disclosed herein may be administered in any suitable form and by any suitable route that will provide sufficient levels of the compounds, vaccines, or compositions for treatment of the disease or disorder. In some embodiments, the Cbl-b inhibitor and/or the cancer vaccine are administered by enteral administration. The compounds, oncolytic viruses, and compositions disclosed herein may be administered in any suitable form and by any suitable route that will provide sufficient levels of the compounds, oncolytic viruses, or compositions for treatment of the disease or disorder. In some embodiments, the Cbl-b inhibitor and/or the oncolytic virus are administered by enteral administration. In some embodiments, the enteral administration is oral administration. In other embodiments, the Cbl-b inhibitor and/or the cancer vaccine are administered by parenteral administration. In other embodiments, the Cbl-b inhibitor and/or the oncolytic virus are administered by parenteral administration. In some embodiments, the parenteral administration is intratumoral injection. In some embodiments, the parenteral administration is by a route selected from the group consisting of intravenous, intraperitoneal, and subcutaneous.

Suitable routes of administration include oral administration, enteral administration, parenteral administration including subcutaneous injection, intravenous injection, intraarterial injection, intramuscular injection, intrasternal injection, intraperitoneal injection, intralesional injection, intraarticular injection, intratumoral injection, or infusion techniques. The compounds, vaccines, and compositions also can be administered sublingually, by mucosal administration, by buccal administration, subcutaneously, by spinal administration, by epidural administration, by administration to cerebral ventricles, by inhalation (e.g., as mists or sprays), nasal administration, vaginal administration, rectal administration, topical administration, or transdermal administration, or by sustained release or extended release mechanisms. The compounds, vaccines, and compositions can be administered in unit dosage formulations containing conventional pharmaceutically acceptable carriers, excipients, adjuvants, and vehicles as desired. The compounds, vaccines, and compositions may be administered directly to a specific or affected organ or tissue. The compounds and/or vaccines can be mixed with pharmaceutically acceptable carriers, excipients, adjuvants, and vehicles to form compositions appropriate for the desired route of administration. The compounds, oncolytic viruses, and compositions also can be administered sublingually, by mucosal administration, by buccal administration, subcutaneously, by spinal administration, by epidural administration, by administration to cerebral ventricles, by inhalation (e.g., as mists or sprays), nasal administration, vaginal administration, rectal administration, topical administration, or transdermal administration, or by sustained release or extended release mechanisms. The compounds, oncolytic viruses, and compositions can be administered in unit dosage formulations containing conventional pharmaceutically acceptable carriers, excipients, adjuvants, and vehicles as desired. The compounds, oncolytic viruses, and compositions may be administered directly to a specific or affected organ or tissue. The compounds and/or oncolytic viruses can be mixed with pharmaceutically acceptable carriers, excipients, adjuvants, and vehicles to form compositions appropriate for the desired route of administration.

In certain embodiments disclosed herein, especially those embodiments where a formulation is used for injection or other parenteral administration, including the routes listed herein, but also including any other route of administration described herein (such as oral, enteric, gastric, etc.), the formulations and preparations used in the methods are sterile, except for the presence of the presence of a microbial vector in certain cancer vaccines. To prepare such preparations, all components of the formulations or preparations are prepared in a sterile manner before combining with the microbial vector. In certain embodiments disclosed herein, especially those embodiments where a formulation is used for injection or other parenteral administration, including the routes listed herein, but also including any other route of administration described herein (such as oral, enteric, gastric, etc.), the formulations and preparations used in the methods are sterile, except for the presence of the oncolytic virus. To prepare such preparations, all components of the formulations or preparations are prepared in a sterile manner before combining with the oncolytic virus. Sterile pharmaceutical formulations are compounded or manufactured according to pharmaceutical-grade sterilization standards (United States Pharmacopeia Chapters 797, 1072, and 1211; California Business & Professions Code 4127.7; 16 California Code of Regulations 1751, 21 Code of Federal Regulations 211) known to those of skill in the art. A "sterile" formulation is aseptic, or free or essentially free from all living microorganisms and their spores. Examples of methods of sterilization of pharmaceutical formulations include, but are not limited to, sterile filtration through sterile filtration membranes, exposure to radiation such as gamma radiation, and heat sterilization.

Oral administration is advantageous due to its ease of implementation and patient compliance. If a patient has difficulty swallowing, introduction of medicine via feeding tube, feeding syringe, or gastrostomy can be employed in order to accomplish enteric administration. The active compound, vaccine, or composition, and, if present, other co-administered agents, can be enterally administered in any other pharmaceutically acceptable excipient suitable for formulation for administration via feeding tube, feeding syringe, or gastrostomy. The active compound, oncolytic virus, or composition, and, if present, other co-administered agents, can be enterally administered in any other pharmaceutically acceptable excipient suitable for formulation for administration via feeding tube, feeding syringe, or gastrostomy.

Intravenous administration also can be used advantageously, for delivery of the compounds, vaccines, or compositions to the bloodstream as quickly as possible and to circumvent the need for absorption from the gastrointestinal tract. Intravenous administration also can be used advantageously, for delivery of the compounds, oncolytic viruses, or compositions to the bloodstream as quickly as possible and to circumvent the need for absorption from the gastrointestinal tract.

The compounds, vaccines, and compositions described for use herein can be administered in solid form, in liquid form, in aerosol form, or in the form of tablets, pills, caplets, capsules (such as hard gelatin capsules or soft elastic gelatin capsules), powder mixtures, granules, injectables, solutions, suppositories, enemas, colonic irrigations, emulsions, dispersions, food premixes, cachets, troches, lozenges, gums, ointments, cataplasms (poultices), pastes, powders, dressings, creams, patches, aerosols (e.g., nasal spray or inhalers), gels, suspensions (e.g., aqueous or non-aqueous liquid suspensions, oil-in-water emulsions or water-in-oil liquid emulsions), elixirs, or in other forms suitable for the route of administration. The compounds, vaccines, and compositions also can be administered in liposome formulations. The compounds, oncolytic viruses, and compositions described for use herein can be administered in solid form, in liquid form, in aerosol form, or in the form of tablets, pills, caplets, capsules (such as hard gelatin capsules or soft elastic gelatin capsules), powder mixtures, granules, injectables, solutions, suppositories, enemas, colonic irrigations, emulsions, dispersions, food premixes, cachets, troches, lozenges, gums, ointments, cataplasms (poultices), pastes, powders, dressings, creams, patches, aerosols (e.g., nasal spray or inhalers), gels, suspensions (e.g., aqueous or non-aqueous liquid suspensions, oil-in-water emulsions or water-in-oil liquid emulsions), elixirs, or in other forms suitable for the route of administration. The compounds, oncolytic viruses, and compositions also can be administered in liposome formulations. The compounds also can be administered as prodrugs, where the prodrug undergoes transformation in the treated subject to a therapeutically effective form.

In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants. Formulations comprising the compound, vaccine, or composition also may contain other substances that have valuable therapeutic properties. Formulations comprising the compound, oncolytic virus, or composition also may contain other substances that have valuable therapeutic properties. Pharmaceutical formulations may be prepared by known pharmaceutical methods. Additional formulations and methods of administration are known in the art. Suitable formulations can be found, e.g., in Remington: The Science and Practice of Pharmacy, Lippincott Williams & Wilkins, 21st ed. (2005), which is incorporated herein by reference.

Injectable preparations, for example, sterile injectable aqueous or oleaginous suspensions of the small molecule Cbl-b inhibitor, may be formulated according to methods known in the art using suitable dispersing or wetting agents and suspending agents. The sterile injectable preparation also may be a sterile injectable solution or suspension in a parenterally acceptable diluent or solvent, for example, as a solution in propylene glycol. Among the acceptable vehicles and solvents that may be employed are water, saline, Ringer's solution, and isotonic sodium chloride solution. In addition, sterile, fixed oils are conventionally employed as a solvent or suspending medium. For this purpose, any bland fixed oil may be employed including synthetic mono or di-glycerides. In addition, fatty acids such as oleic acid may be used in the preparation of injectables.

Solid dosage forms for oral administration may include capsules, tablets, pills, powders, and granules. In such solid dosage forms, the active compound, vaccine, or composition may be admixed with at least one inert diluent such as sucrose, lactose, talc, or starch. In such solid dosage forms, the active compound, oncolytic virus, or composition may be admixed with at least one inert diluent such as sucrose, lactose, talc, or starch. Such dosage forms also may comprise additional excipient substances other than inert diluents, e.g., lubricating agents such as magnesium stearate. In the case of capsules, tablets, and pills, the dosage forms also may comprise buffering agents. Tablets and pills additionally can be prepared with enteric coatings. Acceptable excipients for gel capsules with a soft shell are, for instance, plant oils, wax, fats, semisolid and liquid poly-ols, and so on.

Liquid dosage forms for oral administration may include pharmaceutically acceptable emulsions, solutions, suspensions, syrups, and elixirs containing inert diluents commonly used in the art, such as water. Such compositions also may comprise additional agents, such as wetting agents, emulsifying and suspending agents, cyclodextrins, and sweetening, flavoring, and perfuming agents. Alternatively, the compound also may be administered in neat form if suitable.

The compounds, vaccines, and compositions also can be administered in the form of liposomes. The compounds, oncolytic viruses, and compositions also can be administered in the form of liposomes. As is known in the art, liposomes are generally derived from phospholipids or other lipid substances. Liposomes are formed by mono or multi-lamellar hydrated liquid crystals that are dispersed in an aqueous medium. Any physiologically acceptable and metabolizable lipid capable of forming liposomes can be used. The present compositions in liposome form can contain stabilizers, preservatives, excipients, and the like, in addition to a compound or vaccine as disclosed herein. The present compositions in liposome form can contain stabilizers, preservatives, excipients, and the like, in addition to a compound or oncolytic virus as disclosed herein. Useful lipids include the phospholipids and phosphatidyl cholines (lecithins), both natural and synthetic. Methods to form liposomes are known in the art. See, for example, Gregoriadis, G. Ed., Liposome Technology, Third Edition: Liposome Technology: Liposome Preparation and Related Techniques, CRC Press, Boca Raton, Florida (2006); and Prescott, Ed., Methods in Cell Biology, Volume XIV, Academic Press, New York, N.W., p. 33 et seq (1976).

The amount of active ingredient that may be combined with the carrier materials to produce a single dosage form can vary depending upon the patient to whom the active ingredient is administered and the particular mode of administration. It will be understood, however, that the specific dose level for any particular patient will depend upon a variety of factors including the specific compound or vaccine employed; the age, body weight, body area, body mass index (BMI), general health, sex, and diet of the patient; the time of administration and route of administration used; the rate of excretion; and the drug combination, if any, used. The compounds, vaccines, and compositions can be administered in a unit dosage formulation. It will be understood, however, that the specific dose level for any particular patient will depend upon a variety of factors including the specific compound or oncolytic virus employed; the age, body weight, body area, body mass index (BMI), general health, sex, and diet of the patient; the time of administration and route of administration used; the rate of excretion; and the drug combination, if any, used. The compounds, oncolytic viruses, and compositions can be administered in a unit dosage formulation. The pharmaceutical unit dosage chosen is fabricated and administered to provide sufficient concentration of drug in the patient, subject, or individual.

Although the compounds, vaccines, and compositions for use as described herein can be administered as the sole active pharmaceutical agents, they also can be used in combination with one or more other agents. When additional active agents are used in combination with the compounds, vaccines, or compositions for use as described herein, the additional active agents may generally be employed in therapeutic amounts as indicated in the Physicians' Desk Reference (PDR) 71st Edition (2017), which is incorporated herein by reference, or such therapeutically useful amounts as would be known to one of ordinary skill in the art, or as are determined empirically for each patient. Although the compounds, oncolytic viruses, and compositions for use as described herein can be administered as the sole active pharmaceutical agents, they also can be used in combination with one or more other agents. When additional active agents are used in combination with the compounds, oncolytic viruses, or compositions for use as described herein, the additional active agents may generally be employed in therapeutic amounts as indicated in the Physicians' Desk Reference (PDR) 71st Edition (2017), which is incorporated herein by reference, or such therapeutically useful amounts as would be known to one of ordinary skill in the art, or as are determined empirically for each patient.

Combinations of two or more of the compounds, vaccines, and compositions disclosed herein also can be used. The two or more compounds, vaccines, or compositions can be mixed together shortly before administration and administered together. The two or more compounds, vaccines, or compositions can be administered simultaneously, either by the same route of administration or by different routes of administration. The two or more compounds, vaccines, or compositions can be administered consecutively, either by the same route of administration or by different routes of administration. In one embodiment, a kit form can contain two or more compounds, vaccines, or compositions as individual compounds, vaccines, or compositions, with printed or electronic instructions for administration either as a mixture of compounds, vaccines, or compositions, as separate compounds, vaccines, or compositions administered simultaneously, or as separate compounds, vaccines, or compositions administered consecutively. Where three or more compounds, vaccines, or compositions are administered, they can be administered as a mixture of compounds, vaccines, or compositions, as separate compounds, vaccines, or compositions administered simultaneously, as separate compounds, vaccines, or compositions administered consecutively, as separate compounds, vaccines, or compositions where two or more may be administered simultaneously with the remainder administered consecutively before or after the simultaneous administration, or any other possible combination of mixed administration, simultaneous administration, and consecutive administration.

Combinations of two or more of the compounds, oncolytic viruses, and compositions disclosed herein also can be used. The two or more compounds, oncolytic viruses, or compositions can be mixed together shortly before administration and administered together. The two or more compounds, oncolytic viruses, or compositions can be administered simultaneously, either by the same route of administration or by different routes of administration. The two or more compounds, oncolytic viruses, or compositions can be administered consecutively, either by the same route of administration or by different routes of administration. In one embodiment, a kit form can contain two or more compounds, oncolytic viruses, or compositions as individual compounds, oncolytic viruses, or compositions, with printed or electronic instructions for administration either as a mixture of compounds, oncolytic viruses, or compositions, as separate compounds, oncolytic viruses, or compositions administered simultaneously, or as separate compounds, oncolytic viruses, or compositions administered consecutively. Where three or more compounds, oncolytic viruses, or compositions are administered, they can be administered as a mixture of compounds, oncolytic viruses, or compositions, as separate compounds, oncolytic viruses, or compositions, as separate compounds, oncolytic viruses, or compositions administered simultaneously, as separate compounds, oncolytic viruses, or compositions administered consecutively, as separate compounds, oncolytic viruses, or compositions where two or more may be administered simultaneously with the remainder administered consecutively before or after the simultaneous administration, or any other possible combination of mixed administration, simultaneous administration, and consecutive administration.

A compound as disclosed herein for use in the pharmaceutical compositions and methods described herein may in one aspect be in a purified form and compositions comprising a compound in purified forms are disclosed herein. Compositions comprising a compound as disclosed herein or a salt thereof are provided, such as compositions of substantially pure compounds. In some embodiments, a composition containing a compound as disclosed herein or a salt thereof is in substantially pure form. In one variation, "substantially pure" intends a composition that contains no more than 35% impurity, wherein the impurity denotes a compound other than the compound (or compounds, if combinations of compounds are used) to be administered in the composition, or a salt or solvate of the compound (or compounds, if combinations are used). The weight of any added vehicle, carrier, or excipient is excluded from such a calculation, and the added vehicle, carrier, or excipient is not considered as an impurity. For example, a composition of a substantially pure compound selected from a compound of Table 1 refers to a composition that contains no more than 35% impurity, wherein the impurity denotes a compound other than the compound or a salt or solvate thereof. In one variation, a composition of substantially pure compound or a salt or solvate thereof is provided wherein the composition contains no more than 25% impurity. In another variation, a composition of substantially pure compound or a salt or solvate thereof is provided wherein the composition contains no more than 20% impurity. In still another variation, a composition of substantially pure compound or a salt or solvate thereof is provided wherein the composition contains no more than 10% impurity. In a further variation, a composition of substantially pure compound or a salt or solvate thereof is provided wherein the composition contains no more than 5% impurity. In another variation, a composition of substantially pure compound or a salt or solvate thereof is provided wherein the composition contains no more than 3% impurity. In still another variation, a composition of substantially pure compound or a salt or solvate thereof is provided wherein the composition contains no more than 1% impurity. In a further variation, a composition of substantially pure compound or a salt or solvate thereof is provided wherein the composition contains no more than 0.5% impurity. In yet other variations, a composition of substantially pure compound means that the composition contains no more than 15%, no more than 10%, no more than 5%, no more than 3%, or no more than 1% impurity. An impurity may be the compound in a stereochemical form different from the desired stereochemical form. For instance, a composition of substantially pure (S)-compound means that the composition contains no more than 15%, no more than 10%, no more than 5%, no more than 3%, or no more than 1% of the (R)-form of the compound.

Alternatively, as used herein, "enantiomeric excess (ee)" refers to a dimensionless mol ratio describing the purity of chiral substances that contain, for example, a single stereogenic center. For instance, an enantiomeric excess of zero would indicate a racemic (e.g., 50:50 mixture of enantiomers, or no excess of one enantiomer over the other). By way of further example, an enantiomeric excess of ninety-nine would indicate a nearly stereopure enantiomeric compound (i.e., large excess of one enantiomer over the other). The percentage enantiomeric excess, % ee=([(R)-compound]-[(S)-compound])/([(R)-compound]+[(S)-compound])×100, where the (R)-compound>(S)-compound; or % ee=([(S)-compound]-[(R)-compound])/([(S)-compound]+[(R)-compound])×100, where the (S)-compound>(R)-compound. Moreover, as used herein, "diastereomeric excess (de)" refers to a dimensionless mol ratio describing the purity of chiral substances that contain more than one stereogenic center. For example, a diastereomeric excess of zero would indicate an equimolar mixture of diastereoisomers. By way of further example, diastereomeric excess of ninety-nine would indicate a nearly stereopure diastereomeric compound (i.e., large excess of one diastereomer over the other). Diastereomeric excess may be calculated via a similar method to ee. As would be appreciated by a person of skill, de is usually reported as percent de (% de). % de may be calculated in a similar manner to % ee.

A compound, vaccine, or composition as disclosed herein can be provided in a suitable container. A compound, oncolytic virus, or composition as disclosed herein can be provided in a suitable container. Suitable containers include, for example, bottles, vials (e.g., dual chamber vials), syringes (e.g., single or dual chamber syringes), bags (e.g., an intravenous bag) and tubes (e.g., test tubes). The container may be formed from a variety of materials such as glass or plastic.

V. Articles of Manufacture or Kits

Also provided are articles of manufacture comprising any of the compounds, pharmaceutical compositions, cells, modified immune cells, cell populations, cell compositions, cell cultures, or cell culture compositions described herein. The articles of manufacture include suitable containers or packaging materials for the compounds, pharmaceutical compositions, cells, modified immune cells, cell populations, cell compositions, cell cultures, or cell culture compositions. Examples of a suitable container include, but are not limited to, a bottle, a vial, a syringe, an intravenous bag, or a tube. For cells, modified immune cells, cell populations, cell compositions, cell cultures, or cell culture compositions, a suitable container can be a culture vessel, including, but not limited to, a tube, a dish, a bag, a multiwell plate, or a flask.

Also provided are kits comprising any of the compounds, pharmaceutical compositions, cells, modified immune cells, cell populations, cell compositions, cell cultures, or cell culture compositions described herein. The kits can contain the compounds, pharmaceutical compositions, cells, modified immune cells, cell populations, cell compositions, cell cultures, or cell culture compositions in suitable containers or packaging materials, including, but not limited to, a bottle, a vial, a syringe, an intravenous bag, or a tube. The kits can contain cells, modified immune cells, cell populations, cell compositions, cell cultures, or cell culture compositions in a culture vessel, including, but not limited to, a tube, a dish, a bag, a multiwell plate, or a flask. The kits can comprise the compounds, pharmaceutical compositions, cells, modified immune cells, cell populations, cell compositions, cell cultures, or cell culture compositions for administration to an individual in single-dose form or in multiple-dose form. The kits can further comprise instructions or a label for administering the compounds, pharmaceutical compositions, cells, modified immune cells, cell populations, cell compositions, cell cultures, or cell culture compositions to an individual according to any of the methods disclosed herein. The kits can further comprise equipment for administering the compounds, pharmaceutical compositions, cells, modified immune cells, cell populations, cell compositions, cell cultures, or cell culture compositions to an individual, including, but not limited to, needles, syringes, tubing, or intravenous bags. The kits can further comprise instructions for producing any of the compounds, pharmaceutical compositions, cells, modified immune cells, cell populations, cell compositions, cell cultures, or cell culture compositions disclosed herein.

Also provided are articles of manufacture comprising any of the compounds, vaccines, or pharmaceutical compositions described herein. The articles of manufacture include suitable containers or packaging materials for the compounds, vaccines, or pharmaceutical compositions. Also provided are articles of manufacture comprising any of the compounds, oncolytic viruses, or pharmaceutical compositions described herein. The articles of manufacture include suitable containers or packaging materials for the compounds, oncolytic viruses, or pharmaceutical compositions. Examples of a suitable container include, but are not limited to, a bottle, a vial, a syringe, an intravenous bag or a tube.

Also provided are kits comprising any of the compounds, vaccines, or pharmaceutical compositions described herein. The kits can contain the compounds, vaccines, or pharmaceutical compositions in suitable containers or packaging materials, including, but not limited to, a bottle, a vial, a syringe, an intravenous bag or a tube. The kits can comprise the compounds, vaccines, or pharmaceutical compositions for administration to an individual in single-dose form or in multiple-dose form. The kits can further comprise instructions or a label for administering the compounds, vaccines, or pharmaceutical compositions to an individual according to any of the methods disclosed herein. The kits can further comprise equipment for administering the compounds, vaccines, or pharmaceutical compositions to an individual, including, but not limited to, needles, syringes, tubing, or intravenous bags. The kits can further comprise instructions for producing any of the compounds, vaccines, or pharmaceutical compositions disclosed herein.

Also provided are kits comprising any of the compounds, oncolytic viruses, or pharmaceutical compositions described herein. The kits can contain the compounds, oncolytic viruses, or pharmaceutical compositions in suitable containers or packaging materials, including, but not limited to, a bottle, a vial, a syringe, an intravenous bag or a tube. The kits can comprise the compounds, oncolytic viruses, or pharmaceutical compositions for administration to an individual in single-dose form or in multiple-dose form. The kits can further comprise instructions or a label for administering the compounds, oncolytic viruses, or pharmaceutical compositions to an individual according to any of the methods disclosed herein. The kits can further comprise equipment for administering the compounds, oncolytic viruses, or pharmaceutical compositions to an individual, including, but not limited to, needles, syringes, tubing, or intravenous bags. The kits can further comprise instructions for producing any of the compounds, oncolytic viruses, or pharmaceutical compositions disclosed herein.

The disclosure will be more fully understood by reference to the following examples. They should not, however, be construed as limiting the scope of this disclosure. It is understood that the examples and embodiments described herein are for illustrative purposes only and that various modifications or changes in light thereof will be suggested to persons skilled in the art and are to be included within the spirit and purview of this application and scope of the appended claims.

EXAMPLES

General Work-Up Procedure 1

Aqueous solutions were extracted with ethyl acetate 2-3 times. The combined organic extract was dried over sodium sulfate, or anhydrous magnesium sulfate, or was washed with brine or saturated ammonium chloride aqueous solution before drying, filtration, and concentration under vacuum.

Purification Procedures

Preparative-scale chiral supercritical fluid chromatography (SFC) was performed using various CHIRALPAK columns, such as CHIRALPAK AS-H, CHIRALPAK AD-H, or CHIRALPAK IG, using solvent systems such as $CO_2$/MeOH, $CO_2$/EtOH, or $CO_2$/(MeOH+acetonitrile).

Preparative-scale chiral HPLC was performed using various CHIRALPAK columns, such as CHIRALPAK IA, CHIRAL ART Cellulose-SB, CHIRALPAK IF, and CHIRALPAK IG, using solvent systems such as hexane/methanol, hexane/ethanol, (hexane+dichloromethane)/ethanol, MTBE/methanol, MTBE/ethanol, and (hexane-8 mmol/L $NH_3$)/methanol, Mobile Phase B: ethanol and hexane/IPA.

Preparative-scale HPLC was performed using columns such as SunFire Prep C18 OBD, XBridge Prep OBD C18, and XBridge Shield RP18 OBD, using solvent systems such as (water-0.1% formic acid)/acetonitrile, (water-10 mmol/L $NH_4HCO_3$)/acetonitrile, or (water-10 mmol/L $NH_4HCO_3$)/acetonitrile.

Chromatography A refers to purification over silica gel, typically in pre-packed cartridges, eluting with mixtures of EtOAc in hexanes or petroleum ether; Chromatography B refers to elution with mixtures of MeOH in DCM; Chromatography C refers to use of $C_{18}$ reverse-phase silica gel, eluting with mixtures of acetonitrile in water; Chromatography D refers to elution with mixtures of ethanol, EtOAc, and hexanes. Compounds drawn without stereochemistry in Table 1 were tested as racemic or diasteromeric mixtures in the Biological Examples.

Abbreviations used in the Examples include the following: HATU: 1-[bis(dimethylamino)methylene]-1H-1,2,3-triazolo[4,5-b]pyridinium 3-oxide hexafluorophosphate; T3P: propylphosphonic anhydride; Xantphos: 4,5-Bis(diphenylphosphino)-9,9-dimethylxanthene; NBS: N-bromosuccinimide; BPO: benzoyl peroxide; THF: tetrahydrofuran; EtOAc: ethyl acetate; DCM: dichloromethane; MeOH: methanol; DCE: 1,2-dichloroethane; TEA: triethylamine; DIPEA: N,N-Diisopropylethylamine; and DMF: N,N-dimethylformamide.

Example A: Synthesis of Methyl 2-(bromomethyl)-5-formyl-3-(trifluoromethyl)benzoate

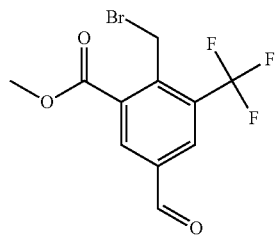 [SMILES: COC(=O)c1cc(C=O)cc(C(F)(F)F)c1CBr]

Step 1: Synthesis of 3-(methoxycarbonyl)-4-methyl-5-(trifluoromethyl)benzoic acid. To a degassed solution of methyl 5-bromo-2-methyl-3-(trifluoromethyl)benzoate (18.0 g, 60.8 mmol), oxalic acid (11.5 g, 91.2 mmol), acetic anhydride (9.3 g, 91.2 mmol), and DIPEA (11.8 g, 91.2 mmol) in DMF (200 mL) were added $Pd(OAc)_2$ (1.4 g, 6.1 mmol) and XantPhos (1.8 g, 3.0 mmol). The mixture was stirred at 100° C. for 16 h under nitrogen. The reaction was quenched by the addition of HCl (1 M, 300 mL) to pH~3, followed by General Work-up Procedure 1. The residue was purified by Chromatography C to afford the title compound (7.5 g, 47%).

Step 2: Synthesis of 4-(bromomethyl)-3-(methoxycarbonyl)-5-(trifluoromethyl)benzoic acid. To a stirred solution of 4-methyl-3-(methoxycarbonyl)-5-(trifluoromethyl)benzoic acid (8 g, 30.5 mmol) and NBS (8.2 g, 46 mmol) in $CCl_4$ (160 mL) was added BPO (2.2 g, 9 mmol). The solution was stirred at 80° C. for 16 h. The mixture was concentrated. The crude product was purified by Chromatography B to afford the title compound (8.0 g, 77%). MS (ESI) calculated for ($C_{11}HgBrF_3O_4$) [M−H]⁻, 339.0; found, 339.1.

Step 3: Synthesis of methyl 2-(bromomethyl)-5-(hydroxymethyl)-3-(trifluoro-methyl)benzoate. To a stirred solution of 4-(bromomethyl)-3-(methoxycarbonyl)-5-(trifluoro-methyl)benzoic acid (2.65 g, 7.77 mmol) in THF (30 mL) was added borane (19.4 mL, 19.4 mmol, 1 M in THF). The solution was stirred at rt for 6 h. The reaction was then quenched by the addition of methanol (10 mL). The mixture was concentrated. The residue was purified by Chromatography A to afford the title compound (1.40 g, 84%).

Step 4: Synthesis of methyl 2-(bromomethyl)-5-formyl-3-(trifluoromethyl)-benzoate. To a stirred solution of methyl 2-(bromomethyl)-5-(hydroxymethyl)-3-(trifluoro-methyl) benzoate (7.1 g, 21.71 mmol) in EtOAc (70 mL) was added 2-iodoxybenzoic acid (9.1 g, 32.5 mmol). The reaction was stirred at 70° C. for 3 h. The solids were removed by filtration, and the filtrate was concentrated in vacuo. The residue was purified by Chromatography A to afford the title compound (6.6 g, 94%).

Example B: Synthesis of (R)-6-((4,4-difluoro-3-methylpiperidin-1-yl)methyl)-4-(trifluoromethyl) isoindolin-1-one

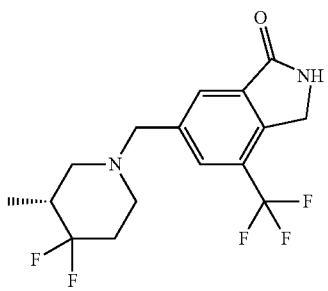 [SMILES: C[C@@H]1CN(Cc2cc3c(c(C(F)(F)F)c2)CNC3=O)CCC1(F)F]

To a stirring solution of (3R)-4,4-difluoro-3-methylpiperidine hydrochloride (5.00 g, 29.1 mmol) in DCM (300.00 mL) was added TEA (24.2 mL, 175 mmol) and sodium triacetoxyborohydride (37.1 g, 175 mmol). The suspension was stirred for 10 min and then cooled to 0° C. before methyl 2-(bromomethyl)-5-formyl-3-(trifluoromethyl)benzoate (9.47 g, 29.1 mmol) in 20 mL of DCM was added. The mixture was stirred at room temperature for about 12 h. The reaction was quenched with saturated ammonium chloride followed by General Work-up Procedure 1 using DCM. After removal of solvent, the crude residue was dissolved in methanol (100 mL) and then ammonia (7 N in methanol, 100 mL) was added to the solution. The mixture was stirred at room temperature for 12 hours. The crude was concentrated and purified by Chromatography B to afford the title compound (7.10 g, 70.0%).

Example C: 4-cyclopropyl-1-oxo-2H,3H-pyrrolo[3,4-c]pyridine-6-carbaldehyde

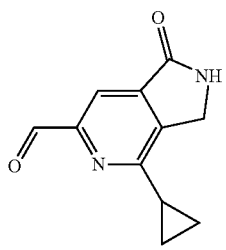 [SMILES: O=Cc1cc2c(c(C3CC3)n1)CNC2=O]

Step 1: Synthesis of 3-amino-6-chloro-2-iodopyridine-4-carboxylic acid. To a solution of 5-amino-2-chloropyridine-4-carboxylic acid (100.0 g, 579.47 mmol) in DMF (1.4 L) was added N-iodosuccinimide (195.6 g, 869.21 mmol) in portions at 0~10° C. After stirring for 30 min, the resulting mixture was heated to 80° C. and stirred for 16 h. The reaction mixture was quenched by the addition of water followed by General Work-up Procedure 1 to afford the title compound (140.0 g, crude), which was used in the next step without purification.

Step 2: Synthesis of methyl 3-amino-6-chloro-2-iodopyridine-4-carboxylate. To a mixture of 3-amino-6-chloro-2-iodopyridine-4-carboxylic acid (70.0 g, 234.80 mmol) in methanol (90.0 mL) and DCM (900 mL) was added TMSCHN$_2$ (176 mL, 2 M in hexane) dropwise at 0° C. The resulting mixture was stirred at room temperature for 16 h. When the reaction was completed, the organic solvents were removed under vacuum. The crude residue was triturated with 15% ethyl acetate in petroleum ether. The solids were collected by filtration and dried to afford the title compound (65.0 g, crude), which was used in the next step without purification.

Step 3: Synthesis of methyl 3-amino-6-chloro-2-cyclopropylpyridine-4-carboxylate. A degassed mixture of methyl 3-amino-6-chloro-2-iodopyridine-4-carboxylate (45.0 g, 144.23 mmol), cyclopropylboronic acid (49.6 g, 576.92 mmol), K$_2$CO$_3$ (59.7 g, 432.69 mmol), and Pd(dppf)Cl$_2$ (10.5 g, 14.42 mmol) in dioxane (1.5 L) was stirred at 100° C. for 16 h under N$_2$ atmosphere. The solids were filtered off and the filtrate was concentrated under vacuum. The crude residue was dissolved in ethyl acetate and water, and General Work-up Procedure 1 was followed before the crude was purified by Chromatography A to afford the title compound (22.1 g, 67% over three steps).

Step 4: Synthesis of methyl 6-chloro-2-cyclopropyl-3-iodopyridine-4-carboxylate. To a mixture of methyl 3-amino-6-chloro-2-cyclopropylpyridine-4-carboxylate (25.0 g, 110.62 mmol) in dichloromethane (1.5 L) were successively added t-BuONO (17.0 g, 169.00 mmol) and BF$_3$·Et$_2$O (19.0 g, 264.70 mmol) dropwise at 0° C. under N$_2$ atmosphere. The resulting mixture was stirred at room temperature for 2 h. The reaction mixture was quenched by the addition of hexane. The solids were collected by filtration and dried to afford 6-chloro-2-cyclopropyl-4-(methoxycarbonyl)pyridine-3-diazonium tetrafluoroborate (33.4 g), which was added to a mixture of KI (34.1 g, 205.52 mmol) in water (250.0 mL) in portions at 50° C. The resulting mixture was stirred at 50° C. for 2 h. When the reaction was completed, General Work-up Procedure 1 was followed, and the resulting residue was purified by Chromatography A to afford the title compound (23.0 g, 62% over two steps).

Step 5: Synthesis of methyl 6-chloro-2-cyclopropyl-3-methylpyridine-4-carboxylate. A degassed mixture of methyl 6-chloro-2-cyclopropyl-3-iodopyridine-4-carboxylate (23.0 g, 68.05 mmol), methylboronic acid (16.3 g, 272.20 mmol), Pd(dppf)Cl$_2$ (4.9 g, 6.81 mmol), and K$_2$CO$_3$ (28.2 g, 204.15 mmol) in dioxane (500 mL) was stirred at 90° C. for 16 h under N$_2$ atmosphere. The solids were filtered off and the filtrate was concentrated under vacuum. The crude residue was dissolved in ethyl acetate and water and General Work-up Procedure 1 was followed before the crude was purified by Chromatography A to afford the title compound (12.5 g, 83%).

Step 6: Synthesis of methyl 3-(bromomethyl)-6-chloro-2-cyclopropylpyridine-4-carboxylate. A mixture of methyl 6-chloro-2-cyclopropyl-3-methylpyridine-4-carboxylate (12.5 g, 55.56 mmol), NBS (19.8 g, 111.11 mmol), and BPO (4.0 g, 16.67 mmol) in CCl$_4$ (150.0 mL) was stirred at 80° C. for 16 h under N$_2$ atmosphere. When the reaction was completed, the solids were filtered off and the filtrate was concentrated under vacuum. The residue was purified by Chromatography A to afford the title compound (7.8 g, 50%).

Step 7: Synthesis of 6-chloro-4-cyclopropyl-2H,3H-pyrrolo[3,4-c]pyridin-1-one. A mixture of methyl 3-(bromomethyl)-6-chloro-2-cyclopropylpyridine-4-carboxylate (7.8 g, 25.83 mmol) in NH$_3$ (7 M in MeOH, 80.0 mL) was stirred at room temperature for 16 h under N$_2$ atmosphere. The resulting mixture was filtered, and the solids were collected and washed with methanol to afford 6-chloro-4-cyclopropyl-2H,3H-pyrrolo[3,4-c]pyridin-1-one (5.0 g, 92.1%).

Step 8: Synthesis of 4-cyclopropyl-6-ethenyl-2H,3H-pyrrolo[3,4-c]pyridin-1-one. A degassed mixture of 6-chloro-4-cyclopropyl-2H,3H-pyrrolo[3,4-c]pyridin-1-one (4.3 g, 43.96 mmol), potassium vinyltrifluoroborate (11.8 g, 87.91 mmol), Pd(dppf)Cl$_2$·CH$_2$Cl$_2$ (3.6 g, 4.39 mmol) and Cs$_2$CO$_3$ (20.8 g, 131.88 mmol) in THF/water (v/v, 10/1, 220.0 mL) was stirred at 80° C. for 4 h under N$_2$ atmosphere. When the reaction was completed, the solvent was removed under vacuum. The crude residue was dissolved with ethyl acetate and water, followed by General Work-up Procedure 1, and the resulting residue was purified by Chromatography B to afford the title compound (3.5 g, 87%).

Step 9: Synthesis of 4-cyclopropyl-1-oxo-2H,3H-pyrrolo[3,4-c]pyridine-6-carbaldehyde. To a solution of 4-cyclopropyl-6-ethenyl-2H,3H-pyrrolo[3,4-c]pyridin-1-one (3.5 g, 17.50 mmol) and 4-methylmorpholine N-oxide (6.1 g, 52.50 mmol) in tetrahydrofuran (50 mL) and water (20 mL) was added K$_2$OsO$_4$·2H$_2$O (127.4 mg, 0.35 mmol) at 0° C. The resulting mixture was stirred at room temperature for 16 h. The reaction mixture was quenched by the addition of NaHSO$_3$ (10.2 g) and stirred for 10 min at room temperature. Then to the mixture was added water (300.0 mL) and the mixture was extracted with ethyl acetate. The aqueous layer was collected to afford a crude solution of 4-cyclopropyl-6-(1,2-dihydroxyethyl)-2H,3H-pyrrolo[3,4-c]pyridin-1-one (350 mL). To a three-necked flask charged with silica gel (65.6 g) was added a solution of NaIO$_4$ (7.5 g, 35.00 mmol) in water (32.8 mL) dropwise while vigorously stirring. After stirring for 20 min at room temperature, to the resulting mixture was added the crude solution of 4-cyclopropyl-6-(1,2-dihydroxyethyl)-2H,3H-pyrrolo[3,4-c]pyridin-1-one (350.0 mL in water) while vigorously stirring. The resulting mixture was stirred at room temperature for 4 h. When the reaction was completed, the solids were filtered off and the filtrate was extracted with DCM. The combined organic layers were dried over anhydrous Na$_2$SO$_4$ and concentrated under vacuum. The residue was purified by Chromatography A to afford the title compound (1.7 g, 48% over two steps).

Example D: (R)-4-cyclopropyl-6-((4,4-difluoro-3-methylpiperidin-1-yl)methyl)-2,3-dihydro-1H-pyrrolo[3,4-c]pyridin-1-one

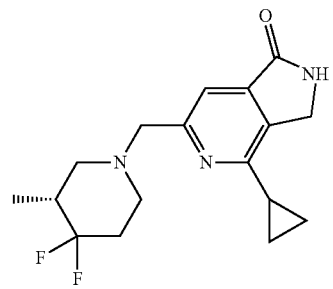 [SMILES: C[C@@H]1CN(Cc2cc3c(c(C4CC4)n2)CNC3=O)CCC1(F)F]

A mixture 4-cyclopropyl-1-oxo-2H,3H-pyrrolo[3,4-c]pyridine-6-carbaldehyde (840 mg, 4.16 mmol), (R)-4,4-difluoro-3-methylpiperidine hydrochloride (783 mg, 4.57 mmol), and TEA (636 µL, 4.56 mmol) in DCM (17 mL) was stirred for 10 min at rt before sodium triacetoxyborohydride (969 mg, 4.57 mmol) was added. After 1.5 h, additional sodium triacetoxyborohydride (177 mg) was added. The reaction was stirred overnight before being quenched with aq. sodium bicarbonate, followed by General Work-up Procedure 1 using DCM. The crude material was purified by Chromatography B, followed by Chromatography C to afford the title compound (626 mg, 47%).

Example E: (S)-4-cyclopropyl-6-((3-methylpiperidin-1-yl)methyl)-2,3-dihydro-1H-pyrrolo[3,4-c]pyridin-1-one

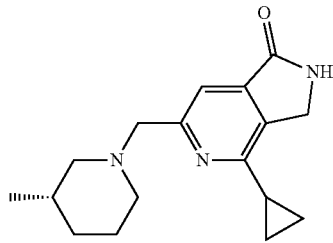 [SMILES: C[C@H]1CCCN(Cc2cc3c(c(C4CC4)n2)CNC3=O)C1]

A solution of 4-cyclopropyl-1-oxo-2H,3H-pyrrolo[3,4-c]pyridine-6-carbaldehyde (1.0 g, 4.95 mmol), (3S)-3-methylpiperidine hydrochloride (804 mg, 5.93 mmol), and TEA (0.69 mL, 4.56 mmol) in DCE (34 mL) was stirred for 15 min at rt before sodium triacetoxyborohydride (1.36 g, 6.43 mmol) was added. The reaction was stirred overnight before being quenched with aq. sodium bicarbonate, followed by General Work-up Procedure 1 using DCM. The crude material was purified by Chromatography B to afford the title compound (1.1 g, 77%).

Example F: (S)-4-cyclopropyl-6-((3-(trifluoromethyl)piperidin-1-yl)methyl)-2,3-dihydro-1H-pyrrolo[3,4-c]pyridin-1-one

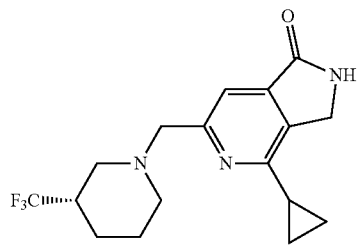 [SMILES: O=C1NCc2c1cc(CN1CCC[C@H](C(F)(F)F)C1)nc2C1CC1]

A solution 4-cyclopropyl-1-oxo-2H,3H-pyrrolo[3,4-c]pyridine-6-carbaldehyde (100 mg, 0.49 mmol), (3S)-3-(trifluoromethyl)piperidine hydrochloride (94 mg, 0.49 mmol), and TEA (0.069 mL, 0.49 mmol) in DCE (3.4 mL) was stirred for 15 min at rt before sodium triacetoxyborohydride (136 mg, 0.64 mmol) was added. The reaction was stirred overnight before being quenched with aq. sodium bicarbonate, followed by General Work-up Procedure 1 using DCM. The crude material was purified by Chromatography B to afford the title compound (91 mg, 54%).

Example G: (1r,3r)-3-(3-aminophenyl)-3-((4-methyl-4H-1,2,4-triazol-3-yl)methyl)cyclobutane-1-carbonitrile

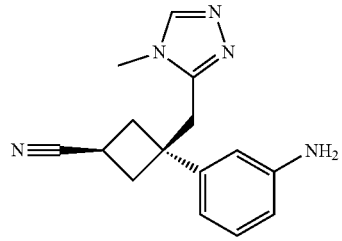 [SMILES: Cn1cnnc1C[C@]1(c2cccc(N)c2)C[C@H](C#N)C1]

Step 1: Synthesis of methyl 2-(3-cyanocyclobutylidene)acetate. To a solution of NaH (20.2 g, 504 mmol, 60.0% purity, 1.20 equiv) in THF (2.50 L) was added a solution of methyl 2-(dimethoxyphosphoryl)acetate (84.3 g, 462 mmol, 66.9 mL, 1.10 equiv) in THF (250 mL) at 0° C. The mixture was stirred at 0° C. for 1 h. Then to the mixture was added a solution of 3-oxocyclobutane-1-carbonitrile (40.0 g, 420 mmol, 1.00 equiv) in THF (250 mL). After the mixture was warmed to 25° C., the mixture was stirred at 25° C. for 12 h. A reaction mixture of two batches was poured into saturated NH$_4$Cl solution (4.0 L) and extracted with ethyl acetate (4.00 L×2). The combined organic layer was washed with brine (2.0 L), dried over Na$_2$SO$_4$, filtered, and concentrated. The residue was purified by Chromatography A to afford the title compound (81.7 g, 64.2% yield).

Step 2: Synthesis of methyl 2-((1r,3r)-1-(3-((tert-butoxycarbonyl)amino)phenyl)-3-cyanocyclobutyl)acetate and methyl 2-((1s,3s)-1-(3-((tert-butoxycarbonyl)amino)phenyl)-3-cyanocyclobutyl)acetate. To a solution of methyl 2-(3-cyanocyclobutylidene)acetate (96.0 g, 635 mmol, 1.00 equiv) in dioxane (1.00 L) and KOH (1.50 M, 550. mL, 1.30 equiv) was added (3-((tert-butoxycarbonyl)amino)phenyl)boronic acid (225 g, 952 mmol, 1.50 equiv) and [Rh(cod)Cl]$_2$ (15.7 g, 31.8 mmol, 0.05 equiv) at 25° C. Then the mixture was stirred at 25° C. for 12 h. A reaction mixture of two batches was poured into saturated NH$_4$Cl solution (2.00 L) and General Work-up Procedure 1 was followed. The residue was purified by Chromatography A with the methyl 2-((1r,3r)-1-(3-((tert-butoxycarbonyl)amino)phenyl)-3-cyanocyclobutyl)acetate eluting first (133 g, 27.4% yield). The second eluting compound was further purified by reversed-phase chromatography to afford isomer methyl 2-((1s,3s)-1-(3-((tert-butoxycarbonyl)amino)phenyl)-3-cyanocyclobutyl)acetate (105 g, 293 mmol, 23.1% yield).

Step 3: Synthesis of 2-((1r,3r)-1-(3-((tert-butoxycarbonyl)amino)phenyl)-3-cyanocyclobutyl)acetic acid. To a solution of methyl 2-((1r,3r)-1-(3-((tert-butoxycarbonyl)amino)phenyl)-3-cyanocyclobutyl)acetate (133 g, 347 mmol, 1.00 equiv) in THF (600 mL) was added LiOH H$_2$O (18.2 g, 434 mmol, 1.25 equiv), and MeOH (120 mL) and H$_2$O (240 mL) at 25° C. Then the mixture was stirred at 25° C. for 12 h. The reaction mixture was concentrated under vacuum at 25° C. Then the mixture was adjusted to pH=3-4 with 0.5 N HCl to generate a precipitate, which was collected by filtration and dried under vacuum. The filter cake was dissolved in ethyl acetate (1.50 L) and the mixture was dried, filtered, and concentrated to afford the title compound (110 g, crude).

Step 4: Synthesis of tert-butyl (3-((1r,3r)-3-cyano-1-((5-mercapto-4-methyl-4H-1,2,4-triazol-3-yl)methyl)cyclobutyl)phenyl)carbamate. To a solution of 2-((1r,3r)-1-(3-

((tert-butoxycarbonyl)amino)phenyl)-3-cyanocyclobutyl)acetic acid (78.0 g, 223 mmol, 1.00 equiv) and N-methylhydrazinecarbothioamide (35.3 g, 335 mmol, 1.50 equiv) in DMF (350 mL) and DIPEA (28.9 g, 223 mmol, 39.0 mL, 1.00 equiv) was added HATU (110 g, 291 mmol, 1.30 equiv) at 25° C. Then the mixture was stirred at 25° C. for 4 h. To the mixture was added NaOH (1.00 M, 470 mL, 2.10 equiv) at 25° C. Then the mixture was heated to 50° C. and stirred at 50° C. for 12 h. After the mixture was cooled to 25° C., the reaction mixture was poured into saturated NH$_4$Cl solution (1.30 L). Solids were precipitated, which were collected by filtration and the filter cake was dried under vacuum. The filter cake was dissolved in ethyl acetate (1.00 L) and the mixture was dried, filtered, and concentrated to afford the title compound (100 g, crude).

Step 5: Synthesis of tert-butyl (3-((1r,3r)-3-cyano-1-((4-methyl-4H-1,2,4-triazol-3-yl)methyl)cyclobutyl)phenyl) carbamate. To a solution of tert-butyl (3-((1r,3r)-3-cyano-1-((5-mercapto-4-methyl-4H-1,2,4-triazol-3-yl)methyl)cyclobutyl)phenyl)carbamate (122 g, 277 mmol, 1.00 equiv) in DCM (1.00 L) and acetic acid (233 g, 3.89 mol, 222 mL, 14.0 equiv) was added H$_2$O$_2$ (78.8 g, 694 mmol, 66.8 mL, 30.0% purity, 2.50 equiv) at 0° C. Then the reaction mixture was stirred at 30° C. for 2 h. The reaction mixture was poured into saturated NaHCO$_3$ solution (2.00 L) and extracted with DCM (500 mL×3). The combined organic layer was washed brine (600 mL). Then the organic layer was dried, filtered, and concentrated. The residue was purified by Chromatography B to afford the title compound (83.0 g, 78.9% yield).

Step 6: Synthesis of (1r,3r)-3-(3-aminophenyl)-3-((4-methyl-4H-1,2,4-triazol-3-yl)methyl)cyclobutane-1-carbonitrile. To a solution of tert-butyl (3-((1r,3r)-3-cyano-1-((4-methyl-4H-1,2,4-triazol-3-yl)methyl)cyclobutyl)phenyl) carbamate (50.0 g, 132 mmol, 1.00 equiv) in DCM (500 mL) was added TMSI (106 g, 528 mmol, 71.9 mL, 4.00 equiv) at 25° C. Then the mixture was stirred at 25° C. for 2 h. To the reaction mixture was added water (300 mL). The aqueous phase was separated and adjusted to pH=7-8 with saturated Na$_2$CO$_3$ solution and extracted with DCM:methanol=10:1 (500 mL×5). The combined organic layers were dried, filtered, and concentrated. The residue was purified by Chromatography B to afford the title compound (10.5 g, 38.6 mmol, 29.2% yield).

Example H: (1r,3r)-3-(3-aminophenyl)-1-methyl-3-((4-methyl-4H-1,2,4-triazol-3-yl)methyl)cyclobutane-1-carbonitrile

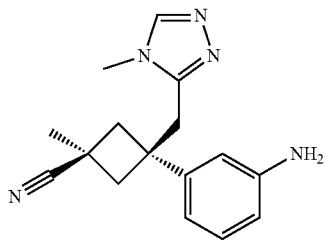 [SMILES: Cn1cnnc1C[C@]1(c2cccc(N)c2)C[C@](C)(C#N)C1]

Step 1: Synthesis of methyl 2-(3-cyano-3-methylcyclobutylidene)acetate. The reaction was carried out analogously to Example G, Step 1, using 1-methyl-3-oxocyclobutane-1-carbonitrile (2.5 g, 22.9 mmol) to generate the title compound (3.5 g, 83%).

Step 2: Synthesis of methyl 2-[(trans)-1-(3-[(tert-butoxycarbonyl)amino]phenyl)-3-cyano-3-methylcyclobutyl]acetate. The reaction was carried out analogously to Example G Step 2, using 1-methyl-3-oxocyclobutane-1-carbonitrile (3.5 g, 21.2 mmol) to generate the title compound (1.1 g, 15%) as the second eluting isomer.

Step 3: Synthesis of 2-((1r,3r)-1-(3-((tert-butoxycarbonyl)amino)phenyl)-3-cyano-3-methylcyclobutyl)acetic acid. The reaction was carried out analogously to Example G, Step 3, using methyl 2-[(trans)-1-(3-[(tert-butoxycarbonyl)amino]phenyl)-3-cyano-3-methylcyclobutyl]acetate (1.1 g, 3.1 mmol). The reaction was worked up by concentrating the mixture to dryness before adding water (50 mL) and acidifying the solution with 1 N HCl (3.8 mL) to give pH~ 5, followed by General Work-up Procedure 1 to give the title compound (1.05 g, 3.1 mmol).

Step 4: Synthesis of tert-butyl (3-((1r,3r)-3-cyano-1-((5-mercapto-4-methyl-4H-1,2,4-triazol-3-yl)methyl)-3-methylcyclobutyl)phenyl)carbamate. The reaction was carried out analogously to Example G, Step 4, using 2-((1r,3r)-1-(3-((tert-butoxycarbonyl)amino)phenyl)-3-cyano-3-methylcyclobutyl)acetic acid (1.05 g, 3.1 mmol) to give the title compound (1.2 g, 91%).

Step 5: Synthesis of tert-butyl (3-((1r,3r)-3-cyano-3-methyl-1-((4-methyl-4H-1,2,4-triazol-3-yl)methyl)cyclobutyl)phenyl)carbamate. The reaction was carried out analogously to Example G, Step 5, using tert-butyl (3-((1r,3r)-3-cyano-1-((5-mercapto-4-methyl-4H-1,2,4-triazol-3-yl)methyl)-3-methylcyclobutyl)phenyl)carbamate (640 mg, 1.6 mmol) to generate the title compound (440 mg, 75%).

Step 6: Synthesis of (1r,3r)-3-(3-aminophenyl)-1-methyl-3-((4-methyl-4H-1,2,4-triazol-3-yl)methyl)cyclobutane-1-carbonitrile. The reaction was carried out analogously to Example G, Step 6, using tert-butyl (3-((1r,3r)-3-cyano-3-methyl-1-((4-methyl-4H-1,2,4-triazol-3-yl)methyl)cyclobutyl)phenyl)carbamate (440 mg, 1.6 mmol) to generate the title compound (290 mg, 89%).

Example I: (1r,3r)-3-(3-bromophenyl)-3-((4-methyl-4H-1,2,4-triazol-3-yl)methyl)cyclobutane-1-carbonitrile

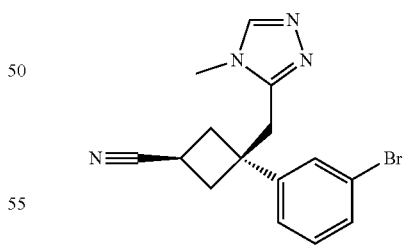

(1r,3r)-3-(3-bromophenyl)-3-((4-methyl-4H-1,2,4-triazol-3-yl)methyl)cyclobutane-1-carbonitrile. To a stirred suspension of Example G (100 mg, 0.37 mmol) and CuBr$_2$ (167 mg, 0.75 mmol) in acetonitrile (4.5 mL) was added t-butyl nitrite (67 μL, 0.56 mmol) dropwise. The reaction was stirred 1 h before being concentrated to half volume and quenched with NH$_4$OH (~6 M, 15 mL) followed by General Work-up Procedure 1 and purification by Chromatography B to provide the title compound (60% yield).

Example 1: N-(3-((1r,3r)-3-cyano-1-((4-methyl-4H-1,2,4-triazol-3-yl)methyl)cyclobutyl)phenyl)-2-cyclopropyl-6-methylpyrimidine-4-carboxamide

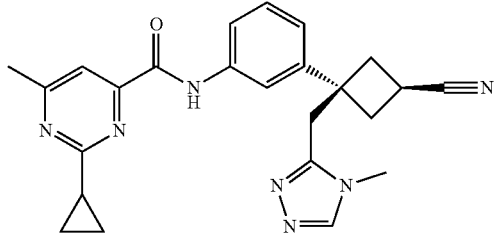 [SMILES: Cc1cc(C(=O)Nc2cccc([C@]3(Cc4nncn4C)C[C@@H](C#N)C3)c2)nc(C2CC2)n1]

To a solution of Example G (53 mg, 0.20 mmol), N-methylmorpholine (65 µL, 0.59 mmol), and 2-cyclopropyl-6-methylpyrimidine-4-carboxylic acid (35 mg, 0.20 mmol) in acetonitrile (1.6 mL) was added 1-Propanephosphonic anhydride solution (50% in DMF, 0.14 mL, 0.25 mmol). The reaction was stirred overnight at rt before addition of aq. 0.5 N HCl (5 mL) and water (5 mL). General Work-up Procedure 1 was followed, keeping the aqueous pH~ 7, and the combined organics were dried and filtered. Chromatography B afforded the title compound (11 mg, 15%). LCMS: $C_{24}H_{25}N_7O$ requires 427.2, found 428.4 [M+H]$^+$. $^1$H NMR (500 MHz, Acetonitrile-$d_3$) δ 9.90 (s, 1H), 7.87 (s, 1H), 7.80-7.70 (m, 2H), 7.40 (t, J=2.0 Hz, 1H), 7.29 (t, J=7.9 Hz, 1H), 6.79 (ddd, J=7.7, 1.9, 1.0 Hz, 1H), 3.29 (s, 2H), 3.15-3.08 (m, 1H), 2.97-2.84 (m, 4H), 2.77 (s, 3H), 2.53 (s, 3H), 2.32 (tt, J=8.0, 4.7 Hz, 1H), 1.19 (tt, J=5.7, 3.0 Hz, 2H), 1.12 (dt, J=8.1, 3.0 Hz, 2H).

Example 2: N-(3-((1s,3s)-3-cyano-1-((4-methyl-4H-1,2,4-triazol-3-yl)methyl)cyclobutyl)phenyl)-2-cyclopropyl-6-methylpyrimidine-4-carboxamide

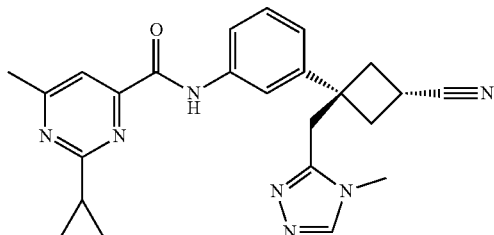 [SMILES: Cc1cc(C(=O)Nc2cccc([C@]3(Cc4nncn4C)C[C@H](C#N)C3)c2)nc(C2CC2)n1]

The title compound was obtained by performing reactions from Example G, Steps 3-6 followed by amide formation from Example 1 using methyl 2-((1s,3s)-1-(3-((tert-butoxycarbonyl)amino)phenyl)-3-cyanocyclobutyl)acetate from Example G, Step 2 to afford the title compound after reverse-phase HPLC (20 mg, 55%). LCMS: $C_{24}H_{25}N_7O$ requires 427.2, found 428.4 [M+H]$^+$. $^1$H NMR (500 MHz, Acetonitrile-$d_3$) δ 9.90 (s, 1H), 8.71 (s, 1H), 7.83 (s, 1H), 7.78-7.67 (m, 1H), 7.39 (t, J=7.9 Hz, 1H), 7.29 (t, J=2.0 Hz, 1H), 6.85 (dt, J=8.0, 1.3 Hz, 1H), 3.61 (p, J=8.9 Hz, 1H), 3.48 (s, 2H), 3.11-2.97 (m, 2H), 2.90 (s, 3H), 2.80 (td, J=9.4, 2.6 Hz, 2H), 2.61 (s, 3H), 2.40 (tt, J=8.1, 4.7 Hz, 1H), 1.29 (tt, J=5.9, 3.1 Hz, 2H), 1.22 (dt, J=8.1, 3.1 Hz, 2H).

Example 3: (1r,3r)-3-((4-methyl-4H-1,2,4-triazol-3-yl)methyl)-3-(3-(1-oxo-4-(trifluoromethyl)isoindolin-2-yl)phenyl)cyclobutane-1-carbonitrile

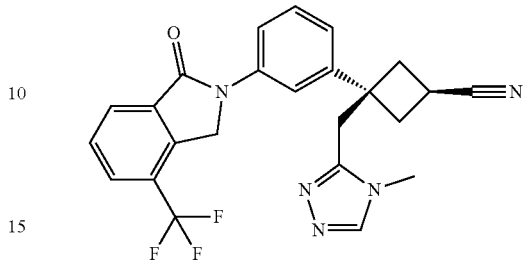

A vial containing Example G (31 mg, 0.12 mmol) was charged with acetonitrile (1.0 mL) and methyl 2-(bromomethyl)-3-(trifluoromethyl)benzoate (35 mg, 0.12 mmol). Silver nitrate (26 mg, 0.15 mmol) was dissolved in water (0.5 mL) and added dropwise, and the reaction was stirred overnight at rt. Solid bicarbonate was added to adjust pH~ 8, followed by brine (1 mL). The reaction was filtered and the filtrate was extracted with DCM:isopropanol (9:1, 3×15 mL), and the combined organics were dried and filtered before reverse phase HPLC purification (10 to 95% MeCN in water with 0.1% TFA gradient over 10 min.) to yield the title compound (6.4 mg, 12%). LCMS: $C_{24}H_{20}F_3N_5O$ requires 451.2, found 452.3 [M+H]$^+$. $^1$H NMR (500 MHz, Acetonitrile-$d_3$) δ 8.13 (s, 1H), 8.05 (d, J=7.6 Hz, 1H), 7.95 (d, J=7.7 Hz, 1H), 7.84 (ddd, J=8.1, 2.2, 0.9 Hz, 1H), 7.73 (t, J=7.7 Hz, 1H), 7.47 (t, J=2.1 Hz, 1H), 7.37 (t, J=8.0 Hz, 1H), 6.92-6.86 (m, 1H), 5.01 (s, 2H), 3.41 (s, 2H), 3.16-3.07 (m, 1H), 2.96 (d, J=7.8 Hz, 4H), 2.83 (d, J=13.4 Hz, 5H).

Example 4: (1r,3r)-3-(3-(6-((5-azaspiro[2.4]heptan-5-yl)methyl)-1-oxo-4-(trifluoromethyl)isoindolin-2-yl)phenyl)-3-((4-methyl-4H-1,2,4-triazol-3-yl)methyl)cyclobutane-1-carbonitrile

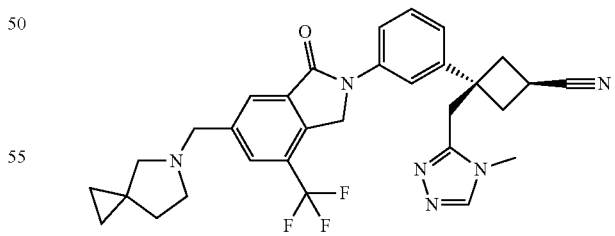

Step 1: Synthesis of (1r,3r)-3-(3-(6-formyl-1-oxo-4-(trifluoromethyl)isoindolin-2-yl)phenyl)-3-((4-methyl-4H-1,2,4-triazol-3-yl)methyl)cyclobutane-1-carbonitrile. The cyclization reaction was carried out analogously to Example 3, using Example G (136 mg, 0.51 mmol) and methyl 2-(bromomethyl)-5-formyl-3-(trifluoromethyl)benzoate (166 mg, 0.51 mmol) to afford the crude title compound (240 mg, 98%) which was used without purification.

Step 2: Synthesis of (1r,3r)-3-(3-(6-((5-azaspiro[2.4]heptan-5-yl)methyl)-1-oxo-4-(trifluoromethyl)isoindolin-2-yl)phenyl)-3-((4-methyl-4H-1,2,4-triazol-3-yl)methyl)cyclobutane-1-carbonitrile. A solution of (1r,3r)-3-(3-(6-formyl-1-oxo-4-(trifluoromethyl)isoindolin-2-yl)phenyl)-3-((4-methyl-4H-1,2,4-triazol-3-yl)methyl)cyclobutane-1-carbonitrile (50 mg, 0.10 mmol), 5-azaspiro[2.4]heptane hydrochloride (21 mg, 0.16 mmol), and TEA (14.6 μL, 0.10 mmol) in DCE (0.42 mL) was stirred for 15 min before sodium triacetoxyborohydride (33 mg, 0.16 mmol) was added. The reaction was stirred overnight before being quenched with aq. sodium bicarbonate, followed by General Work-up Procedure 1 using DCM. The crude material was purified by Chromatography B, followed by Chromatography C to afford the title compound (10 mg, 17%). LCMS: $C_{31}H_{31}F_3N_6O$ requires 560.3, found 561.4 [M+H]$^+$. $^1$H NMR (500 MHz, Acetonitrile-$d_3$) δ 8.00 (s, 1H), 7.94 (s, 1H), 7.89 (s, 1H), 7.88-7.83 (m, 1H), 7.43 (t, J=2.0 Hz, 1H), 7.37 (t, J=8.0 Hz, 1H), 6.88 (ddd, J=7.7, 1.8, 0.9 Hz, 1H), 4.98 (d, J=1.5 Hz, 2H), 3.81 (s, 2H), 3.34 (s, 2H), 3.21-3.10 (m, 1H), 3.04-2.90 (m, 4H), 2.77 (d, J=9.0 Hz, 5H), 2.52 (s, 2H), 1.83 (t, J=6.9 Hz, 2H), 0.55 (d, J=1.6 Hz, 4H).

Example 5: (1r,3r)-3-(3-(6-((2-ethyl-1,4-oxazepan-4-yl)methyl)-1-oxo-4-(trifluoromethyl)isoindolin-2-yl)phenyl)-3-((4-methyl-4H-1,2,4-triazol-3-yl)methyl)cyclobutane-1-carbonitrile

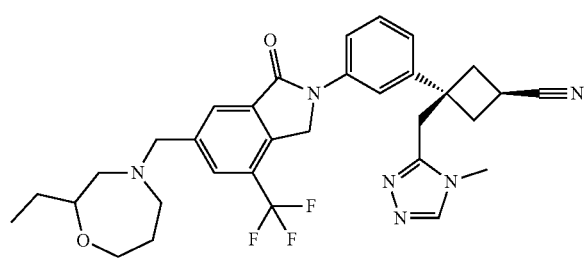 [SMILES: CCC1CN(Cc2cc3c(c(C(F)(F)F)c2)CN(c2cccc([C@]4(Cc5nncn5C)C[C@@H](C#N)C4)c2)C3=O)CCCO1]

The reductive amination was carried out analogously to Example 13, using (1r,3r)-3-(3-(6-formyl-1-oxo-4-(trifluoromethyl)isoindolin-2-yl)phenyl)-1-methyl-3-((4-methyl-4H-1,2,4-triazol-3-yl)methyl)cyclobutane-1-carbonitrile (60 mg, 0.13 mmol) and 2-ethyl-1,4-oxazepane (32 mg, 0.25 mmol), to afford the title compound after Chromatography C (29 mg, 39%). LCMS: $C_{32}H_{35}F_3N_6O_2$ requires 592.3, found 593.5 [M+H]$^+$. $^1$H NMR (500 MHz, Acetonitrile-$d_3$) δ 8.03 (s, 1H), 7.97 (s, 1H), 7.93-7.84 (m, 2H), 7.44 (t, J=2.1 Hz, 1H), 7.37 (t, J=8.0 Hz, 1H), 6.91-6.82 (m, 1H), 4.99 (s, 2H), 3.94-3.79 (m, 3H), 3.79-3.67 (m, 1H), 3.50 (tdd, J=7.7, 5.0, 2.4 Hz, 1H), 3.34 (s, 2H), 3.22-3.07 (m, 1H), 3.03-2.91 (m, 4H), 2.88-2.72 (m, 5H), 2.64 (ddd, J=12.8, 9.0, 3.9 Hz, 1H), 2.42 (dd, J=13.3, 8.9 Hz, 1H), 1.96-1.85 (m, 1H), 1.86-1.76 (m, 1H), 1.45-1.26 (m, 2H), 0.86 (t, J=7.4 Hz, 3H).

Example 6: (1r,3r)-3-((4-methyl-4H-1,2,4-triazol-3-yl)methyl)-3-(3-(6-(((R)-2-methylmorpholino)methyl)-1-oxo-4-(trifluoromethyl)isoindolin-2-yl)phenyl)cyclobutane-1-carbonitrile

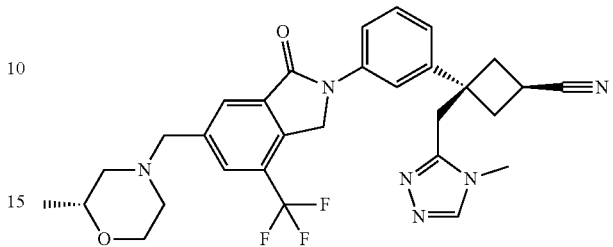

The reductive amination was carried out analogously to Example 14, Step 2, using (1r,3r)-3-(3-(6-formyl-1-oxo-4-(trifluoromethyl)isoindolin-2-yl)phenyl)-3-((4-methyl-4H-1,2,4-triazol-3-yl)methyl)cyclobutane-1-carbonitrile (35 mg, 0.07 mmol) and (2R)-2-methylmorpholine (22 mg, 0.22 mmol), to afford the title compound after Chromatography C using 0.1% TFA additive. The fractions containing the product were concentrated, dissolved in DCM, and washed with aq. sodium bicarbonate. The organic layer was dried and concentrated to give the product (15 mg, 36%). LCMS: $C_{30}H_{31}F_5N_6O_2$ requires 564.2, found 565.5 [M+H]$^+$. $^1$H NMR (500 MHz, Acetonitrile-$d_3$) δ 8.01 (s, 1H), 7.98-7.83 (m, 3H), 7.43 (t, J=2.0 Hz, 1H), 7.37 (t, J=8.0 Hz, 1H), 6.88 (ddd, J=7.8, 1.8, 0.9 Hz, 1H), 4.99 (s, 2H), 3.81 (ddd, J=11.3, 3.4, 1.6 Hz, 1H), 3.68 (d, J=1.8 Hz, 2H), 3.61 (ddt, J=11.5, 9.3, 2.4 Hz, 2H), 3.34 (s, 2H), 3.21-3.08 (m, 1H), 3.04-2.90 (m, 4H), 2.73 (dt, J=11.2, 2.0 Hz, 1H), 2.66 (dd, J=11.2, 2.1 Hz, 1H), 1.87 (dd, J=11.3, 9.8 Hz, 1H), 1.09 (d, J=6.2 Hz, 3H).

Example 7: (1r,3r)-1-methyl-3-((4-methyl-4H-1,2,4-triazol-3-yl)methyl)-3-(3-(6-(((R)-2-methylmorpholino)methyl)-1-oxo-4-(trifluoromethyl)isoindolin-2-yl)phenyl)cyclobutane-1-carbonitrile

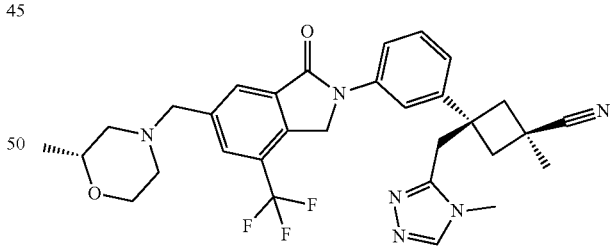

Step 1. Synthesis of (1r,3r)-3-(3-(6-formyl-1-oxo-4-(trifluoromethyl)isoindolin-2-yl)phenyl)-1-methyl-3-((4-methyl-4H-1,2,4-triazol-3-yl)methyl)cyclobutane-1-carbonitrile. The reaction was carried out analogously to Example 3, using Example H (234 mg, 0.83 mmol) and methyl 2-(bromomethyl)-5-formyl-3-(trifluoromethyl)benzoate (270 mg, 0.83 mmol) to generate the title compound after Chromatography B (200 mg, 49%).

Step 2. Synthesis of (1r,3r)-1-methyl-3-((4-methyl-4H-1,2,4-triazol-3-yl)methyl)-3-(3-(6-(((R)-2-methylmorpholino)methyl)-1-oxo-4-(trifluoromethyl)isoindolin-2-yl)phenyl)cyclobutane-1-carbonitrile. The reductive amination was carried out analogously to Example 4, Step 2, using (1r,3r)-3-(3-(6-formyl-1-oxo-4-(trifluoromethyl)isoindolin-2-yl)phenyl)-1-methyl-3-((4-methyl-4H-1,2,4-triazol-3-yl)methyl)cyclobutane-1-carbonitrile (53 mg, 0.11 mmol) and (2R)-2-methylmorpholine hydrochloride (22 mg, 0.16 mmol), to afford the title compound after Chromatography C. (19 mg, 31%). LCMS: $C_{31}H_{33}F_3N_6O_2$ requires 578.3, found 579.5 [M+H]$^+$. $^1$H NMR (500 MHz, Acetonitrile-d$_3$) δ 8.02 (d, J=3.2 Hz, 1H), 7.98-7.83 (m, 3H), 7.51 (q, J=2.1 Hz, 1H), 7.40 (t, J=8.1 Hz, 1H), 6.98 (d, J=7.8 Hz, 1H), 5.01 (s, 2H), 3.88-3.76 (m, 1H), 3.74-3.54 (m, 4H), 3.20 (d, J=3.3 Hz, 2H), 3.16-3.04 (m, 2H), 2.88 (dt, J=11.6, 2.7 Hz, 2H), 2.81-2.70 (m, 4H), 2.66 (dt, J=11.5, 2.0 Hz, 1H), 1.87 (t, J=10.6 Hz, 1H), 1.66 (d, J=1.3 Hz, 3H), 1.09 (dd, J=6.4, 1.4 Hz, 3H).

Example 8: N-(3-((1r,3r)-3-cyano-3-methyl-1-((4-methyl-4H-1,2,4-triazol-3-yl)methyl)cyclobutyl)phenyl)-2-cyclopropyl-6-methylpyrimidine-4-carboxamide

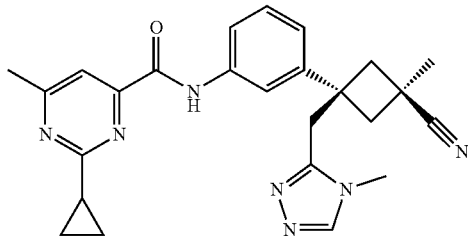 [SMILES: Cc1cc(C(=O)Nc2cccc([C@]3(Cc4nncn4C)C[C@@](C)(C#N)C3)c2)nc(C2CC2)n1]

The reaction was carried out analogously to Example 1, using Example H (47 mg, 0.17 mmol) to yield the title compound (45 mg, 61%) after Chromatography C. LCMS: $C_{25}H_{27}N_7O$ requires 441.2, found 442.4 [M+H]$^+$. $^1$H NMR (500 MHz, DMSO-d$_6$) δ 10.42 (s, 1H), 8.18 (s, 1H), 7.83 (dd, J=8.1, 2.0 Hz, 1H), 7.72 (s, 1H), 7.59 (t, J=1.9 Hz, 1H), 7.30 (t, J=7.9 Hz, 1H), 6.81 (dd, J=7.8, 1.7 Hz, 1H), 3.16 (s, 2H), 3.01-2.89 (m, 2H), 2.78 (d, J=18.0 Hz, 5H), 2.52 (s, 2H), 2.34 (tt, J=8.1, 4.7 Hz, 1H), 1.58 (s, 3H), 1.21-1.01 (m, 4H).

Example 9: (1S,3s)-1-methyl-3-((4-methyl-4H-1,2,4-triazol-3-yl)methyl)-3-(3-(6-(((R)-2-methylmorpholino)methyl)-1-oxo-4-(trifluoromethyl)isoindolin-2-yl)phenyl)cyclobutane-1-carbonitrile

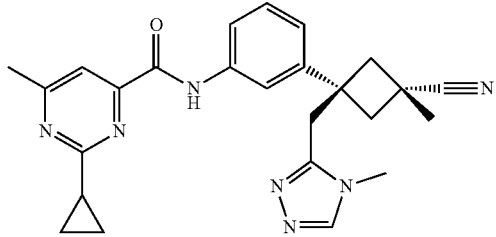 [SMILES: Cc1cc(C(=O)Nc2cccc([C@]3(Cc4nncn4C)C[C@](C)(C#N)C3)c2)nc(C2CC2)n1]

The title compound was synthesized analogously to Example H, Steps 3-6, using the first eluting isomer isolated from Example H, Step 2. After Step 6, the reaction was carried out analogously to Example 1 and following Chromatography C provided the title compound (27 mg, 38%). LCMS: $C_{31}H_{33}F_3N_6O_2$ requires 578.3, found 579.5 [M+H]$^+$. $^1$H NMR (500 MHz, DMSO-d6) δ 8.16 (s, 1H), 8.00 (s, 1H), 7.95 (s, 1H), 7.88-7.80 (m, 1H), 7.37-7.27 (m, 2H), 6.68 (dd, J=7.8, 1.7 Hz, 1H), 5.09 (s, 2H), 3.80-3.62 (m, 3H), 3.62-3.46 (m, 2H), 3.26-3.17 (m, 2H), 2.75-2.55 (m, 8H), 2.11 (td, J=11.4, 3.4 Hz, 1H), 1.81 (t, J=10.5 Hz, 1H), 1.41 (s, 3H), 1.04 (d, J=6.3 Hz, 3H).

Example 10: (1S,3s)-1-methyl-3-((4-methyl-4H-1,2,4-triazol-3-yl)methyl)-3-(3-(6-(((R)-2-methylmorpholino)methyl)-1-oxo-4-(trifluoromethyl)isoindolin-2-yl)phenyl)cyclobutane-1-carbonitrile

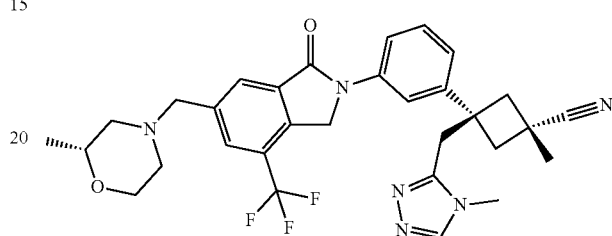

The title compound was synthesized analogously to Example 7, using the first eluting isomer from Example H, Step 2. LCMS: $C_{31}H_{33}F_3N_6O_2$ requires 578.3, found 579.5 [M+H]$^+$. $^1$H NMR (500 MHz, DMSO-d$_6$) δ 8.16 (s, 1H), 8.00 (s, 1H), 7.95 (s, 1H), 7.88-7.80 (m, 1H), 7.37-7.27 (m, 2H), 6.68 (dd, J=7.8, 1.7 Hz, 1H), 5.09 (s, 2H), 3.80-3.62 (m, 3H), 3.62-3.46 (m, 2H), 3.26-3.17 (m, 2H), 2.75-2.55 (m, 8H), 2.11 (td, J=11.4, 3.4 Hz, 1H), 1.81 (t, J=10.5 Hz, 1H), 1.41 (s, 3H), 1.04 (d, J=6.3 Hz, 3H).

Example 11: (1R,3r)-3-(3-(6-(((R)-4,4-difluoro-3-methylpiperidin-1-yl)methyl)-1-oxo-4-(trifluoromethyl)isoindolin-2-yl)phenyl)-3-((4-methyl-4H-1,2,4-triazol-3-yl)methyl)cyclobutane-1-carbonitrile

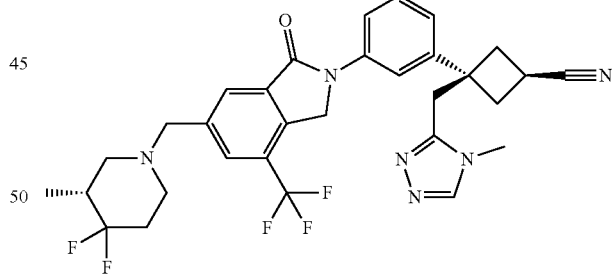

A mixture of Example I (70 mg, 0.21 mmol), (R)-6-((4,4-difluoro-3-methylpiperidin-1-yl)methyl)-4-(trifluoromethyl)isoindolin-1-one (74 mg, 0.21 mmol), Cs$_2$CO$_3$ (152 mg, 0.46 mmol), xantphos (25 mg, 0.04 mmol), and Pd(OAc)$_2$ (4.7 mg, 0.02 mmol) in dioxane (0.72 mL) was heated at 120° C. for 1 h. This mixture was concentrated directly onto Celite and purified using Chromatography C to afford the title compound (35 mg, 27%). LCMS: $C_{31}H_{31}F_5N_6O$ requires 598.2, found 599.4 [M+H]$^+$. $^1$H NMR (500 MHz, Acetonitrile-d$_3$) δ 7.99 (s, 1H), 7.91 (s, 1H), 7.86 (s, 1H), 7.84 (dd, J=8.2, 2.2 Hz, 1H), 7.41 (t, J=2.0 Hz, 1H), 7.34 (t, J=8.0 Hz, 1H), 6.85 (dt, J=7.8, 1.2 Hz, 1H), 4.96 (s, 2H), 3.71 (s, 2H), 3.35-3.26 (m, 2H), 3.20-3.07 (m, 1H), 3.01-2.85 (m, 4H), 2.83-2.64 (m, 5H), 2.37 (t, J=11.4 Hz, 1H), 2.14-1.97 (m, 4H), 0.97 (d, J=6.3 Hz, 3H).

Example 12: (1r,3r)-3-(3-(6-(((6,6-difluorobicyclo[3.1.0]hexan-3-yl)amino)methyl)-1-oxo-4-(trifluoromethyl)isoindolin-2-yl)phenyl)-3-((4-methyl-4H-1,2,4-triazol-3-yl)methyl)cyclobutane-1-carbonitrile

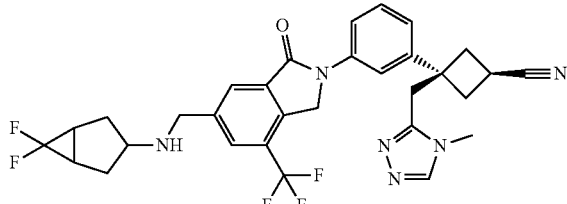

The reductive amination was carried out analogously to Example 4, Step 2, using (1r,3r)-3-(3-(6-formyl-1-oxo-4-(trifluoromethyl)isoindolin-2-yl)phenyl)-1-methyl-3-((4-methyl-4H-1,2,4-triazol-3-yl)methyl)cyclobutane-1-carbonitrile (35 mg, 0.07 mmol) and 6,6-difluorobicyclo[3.1.0]hexan-3-amine hydrochloride (25 mg, 0.15 mmol), to afford the title compound after Chromatography C. LCMS: $C_{31}H_{29}F_5N_6O$ requires 596.2, found 597.5 [M+H]$^+$.
$^1$H NMR (500 MHz, Acetonitrile-d$_3$) δ 8.00 (s, 1H), 7.93 (s, 1H), 7.86 (s, 1H), 7.84 (dd, J=8.2, 2.2 Hz, 1H), 7.40 (d, J=2.0 Hz, 1H), 7.34 (t, J=8.0 Hz, 1H), 6.85 (d, J=7.3 Hz, 1H), 4.95 (s, 2H), 3.93 (s, 2H), 3.31 (s, 2H), 3.21-3.07 (m, 2H), 2.98-2.91 (m, 4H), 2.75 (s, 3H), 2.26 (dd, J=13.5, 7.2 Hz, 2H), 2.06-2.02 (m, 2H), 1.90-1.79 (m, 3H).

Example 13: (1r,3r)-3-((4-methyl-4H-1,2,4-triazol-3-yl)methyl)-3-(3-(6-((4-methylazepan-1-yl)methyl)-1-oxo-4-(trifluoromethyl)isoindolin-2-yl)phenyl)cyclobutane-1-carbonitrile

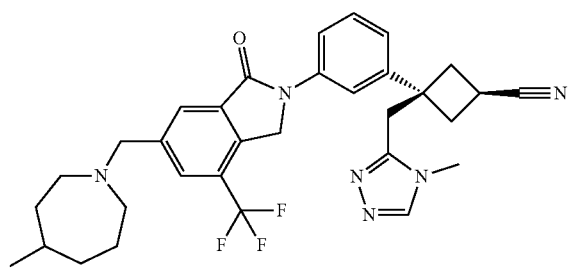 [SMILES: CC1CCCN(Cc2cc3c(c(C(F)(F)F)c2)CN(c2cccc([C@]4(Cc5nncn5C)C[C@@H](C#N)C4)c2)C3=O)CC1]

A mixture of (1r,3r)-3-(3-(6-formyl-1-oxo-4-(trifluoromethyl)isoindolin-2-yl)phenyl)-3-((4-methyl-4H-1,2,4-triazol-3-yl)methyl)cyclobutane-1-carbonitrile (50 mg, 0.10 mmol), 4-methylazepane (24 mg, 0.21 mmol), and acetic acid (6 µL, 0.10 mmol) in DCE (0.71 mL) was stirred for 15 min before sodium triacetoxyborohydride (30 mg, 0.14 mmol) was added. The reaction was stirred overnight before being quenched with aq. sodium bicarbonate, followed by General Work-up Procedure 1 using DCM. The crude material was purified by Chromatography C to afford the title compound (29 mg, 47%). LCMS: $C_{32}H_{35}F_3N_6O$ requires 576.3, found 577.5 [M+H]$^+$. $^1$H NMR (500 MHz, Acetonitrile-d$_3$) δ 7.99 (s, 1H), 7.93 (s, 1H), 7.86 (s, 1H), 7.84 (dd, J=8.2, 2.2 Hz, 1H), 7.41 (t, J=2.0 Hz, 1H), 7.34 (t, J=8.0 Hz, 1H), 6.85 (dt, J=7.8, 1.2 Hz, 1H), 4.95 (s, 2H), 3.78 (s, 2H), 3.31 (s, 2H), 3.19-3.08 (m, 1H), 2.97-2.90 (m, 4H), 2.75 (s, 3H), 2.71-2.53 (m, 5H), 1.77-1.50 (m, 3H), 1.40-1.29 (m, 2H), 0.93 (d, J=6.6 Hz, 3H).

Example 14: (1R,3r)-3-((4-methyl-4H-1,2,4-triazol-3-yl)methyl)-3-(3-(1-oxo-4-(trifluoromethyl)-6-(((S)-3-(trifluoromethyl)piperidin-1-yl)methyl)isoindolin-2-yl)phenyl)cyclobutane-1-carbonitrile

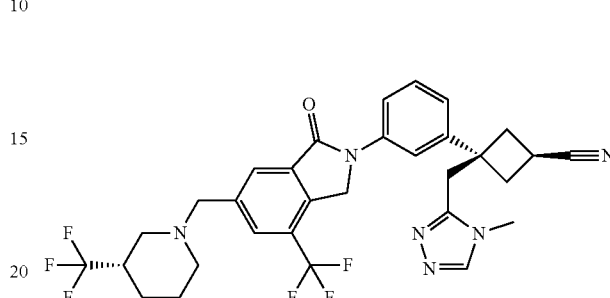

The reductive amination was carried out analogously to Example 4, Step 2, using (1r,3r)-3-(3-(6-formyl-1-oxo-4-(trifluoromethyl)isoindolin-2-yl)phenyl)-1-methyl-3-((4-methyl-4H-1,2,4-triazol-3-yl)methyl)cyclobutane-1-carbonitrile (35 mg, 0.07 mmol) and (3S)-3-(trifluoromethyl)piperidine hydrochloride (21 mg, 0.11 mmol), to afford the title compound after Chromatography C (19 mg, 41%). LCMS: $C_{31}H_{30}F_6N_6O$ requires 616.2, found 617.5 [M+H]$^+$.
$^1$H NMR (500 MHz, Acetonitrile-d$_3$) δ 7.98 (s, 1H), 7.90 (s, 1H), 7.86 (s, 1H), 7.84 (dd, J=7.9, 1.8 Hz, 1H), 7.41 (t, J=2.0 Hz, 1H), 7.34 (t, J=8.0 Hz, 1H), 6.88-6.82 (m, 1H), 4.96 (s, 2H), 3.71 (s, 2H), 3.31 (s, 2H), 3.17-3.09 (m, 1H), 2.99-2.88 (m, 5H), 2.82 (d, J=11.6 Hz, 1H), 2.75 (s, 3H), 2.47 (t, J=11.4 Hz, 1H), 2.11-2.00 (m, 3H), 1.75 (d, J=13.6 Hz, 1H), 1.63-1.52 (m, 1H), 1.32 (qd, J=12.5, 4.3 Hz, 1H).

Example 15: (1R,3r)-3-(3-(6-(((2R,6S)-2,6-dimethylmorpholino)methyl)-1-oxo-4-(trifluoromethyl)isoindolin-2-yl)phenyl)-3-((4-methyl-4H-1,2,4-triazol-3-yl)methyl)cyclobutane-1-carbonitrile

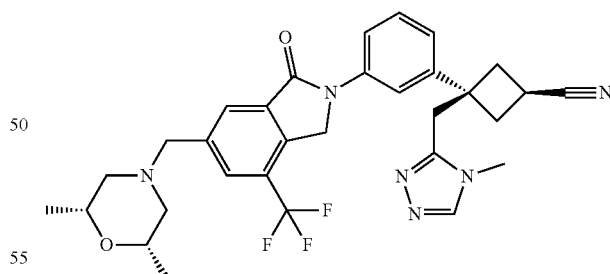

The reductive amination was carried out analogously to Example 13, using (1r,3r)-3-(3-(6-formyl-1-oxo-4-(trifluoromethyl)isoindolin-2-yl)phenyl)-1-methyl-3-((4-methyl-4H-1,2,4-triazol-3-yl)methyl)cyclobutane-1-carbonitrile (40 mg, 0.09 mmol) and cis-2,6-dimethylmorpholine (20 mg, 0.17 mmol), to afford the title compound after Chromatography C (20 mg, 41%). LCMS: $C_{29}H_{30}F_3N_7O_2$ requires 565.2, found 565.5 [M+H]$^+$. $^1$H NMR (500 MHz, Acetonitrile-d$_3$) δ 8.11 (s, 1H), 8.05-7.93 (m, 3H), 7.89 (s, 1H), 7.74 (s, 1H), 7.52 (t, J=7.9 Hz, 1H), 7.21 (dt, J=7.7, 1.2 Hz, 1H), 5.04 (s, 2H), 3.90 (s, 3H), 3.68-3.58 (m, 4H), 3.36 (s, 3H), 2.69 (dt, J=10.5, 1.9 Hz, 2H), 1.76 (t, J=10.7 Hz, 2H), 1.06 (d, J=6.2 Hz, 6H).

Example 16: (1S,3r)-3-((4-methyl-4H-1,2,4-triazol-3-yl)methyl)-3-(3-(1-oxo-4-(trifluoromethyl)-6-(((S)-2-(trifluoromethyl)morpholino)methyl)isoindolin-2-yl)phenyl)cyclobutane-1-carbonitrile

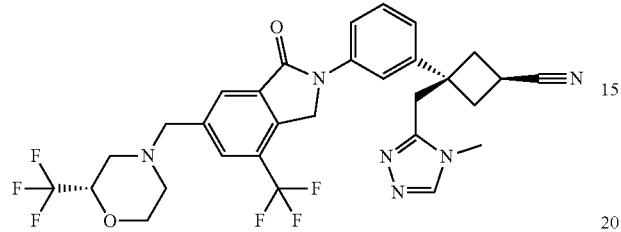

The reductive amination was carried out analogously to Example 14, Step 2, using (1r,3r)-3-(3-(6-formyl-1-oxo-4-(trifluoromethyl)isoindolin-2-yl)phenyl)-1-methyl-3-((4-methyl-4H-1,2,4-triazol-3-yl)methyl)cyclobutane-1-carbonitrile (30 mg, 0.06 mmol) and (2S)-3-(trifluoromethyl)morpholine hydrochloride (18 mg, 0.09 mmol), to afford the title compound after Chromatography C (19 mg, 41%). LCMS: $C_{31}H_{28}F_6N_6O_2$ requires 618.2, found 619.5 $[M+H]^+$. $^1H$ NMR (500 MHz, Acetonitrile-$d_3$) δ 8.04 (s, 1H), 7.95 (s, 1H), 7.91-7.84 (m, 2H), 7.43 (t, J=2.0 Hz, 1H), 7.37 (t, J=8.0 Hz, 1H), 6.89 (d, J=7.7 Hz, 1H), 5.00 (s, 2H), 4.17-4.06 (m, 1H), 4.03-3.94 (m, 1H), 3.78 (s, 2H), 3.72 (td, J=11.4, 2.5 Hz, 1H), 3.34 (s, 2H), 3.21-3.09 (m, 1H), 3.05-2.88 (m, 5H), 2.78 (s, 3H), 2.72 (d, J=11.9 Hz, 1H), 2.37-2.24 (m, 2H).

Example 17: (1r,3r)-3-(3-(6-((4,4-difluoroazepan-1-yl)methyl)-1-oxo-4-(trifluoromethyl)isoindolin-2-yl)phenyl)-3-((4-methyl-4H-1,2,4-triazol-3-yl)methyl)cyclobutane-1-carbonitrile

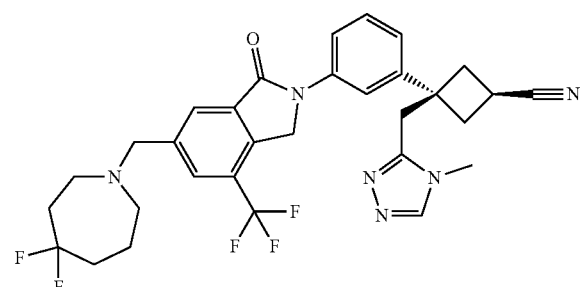

The reductive amination was carried out analogously to Example 14, Step 2, using (1r,3r)-3-(3-(6-formyl-1-oxo-4-(trifluoromethyl)isoindolin-2-yl)phenyl)-1-methyl-3-((4-methyl-4H-1,2,4-triazol-3-yl)methyl)cyclobutane-1-carbonitrile (30 mg, 0.06 mmol) and 4,4-difluoroazepane hydrochloride (16 mg, 0.09 mmol), to afford the title compound after Chromatography C (23 mg, 58%). LCMS: $C_{31}H_{31}F_5N_6O$ requires 598.2, found 599.5 $[M+H]^+$. $^1H$ NMR (500 MHz, Acetonitrile-$d_3$) δ 7.99 (s, 1H), 7.93 (s, 1H), 7.86 (s, 1H), 7.84 (dd, J=8.1, 2.2 Hz, 1H), 7.41 (s, 1H), 7.34 (t, J=8.0 Hz, 1H), 6.85 (d, J=7.8 Hz, 1H), 4.96 (s, 2H), 3.81 (s, 2H), 3.31 (s, 2H), 3.18-3.07 (m, 1H), 2.99-2.89 (m, 4H), 2.75 (s, 3H), 2.71 (t, J=5.9 Hz, 2H), 2.69-2.61 (m, 2H), 2.24-2.14 (m, 3H), 1.79-1.70 (m, 3H).

Example 18: (1R,3r)-3-(3-(6-(((3S,5R)-3,5-dimethylpiperidin-1-yl)methyl)-1-oxo-4-(trifluoromethyl)isoindolin-2-yl)phenyl)-3-((4-methyl-4H-1,2,4-triazol-3-yl)methyl)cyclobutane-1-carbonitrile

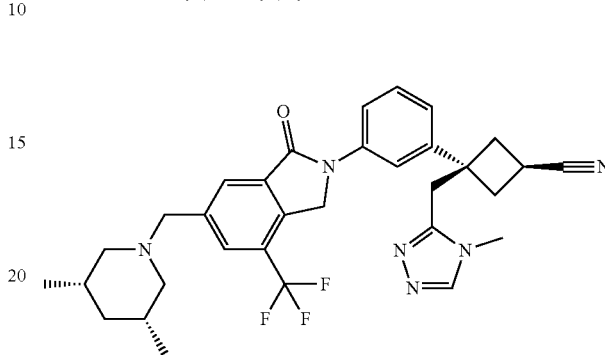

The reductive amination was carried out analogously to Example 13, using (1r,3r)-3-(3-(6-formyl-1-oxo-4-(trifluoromethyl)isoindolin-2-yl)phenyl)-1-methyl-3-((4-methyl-4H-1,2,4-triazol-3-yl)methyl)cyclobutane-1-carbonitrile (30 mg, 0.06 mmol) and (3R,5S)-3,5-dimethylpiperidine (10 mg, 0.09 mmol), to afford the title compound after Chromatography C (18 mg, 50%). LCMS: $C_{32}H_{35}F_3N_6O$ requires 576.3, found 577.6 $[M+H]^+$. $^1H$ NMR (500 MHz, Acetonitrile-$d_3$) δ 7.96 (s, 1H), 7.90-7.81 (m, 3H), 7.41 (t, J=2.0 Hz, 1H), 7.34 (t, J=8.0 Hz, 1H), 6.85 (dt, J=8.0, 1.1 Hz, 1H), 4.96 (s, 2H), 3.63 (s, 2H), 3.31 (s, 2H), 3.17-3.07 (m, 1H), 3.02-2.89 (m, 4H), 2.81-2.71 (m, 5H), 1.75-1.59 (m, 3H), 1.54 (t, J=10.8 Hz, 2H), 0.83 (d, J=6.4 Hz, 6H), 0.54 (q, J=11.8 Hz, 1H).

Example 19: (1R,3r)-3-((4-methyl-4H-1,2,4-triazol-3-yl)methyl)-3-(3-(6-(((S)-3-methylpiperidin-1-yl)methyl)-1-oxo-4-(trifluoromethyl)isoindolin-2-yl)phenyl)cyclobutane-1-carbonitrile

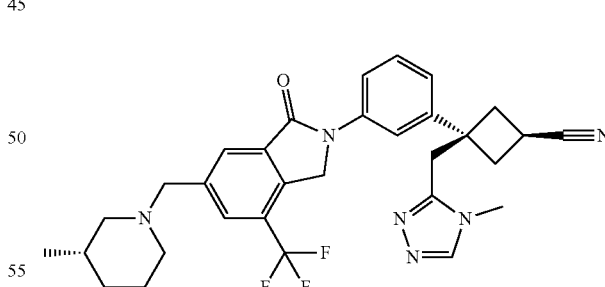

The reductive amination was carried out analogously to Example 4, Step 2, using (1r,3r)-3-(3-(6-formyl-1-oxo-4-(trifluoromethyl)isoindolin-2-yl)phenyl)-1-methyl-3-((4-methyl-4H-1,2,4-triazol-3-yl)methyl)cyclobutane-1-carbonitrile (50 mg, 0.10 mmol) and (3S)-3-methylpiperidine hydrochloride (25 mg, 0.18 mmol), to afford the title compound after Chromatography (39 mg, 66%). LCMS: $C_{31}H_{33}F_3N_6O$ requires 562.3, found 563.6 $[M+H]^+$. $^1H$ NMR (500 MHz, Acetonitrile-$d_3$) δ 7.96 (s, 1H), 7.89 (s, 1H), 7.86 (s, 1H), 7.84 (dd, J=8.2, 2.1 Hz, 1H), 7.40 (t, J=2.1

Hz, 1H), 7.34 (t, J=8.0 Hz, 1H), 6.85 (dt, J=7.8, 1.4 Hz, 1H), 4.95 (s, 2H), 3.62 (s, 2H), 3.31 (s, 2H), 3.18-3.09 (m, 1H), 3.00-2.89 (m, 4H), 2.81-2.66 (m, 5H), 1.73-1.46 (m, 6H), 0.96-0.87 (m, 1H), 0.84 (d, J=6.1 Hz, 3H).

Example 20: (1R³r)-3-(3-(6-((((S)-3,3-difluorocyclopentyl)amino)methyl)-1-oxo-4-(trifluoromethyl)isoindolin-2-yl)phenyl)-3-((4-methyl-4H-1,2,4-triazol-3-yl)methyl)cyclobutane-1-carbonitrile

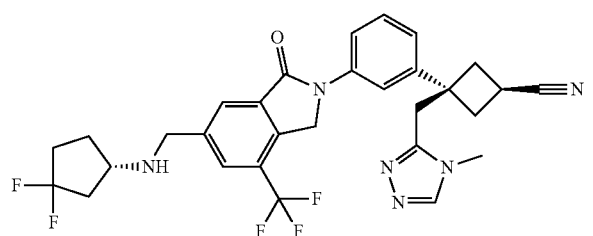

The reductive amination was carried out analogously to Example 4, Step 2, using (1r,3r)-3-(3-(6-formyl-1-oxo-4-(trifluoromethyl)isoindolin-2-yl)phenyl)-1-methyl-3-((4-methyl-4H-1,2,4-triazol-3-yl)methyl)cyclobutane-1-carbonitrile (150 mg, 0.30 mmol) and (1S)-3,3-difluorocyclopentan-1-amine hydrochloride (61 mg, 0.39 mmol), to afford the title compound after Chromatography C (79 mg, 41%). LCMS: $C_{30}H_{29}F_5N_6O$ requires 584.2, found 585.5 [M+H]⁺. ¹H NMR (500 MHz, Acetonitrile-d₃) δ 8.00 (s, 1H), 7.92 (s, 1H), 7.86 (s, 1H), 7.84 (dd, J=8.3, 2.2 Hz, 1H), 7.40 (t, J=2.0 Hz, 1H), 7.34 (t, J=8.0 Hz, 1H), 6.85 (dt, J=7.8, 1.2 Hz, 1H), 4.95 (s, 2H), 3.91 (s, 2H), 3.35-3.24 (m, 3H), 3.17-3.08 (m, 1H), 2.99-2.89 (m, 4H), 2.75 (s, 3H), 2.43-2.30 (m, 1H), 2.29-2.17 (m, 1H), 2.10-1.96 (m, 4H), 1.68-1.57 (m, 1H).

Example 21: (1R,3r)-3-(3-(6-((((R)-3,3-difluorocyclopentyl)amino)methyl)-1-oxo-4-(trifluoromethyl)isoindolin-2-yl)phenyl)-3-((4-methyl-4H-1,2,4-triazol-3-yl)methyl)cyclobutane-1-carbonitrile

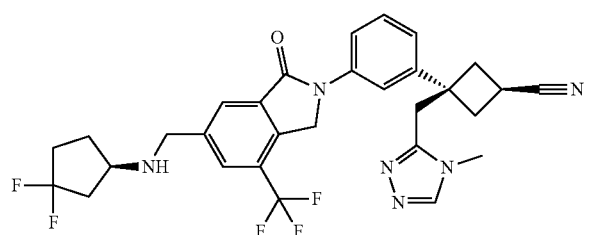

The reductive amination was carried out analogously to Example 4, Step 2, using (1r,3r)-3-(3-(6-formyl-1-oxo-4-(trifluoromethyl)isoindolin-2-yl)phenyl)-1-methyl-3-((4-methyl-4H-1,2,4-triazol-3-yl)methyl)cyclobutane-1-carbonitrile (150 mg, 0.30 mmol) and (1R)-3,3-difluorocyclopentan-1-amine hydrochloride (61 mg, 0.39 mmol), to afford the title compound after Chromatography C (70 mg, 37%). LCMS: $C_{30}H_{29}F_5N_6O$ requires 584.2, found 585.5 [M+H]⁺. ¹H NMR (500 MHz, Acetonitrile-d₃) δ 8.00 (s, 1H), 7.92 (s, 1H), 7.86 (s, 1H), 7.84 (dd, J=8.3, 2.2 Hz, 1H), 7.40 (t, J=2.0 Hz, 1H), 7.34 (t, J=8.0 Hz, 1H), 6.85 (dt, J=7.8, 1.2 Hz, 1H), 4.95 (s, 2H), 3.91 (s, 2H), 3.35-3.24 (m, 3H), 3.17-3.08 (m, 1H), 2.99-2.89 (m, 4H), 2.75 (s, 3H), 2.43-2.30 (m, 1H), 2.29-2.17 (m, 1H), 2.10-1.96 (m, 4H), 1.68-1.57 (m, 1H).

Example 22: (1r,3r)-3-(3-(6-(((3,3-difluorocyclobutyl)(methyl)amino)methyl)-1-oxo-4-(trifluoromethyl)isoindolin-2-yl)phenyl)-3-((4-methyl-4H-1,2,4-triazol-3-yl)methyl)cyclobutane-1-carbonitrile

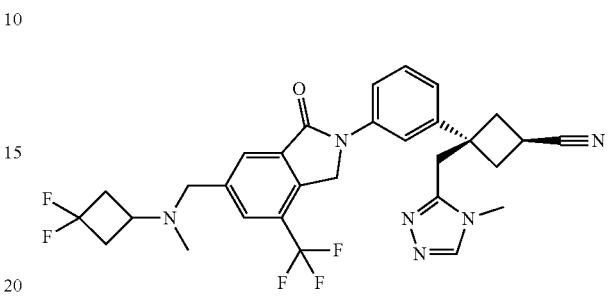

The reductive amination was carried out analogously to Example 4, Step 2, using (1r,3r)-3-(3-(6-formyl-1-oxo-4-(trifluoromethyl)isoindolin-2-yl)phenyl)-1-methyl-3-((4-methyl-4H-1,2,4-triazol-3-yl)methyl)cyclobutane-1-carbonitrile (30 mg, 0.06 mmol) and 3,3-difluoro-N-methylcyclobutan-1-amine hydrochloride (15 mg, 0.09 mmol), to afford the title compound after Chromatography C (17 mg, 47%). LCMS: $C_{30}H_{29}F_5N_6O$ requires 584.2, found 585.5 [M+H]⁺. ¹H NMR (500 MHz, Acetonitrile-d₃) δ 7.98 (s, 1H), 7.90 (s, 1H), 7.89-7.81 (m, 2H), 7.40 (t, J=2.1 Hz, 1H), 7.34 (t, J=8.0 Hz, 1H), 6.86 (d, J=7.8 Hz, 1H), 4.96 (s, 2H), 3.59 (s, 2H), 3.31 (s, 2H), 3.18-3.08 (m, 1H), 3.01-2.87 (m, 5H), 2.79-2.68 (m, 5H), 2.57-2.43 (m, 2H), 2.04 (s, 3H).

Example 23: (1r,3r)-3-(3-(6-(((1,1-difluorospiro[2.3]hexan-5-yl)amino)methyl)-1-oxo-4-(trifluoromethyl)isoindolin-2-yl)phenyl)-3-((4-methyl-4H-1,2,4-triazol-3-yl)methyl)cyclobutane-1-carbonitrile

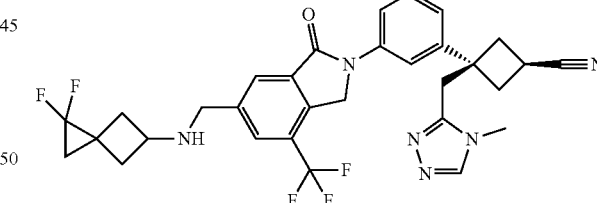

The reductive amination was carried out analogously to Example 4, Step 2, using (1r,3r)-3-(3-(6-formyl-1-oxo-4-(trifluoromethyl)isoindolin-2-yl)phenyl)-1-methyl-3-((4-methyl-4H-1,2,4-triazol-3-yl)methyl)cyclobutane-1-carbonitrile (35 mg, 0.07 mmol) and 1,1-difluorospiro[2.3]hexan-5-amine hydrochloride (25 mg, 0.15 mmol), to afford the title compound after Chromatography C (6 mg, 13%). LCMS: $C_{31}H_{29}F_5N_6O$ requires 596.2, found 597.5 [M+H]⁺. ¹H NMR (500 MHz, Acetonitrile-d₃) δ 8.00 (s, 1H), 7.94 (s, 1H), 7.90-7.81 (m, 2H), 7.41 (t, J=2.0 Hz, 1H), 7.34 (t, J=8.0 Hz, 1H), 6.85 (d, J=8.1 Hz, 1H), 4.95 (s, 2H), 3.89 (s, 2H), 3.46 (dp, J=74.4, 7.2 Hz, 1H), 3.31 (s, 2H), 3.19-3.05 (m, 1H), 3.00-2.87 (m, 5H), 2.75 (s, 3H), 2.45-2.37 (m, 1H), 2.28-2.19 (m, 2H), 1.26 (dt, J=22.2, 8.4 Hz, 3H).

Example 24: (1r,3r)-3-(3-(6-(((5,5-dimethyltetrahydrofuran-3-yl)amino)methyl)-1-oxo-4-(trifluoromethyl)isoindolin-2-yl)phenyl)-3-((4-methyl-4H-1,2,4-triazol-3-yl)methyl)cyclobutane-1-carbonitrile

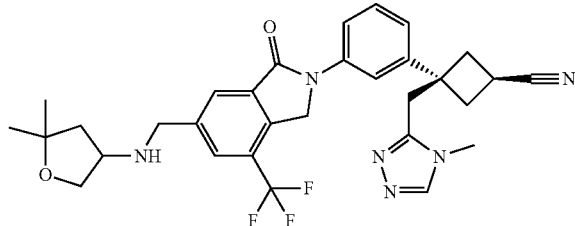 [SMILES: Cn1cnnc1C[C@]1(c2cccc(N3Cc4c(cc(CNC5COC(C)(C)C5)cc4C(F)(F)F)C3=O)c2)C[C@H](C#N)C1]

The reductive amination was carried out analogously to Example 13, using (1r,3r)-3-(3-(6-formyl-1-oxo-4-(trifluoromethyl)isoindolin-2-yl)phenyl)-1-methyl-3-((4-methyl-4H-1,2,4-triazol-3-yl)methyl)cyclobutane-1-carbonitrile (35 mg, 0.07 mmol) and 5,5-dimethyloxolan-3-amine (16 mg, 0.15 mmol), to afford the title compound after Chromatography C (3 mg, 6%). LCMS: $C_{31}H_{33}F_3N_6O_2$ requires 578.3, found 579.5 [M+H]$^+$. $^1$H NMR (500 MHz, Acetonitrile-d$_3$) δ 8.00 (s, 1H), 7.92 (s, 1H), 7.86 (s, 1H), 7.84 (dd, J=8.3, 2.2 Hz, 1H), 7.40 (t, J=2.0 Hz, 1H), 7.34 (t, J=8.0 Hz, 1H), 6.85 (d, J=7.9 Hz, 1H), 4.95 (s, 2H), 3.94-3.84 (m, 3H), 3.54 (dd, J=8.8, 5.6 Hz, 1H), 3.48-3.40 (m, 1H), 3.31 (s, 2H), 3.16-3.09 (m, 1H), 2.98-2.92 (m, 4H), 2.75 (s, 3H), 2.50 (s, 1H), 2.02 (dd, J=12.5, 7.6 Hz, 1H), 1.58 (dd, J=12.5, 6.1 Hz, 1H), 1.28 (s, 3H), 1.15 (s, 3H).

Example 25: (1r,3r)-3-((4-methyl-4H-1,2,4-triazol-3-yl)methyl)-3-(3-(6-((3-methylazepan-1-yl)methyl)-1-oxo-4-(trifluoromethyl)isoindolin-2-yl)phenyl)cyclobutane-1-carbonitrile

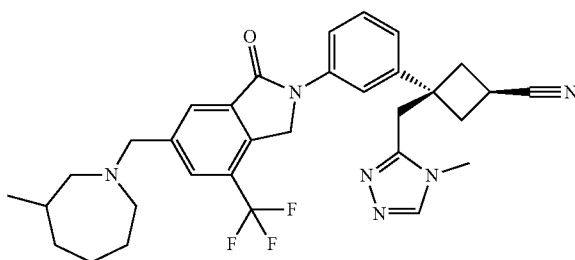

The reductive amination was carried out analogously to Example 4, Step 2, using (1r,3r)-3-(3-(6-formyl-1-oxo-4-(trifluoromethyl)isoindolin-2-yl)phenyl)-1-methyl-3-((4-methyl-4H-1,2,4-triazol-3-yl)methyl)cyclobutane-1-carbonitrile (50 mg, 0.10 mmol) and 3-methylazepane hydrochloride (47 mg, 0.31 mmol), to afford the title compound after Chromatography C (27 mg, 42%). LCMS: $C_{32}H_{35}F_3N_6O$ requires 576.3, found 577.5 [M+H]. $^1$H NMR (500 MHz, Acetonitrile-d$_3$) δ 7.99 (s, 1H), 7.94 (s, 1H), 7.86 (s, 1H), 7.84 (dd, J=8.0, 2.3 Hz, 2H), 7.41 (t, J=2.1 Hz, 1H), 7.34 (t, J=8.0 Hz, 1H), 6.85 (dt, J=7.8, 1.3 Hz, 1H), 4.95 (s, 2H), 3.80 (s, 2H), 3.31 (s, 2H), 3.18-3.04 (m, 1H), 3.00-2.89 (m, 4H), 2.83-2.62 (m, 5H), 2.62-2.53 (m, 1H), 2.32 (dd, J=13.1, 9.0 Hz, 1H), 1.76-1.46 (m, 5H), 1.34-1.24 (m, 1H), 0.80 (d, J=6.7 Hz, 3H).

Example 26: (1r,3r)-3-(3-(6-((3-fluoro-3-methylazepan-1-yl)methyl)-1-oxo-4-(trifluoromethyl)isoindolin-2-yl)phenyl)-3-((4-methyl-4H-1,2,4-triazol-3-yl)methyl)cyclobutane-1-carbonitrile

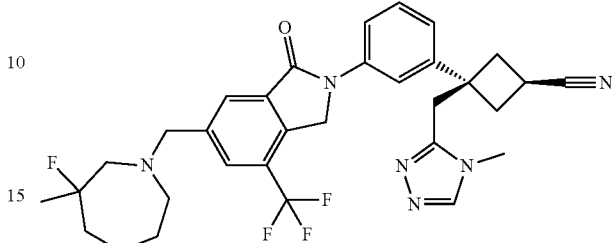

The reductive amination was carried out analogously to Example 13, using (1r,3r)-3-(3-(6-formyl-1-oxo-4-(trifluoromethyl)isoindolin-2-yl)phenyl)-1-methyl-3-((4-methyl-4H-1,2,4-triazol-3-yl)methyl)cyclobutane-1-carbonitrile (50 mg, 0.10 mmol) and 3-fluoro-3-methylazepane (27 mg, 0.21 mmol), to afford the title compound after Chromatography C (29 mg, 46%). LCMS: $C_{32}H_{34}F_4N_6O$ requires 594.3, found 595.5 [M+H]$^+$. $^1$H NMR (500 MHz, Acetonitrile-d$_3$) δ 8.01 (s, 1H), 7.97 (s, 1H), 7.86 (s, 1H), 7.84 (dd, J=8.2, 2.2 Hz, 1H), 7.41 (t, J=2.0 Hz, 1H), 7.34 (t, J=8.0 Hz, 1H), 6.85 (dt, J=7.9, 1.4 Hz, 1H), 4.96 (s, 2H), 3.91-3.81 (m, 2H), 3.31 (s, 2H), 3.17-3.08 (m, 1H), 3.02-2.83 (m, 5H), 2.80-2.60 (m, 6H), 1.88-1.66 (m, 4H), 1.65-1.54 (m, 1H), 1.47-1.39 (m, 1H), 1.22 (d, J=21.5 Hz, 3H).

Example 27: (1r,3r)-3-(3-(6-(((7,7-difluoro-3-azabicyclo[4.1.0]heptan-3-yl)methyl)-1-oxo-4-(trifluoromethyl)isoindolin-2-yl)phenyl)-3-((4-methyl-4H-1,2,4-triazol-3-yl)methyl)cyclobutane-1-carbonitrile

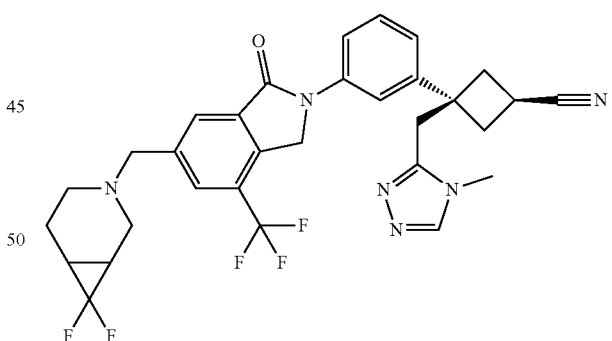

The reductive amination was carried out analogously to Example 4, Step 2, using (1r,3r)-3-(3-(6-formyl-1-oxo-4-(trifluoromethyl)isoindolin-2-yl)phenyl)-1-methyl-3-((4-methyl-4H-1,2,4-triazol-3-yl)methyl)cyclobutane-1-carbonitrile (35 mg, 0.07 mmol) and 7,7-difluoro-3-azabicyclo[4.1.0]heptane hydrochloride (19 mg, 0.11 mmol), to afford the title compound after Chromatography C (22 mg, 49%). LCMS: $C_{31}H_{29}F_5N_6O$ requires 596.2, found 597.5 [M+H]. $^1$H NMR (500 MHz, Acetonitrile-d$_3$) δ 7.96 (s, 1H), 7.89 (s, 1H), 7.86 (s, 1H), 7.84 (dd, J=8.0, 2.1 Hz, 1H), 7.41 (t, J=2.0 Hz, 1H), 7.34 (t, J=8.0 Hz, 1H), 6.85 (dt, J=7.7, 1.3 Hz, 1H), 4.96 (s, 2H), 3.69-3.55 (m, 2H), 3.31 (s, 2H), 3.18-3.07 (m, 1H), 3.00-2.90 (m, 4H), 2.80-2.71 (m, 4H), 2.62 (d, J=12.0 Hz, 1H), 2.34-2.25 (m, 1H), 2.25-2.18 (m, 1H), 2.01-1.95 (m, 1H), 1.83-1.68 (m, 3H).

Example 28: (1r,3r)-3-(3-(6-((7,8-dihydro-1,6-naph-thyridin-6(5H)-yl)methyl)-1-oxo-4-(trifluoromethyl) isoindolin-2-yl)phenyl)-3-((4-methyl-4H-1,2,4-tri-azol-3-yl)methyl)cyclobutane-1-carbonitrile

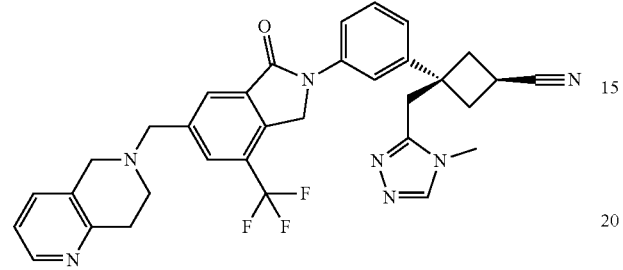

The reductive amination was carried out analogously to Example 4, Step 2, using (1r,3r)-3-(3-(6-formyl-1-oxo-4-(trifluoromethyl)isoindolin-2-yl)phenyl)-1-methyl-3-((4-methyl-4H-1,2,4-triazol-3-yl)methyl)cyclobutane-1-carbonitrile (35 mg, 0.07 mmol) and 5,6,7,8-tetrahydro-1,6-naphthyridine dihydrochloride (23 mg, 0.11 mmol), to afford the title compound after Chromatography C (12 mg, 26%). LCMS: $C_{33}H_{30}F_3N_7O$ requires 597.2, found 598.5 [M+H]$^+$. $^1$H NMR (500 MHz, Acetonitrile-d$_3$) δ 8.35 (dd, J=4.8, 1.6 Hz, 1H), 8.04 (s, 1H), 7.97 (s, 1H), 7.87 (s, 1H), 7.85 (dd, J=8.0, 2.2 Hz, 1H), 7.41 (t, J=2.0 Hz, 1H), 7.38-7.32 (m, 2H), 7.09 (dd, J=7.8, 4.8 Hz, 1H), 6.85 (d, J=7.8 Hz, 1H), 4.98 (s, 2H), 3.88 (s, 2H), 3.66 (s, 2H), 3.31 (s, 2H), 3.18-3.08 (m, 1H), 3.01-2.83 (m, 8H), 2.75 (s, 3H).

Example 29: (1r,3r)-3-(3-(6-((1,4-oxazepan-4-yl) methyl)-1-oxo-4-(trifluoromethyl)isoindolin-2-yl) phenyl)-3-((4-methyl-4H-1,2,4-triazol-3-yl)methyl) cyclobutane-1-carbonitrile

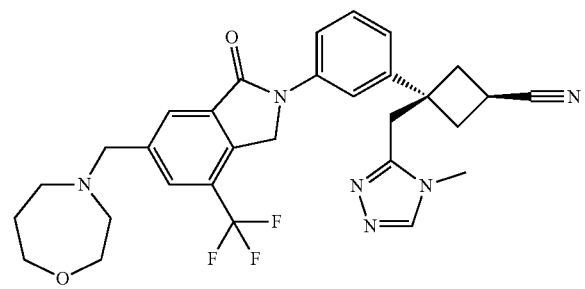 [SMILES: Cn1cnnc1C[C@]1(c2cccc(N3Cc4c(cc(CN5CCCOCC5)cc4C(F)(F)F)C3=O)c2)C[C@H](C#N)C1]

The reductive amination was carried out analogously to Example 4, Step 2, using (1r,3r)-3-(3-(6-formyl-1-oxo-4-(trifluoromethyl)isoindolin-2-yl)phenyl)-1-methyl-3-((4-methyl-4H-1,2,4-triazol-3-yl)methyl)cyclobutane-1-carbonitrile (35 mg, 0.07 mmol) and 1,4-oxazepane hydrochloride (20 mg, 0.15 mmol), to afford the title compound after Chromatography C (22 mg, 51%). LCMS: $C_{31}H_{29}F_5N_6O$ requires 564.2, found 565.5 [M+H]$^+$. $^1$H NMR (500 MHz, Acetonitrile-d$_3$) δ 8.00 (s, 1H), 7.93 (s, 1H), 7.86 (s, 1H), 7.84 (dd, J=8.2, 2.2 Hz, 1H), 7.41 (t, J=2.0 Hz, 1H), 7.34 (t, J=8.0 Hz, 1H), 6.85 (d, J=7.8 Hz, 1H), 4.96 (s, 2H), 3.83 (s, 2H), 3.76 (t, J=6.0 Hz, 2H), 3.69-3.64 (m, 2H), 3.31 (s, 2H), 3.13 (tt, J=9.6, 7.1 Hz, 1H), 2.99-2.92 (m, 4H), 2.75 (s, 3H), 2.73-2.67 (m, 4H), 1.89-1.85 (m, 2H).

Example 30: (1r,3r)-3-(3-(6-((5-oxa-8-azaspiro[2.6] nonan-8-yl)methyl)-1-oxo-4-(trifluoromethyl)isoin-dolin-2-yl)phenyl)-3-((4-methyl-4H-1,2,4-triazol-3-yl)methyl)cyclobutane-1-carbonitrile

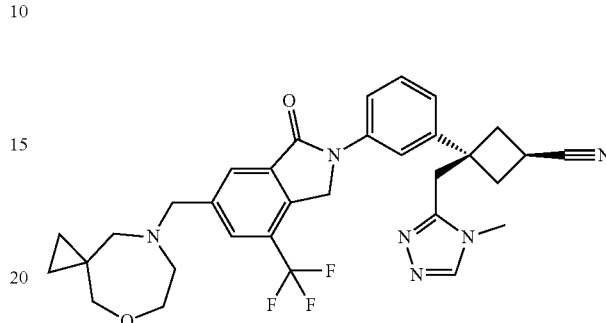

The reductive amination was carried out analogously to Example 13, using (1r,3r)-3-(3-(6-formyl-1-oxo-4-(trifluoromethyl)isoindolin-2-yl)phenyl)-1-methyl-3-((4-methyl-4H-1,2,4-triazol-3-yl)methyl)cyclobutane-1-carbonitrile (62 mg, 0.13 mmol) and 5-oxa-8-azaspiro[2.6]nonane (49 mg, 0.39 mmol), to afford the title compound after Chromatography C (38 mg, 50%). LCMS: $C_{32}H_{33}F_3N_6O_2$ requires 590.3, found 591.5 [M+H]$^+$. $^1$H NMR (500 MHz, Acetonitrile-d$_3$) δ 7.99 (s, 1H), 7.94 (s, 1H), 7.86 (s, 1H), 7.84 (dd, J=8.1, 2.2 Hz, 1H), 7.41 (t, J=2.0 Hz, 1H), 7.34 (t, J=8.0 Hz, 1H), 6.85 (dt, J=7.7, 1.1 Hz, 1H), 4.95 (s, 2H), 3.82 (s, 2H), 3.80-3.73 (m, 2H), 3.52 (s, 2H), 3.31 (s, 2H), 3.13 (tt, J=9.4, 6.9 Hz, 1H), 3.01-2.88 (m, 4H), 2.83-2.77 (m, 2H), 2.75 (s, 3H), 2.54 (s, 2H), 0.44 (d, J=9.9 Hz, 4H).

Example 31: (1r,3r)-3-(3-(6-(((3,3-dimethylcyclo-pentyl)amino)methyl)-1-oxo-4-(trifluoromethyl) isoindolin-2-yl)phenyl)-3-((4-methyl-4H-1,2,4-tri-azol-3-yl)methyl)cyclobutane-1-carbonitrile

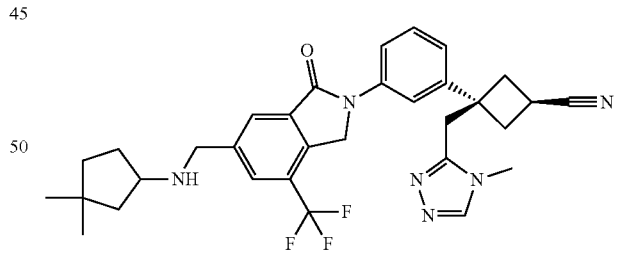

The reductive amination was carried out analogously to Example 4, Step 2, using (1r,3r)-3-(3-(6-formyl-1-oxo-4-(trifluoromethyl)isoindolin-2-yl)phenyl)-1-methyl-3-((4-methyl-4H-1,2,4-triazol-3-yl)methyl)cyclobutane-1-carbonitrile (50 mg, 0.10 mmol) and 3,3-dimethylcyclopentan-1-amine hydrochloride (27 mg, 0.18 mmol), to afford the title compound after Chromatography C (34 mg, 37%). LCMS: $C_{32}H_{35}F_3N_6O$ requires 576.3, found 577.5 [M+H]$^+$.
$^1$H NMR (500 MHz, Acetonitrile-d$_3$) δ 8.01 (s, 1H), 7.94 (s, 1H), 7.91-7.84 (m, 2H), 7.43 (t, J=2.0 Hz, 1H), 7.37 (t, J=8.0 Hz, 1H), 6.88 (dd, J=7.7, 1.4 Hz, 1H), 4.98 (s, 2H), 3.91 (s, 2H), 3.34 (s, 2H), 3.24 (p, J=7.2 Hz, 1H), 3.21-3.09

(m, 1H), 3.03-2.90 (m, 4H), 2.78 (s, 3H), 2.02-1.99 (m, 1H), 1.77 (dd, J=12.6, 7.3 Hz, 1H), 1.61-1.45 (m, 2H), 1.45-1.35 (m, 1H), 1.26 (dd, J=12.6, 7.5 Hz, 1H), 1.10 (s, 3H), 0.99 (s, 3H).

Example 32: (1r,3r)-3-(3-(6-(((3,3-difluorocyclopentyl)(methyl)amino)methyl)-1-oxo-4-(trifluoromethyl)isoindolin-2-yl)phenyl)-3-((4-methyl-4H-1,2,4-triazol-3-yl)methyl)cyclobutane-1-carbonitrile

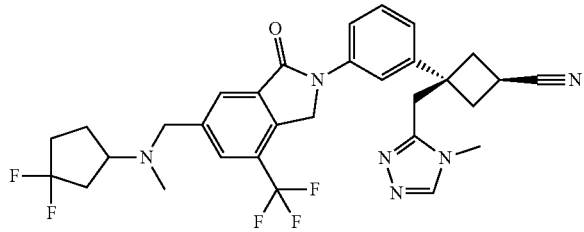 [SMILES: CN(Cc1cc2c(c(C(F)(F)F)c1)CN(c1cccc([C@]3(Cc4nncn4C)C[C@@H](C#N)C3)c1)C2=O)C1CCC(F)(F)C1]

The reductive amination was carried out analogously to Example 4, Step 2, using (1r,3r)-3-(3-(6-formyl-1-oxo-4-(trifluoromethyl)isoindolin-2-yl)phenyl)-1-methyl-3-((4-methyl-4H-1,2,4-triazol-3-yl)methyl)cyclobutane-1-carbonitrile (75 mg, 0.16 mmol) and 3,3-difluoro-N-methylcyclopentan-1-amine hydrochloride (47 mg, 0.27 mmol), to afford the title compound after Chromatography C (34 mg, 37%). LCMS: $C_{31}H_{31}F_5N_6O$ requires 598.2, found 599.5 [M+H]$^+$. $^1$H NMR (500 MHz, Acetonitrile-d$_3$) δ 8.00 (s, 1H), 7.92 (s, 1H), 7.89 (s, 1H), 7.87 (ddd, J=8.2, 2.3, 0.9 Hz, 1H), 7.43 (t, J=2.0 Hz, 1H), 7.37 (t, J=8.0 Hz, 1H), 6.88 (dt, J=7.8, 1.3 Hz, 1H), 4.99 (s, 2H), 3.71 (dd, J=17, 14 Hz, 2H), 3.34 (s, 2H), 3.20-3.12 (m, 2H), 3.02-2.92 (m, 4H), 2.78 (s, 3H), 2.48-2.35 (m, 1H), 2.30-2.20 (m, 1H), 2.15 (s, 3H), 2.15-1.99 (m, 3H), 1.87-1.75 (m, 1H).

Example 33: (1r,3r)-3-(3-(6-((2-methyl-1,4-oxazepan-4-yl)methyl)-1-oxo-4-(trifluoromethyl)isoindolin-2-yl)phenyl)-3-((4-methyl-4H-1,2,4-triazol-3-yl)methyl)cyclobutane-1-carbonitrile

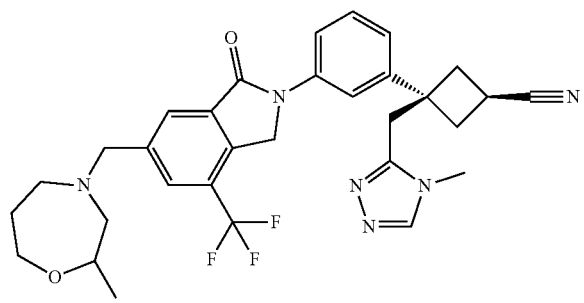 [SMILES: CC1CN(Cc2cc3c(c(C(F)(F)F)c2)CN(c2cccc([C@]4(Cc5nncn5C)C[C@@H](C#N)C4)c2)C3=O)CCCO1]

The reductive amination was carried out analogously to Example 13, using (1r,3r)-3-(3-(6-formyl-1-oxo-4-(trifluoromethyl)isoindolin-2-yl)phenyl)-1-methyl-3-((4-methyl-4H-1,2,4-triazol-3-yl)methyl)cyclobutane-1-carbonitrile (75 mg, 0.16 mmol) and 2-methyl-1,4-oxazepane (36 mg, 0.31 mmol), to afford the title compound after Chromatography C (55 mg, 58%). LCMS: $C_{31}H_{33}F_3N_6O_2$ requires 578.3, found 579.5 [M+H]$^+$. $^1$H NMR (500 MHz, Acetonitrile-d$_3$) δ 8.00 (s, 1H), 7.94 (s, 1H), 7.86 (s, 1H), 7.84 (dd, J=8.2, 2.2 Hz, 1H), 7.41 (t, J=2.0 Hz, 1H), 7.34 (t, J=8.0 Hz, 1H), 6.85 (d, J=7.9 Hz, 1H), 4.96 (s, 2H), 3.84-3.77 (m, 3H), 3.77-3.68 (m, 2H), 3.31 (s, 2H), 3.16-3.08 (m, 1H), 2.99-2.90 (m, 4H), 2.83-2.73 (m, 5H), 2.61 (ddd, J=12.9, 8.8, 4.3 Hz, 1H), 2.39 (dd, J=13.4, 8.9 Hz, 1H), 1.82-1.75 (m, 2H), 1.01 (d, J=6.3 Hz, 3H).

Example 34: (1r,3r)-3-(3-(6-((2,7-dimethyl-1,4-oxazepan-4-yl)methyl)-1-oxo-4-(trifluoromethyl)isoindolin-2-yl)phenyl)-3-((4-methyl-4H-1,2,4-triazol-3-yl)methyl)cyclobutane-1-carbonitrile

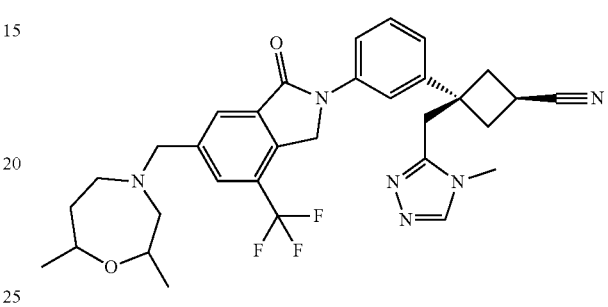

The reductive amination was carried out analogously to Example 13, using (1r,3r)-3-(3-(6-formyl-1-oxo-4-(trifluoromethyl)isoindolin-2-yl)phenyl)-1-methyl-3-((4-methyl-4H-1,2,4-triazol-3-yl)methyl)cyclobutane-1-carbonitrile (100 mg, 0.21 mmol) and 2,7-dimethyl-1,4-oxazepane (40 mg, 0.31 mmol), to afford the title compound after Chromatography C (52 mg, 39%). LCMS: $C_{32}H_{35}F_3N_6O_2$ requires 592.3, found 593.5 [M+H]$^+$. $^1$H NMR (500 MHz, Acetonitrile-d$_3$) δ 8.00 (s, 1H), 7.93 (s, 1H), 7.86 (s, 1H), 7.84 (d, J=8.1 Hz, 1H), 7.41 (s, 1H), 7.34 (t, J=7.9 Hz, 1H), 6.85 (d, J=7.7 Hz, 1H), 4.96 (s, 2H), 3.99-3.87 (m, 1H), 3.83-3.71 (m, 3H), 3.31 (s, 2H), 3.13 (p, J=8.0 Hz, 1H), 3.02-2.89 (m, 5H), 2.80-2.60 (m, 7H), 2.36 (dd, J=13.0, 8.9 Hz, 1H), 1.56 (ddd, J=14.0, 11.3, 6.3 Hz, 1H), 1.10 (d, J=6.3 Hz, 3H), 1.01 (d, J=6.3 Hz, 3H).

Example 35: (1r,3r)-3-(3-(6-((6-methyl-1,4-oxazepan-4-yl)methyl)-1-oxo-4-(trifluoromethyl)isoindolin-2-yl)phenyl)-3-((4-methyl-4H-1,2,4-triazol-3-yl)methyl)cyclobutane-1-carbonitrile

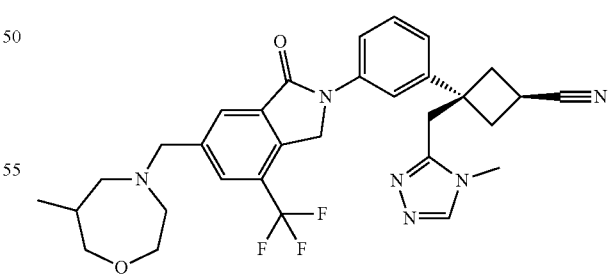

The reductive amination was carried out analogously to Example 13, using (1r,3r)-3-(3-(6-formyl-1-oxo-4-(trifluoromethyl)isoindolin-2-yl)phenyl)-1-methyl-3-((4-methyl-4H-1,2,4-triazol-3-yl)methyl)cyclobutane-1-carbonitrile (50 mg, 0.10 mmol) and 6-methyl-1,4-oxazepane (18 mg, 0.16 mmol), to afford the title compound after Chromatography C (16 mg, 26%). LCMS: $C_{31}H_{33}F_3N_6O_2$ requires 578.3, found 579.5 [M+H]⁺. ¹H NMR (500 MHz, Acetonitrile-d₃) δ 8.03 (s, 1H), 7.98 (s, 1H), 7.89 (s, 1H), 7.87 (dd, J=8.1, 2.2 Hz, 1H), 7.44 (t, J=2.0 Hz, 1H), 7.37 (t, J=8.0 Hz, 1H), 6.88 (d, J=7.8 Hz, 1H), 4.99 (s, 2H), 3.86 (d, J=4.4 Hz, 2H), 3.82 (dd, J=11.9, 5.1 Hz, 1H), 3.75 (ddd, J=12.4, 7.8, 3.3 Hz, 1H), 3.63 (ddd, J=12.4, 5.5, 3.4 Hz, 1H), 3.39 (dd, J=12.0, 8.4 Hz, 1H), 3.34 (s, 2H), 3.20-3.12 (m, 1H), 3.03-2.93 (m, 4H), 2.82-2.74 (m, 6H), 2.68 (ddd, J=13.4, 7.8, 3.4 Hz, 1H), 2.45 (dd, J=12.9, 8.1 Hz, 1H), 0.80 (d, J=7.0 Hz, 3H).

Example 36: (1r,3r)-3-(3-(6-((7-methyl-1,4-oxazepan-4-yl)methyl)-1-oxo-4-(trifluoromethyl)isoindolin-2-yl)phenyl)-3-((4-methyl-4H-1,2,4-triazol-3-yl)methyl)cyclobutane-1-carbonitrile

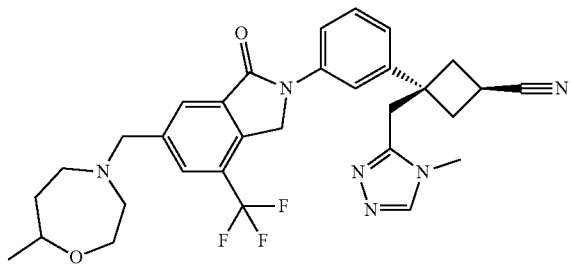 [SMILES: CC1CCN(Cc2cc3c(c(C(F)(F)F)c2)CN(c2cccc([C@]4(Cc5nncn5C)C[C@@H](C#N)C4)c2)C3=O)CCO1]

The reductive amination was carried out analogously to Example 13, using (1r,3r)-3-(3-(6-formyl-1-oxo-4-(trifluoromethyl)isoindolin-2-yl)phenyl)-1-methyl-3-((4-methyl-4H-1,2,4-triazol-3-yl)methyl)cyclobutane-1-carbonitrile (50 mg, 0.10 mmol) and 7-methyl-1,4-oxazepane (18 mg, 0.16 mmol), to afford the title compound after Chromatography C (26 mg, 41%). LCMS: C₃₁H₃₃F₃N₆O₂ requires 578.3, found 579.5 [M+H]⁺. ¹H NMR (500 MHz, Acetonitrile-d₃) δ 7.99 (s, 1H), 7.92 (s, 1H), 7.86 (s, 1H), 7.84 (dd, J=7.9, 2.2 Hz, 1H), 7.40 (t, J=2.1 Hz, 1H), 7.34 (t, J=8.0 Hz, 1H), 6.85 (d, J=8.2 Hz, 1H), 4.96 (s, 2H), 3.93-3.85 (m, 1H), 3.82-3.74 (m, 3H), 3.60-3.52 (m, 1H), 3.31 (s, 2H), 3.17-3.08 (m, 1H), 2.99-2.91 (m, 4H), 2.81-2.58 (m, 8H), 1.72-1.62 (m, 1H), 1.11 (d, J=6.3 Hz, 3H).

Example 37: (1r,3r)-3-(3-(6-((9-oxa-3-azabicyclo[4.2.1]nonan-3-yl)methyl)-1-oxo-4-(trifluoromethyl)isoindolin-2-yl)phenyl)-3-((4-methyl-4H-1,2,4-triazol-3-yl)methyl)cyclobutane-1-carbonitrile

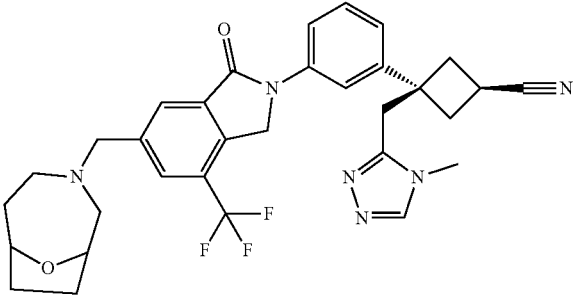 [SMILES: Cn1cnnc1C[C@]1(c2cccc(N3Cc4c(cc(CN5CCC6CCC(C5)O6)cc4C(F)(F)F)C3=O)c2)C[C@H](C#N)C1]

The reductive amination was carried out analogously to Example 13, using (1r,3r)-3-(3-(6-formyl-1-oxo-4-(trifluoromethyl)isoindolin-2-yl)phenyl)-1-methyl-3-((4-methyl-4H-1,2,4-triazol-3-yl)methyl)cyclobutane-1-carbonitrile (62 mg, 0.13 mmol) and 9-oxa-3-azabicyclo[4.2.1]nonane (25 mg, 0.19 mmol), to afford the title compound after Chromatography C (27 mg, 35%). LCMS: C₃₂H₃₃F₃N₆O₂ requires 590.3, found 591.5 [M+H]⁺. ¹H NMR (500 MHz, Acetonitrile-d₃) δ 8.01 (s, 1H), 7.97 (s, 1H), 7.86 (s, 1H), 7.84 (dd, J=8.0, 1.6 Hz, 1H), 7.42 (t, J=2.0 Hz, 1H), 7.38-7.30 (m, 1H), 6.85 (d, J=7.9 Hz, 1H), 4.96 (s, 2H), 4.39 (t, J=8.6 Hz, 1H), 4.23 (ddd, J=7.5, 5.1, 2.6 Hz, 1H), 3.76 (s, 2H), 3.31 (s, 2H), 3.18-3.08 (m, 1H), 3.00-2.91 (m, 4H), 2.75 (s, 3H), 2.66 (ddt, J=13.1, 6.1, 2.3 Hz, 1H), 2.57 (dt, J=12.1, 1.9 Hz, 1H), 2.50 (ddd, J=13.2, 11.6, 4.5 Hz, 1H), 2.41 (dd, J=12.2, 2.8 Hz, 1H), 2.12-2.07 (m, 1H), 1.93-1.82 (m, 4H), 1.57-1.46 (m, 1H).

Example 38: (1r,3r)-3-(3-(6-((6-oxa-3-azabicyclo[3.2.1]octan-3-yl)methyl)-1-oxo-4-(trifluoromethyl)isoindolin-2-yl)phenyl)-3-((4-methyl-4H-1,2,4-triazol-3-yl)methyl)cyclobutane-1-carbonitrile

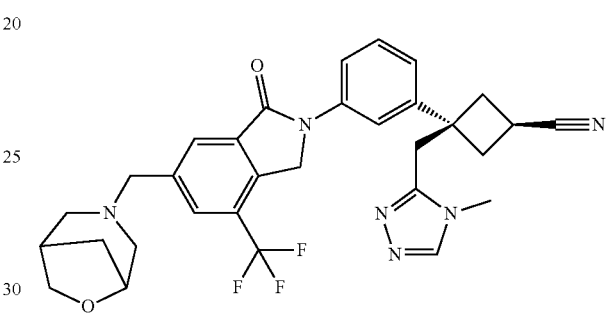

The reductive amination was carried out analogously to Example 4, Step 2, using (1r,3r)-3-(3-(6-formyl-1-oxo-4-(trifluoromethyl)isoindolin-2-yl)phenyl)-1-methyl-3-((4-methyl-4H-1,2,4-triazol-3-yl)methyl)cyclobutane-1-carbonitrile (44 mg, 0.09 mmol) and 6-oxa-3-azabicyclo[3.2.1]octane hydrochloride (28 mg, 0.18 mmol), to afford the title compound after Chromatography C (23 mg, 44%). LCMS: C₃₂H₃₃F₃N₆O₂ requires 576.2, found 577.5 [M+H]⁺. ¹H NMR (500 MHz, Acetonitrile-d₃) δ 7.98 (s, 1H), 7.90 (s, 1H), 7.87 (s, 1H), 7.84 (dd, J=8.2, 2.2 Hz, 1H), 7.41 (t, J=2.0 Hz, 1H), 7.34 (t, J=8.0 Hz, 1H), 6.85 (d, J=7.6 Hz, 1H), 4.95 (s, 2H), 4.15 (t, J=4.9 Hz, 1H), 4.01 (d, J=6.9 Hz, 1H), 3.71 (d, J=8.5 Hz, 3H), 3.31 (s, 2H), 3.16-3.09 (m, 1H), 3.01-2.89 (m, 4H), 2.79 (dd, J=10.0, 4.9 Hz, 2H), 2.75 (s, 3H), 2.40 (q, J=4.3 Hz, 1H), 2.32 (d, J=10.5 Hz, 1H), 2.11-2.06 (m, 2H), 1.61 (d, J=10.9 Hz, 1H).

Example 39: (1r,3r)-3-(3-(4-cyclopropyl-6-(((3,3-difluorocyclopentyl)amino)methyl)-1-oxo-1,3-dihydro-2H-pyrrolo[3,4-c]pyridin-2-yl)phenyl)-3-((4-methyl-4H-1,2,4-triazol-3-yl)methyl)cyclobutane-1-carbonitrile

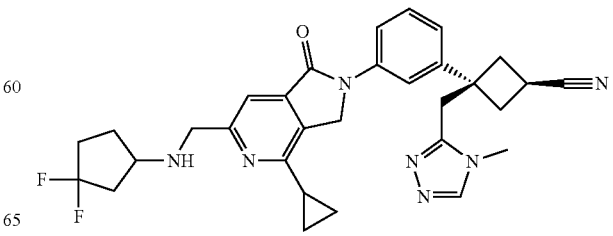

Step 1: Synthesis of 4-cyclopropyl-6-(((3,3-difluorocyclopentyl)amino)methyl)-2,3-dihydro-1H-pyrrolo[3,4-c]pyridin-1-one. The title compound was synthesized analogously to Example E, using 4-cyclopropyl-1-oxo-2H,3H-pyrrolo[3,4-c]pyridine-6-carbaldehyde (50 mg, 0.25 mmol) and 3,3-difluorocyclopentan-1-amine hydrochloride (39 mg, 0.25 mmol). Following General Work-up Procedure 1 and Chromatography B, the title compound was obtained (52 mg, 68%).

Step 2: Synthesis of (1r,3r)-3-(3-(4-cyclopropyl-6-(((3,3-difluorocyclopentyl)amino)methyl)-1-oxo-1,3-dihydro-2H-pyrrolo[3,4-c]pyridin-2-yl)phenyl)-3-((4-methyl-4H-1,2,4-triazol-3-yl)methyl)cyclobutane-1-carbonitrile. The title compound was synthesized analogously to Example 11, using 4-cyclopropyl-6-(((3,3-difluorocyclopentyl)amino)methyl)-2,3-dihydro-1H-pyrrolo[3,4-c]pyridin-1-one (46 mg, 0.15 mmol), and Example I (50 mg, 0.15 mmol) followed by Chromatography C to afford the title compound (15 mg, 16%). LCMS: $C_{31}H_{33}F_2N_7O$ requires 557.3, found 558.5 [M+H]$^+$. $^1$H NMR (500 MHz, Acetonitrile-$d_3$) δ 7.92-7.81 (m, 2H), 7.47-7.39 (m, 2H), 7.39-7.31 (m, 1H), 6.87 (d, J=7.6 Hz, 1H), 4.90 (s, 2H), 3.84 (s, 2H), 3.31 (s, 2H), 3.29-3.23 (m, 1H), 3.19-3.06 (m, 1H), 3.02-2.89 (m, 5H), 2.76 (s, 3H), 2.40-2.26 (m, 1H), 2.27-2.17 (m, 1H), 2.06-1.96 (m, 2H) 1.67-1.56 (m, 2H), 1.21-1.11 (m, 2H), 1.14-1.04 (m, 2H).

Example 40: (1r,3r)-3-(3-(4-cyclopropyl-6-(((S)-3-methylpiperidin-1-yl)methyl)-1-oxo-1,3-dihydro-2H-pyrrolo[3,4-c]pyridin-2-yl)phenyl)-3-((4-methyl-4H-1,2,4-triazol-3-yl)methyl)cyclobutane-1-carbonitrile

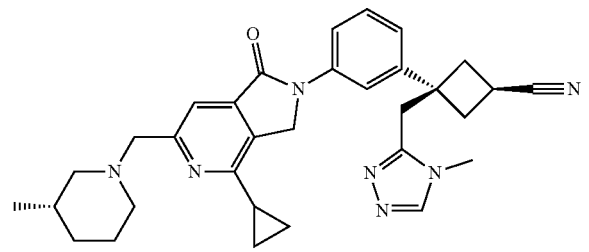 [SMILES: C[C@H]1CCCN(Cc2cc3c(c(C4CC4)n2)CN(c2cccc([C@]4(Cc5nncn5C)C[C@@H](C#N)C4)c2)C3=O)C1]

The title compound was synthesized analogously to Example 11, using (S)-4-cyclopropyl-6-((3-methylpiperidin-1-yl)methyl)-2,3-dihydro-1H-pyrrolo[3,4-c]pyridin-1-one (Example E, 86 mg, 0.30 mmol), and Example I (100 mg, 0.30 mmol) followed by Chromatography C to afford the title compound (38 mg, 21%). LCMS: $C_{32}H_{37}N_7O$ requires 535.3, found 536.5 [M+H]$^+$. $^1$H NMR (500 MHz, Acetonitrile-$d_3$) δ 7.94-7.89 (m, 2H), 7.53 (s, 1H), 7.45 (t, J=2.0 Hz, 1H), 7.38 (t, J=8.0 Hz, 1H), 6.90 (d, J=7.8 Hz, 1H), 4.94 (s, 2H), 3.62 (s, 2H), 3.34 (s, 2H), 3.25-3.08 (m, 1H), 3.08-2.90 (m, 5H), 2.83-2.74 (m, 5H), 1.76-1.52 (m, 6H), 1.18-1.04 (m, 4H), 0.97-0.88 (m, 1H), 0.87 (d, J=6.2 Hz, 3H).

Example 41: (1r,3r)-3-(3-(6-((2-(hydroxymethyl)-1,4-oxazepan-4-yl)methyl)-1-oxo-4-(trifluoromethyl)isoindolin-2-yl)phenyl)-3-((4-methyl-4H-1,2,4-triazol-3-yl)methyl)cyclobutane-1-carbonitrile

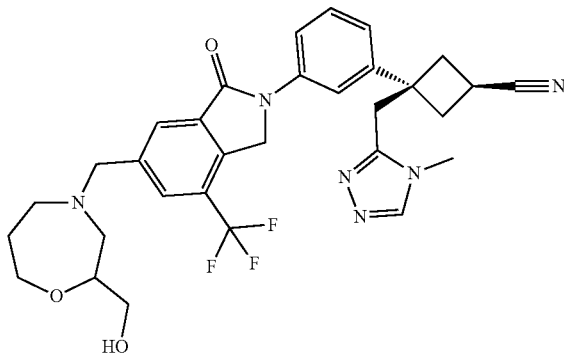 [SMILES: Cn1cnnc1C[C@]1(c2cccc(N3Cc4c(cc(CN5CCCOC(CO)C5)cc4C(F)(F)F)C3=O)c2)C[C@H](C#N)C1]

The reductive amination was carried out analogously to Example 4, Step 2, using (1r,3r)-3-(3-(6-formyl-1-oxo-4-(trifluoromethyl)isoindolin-2-yl)phenyl)-1-methyl-3-((4-methyl-4H-1,2,4-triazol-3-yl)methyl)cyclobutane-1-carbonitrile (40 mg, 0.08 mmol) and 1,4-oxazepan-2-ylmethanol hydrochloride (21 mg, 0.13 mmol), to afford the title compound after Chromatography C (26 mg, 52%). LCMS: $C_{31}H_{33}F_3N_6O_3$ requires 594.3, found 595.5 [M+H]$^+$. $^1$H NMR (500 MHz, Acetonitrile-$d_3$) δ 8.03 (s, 1H), 7.96 (s, 1H), 7.91-7.84 (m, 2H), 7.44 (t, J=2.0 Hz, 1H), 7.37 (t, J=8.0 Hz, 1H), 6.88 (dt, J=7.6, 1.1 Hz, 1H), 4.99 (s, 2H), 3.94-3.83 (m, 3H), 3.79 (ddd, J=11.8, 6.8, 4.6 Hz, 1H), 3.67 (dtd, J=8.4, 5.8, 2.4 Hz, 1H), 3.42 (ddd, J=10.8, 6.4, 4.3 Hz, 1H), 3.37-3.26 (m, 3H), 3.16 (dq, J=9.7, 7.0 Hz, 1H), 3.05-2.91 (m, 5H), 2.91-2.86 (m, 1H), 2.86-2.71 (m, 5H), 2.66 (ddd, J=12.5, 8.6, 3.6 Hz, 1H), 2.47 (dd, J=13.4, 8.5 Hz, 1H).

Example 42: (1R,3r)-3-(3-(4-cyclopropyl-6-(((R)-4,4-difluoro-3-methylpiperidin-1-yl)methyl)-1-oxo-1,3-dihydro-2H-pyrrolo[3,4-c]pyridin-2-yl)phenyl)-3-((4-methyl-4H-1,2,4-triazol-3-yl)methyl)cyclobutane-1-carbonitrile

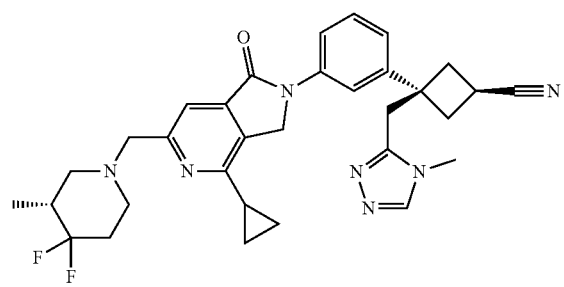 [SMILES: C[C@@H]1CN(Cc2cc3c(c(C4CC4)n2)CN(c2cccc([C@]4(Cc5nncn5C)C[C@@H](C#N)C4)c2)C3=O)CCC1(F)F]

The title compound was synthesized analogously to Example 11, using (R)-4-cyclopropyl-6-((4,4-difluoro-3-methylpiperidin-1-yl)methyl)-2,3-dihydro-1H-pyrrolo[3,4-c]pyridin-1-one (Example D, 80 mg, 0.25 mmol), and Example I (82 mg, 0.25 mmol) followed by Chromatography C to afford the title compound (40 mg, 26%). LCMS: $C_{32}H_{35}F_2N_7O$ requires 571.3, found 572.5 [M+H]$^+$. $^1$H NMR (500 MHz, Acetonitrile-$d_3$) δ 7.95-7.87 (m, 2H), 7.55

(s, 1H), 7.46 (t, J=2.0 Hz, 1H), 7.38 (t, J=8.0 Hz, 1H), 6.91 (d, J=8.3 Hz, 1H), 4.94 (s, 2H), 3.72 (s, 2H), 3.34 (s, 2H), 3.23-3.11 (m, 1H), 3.03-2.91 (m, 5H), 2.79 (d, J=10.6 Hz, 6H), 2.48-2.37 (m, 1H), 2.10-2.01 (m, 3H), 1.20-1.05 (m, 4H), 1.00 (d, J=6.1 Hz, 3H).

Example 43: (1r,3r)-3-(3-(6-(((6-ethyl-1,4-oxazepan-4-yl)methyl)-1-oxo-4-(trifluoromethyl)isoindolin-2-yl)phenyl)-3-((4-methyl-4H-1,2,4-triazol-3-yl)methyl)cyclobutane-1-carbonitrile

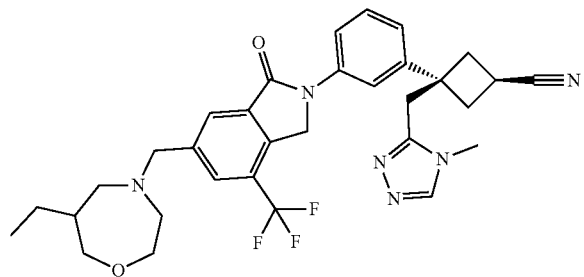 [SMILES: CCC1COCCN(Cc2cc3c(c(C(F)(F)F)c2)CN(c2cccc([C@]4(Cc5nncn5C)C[C@@H](C#N)C4)c2)C3=O)C1]

The reductive amination was carried out analogously to Example 13, using (1r,3r)-3-(3-(6-formyl-1-oxo-4-(trifluoromethyl)isoindolin-2-yl)phenyl)-1-methyl-3-((4-methyl-4H-1,2,4-triazol-3-yl)methyl)cyclobutane-1-carbonitrile (80 mg, 0.17 mmol) and 6-ethyl-1,4-oxazepane (43 mg, 0.33 mmol), to afford the title compound after Chromatography C (52 mg, 49%). LCMS: $C_{32}H_{35}F_3N_6O_2$ requires 576.2, found 577.5 [M+H]$^+$. $^1$H NMR (500 MHz, Acetonitrile-d$_3$) δ 8.03 (s, 1H), 7.99 (s, 1H), 7.89 (s, 1H), 7.89-7.83 (m, 1H), 7.44 (t, J=2.0 Hz, 1H), 7.37 (t, J=8.0 Hz, 1H), 6.88 (dt, J=7.8, 1.3 Hz, 1H), 4.99 (s, 2H), 3.85 (q, J=5.8 Hz, 3H), 3.73 (ddd, J=12.4, 7.6, 3.0 Hz, 1H), 3.63 (ddd, J=12.4, 5.8, 3.3 Hz, 1H), 3.45 (dd, J=12.0, 8.3 Hz, 1H), 3.34 (s, 2H), 3.20-3.11 (m, 1H), 3.02-2.92 (m, 4H), 2.83-2.71 (m, 5H), 2.66 (ddd, J=13.4, 7.6, 3.3 Hz, 1H), 2.49 (dd, J=13.0, 7.7 Hz, 1H), 1.89-1.87 (m, 1H), 1.27-1.11 (m, 2H), 0.79 (t, J=7.5 Hz, 3H).

Example 44: (1r,3r)-3-(3-(6-(((6-(hydroxymethyl)-1,4-oxazepan-4-yl)methyl)-1-oxo-4-(trifluoromethyl)isoindolin-2-yl)phenyl)-3-((4-methyl-4H-1,2,4-triazol-3-yl)methyl)cyclobutane-1-carbonitrile

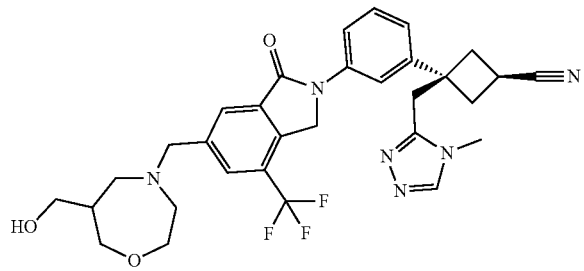 [SMILES: Cn1cnnc1C[C@]1(c2cccc(N3Cc4c(cc(CN5CCOCC(CO)C5)cc4C(F)(F)F)C3=O)c2)C[C@H](C#N)C1]

Step 1: Synthesis of 1,4-oxazepan-6-ylmethanol trifluoroacetate. To a DCM (4 mL) solution of tert-butyl 6-(hydroxymethyl)-1,4-oxazepane-4-carboxylate (200 mg) was added 1 mL of TFA. The reaction was stirred at rt for 16 h before being concentrated and used directly in the next step.

Step 2: (1r,3r)-3-(3-(6-(((6-(hydroxymethyl)-1,4-oxazepan-4-yl)methyl)-1-oxo-4-(trifluoromethyl)isoindolin-2-yl)phenyl)-3-((4-methyl-4H-1,2,4-triazol-3-yl)methyl)cyclobutane-1-carbonitrile. The reductive amination was carried out analogously to Example 4, Step 2, using (1r,3r)-3-(3-(6-formyl-1-oxo-4-(trifluoromethyl)isoindolin-2-yl)phenyl)-1-methyl-3-((4-methyl-4H-1,2,4-triazol-3-yl)methyl)cyclobutane-1-carbonitrile (40 mg, 0.08 mmol) and 1,4-oxazepan-6-ylmethanol trifluoroacetate (41 mg, 0.17 mmol), to afford the title compound after Chromatography C (9.7 mg, 19%). LCMS: $C_{31}H_{33}F_3N_6O_3$ requires 594.3, found 595.5 [M+H]$^+$. $^1$H NMR (500 MHz, Acetonitrile-d$_3$) δ 8.04 (s, 1H), 7.97 (s, 1H), 7.89 (s, 1H), 7.89-7.85 (m, 1H), 7.44 (t, J=2.0 Hz, 1H), 7.37 (t, J=8.0 Hz, 1H), 6.88 (dt, J=7.7, 1.3 Hz, 1H), 4.99 (s, 2H), 3.91-3.83 (m, 3H), 3.72 (ddd, J=12.5, 7.3, 3.1 Hz, 1H), 3.65 (ddd, J=12.4, 5.8, 3.2 Hz, 1H), 3.59 (dd, J=12.1, 7.5 Hz, 1H), 3.40 (dd, J=10.6, 6.4 Hz, 1H), 3.34 (s, 3H), 3.21-3.11 (m, 1H), 3.00-2.89 (m, 4H), 2.83 (dd, J=13.1, 4.6 Hz, 1H), 2.80-2.63 (m, 6H), 2.58 (dd, J=13.0, 7.5 Hz, 1H).

Example 45: (1r,3r)-3-(3-(6-((3-(methoxymethyl)azepan-1-yl)methyl)-1-oxo-4-(trifluoromethyl)isoindolin-2-yl)phenyl)-3-((4-methyl-4H-1,2,4-triazol-3-yl)methyl)cyclobutane-1-carbonitrile

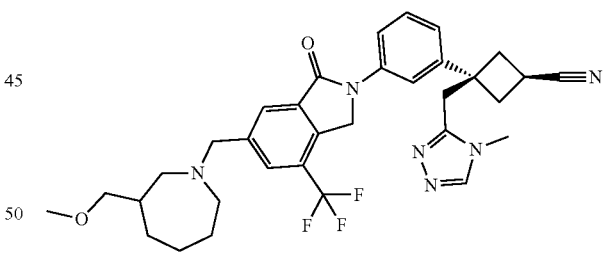

The reductive amination was carried out analogously to Example 13, using (1r,3r)-3-(3-(6-formyl-1-oxo-4-(trifluoromethyl)isoindolin-2-yl)phenyl)-1-methyl-3-((4-methyl-4H-1,2,4-triazol-3-yl)methyl)cyclobutane-1-carbonitrile (80 mg, 0.17 mmol) and 3-(methoxymethyl)azepane (44 mg, 0.31 mmol), to afford the title compound after Chromatography C (35 mg, 34%). LCMS: $C_{33}H_{37}F_3N_6O_2$ requires 606.3, found 607.5 [M+H]$^+$. $^1$H NMR (500 MHz, Acetonitrile-d$_3$) δ 8.02 (s, 1H), 7.96 (s, 1H), 7.92-7.82 (m, 2H), 7.44 (d, J=2.2 Hz, 1H), 7.37 (t, J=8.0 Hz, 1H), 6.88 (d, J=7.9 Hz, 1H), 4.98 (s, 2H), 3.82 (s, 2H), 3.34 (s, 2H), 3.24-3.03 (m, 6H), 3.03-2.89 (m, 4H), 2.84-2.60 (m, 7H), 2.48 (dd, J=13.2, 7.9 Hz, 1H), 1.79-1.69 (m, 3H), 1.65-1.55 (m, 2H), 1.38-1.25 (m, 1H).

Example 46: (1r,3r)-3-(3-(6-((6-(methoxymethyl)-1,4-oxazepan-4-yl)methyl)-1-oxo-4-(trifluoromethyl)isoindolin-2-yl)phenyl)-3-((4-methyl-4H-1,2,4-triazol-3-yl)methyl)cyclobutane-1-carbonitrile

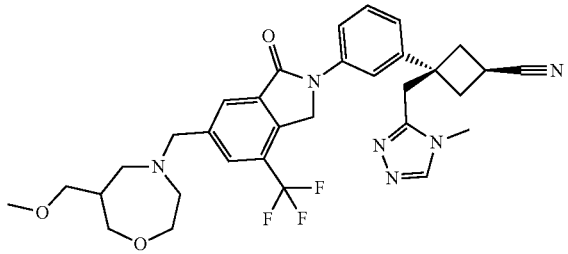 [SMILES: COCC1COCCN(Cc2cc3c(c(C(F)(F)F)c2)CN(c2cccc([C@]4(Cc5nncn5C)C[C@@H](C#N)C4)c2)C3=O)C1]

Step 1: Synthesis of tert-butyl 6-(methoxymethyl)-1,4-oxazepane-4-carboxylate. To a DMF (4.3 mL) solution of tert-butyl 6-(hydroxymethyl)-1,4-oxazepane-4-carboxylate (270 mg, 1.17 mmol) at 0° C. was added sodium hydride (60% dispersion in oil, 56 mg, 1.4 mmol). This mixture was stirred for 10 min at rt before addition of methyl iodide (0.11 mL, 1.75 mmol). The reaction was then stirred overnight before being quenched with water followed by General Work-up Procedure 1. The material was purified using Chromatography A to yield the title compound (0.188 g, 66%).

Step 2: Synthesis of 6-(methoxymethyl)-1,4-oxazepane trifluoroacetate. To a solution of tert-butyl 6-(methoxymethyl)-1,4-oxazepane-4-carboxylate (0.185 mg, 0.75 mmol) in DCM (3.6 mL) was added trifluoroacetic acid (0.9 mL) and the reaction was stirred at rt for 16 hr. After this time, the reaction was concentrated, and the material was used without purification.

Step 3: Synthesis of (1r,3r)-3-(3-(6-((6-(methoxymethyl)-1,4-oxazepan-4-yl)methyl)-1-oxo-4-(trifluoromethyl)isoindolin-2-yl)phenyl)-3-((4-methyl-4H-1,2,4-triazol-3-yl)methyl)cyclobutane-1-carbonitrile. The reductive amination was carried out analogously to Example 4, Step 2, using (1r,3r)-3-(3-(6-formyl-1-oxo-4-(trifluoromethyl)isoindolin-2-yl)phenyl)-1-methyl-3-((4-methyl-4H-1,2,4-triazol-3-yl)methyl)cyclobutane-1-carbonitrile (75 mg, 0.16 mmol) and 6-(methoxymethyl)-1,4-oxazepane trifluoroacetic acetate (67 mg, 0.26 mmol), to afford the title compound after Chromatography C (45 mg, 46%). LCMS: $C_{32}H_{35}F_3N_6O_3$ requires 608.3, found 609.5 [M+H]$^+$. $^1$H NMR (500 MHz, Acetonitrile-d$_3$) δ 8.03 (s, 1H), 7.98 (s, 1H), 7.89 (s, 1H), 7.87 (ddd, J=8.1, 2.3, 0.9 Hz, 1H), 7.44 (t, J=2.0 Hz, 1H), 7.37 (t, J=8.0 Hz, 1H), 6.88 (dt, J=8.0, 1.1 Hz, 1H), 4.99 (s, 2H), 3.89-3.80 (m, 3H), 3.71 (ddd, J=12.5, 7.2, 3.1 Hz, 1H), 3.65 (ddd, J=12.4, 5.9, 3.4 Hz, 1H), 3.54 (dd, J=12.1, 7.5 Hz, 1H), 3.34 (s, 2H), 3.23-3.11 (m, 6H), 3.03-2.91 (m, 4H), 2.81-2.71 (m, 5H), 2.67 (ddd, J=13.4, 7.3, 3.4 Hz, 1H), 2.56 (dd, J=13.0, 7.3 Hz, 1H), 2.27-2.18 (m, 1H).

Example 47: (1r,3r)-3-(3-(6-((4,4-difluorohexahydrocyclopenta[c]pyrrol-2(1H)-yl)methyl)-1-oxo-4-(trifluoromethyl)isoindolin-2-yl)phenyl)-3-((4-methyl-4H-1,2,4-triazol-3-yl)methyl)cyclobutane-1-carbonitrile

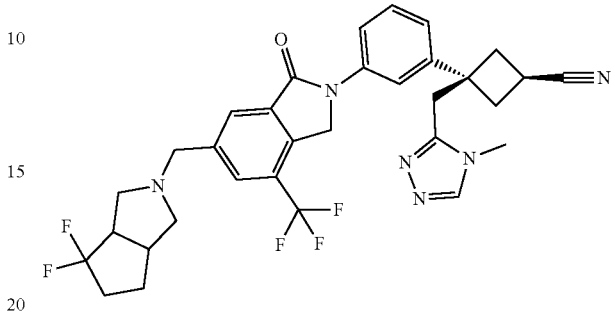

The reductive amination was carried out analogously to Example 13, using (1r,3r)-3-(3-(6-formyl-1-oxo-4-(trifluoromethyl)isoindolin-2-yl)phenyl)-1-methyl-3-((4-methyl-4H-1,2,4-triazol-3-yl)methyl)cyclobutane-1-carbonitrile (75 mg, 0.16 mmol) and cis-4,4-difluoro-octahydrocyclopenta[c]pyrrole (46 mg, 0.31 mmol), to afford the title compound after Chromatography C (61 mg, 61%). LCMS: $C_{32}H_{31}F_5N_6O$ requires 610.2, found 611.5 [M+H]$^+$. $^1$H NMR (500 MHz, Acetonitrile-d$_3$) δ 8.00 (s, 1H), 7.93 (s, 1H), 7.89 (s, 1H), 7.89-7.82 (m, 1H), 7.45 (t, J=2.0 Hz, 1H), 7.37 (t, J=8.0 Hz, 1H), 6.87 (dt, J=7.8, 1.3 Hz, 1H), 4.99 (s, 2H), 3.80 (d, J=13.8 Hz, 1H), 3.71 (d, J=13.8 Hz, 1H), 3.34 (s, 2H), 3.23-3.13 (m, 1H), 3.03-2.86 (m, 6H), 2.86-2.68 (m, 6H), 2.63 (d, J=9.1 Hz, 1H), 2.55 (dd, J=9.1, 7.1 Hz, 1H), 2.42-2.33 (m, 1H), 2.32-2.21 (m, 1H), 1.62 (ddd, J=12.3, 7.2, 3.2 Hz, 1H).

Example 48: (1r,3r)-3-(3-(6-((3-(hydroxymethyl)azepan-1-yl)methyl)-1-oxo-4-(trifluoromethyl)isoindolin-2-yl)phenyl)-3-((4-methyl-4H-1,2,4-triazol-3-yl)methyl)cyclobutane-1-carbonitrile

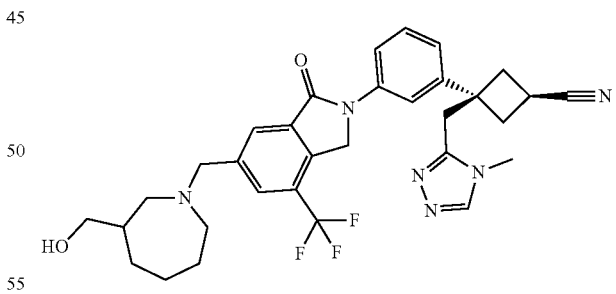

The reductive amination was carried out analogously to Example 4, Step 2, using (1r,3r)-3-(3-(6-formyl-1-oxo-4-(trifluoromethyl)isoindolin-2-yl)phenyl)-1-methyl-3-((4-methyl-4H-1,2,4-triazol-3-yl)methyl)cyclobutane-1-carbonitrile (60 mg, 0.13 mmol) and azepan-3-ylmethanol hydrochloride (31 mg, 0.19 mmol), to afford the title compound after Chromatography C (19 mg, 24%). LCMS: $C_{32}H_{35}F_3N_6O_2$ requires 592.3, found 593.5 [M+H]$^+$. $^1$H NMR (500 MHz, Acetonitrile-d$_3$) δ 8.03 (s, 1H), 7.97 (s, 1H), 7.92-7.83 (m, 2H), 7.44 (t, J=2.1 Hz, 1H), 7.37 (t, J=8.0 Hz, 1H), 6.92-6.86 (m, 1H), 4.99 (s, 2H), 3.84 (s, 2H), 3.42-3.30 (m, 3H), 3.25 (dd, J=10.5, 7.2 Hz, 1H), 3.22-3.10 (m, 1H), 3.03-2.94 (m, 4H), 2.89-2.73 (m, 5H), 2.73-2.60 (m, 2H), 2.51 (dd, J=13.1, 7.9 Hz, 1H), 1.78-1.71 (m, 4H), 1.65-1.55 (m, 2H), 1.41-1.28 (m, 1H).

Example 49: (1r,3r)-3-(3-(4-cyclopropyl-1-oxo-6-(((S)-3-(trifluoromethyl)piperidin-1-yl)methyl)-1,3-dihydro-2H-pyrrolo[3,4-c]pyridin-2-yl)phenyl)-3-((4-methyl-4H-1,2,4-triazol-3-yl)methyl)cyclobutane-1-carbonitrile

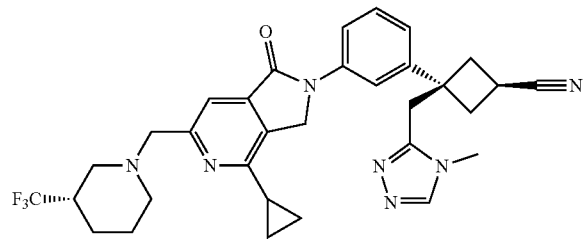 [SMILES: Cn1cnnc1C[C@]1(c2cccc(N3Cc4c(cc(CN5CCC[C@H](C(F)(F)F)C5)nc4C4CC4)C3=O)c2)C[C@H](C#N)C1]

The title compound was synthesized analogously to Example 11, using Example F, (112 mg, 0.33 mmol), and Example I (110 mg, 0.33 mmol) followed by prep HPLC. The solvents were then removed under reduced pressure and the compound was neutralized by passing through an Agilent PL-HCO3 cartridge to afford the title compound (19 mg, 10%). LCMS: $C_{32}H_{34}F_3N_7O$ requires 589.3, found 590.5 [M+H]$^+$. $^1$H NMR (500 MHz, Acetonitrile-d$_3$) δ 7.93-7.87 (m, 2H), 7.53 (s, 1H), 7.45 (t, J=2.0 Hz, 1H), 7.38 (t, J=8.0 Hz, 1H), 6.94-6.87 (m, 1H), 4.94 (s, 2H), 3.72 (s, 2H), 3.34 (s, 2H), 3.22-3.11 (m, 1H), 3.11-3.03 (m, 1H), 3.03-2.92 (m, 4H), 2.87 (d, J=11.6 Hz, 1H), 2.79 (s, 3H), 2.55-2.43 (m, 1H), 2.13-2.04 (m, 4H), 1.80-1.73 (m, 1H), 1.65-1.54 (m, 1H), 1.32 (qd, J=12.4, 4.3 Hz, 1H), 1.19-1.06 (m, 4H).

Example 50: (1r,3r)-3-(3-(6-((3,3-difluoroazepan-1-yl)methyl)-1-oxo-4-(trifluoromethyl)isoindolin-2-yl)phenyl)-3-((4-methyl-4H-1,2,4-triazol-3-yl)methyl)cyclobutane-1-carbonitrile

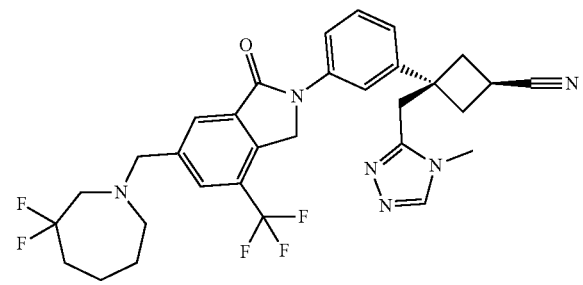 [SMILES: Cn1cnnc1C[C@]1(c2cccc(N3Cc4c(cc(CN5CCCCC(F)(F)C5)cc4C(F)(F)F)C3=O)c2)C[C@H](C#N)C1]

The reductive amination was carried out analogously to Example 4, Step 2, using (1r,3r)-3-(3-(6-formyl-1-oxo-4-(trifluoromethyl)isoindolin-2-yl)phenyl)-1-methyl-3-((4-methyl-4H-1,2,4-triazol-3-yl)methyl)cyclobutane-1-carbonitrile (50 mg, 0.10 mmol) and 3,3-difluoroazepane hydrochloride (31 mg, 0.18 mmol), to afford the title compound after Chromatography C (23 mg, 35%). LCMS: $C_{31}H_{31}F_5N_6O$ requires 598.2, found 599.5 [M+H]$^+$. $^1$H NMR (500 MHz, Acetonitrile-d$_3$) δ 8.03 (s, 1H), 7.98 (s, 1H), 7.89 (s, 1H), 7.88-7.84 (m, 1H), 7.44 (t, J=2.0 Hz, 1H), 7.37 (t, J=8.0 Hz, 1H), 6.88 (d, J=7.9 Hz, 1H), 4.99 (s, 2H), 3.94 (s, 2H), 3.34 (s, 2H), 3.15 (dt, J=9.6, 6.9 Hz, 1H), 3.07 (t, J=14.0 Hz, 2H), 3.02-2.92 (m, 4H), 2.83-2.72 (m, 5H), 2.23-2.08 (m, 2H), 1.79-1.65 (m, 4H).

Example 51: [(1r,3r)-3-[3-(6-{[(3R)-4,4-difluoro-3-methylpiperidin-1-yl]methyl}-1-oxo-4-(trifluoromethyl)-3H-isoindol-2-yl)phenyl]-3-[(4-methyl-1,2,4-triazol-3-yl)methyl]cyclobutyl]acetonitrile

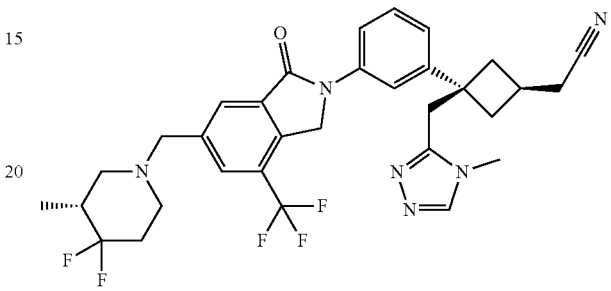

Step 1: Synthesis of methyl 2-[3-(cyanomethyl)cyclobutylidene]acetate. The reaction was carried out analogously to Example G, Step 1, using 2-(3-oxocyclobutyl)acetonitrile (2.0 g, 18.3 mmol) to generate the title compound (2.8 g, 92%).

Step 2: Synthesis of cis-methyl 2-[(1r,3r)-1-{3-[(tert-butoxycarbonyl)amino]phenyl}-3-(cyanomethyl)cyclobutyl]acetate. The reaction was carried out analogously to Example G, Step 2, using methyl 2-[3-(cyanomethyl)cyclobutylidene]acetate (2.8 g, 18.3 mmol) to generate the title compound (2.1 g, 35%) as the first eluting isomer from Chromatography A.

Step 3: Synthesis of 2-((1r,3r)-1-(3-((tert-butoxycarbonyl)amino)phenyl)-3-(cyanomethyl)cyclobutyl)acetic acid. The reaction was carried out analogously to Example G, Step 3, using cis-methyl 2-[(1r,3r)-1-{3-[(tert-butoxycarbonyl)amino]phenyl}-3-(cyanomethyl)cyclobutyl]acetate (2.1 g, 5.86 mmol). The reaction was worked up by concentrating the whole mixture to dryness before adding water (50 mL) and acidifying the solution with 1 N HCl (3.8 mL) to give pH~ 5, followed by General Work-up Procedure 1 to give the title compound (2.05 g, 99%).

Step 4: Synthesis of tert-butyl N-{3-[(1r,3r)-3-(cyanomethyl)-1-[(4-methyl-5-sulfanyl-1,2,4-triazol-3-yl)methyl]cyclobutyl]phenyl}carbamate. The reaction was carried out analogously to Example G, Step 4, using 2-((1r,3r)-1-(3-((tert-butoxycarbonyl)amino)phenyl)-3-(cyanomethyl)cyclobutyl)acetic acid (2.05 g, 5.8 mmol) to give the title compound (0.5 g, 20%).

Step 5: Synthesis of tert-butyl N-{3-[(1r,3r)-3-(cyanomethyl)-1-[(4-methyl-1,2,4-triazol-3-yl)methyl]cyclobutyl]phenyl}carbamate. The reaction was carried out analogously to Example G, Step 5, using tert-butyl N-{3-[(1r,3r)-3-(cyanomethyl)-1-[(4-methyl-5-sulfanyl-1,2,4-triazol-3-yl)methyl]cyclobutyl]phenyl}carbamate (560 mg, 1.35 mmol) to generate the title compound (100 mg, 19%).

Step 6: Synthesis of 2-((1r,3r)-3-(3-aminophenyl)-3-((4-methyl-4H-1,2,4-triazol-3-yl)methyl)cyclobutyl)acetonitrile. The reaction was carried out analogously to Example G, Step 6, using tert-butyl N-{3-[(1r,3r)-3-(cyanomethyl)-

1-[(4-methyl-1,2,4-triazol-3-yl)methyl]cyclobutyl]phenyl}carbamate (100 mg, 0.26 mmol) to generate the title compound (80 mg, 99%).

Step 7: Synthesis of 2-[(1r,3r)-3-{3-[6-formyl-1-oxo-4-(trifluoromethyl)-3H-isoindol-2-yl]phenyl}-3-[(4-methyl-1,2,4-triazol-3-yl)methyl]cyclobutyl]acetonitrile. The reaction was carried out analogously to Example 3, using 2-((1r,3r)-3-(3-aminophenyl)-3-((4-methyl-4H-1,2,4-triazol-3-yl)methyl)cyclobutyl)acetonitrile (80 mg, 0.83 mmol) and methyl 2-(bromomethyl)-5-formyl-3-(trifluoromethyl)benzoate (101 mg, 0.31 mmol) to generate the title compound after Chromatography B (60 mg, 43%).

Step 8: Synthesis of [(1r,3r)-3-[3-(6-{[(3R)-4,4-difluoro-3-methylpiperidin-1-yl]methyl}-1-oxo-4-(trifluoromethyl)-3H-isoindol-2-yl)phenyl]-3-[(4-methyl-1,2,4-triazol-3-yl)methyl]cyclobutyl]acetonitrile. The reductive amination was carried out analogously to Example 13, using 2-[(1r,3r)-3-{3-[6-formyl-1-oxo-4-(trifluoromethyl)-3H-isoindol-2-yl]phenyl}-3-[(4-methyl-1,2,4-triazol-3-yl)methyl]cyclobutyl]acetonitrile (20 mg, 0.04 mmol) and (R)-4,4-difluoro-3-methylpiperidine hydrochloride (8.7 mg, 0.05 mmol), to afford the title compound after Chromatography C (41 mg, 15%). LCMS: $C_{32}H_{33}F_5N_6O$ requires 612.3, found 613.5 [M+H]$^+$. $^1$H NMR (500 MHz, Acetonitrile-d$_3$) δ 8.01 (s, 1H), 7.93 (s, 1H), 7.91-7.79 (m, 2H), 7.33 (t, J=7.9 Hz, 1H), 7.25 (t, J=2.0 Hz, 1H), 6.73 (dt, J=7.9, 1.2 Hz, 1H), 4.97 (s, 2H), 3.74 (s, 2H), 3.24 (d, J=4.0 Hz, 2H), 3.00-2.86 (m, 3H), 2.86-2.73 (m, 2H), 2.69 (s, 3H), 2.58 (d, J=5.7 Hz, 2H), 2.48-2.29 (m, 1H), 2.25-2.18 (m, 4H), 2.15-2.10 (m, 2H), 1.00 (d, J=6.3 Hz, 3H).

Example 52: ((1S,3s)-3-(3-(6-(((R)-4,4-difluoro-3-methylpiperidin-1-yl)methyl)-1-oxo-4-(trifluoromethyl)isoindolin-2-yl)phenyl)-3-((4-methyl-4H-1,2,4-triazol-3-yl)methyl)cyclobutyl)acetonitrile

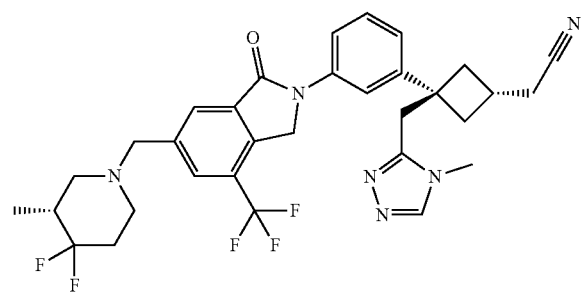 [SMILES: C[C@@H]1CN(Cc2cc3c(c(C(F)(F)F)c2)CN(c2cccc([C@]4(Cc5nncn5C)C[C@H](CC#N)C4)c2)C3=O)CCC1(F)F]

The title compound was synthesized analogously to Example 51, Steps 3-8, using the second eluting isomer from Example 51, Step 2. LCMS: $C_{32}H_{33}F_5N_6O$ requires 612.3, found 613.5 [M+H]$^+$. $^1$H NMR (500 MHz, Acetonitrile-d$_3$) δ 8.02 (s, 1H), 7.94 (s, 1H), 7.91-7.82 (m, 2H), 7.59 (t, J=2.0 Hz, 1H), 7.39 (t, J=8.0 Hz, 1H), 7.05 (d, J=7.3 Hz, 1H), 5.02 (s, 2H), 3.74 (s, 2H), 3.17 (s, 2H), 2.85-2.74 (m, 7H), 2.69 (d, J=6.1 Hz, 1H), 2.61 (s, 2H), 2.52-2.31 (m, 3H), 2.17-2.11 (m, 4H), 1.00 (d, J=6.2 Hz, 3H).

Example 53: 4-((5-azaspiro[2.4]heptan-5-yl)methyl)-N-(3-((1r,3r)-3-cyano-1-((4-methyl-4H-1,2,4-triazol-3-yl)methyl)cyclobutyl)phenyl)-6-cyclopropylpicolinamide

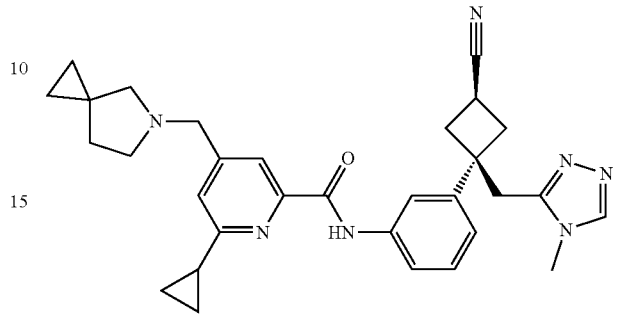

Step 1: Synthesis of ethyl 6-chloro-4-methylpicolinate. To a solution of 6-chloro-4-methylpyridine-2-carboxylic acid (50.0 g, 58.48 mmol) in EtOH (300.0 mL) was added H$_2$SO$_4$ (4.00 mL) dropwise. The resulting mixture was stirred at 70° C. for 16 h then concentrated under vacuum. The residue was dissolved in EtOAc and washed sequentially with NaHCO$_3$ (sat. aq.) and water. The combined organic phases were dried, filtered, and concentrated to afford the title compound (53.1 g, crude), which was used in next step without purification. MS (ESI) calculated for ($C_9H_{10}ClNO_2$) [M+H]$^+$, 200.0, found, 200.0.

Step 2: Synthesis of ethyl 6-cyclopropyl-4-methylpicolinate. A degassed solution of ethyl 6-chloro-4-methylpyridine-2-carboxylate (30.0 g, 0.15 mol), cyclopropylboronic acid (25.0 g, 0.29 mol), tetrakis(triphenylphosphine)palladium (17.0 g, 14.71 mmol) and potassium carbonate (62.0 g, 0.45 mmol) in dioxane (450 mL) was stirred at 100° C. for 2 h under N$_2$. The reaction mixture was quenched by the addition of water and extracted with EtOAc. The organic layer was dried over anhydrous sodium sulfate, filtered, and concentrated under vacuum. The residue was purified by chromatography A to provide the title compound (20.1 g, 64.8%). MS (ESI) calculated for ($C_{12}H_{15}NO_2$) [M+H]$^+$, 206.1, found, 206.0.

Step 3: Synthesis of ethyl 6-cyclopropyl-4-formylpyridine-2-carboxylate. To a mixture of ethyl 6-cyclopropyl-4-methylpyridine-2-carboxylate (14.0 g, 68.21 mmol) and Ac$_2$O (31.5 g) in HOAc (120 mL), was added SeO$_2$ (10.5 g, 94.81 mmol). The resulting mixture was stirred at 120° C. for 16 h. The reaction mixture was cooled to room temperature and filtered. The filtrate was concentrated under vacuum. The crude residue was purified by chromatography C to afford the title compound (9.8 g, 46.2%). MS (ESI) calculated for ($C_{12}H_{13}NO_3$) [M+H]$^+$, 220.1, found, 220.0.

Step 4: Synthesis of ethyl 4-{5-azaspiro[2.4]heptan-5-ylmethyl}-6-cyclopropylpyridine-2-carboxylate. A mixture of ethyl 6-cyclopropyl-4-formylpyridine-2-carboxylate (360 mg, 1.64 mmol), 5-azaspiro[2.4]heptane hydrochloride (440 mg, 3.3 mmol), triethylamine (460 μL, 3.3 mmol), sodium triacetoxyborohydride (529 mg, 2.5 mmol), and DCM (3.0 mL) was heated in a sealed vial at 40-50° C. until LCMS indicated consumption of aldehyde. The mixture was diluted with MeOH and EtOAc, concentrated onto Celite, and purified by Chromatography D to afford the title compound (255 mg, 52%).

Step 5: Synthesis of lithium 4-((5-azaspiro[2.4]heptan-5-yl)methyl)-6-cyclopropylpicolinate. A mixture of ethyl 4-{5-azaspiro[2.4]heptan-5-ylmethyl}-6-cyclopropylpyridine-2-carboxylate (250 mg, 0.84 mmol,) LiOH H₂O (35 mg, 0.84 mmol), THF (2 mL), and water (1 mL) was stirred vigorously until complete. The THF was removed under reduced pressure to afford the title compound.

Step 6: Example 53. 1-Propanephosphonic anhydride (0.81 mL, 0.14 mmol) was added to a solution of lithium 4-((5-azaspiro[2.4]heptan-5-yl)methyl)-6-cyclopropylpicolinate (31 mg, 0.11 mmol), Example G (30 mg, 0.11 mmol), and 4-methylmorpholine (64 μL, 0.6 mmol) in DMF (0.5 mL) at rt. The solution was heated at 45-50° C. until complete. The mixture was diluted with water and acetonitrile, concentrated onto Celite, and purified by Chromatography C to afford the title compound (27 mg, 47%): ¹H NMR (500 MHz, DMSO-d₆) δ 10.11 (s, 1H), 8.18 (s, 1H), 7.83 (d, J=1.4 Hz, 1H), 7.73 (dd, J=8.1, 2.0 Hz, 1H), 7.49 (t, J=2.0 Hz, 1H), 7.43 (d, J=1.4 Hz, 1H), 7.27 (t, J=7.9 Hz, 1H), 6.75-6.65 (m, 1H), 3.67 (s, 2H), 3.29-3.18 (m, 3H), 2.86 (td, J=10.5, 9.1, 7.3 Hz, 4H), 2.80 (s, 3H), 2.68 (t, J=6.8 Hz, 2H), 2.25 (tt, J=8.1, 4.9 Hz, 1H), 1.77 (t, J=6.8 Hz, 2H), 1.14 (dt, J=5.9, 3.1 Hz, 2H), 1.04 (dt, J=8.3, 3.2 Hz, 2H), 0.51 (dt, J=8.1, 1.9 Hz, 4H). LCMS: C₃₁H₃₅N₇O requires: 521, found: m/z 522 [M+H]⁺.

Example 54: Synthesis of N-(3-((1r,3R)-3-cyano-1-((4-methyl-4H-1,2,4-triazol-3-yl)methyl)cyclobutyl)phenyl)-6-cyclopropyl-4-(((3S,5R)-3,5-dimethylpiperidin-1-yl)methyl)picolinamide Example 55: Synthesis of N-(3-((1r,3S)-3-cyano-1-((4-methyl-4H-1,2,4-triazol-3-yl)methyl)cyclobutyl)phenyl)-6-cyclopropyl-4-(((S)-3-methylpiperidin-1-yl)methyl)picolinamide

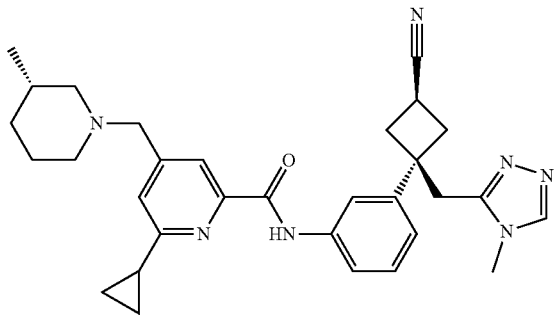

The title compound was prepared according to the procedure of Example 53 using (3S)-3-methylpiperidine hydrochloride in Step 4: ¹H NMR (500 MHz, DMSO-d₆) δ 10.12 (s, 1H), 8.18 (s, 1H), 7.82 (s, 1H), 7.72 (dd, J=8.0, 1.9 Hz, 1H), 7.50 (d, J=2.1 Hz, 1H), 7.40 (s, 1H), 7.26 (t, J=7.9 Hz, 1H), 6.70 (d, J=7.6 Hz, 1H), 3.51 (s, 2H), 3.28 (s, 2H), 3.26-3.18 (m, 1H), 2.91-2.82 (m, 4H), 2.80 (s, 3H), 2.69 (t, J=10.8 Hz, 2H), 2.24 (tt, J=8.4, 4.9 Hz, 1H), 1.95-1.85 (m, 1H), 1.71-1.55 (m, 4H), 1.55-1.43 (m, 1H), 1.14 (dt, J=5.8, 3.1 Hz, 2H), 1.04 (dt, J=8.2, 3.2 Hz, 2H), 0.86 (d, J=10.6 Hz, 1H), 0.82 (d, J=5.2 Hz, 3H); LCMS: C₃₁H₃₇N₇O requires: 523, found: m/z 524 [M+H]⁺.

Example 56: N-(3-((1r,3R)-3-cyano-1-((4-methyl-4H-1,2,4-triazol-3-yl)methyl)cyclobutyl)phenyl)-6-cyclopropyl-4-(((R)-2-methylmorpholino)methyl)picolinamide

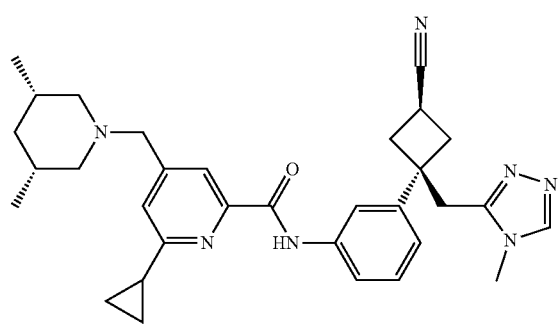 [SMILES: C[C@@H]1C[C@H](C)CN(Cc2cc(C(=O)Nc3cccc([C@]4(Cc5nncn5C)C[C@@H](C#N)C4)c3)nc(C3CC3)c2)C1]

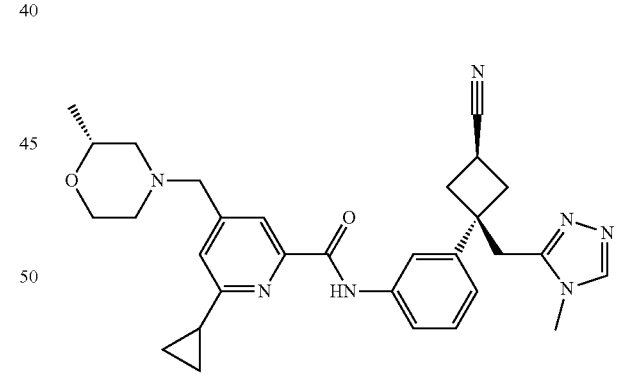

The title compound was prepared according to the procedure of Example 53 using (3R,5S)-3,5-dimethylpiperidine in Step 4: ¹H NMR (500 MHz, DMSO-d₆) δ 10.12 (s, 1H), 8.18 (s, 1H), 7.82 (s, 1H), 7.72 (dd, J=8.1, 1.9 Hz, 1H), 7.50 (t, J=1.9 Hz, 1H), 7.41 (s, 1H), 7.26 (t, J=7.9 Hz, 1H), 6.71 (d, J=7.5 Hz, 1H), 3.52 (s, 2H), 3.28 (s, 2H), 3.27-3.20 (m, 1H), 2.91-2.82 (m, 4H), 2.80 (s, 3H), 2.75-2.68 (m, 2H), 2.24 (tt, J=8.3, 4.8 Hz, 1H), 1.72-1.59 (m, 2H), 1.49 (t, J=10.8 Hz, 2H), 1.14 (dt, J=6.0, 3.2 Hz, 2H), 1.04 (dt, J=8.2, 3.3 Hz, 2H), 0.80 (d, J=6.4 Hz, 6H), 0.50 (q, J=11.9 Hz, 1H); LCMS: C₃₂H₃₉N₇O requires: 537, found: m/z 538 [M+H]⁺.

The title compound was prepared according to the procedure of Example 53 using ((2R)-2-methylmorpholine in Step 4: ¹H NMR (500 MHz, DMSO-d₆) δ 10.12 (s, 1H), 8.18 (s, 1H), 7.84 (d, J=1.4 Hz, 1H), 7.72 (dd, J=8.0, 2.0 Hz, 1H), 7.50 (t, J=1.9 Hz, 1H), 7.43 (d, J=1.4 Hz, 1H), 7.27 (t, J=7.9 Hz, 1H), 6.74-6.68 (m, 1H), 3.74 (ddd, J=11.4, 3.2, 1.5 Hz, 1H), 3.59-3.48 (m, 4H), 3.28 (s, 2H), 3.27-3.19 (m, 1H), 2.91-2.81 (m, 4H), 2.80 (s, 3H), 2.67 (dt, J=11.0, 2.0 Hz, 1H), 2.63-2.58 (m, 1H), 2.24 (tt, J=8.4, 4.8 Hz, 1H), 2.08 (td, J=11.2, 3.2 Hz, 1H), 1.78 (t, J=10.5 Hz, 1H), 1.14 (dt, J=5.9, 3.1 Hz, 2H), 1.04 (t, J=5.8 Hz, 5H); LCMS: C₃₀H₃₅N₇O₂ requires: 525, found: m/z 526 [M+H]⁺.

177

Example 57: N-(3-((1r,3R)-3-cyano-1-((4-methyl-4H-1,2,4-triazol-3-yl)methyl)cyclobutyl)phenyl)-2-cyclopropyl-6-(((R)-4,4-difluoro-3-methylpiperidin-1-yl)methyl)pyrimidine-4-carboxamide

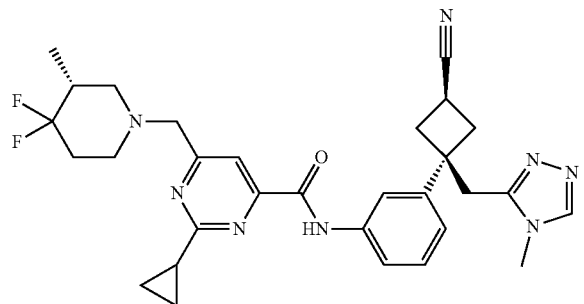 [SMILES: C[C@@H]1CN(Cc2cc(C(=O)Nc3cccc([C@]4(Cc5nncn5C)C[C@@H](C#N)C4)c3)nc(C3CC3)n2)CCC1(F)F]

Step 1: Synthesis of ethyl 2-cyclopropyl-6-methylpyrimidine-4-carboxylate. To a solution of ethyl 2,4-dioxopentanoate (10.0 g, 63.29 mmol) and cyclopropanecarboximidamide (6.9 g, 57.5 mmol) in DMF (200 mL) was added pTsOH H$_2$O (1.1 g, 5.8 mmol). The solution was stirred at 100° C. for 72 h. The mixture was cooled to rt and diluted with water, followed by General Work-up Procedure 1. The residue was purified by chromatography A to afford the title compound (4.8 g, 40%).

Step 2: Synthesis of ethyl 6-(bromomethyl)-2-cyclopropylpyrimidine-4-carboxylate. To a solution of ethyl 2-cyclopropyl-6-methylpyrimidine-4-carboxylate (5.0 g, 24.2 mmol) in HOAc (50 mL) was added bromine (3.86 g, 24.2 mmol). The solution was stirred at 80° C. for 1 h. The solvent was removed under vacuum. The residue was purified by Chromatography A to afford the title compound (2.0 g, 30%).

Step 3: Synthesis of ethyl 2-cyclopropyl-6-{[(3R)-4,4-difluoro-3-methylpiperidin-1-yl]methyl}pyrimidine-4-carboxylate. A solution of ethyl 6-(bromomethyl)-2-cyclopropylpyrimidine-4-carboxylate (50 mg, 0.18 mmol), 4,4-difluoro-3-methylpiperidine hydrochloride (30 mg, 0.18 mmol), N,N-diisopropylethylamine (0.061 mL, 0.36 mmol), and acetonitrile was maintained at rt for 5 h. The mixture was concentrated to afford the title compound.

Step 4: Synthesis of lithio 2-cyclopropyl-6-{[(3R)-4,4-difluoro-3-methylpiperidin-1-yl]methyl}pyrimidine-4-carboxylate. A mixture of ethyl 2-cyclopropyl-6-{[(3R)-4,4-difluoro-3-methylpiperidin-1-yl]methyl}pyrimidine-4-carboxylate (61 mg, 0.18 mmol,) LiOH H$_2$O (15 mg, 0.36 mmol), THF (0.5 mL), and water (0.25 mL) was stirred vigorously until complete. The THF was removed under reduced pressure to afford the title compound.

Step 5: Example 57: The title compound was prepared according to the procedure of Example 53, Step 6: $^1$H NMR (500 MHz, DMSO-d$_6$) δ 10.43 (s, 1H), 8.18 (s, 1H), 7.87 (s, 1H), 7.78 (dd, J=8.2, 2.0 Hz, 1H), 7.56 (d, J=2.0 Hz, 1H), 7.28 (t, J=7.9 Hz, 1H), 3.76-3.65 (m, 2H), 3.28 (s, 2H), 3.27-3.20 (m, 1H), 2.90-2.82 (m, 4H), 2.81 (s, 3H), 2.78-2.72 (m, 2H), 2.44-2.31 (m, 3H), 2.19-2.08 (m, 2H), 2.04 (td, J=11.2, 4.1 Hz, 1H), 2.00-1.91 (m, 1H), 1.17 (dt, J=5.4, 2.8 Hz, 2H), 1.13 (dq, J=8.4, 3.1, 2.3 Hz, 2H), 0.95 (d, J=5.9 Hz, 3H); LCMS: C$_{30}$H$_{34}$F$_2$N$_7$O$_2$ requires: 560, found: m/z 561 [M+H]$^+$.

178

Example 58: (1R,3r)-3-((4-methyl-4H-1,2,4-triazol-3-yl)methyl)-3-(3-(6-(2-((R)-2-methylmorpholino)propan-2-yl)-1-oxo-4-(trifluoromethyl)isoindolin-2-yl)phenyl)cyclobutane-1-carbonitrile

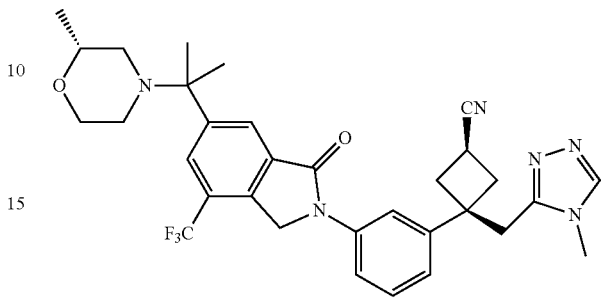

Step 1: Synthesis of methyl 5-bromo-2-methyl-3-(trifluoromethyl)benzoate. To a mixture of methyl 2-methyl-3-(trifluoromethyl)benzoate (15 g, 73.34 mmol) in acetic acid (100 mL) were added HNO$_3$ (46 g) and bromine (12.8 g, 80.10 mmol). Then AgNO$_3$ (16.1 g, 2.5 M in water) was added to the above mixture over ~30 min. After the mixture stirred for 16 h at rt, the mixture was diluted with water. General Work-up Procedure 1 was followed. The residue was purified by Chromatography A to afford the title compound (14.0 g, 70%).

Step 2: Synthesis of methyl 5-bromo-2-(bromomethyl)-3-(trifluoromethyl)benzoate. A mixture of methyl 5-bromo-2-methyl-3-(trifluoromethyl)benzoate (14.0 g, 47.1 mmol), N-bromosuccinimide (NBS) (16.8 g, 94.4 mmol), and benzoyl peroxide (BPO) (2.3 g, 8.9 mmol) in CCl$_4$ (150 mL) was stirred at 80° C. for 5 h. Then the solids were filtered off. The filtrate was concentrated. The residue was purified by flash column chromatography with 0-10% ethyl acetate in petroleum ether to provide the title compound (11.2 g, 63%).

Step 3: Synthesis of 6-bromo-4-(trifluoromethyl)isoindolin-1-one. To a stirred solution of methyl 5-bromo-2-(bromomethyl)-3-(trifluoromethyl)benzoate (11.2 g, 29.79 mmol) in tetrahydrofuran (50 mL) was added NH$_3$ (7 M in methanol, 50 mL). The mixture was stirred at rt for 16 h. The mixture was concentrated. The residue was diluted with water. General Work-up Procedure 1 was followed. The title compound (8.1 g, 53%) was obtained using standard flash chromatography purification methods. MS (ESI) calc'd for (C$_9$H$_5$BrF$_3$NO) [M+H]$^+$, 280.0; found, 280.1.

Step 4: Synthesis of 6-acetyl-4-(trifluoromethyl)isoindolin-1-one. A mixture of 6-bromo-4-(trifluoromethyl)-2,3-dihydroisoindol-1-one (9.6 g, 34 mmol), tributyl(1-ethoxyethenyl)stannane (18.6 g, 51.6 mmol), and Pd(dppf)Cl$_2$·CH$_2$Cl$_2$ (2.8 g, 3.4 mmol) in dioxane (100.0 mL) was stirred at 100° C. for 16 h under nitrogen atmosphere. The solvent was removed under reduced pressure. The resulting mixture was diluted with water and General Work-up Procedure 1 was followed. After filtration, the filtrate was concentrated under vacuum. Then to the crude residue was added HCl (1 N, 100.0 mL) and THF (200.0 mL). The resulting mixture was stirred at 60° C. for 1 h under nitrogen atmosphere. The organic solvent was removed under vacuum and General Work-up Procedure 1 was followed. The residue was purified by Chromatography A to afford 6-acetyl-4-(trifluoromethyl)isoindolin-1-one (4.2 g, 50%). MS (ESI) calculated for (C$_{11}$H$_8$F$_3$NO$_2$) [M+H]$^+$, 244.1; found, 244.0.

Step 5: Synthesis of 2-[(2R)-2-methylmorpholin-4-yl]-2-[3-oxo-7-(trifluoromethyl)-1,2-dihydroisoindol-5-yl]propanenitrile. A solution of 6-acetyl-4-(trifluoromethyl)-2,3-dihydroisoindol-1-one (650.0 mg, 2.67 mmol), (2R)-2-methylmorpholine (270.4 mg, 2.67 mmol), and Ti(OEt)$_4$ (1.2 g, 5.4 mmol) in THF (20.0 mL) was stirred at room temperature for 3 h. Trimethylsilyl cyanide (397.8 mg, 4.01 mmol) was added to the above mixture and stirred at 60° C. for 16 h under nitrogen atmosphere. General Work-up Pro- 2.97-2.83 (m, 4H), 2.72 (s, 3H), 2.52 (ddt, J=33.2, 11.4, 2.2 Hz, 2H), 2.28 (td, J=11.2, 3.1 Hz, 1H), 1.92 (p, J 2.5 Hz, 1H), 1.38-1.32 (m, 6H), 1.00 (d, J=6.2 Hz, 3H).

Example 59: (R)-6-cyclopropyl-5-(17-(5,5-difluoro-7,9-dimethyl-5H-$\lambda^4$,6$\lambda^4$-dipyrrolo[1,2-c:2',1'-f][1,3,2]diazaborinin-3-yl)-15-oxo-5,8,11-trioxa-2,14-diazaheptadecyl)-N-(3-(1-(4-methyl-4H-1,2,4-triazol-3-yl)propan-2-yl)phenyl)picolinamide

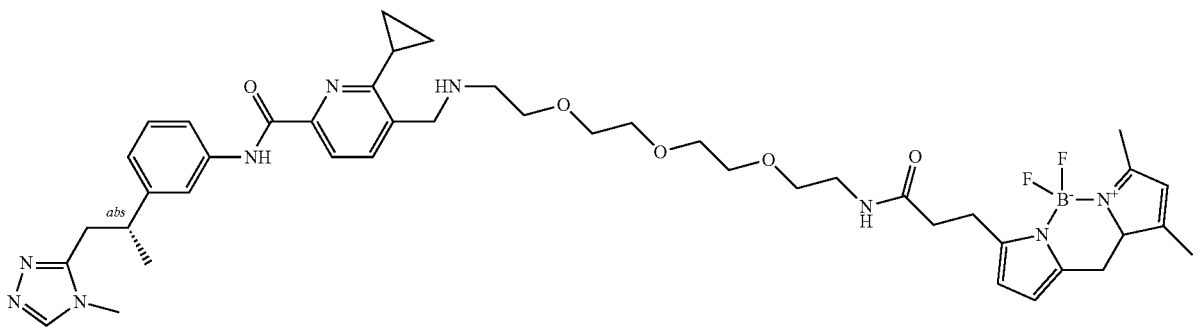 [SMILES: CC1=CC(C)=[N+]2C1Cc1ccc(CCC(=O)NCCOCCOCCOCCNCc3ccc(C(=O)Nc4cccc([C@H](C)Cc5nncn5C)c4)nc3C3CC3)n1[B-]2(F)F]

cedure 1 was followed. The residue was purified by reverse phase flash column chromatography with 5~50% acetonitrile in water to afford 2-[(2R)-2-methylmorpholin-4-yl]-2-[3-oxo-7-(trifluoromethyl)-1,2-dihydroisoindol-5-yl]propanenitrile (550.0 mg, 58%). MS (ESI) calculated for (C$_{17}$H$_{18}$F$_3$N$_3$O$_2$) [M+H]$^+$, 354.1; found, 354.0.

Step 6: Synthesis of (R)-6-(2-(2-methylmorpholino)propan-2-yl)-4-(trifluoromethyl)isoindolin-1-one. To a degassed solution of 2-[(2R)-2-methylmorpholin-4-yl]-2-[3-oxo-7-(trifluoromethyl)-1,2-dihydroisoindol-5-yl] propanenitrile (550.0 mg, 1.55 mmol) in THF (20.0 mL) was added methylmagnesium bromide (31.0 mL, 3 M in THF) dropwise at −60° C. The reaction mixture was warmed to room temperature and stirred for 2 h under nitrogen atmosphere. The reaction mixture was quenched with saturated aqueous NH$_4$Cl solution at 0° C. and General Work-up Procedure 1 was followed. The residue was purified by reverse phase flash column chromatography with 5~50% acetonitrile in water to afford (R)-6-(2-(2-methylmorpholino)propan-2-yl)-4-(trifluoromethyl)isoindolin-1-one (135.3 mg, 33%). MS (ESI) calculated for (C$_{17}$H$_{21}$F$_3$N$_2$O$_2$) [M+H]$^+$, 343.2; found, 343.2.

Step 7: Synthesis of (1R,3r)-3-((4-methyl-4H-1,2,4-triazol-3-yl)methyl)-3-(3-(6-(2-((R)-2-methylmorpholino)propan-2-yl)-1-oxo-4-(trifluoromethyl)isoindolin-2-yl)phenyl)cyclobutane-1-carbonitrile. The title compound was synthesized analogously to Example 11, using (R)-6-(2-(2-methylmorpholino)propan-2-yl)-4-(trifluoromethyl)isoindolin-1-one (53.1 mg, 0.16 mmol) and (1r,3r)-3-(3-bromophenyl)-3-((4-methyl-4H-1,2,4-triazol-3-yl)methyl)cyclobutane-1-carbonitrile (52.1 mg, 0.16 mmol) to afford (1R,3r)-3-((4-methyl-4H-1,2,4-triazol-3-yl)methyl)-3-(3-(6-(2-((R)-2-methylmorpholino)propan-2-yl)-1-oxo-4-(trifluoromethyl)isoindolin-2-yl)phenyl)cyclobutane-1-carbonitrile obtained as the trifluoroacetate salt (13.3 mg, 12%). MS (ESI) calculated for (C$_{32}$H$_{35}$F$_3$N$_6$O$_2$) [M+H]$^+$, 593.3; found, 593.7. $^1$H NMR (500 MHz, Acetonitrile-d3) δ 8.13 (d, J=3.9 Hz, 2H), 7.84 (s, 1H), 7.81 (dd, J=8.1, 2.2 Hz, 1H), 7.39 (d, J=2.0 Hz, 1H), 7.31 (t, J=8.0 Hz, 1H), 6.82 (d, J=7.8 Hz, 1H), 4.93 (s, 2H), 3.74 (dt, J=11.0, 2.4 Hz, 1H), 3.64-3.46 (m, 2H), 3.29 (s, 2H), 3.10 (ddd, J=16.3, 9.3, 7.0 Hz, 1H), Step 1: Synthesis of methyl 6-cyclopropyl-5-(hydroxymethyl)pyridine-2-carboxylate. A mixture of methyl 6-chloro-5-(hydroxymethyl)pyridine-2-carboxylate (Gangadasu, B. et al., Tetrahedron 2006, 62, 8398-8403) (1.0 g, 5.0 mmol), potassium cyclopropyltrifluoroboranuide (2.1 g, 14.1 mmol), Pd(dppf)Cl$_2$ (770 mg, 1.05 mmol) and K$_3$PO$_4$ (3.8 g, 18.1 mmol) in toluene (40 mL) and water (4 mL) was heated to 100° C. for 16 h under nitrogen. The mixture was cooled to rt and then filtered. The filtrate was evaporated under vacuum. The residue was purified by Chromatography A to afford the title compound (834.0 mg, 81%). LCMS: C$_{11}$H$_{13}$NO$_3$ requires 207.2, found 207.9 [M+H]$^+$.

Step 2: Synthesis of 6-cyclopropyl-5-(hydroxymethyl)pyridine-2-carboxylic acid. A mixture of methyl 6-cyclopropyl-5-(hydroxymethyl)pyridine-2-carboxylate (170.0 mg, 0.82 mmol) and LiOH (45.0 mg, 1.88 mmol) in THF (6 mL) and water (2 mL) was stirred at rt for 3 h. The pH of the mixture was adjusted to ~5 with HCl (1 N). The mixture was evaporated under vacuum to afford the title compound (200.0 mg, crude), which was used without purification. MS (ESI) calculated for (C$_{10}$H$_{11}$NO$_3$) [M+H]$^+$, 194.1, found, 193.9.

Step 3: Synthesis of 6-cyclopropyl-5-(hydroxymethyl)-N-[3-[(2R)-1-(4-methyl-4H-1,2,4-triazol-3-yl)propan-2-yl]phenyl]pyridine-2-carboxamide. To a mixture of 6-cyclopropyl-5-(hydroxymethyl)pyridine-2-carboxylic acid (200.0 mg, crude) in DMF (3 mL) were added DIEA (1 mL, 6.05 mmol), 3-[(2R)-1-(4-methyl-4H-1,2,4-triazol-3-yl)propan-2-yl]aniline (173.6 mg, 0.80 mmol) and HATU (883.0 mg, 2.32 mmol). The mixture was stirred at rt for 2 h. The mixture was purified by Chromatography C, then purified by Prep-HPLC to afford the title compound (31.6 mg, 10%). MS (ESI) calculated for (C$_{22}$H$_{25}$N$_5$O$_2$) [M+H]$^+$, 392.2, found, 392.2.

Step 4: Synthesis of (R)-6-cyclopropyl-5-formyl-N-(3-(1-(4-methyl-4H-1,2,4-triazol-3-yl)propan-2-yl)phenyl)picolinamide. To a solution of (R)-6-cyclopropyl-5-(hydroxymethyl)-N-(3-(1-(4-methyl-4H-1,2,4-triazol-3-yl)propan-2-yl)phenyl)picolinamide (3.1 g, 7.9 mmol) in methylene chloride (30 mL) was added Dess-Martin reagent (4.0 g, 9.5 mmol) at 0° C. The mixture was stirred at 0° C.

for 1 h, and then quenched by the addition of saturated aqueous NaHCO₃. The aqueous phase was extracted with EtOAc. The organic layers were combined, washed with brine, dried, and filtered. The filtrate was concentrated. The residue was purified by Chromatography B to afford the title compound (1.8 g, 58%). MS (ESI) calculated for ($C_{22}H_{23}N_5O_2$) [M+H]⁺, 390.2; found 390.2.

Step 5. Synthesis of (R)-5-(13-amino-5,8,11-trioxa-2-azatridecyl)-6-cyclopropyl-N-(3-(1-(4-methyl-4H-1,2,4-triazol-3-yl)propan-2-yl)phenyl)picolinamide. Sodium triacetoxyborohydride (0.05 g, 0.23 mmol) was added to a DCM (1.00 mL) solution containing tert-butyl N-(2-{2-[2-(2-aminoethoxy)ethoxy]ethoxy}ethyl)carbamate (45 mg, 0.15 mmol) (R)-6-cyclopropyl-5-formyl-N-(3-(1-(4-methyl-4H-1,2,4-triazol-3-yl)propan-2-yl)phenyl)picolinamide (60 mg, 0.15 mmol). The mixture was stirred at room temperature for 3 h. After concentration, the crude reaction mixture was purified by reverse phase preparative HPLC (Waters 5 mM CSH C18 column, 50×50 mm), eluting with acetonitrile in water with 0.1% TFA. The desired fractions were combined and concentrated to give tert-butyl (R)-(1-(2-cyclopropyl-6-((3-(1-(4-methyl-4H-1,2,4-triazol-3-yl)propan-2-yl)phenyl)carbamoyl)pyridin-3-yl)-5,8,11-trioxa-2-azatridecan-13-yl)carbamate, which was treated with DCM/TFA 1:1 solution at room temperature. After 1 h the reaction was concentrated to afford the title compound (51 mg); LCMS: $C_{30}H_{43}N_7O_4$ requires m/z=565, found 566 [M+H]⁺.

Step 6. Synthesis of (R)-6-cyclopropyl-5-(17-(5,5-difluoro-7,9-dimethyl-5H-5$\lambda^4$,6$\lambda^4$-dipyrrolo[1,2-c:2',1'-f][1,3,2]diazaborinin-3-yl)-15-oxo-5,8,11-trioxa-2,14-diazaheptadecyl)-N-(3-(1-(4-methyl-4H-1,2,4-triazol-3-yl)propan-2-yl)phenyl)picolinamide. Triethylamine (0.01 mL, 6.08 mg, 0.06 mmol) was added to a DMF solution (1 mL) containing HATU (17 mg, 0.05 mmol) and 3-(5,5-difluoro-7,9-dimethyl-5H-5$\lambda^4$,6$\lambda^4$-dipyrrolo[1,2-c:2',1'-f][1,3,2]diazaborinin-3-yl)propanoic acid (9 mg, 0.03 mmol). After stirring for 5 min at room temperature, 5-(13-amino-5,8,11-trioxa-2-azatridecan-1-yl)-6-cyclopropyl-N-{3-[(2R)-1-(4-methyl-4H-1,2,4-triazol-3-yl)propan-2-yl]phenyl}pyridine-2-carboxamide (17 mg, 0.03 mmol) was added, and the resulting solution was stirred at rt for 4 h. The crude reaction mixture was purified by reverse phase preparative HPLC, eluting with acetonitrile in water with 0.1% TFA, to afford the title compound. ¹H NMR (500 MHz, Methanol-d₄) δ 8.00 (s, 2H), 7.67 (t, J=2.0 Hz, 1H), 7.55-7.45 (m, 1H), 7.38 (s, 1H), 7.33 (t, J=7.9 Hz, 1H), 7.05 (d, J=7.7 Hz, 1H), 6.97 (d, J=4.0 Hz, 1H), 4.57 (s, 2H), 3.82 (dd, J=5.7, 4.2 Hz, 2H), 3.68 (hd, J=3.9, 2.6 Hz, 4H), 3.65-3.62 (m, 3H), 3.61 (s, 3H), 3.60-3.56 (m, 2H), 3.48 (t, J=5.6 Hz, 3H), 3.39 (q, J=6.2, 5.6 Hz, 3H), 3.34 (s, 4H), 3.18 (t, J=7.8 Hz, 3H), 2.59 (t, J=7.7 Hz, 2H), 2.47 (s, 3H), 2.35 (tt, J=8.3, 4.7 Hz, 1H), 2.24 (s, 3H), 1.46 (d, J=6.7 Hz, 3H), 1.37-1.28 (m, 2H), 1.19 (dt, J=8.2, 3.3 Hz, 3H); LCMS: $C_{44}H_{56}BF_2N_9O_5$ requires m/z=840, found 841 [M+H]⁺.

Biological Examples

The following abbreviations apply: ACT (adoptive cell therapy); AUC (area under curve); Cmpd (compound); CP (cell proliferation); E/T (Effector:Target cell ratio); ID (identification); MFI (mean fluorescence intensity); mpk (milligram per kilogram); PBMC (peripheral blood mononuclear cells); TIL (tumor infiltrating lymphocyte); DPBS (Dulbecco's phosphate-buffered saline); and Ub (ubiquitin).

Biological Example 1: Evaluation of Cbl-b Inhibition by Candidate Inhibitors

Candidate compounds were evaluated for their ability to bind and inhibit Cbl-b, an E3 ubiquitin-protein ligase, as evidenced by their ability to displace a fluorophore-labeled probe (Example 59) bound to Cbl-b.

Materials and Methods

Cbl-b Displacement Assay (Cbl-b Inhibition Assay)

The ability of candidate compounds to displace a known inhibitor and thereby inhibit Cbl-b activity was measured by monitoring the interaction of Cbl-b with a fluorophore-labeled probe in the presence of the candidate compound. A truncated variant of Cbl-b (UniProt number Q13191; SEQ ID NO:1) containing an Avitag at its N-terminus was co-expressed with BirA biotin ligase and purified using a standard protocol (see Dou et al., Nature Structural and Molecular Biology, 8: 982-987, 2013; Avidity LLC).

Cbl-b Amino Acid Residues 36-427:

(SEQ ID NO: 1)
PKQAAADRRTVEKTWKLMDKVVRLCQNPKLQLKNSPPYILDILPDTYQHL

RLILSKYDDNQKLAQLSENEYFKIYIDSLMKKSKRAIRLFKEGKERMYEE

QSQDRRNLTKLSLIFSHMLAEIKAIFPNGQFQGDNFRITKADAAEFWRKF

FGDKTIVPWKVFRQCLHEVHQISSGLEAMALKSTIDLTCNDYISVFEFDI

FTRLFQPWGSILRNWNFLAVTHPGYMAFLTYDEVKARLQKYSTKPGSYIF

RLSCTRLGQWAIGYVTGDGNILQTIPHNKPLFQALIDGSREGFYLYPDGR

SYNPDLTGLCEPTPHDHIKVTQEQYELYCEMGSTFQLCKICAENDKDVKI

EPCGHLMCTSCLTAWQESDGQGCPFCRCEIKGTEPIIVDPFD

Fluorescently-labeled inhibitor probe was synthesized and tagged with BODIPY FL (Example 59). Cbl-b displacement assays were performed in a 384-well plate at room temperature in a 10 µL reaction volume by pre-incubating 0.5 nM Cbl-b or 0.125 nM Cbl-b (final concentration, indicated as "High" and "Low", respectively) in an assay buffer containing 20 mM HEPES pH 7.5, 150 mM NaCl, 0.01% Triton X-100, 0.01% BSA and 0.5 mM TCEP in the presence of a candidate compound in 1% DMSO (final concentration) for 1 hour. After incubation in the presence of the candidate compound, the plate was incubated for an additional 1 hour in the presence of an approximate $EC_{40}$ binding saturation consisting of 150 nM fluorescently-labeled inhibitor probe and 2 nM Streptavidin-Terbium (Cisbio) (final concentrations). Following the 1 hour incubation, the plates were read for TR-FRET signal at 520/620 nM using an Envision plate reader (Perkin Elmer). The presence of a TR-FRET signal indicated that the probe was not displaced from Cbl-b by the compound candidate. The absence of a FRET signal indicated that the probe was displaced from Cbl-b by the compound candidate.

Compounds were ranked into bins A through E as follows for $IC_{50}$: A indicates <1 nM; B indicates 1 nM≤$IC_{50}$<2 nM; C indicates 2 nM≤$IC_{50}$<5 nM; D indicates 5 nM≤$IC_{50}$<20 nM; E indicates 20 nM≤$IC_{50}$.

TABLE 2

| Cbl-b inhibition by tested compounds | | |
|---|---|---|
| Cmpd No. | Cbl-b activity $IC_{50}$ (High) | Cbl-b activity $IC_{50}$ (Low) |
| 1 | C | |
| 2 | C | |
| 3 | | E |
| 4 | | B |
| 5 | | C |

TABLE 2-continued

Cbl-b inhibition by tested compounds

| Cmpd No. | Cbl-b activity IC$_{50}$ (High) | Cbl-b activity IC$_{50}$ (Low) |
|---|---|---|
| 6 | | C |
| 7 | | D |
| 8 | | E |
| 9 | | D |
| 10 | | E |
| 11 | | B |
| 12 | | A |
| 13 | | C |
| 14 | | C |
| 15 | | C |
| 16 | | B |
| 17 | | B |
| 18 | | A |
| 19 | | A |
| 20 | | A |
| 21 | | A |
| 22 | | C |
| 23 | | B |
| 24 | | C |
| 25 | | A |
| 26 | | C |
| 27 | | C |
| 28 | | C |
| 29 | | C |
| 30 | | C |
| 31 | | A |
| 32 | | C |
| 33 | | C |
| 34 | | C |
| 35 | | C |
| 36 | | C |
| 37 | | C |
| 38 | | D |
| 39 | | B |
| 40 | | B |
| 41 | | C |
| 42 | | C |
| 43 | | C |
| 44 | | B |
| 45 | | C |
| 46 | | D |
| 47 | | C |
| 48 | | B |
| 49 | | A |
| 50 | | C |
| 51 | | E |
| 52 | | D |
| 53 | A | |
| 54 | | A |
| 55 | | A |
| 56 | | A |
| 57 | | A |
| 58 | | C |

Blank cell indicates data not available.

Biological Example 2: Evaluation of T-cell Activation by Cbl-b Inhibitors

Loss of Cbl-b function in both T-cells and mice by genetic knockout of the cbl-b gene results in loss of the CD28 co-stimulation requirement for T-cell activation and T-cell resistance to anergy (see Bachmaier et al., Nature, 403: 211-216, 2000; and Jeon et al., Immunity, 21: 167-177, 2004). Cbl-b inhibitors described herein were evaluated for their ability to activate T-cells.

Materials and Methods

Purification and Assessment of Primary Human Total T-Cell Activation

Peripheral blood mononuclear cells (PBMC) were obtained either: 1) by using Ficoll-Paque™ (GE Healthcare) for separation of peripheral blood hematopoietic cells from buffy coats of healthy human donors; or 2) directly from LeukoPak donations. Total human primary T-cells were isolated from the PMBCs utilizing negative selection with commercial kits following the manufacturer's protocol (Miltenyi Biotec Catalog #130-096-535 (i.e., cocktail of antibodies against surface markers CD14, CD15, CD16, CD19, CD34, CD36, CD56, CD123, and CD235a were incubated with the PBMCs before passing the samples by magnetic beads for removal of cells expressing those surface markers) or Stemcell Technolgies Catalog #17951) to yield >95% CD3+ cells as assessed by flow cytometry. The cells were rested overnight at 37° C. 5% CO$_2$. The Cbl-inhibitor was added to 1×10$^5$ cells per well and the plate was incubated for one hour at 37° C. in 5% CO$_2$ at the concentrations indicated (Table 3) with a final DMSO concentration of <0.1%. For samples stimulated with anti-CD3 antibody and anti-CD28 antibody (anti-CD3/anti-CD28), the Cbl-b inhibitor concentrations tested were 1 µM, and 0.3 µM. For samples stimulated with anti-CD3 antibody alone (anti-CD3), the Cbl-b inhibitor concentrations tested were 3 µM, and 1 µM. Following incubation with the Cbl-b inhibitor, primary human total T-cells were stimulated with either plate bound anti-CD3 antibody (OKT3) alone or plate bound anti-CD3 antibody (OKT3) with soluble anti-CD28 antibody (28.2) (Life Technologies). To prepare plates with plate bound anti-CD3 antibody (OKT3), 96-well round bottom tissue culture plates were coated with 100 µL of anti-CD3 antibody (OKT3) at 10 µg/mL for 4 hours at 37° C. 5% CO$_2$ in phosphate buffered saline (PBS). The plates were washed with PBS once prior to adding the cells with or without soluble anti-CD28 antibody (28.2) to each well at a final concentration of 5 µg/mL. Cells were stimulated for 48 hours prior to harvesting the cell free supernatant and staining the cell population for surface marker assessment by flow cytometry. Supernatants were analyzed for cytokine secretion, including IL-2 by ELISA (R&D Systems, Pepro-tech or Life Technologies) or Luminex multiplex kits (Pro-carta Life Technologies) following the manufacturer's protocol. Cells were stained with anti-CD25 antibody (BD Biosciences) to assess levels of surface marker of activation.

Results

Readouts were reported as fold change over baseline. Baseline for this study was the measurement obtained from total human T-cells stimulated with anti-CD3 antibody and with soluble anti-CD28 antibody, wherein the cells were not incubated with a Cbl-b inhibitor (Table 3). For T-cells stimulated with anti-CD3/anti-CD28, changes greater than 2.5-fold over baseline for IL-2 secretion and greater than 1.3-fold over baseline for CD25 surface staining were considered significant and a positive response (Table 3). For T-cells stimulated with anti-CD3 alone, changes greater than 0.1-fold over baseline for IL-2 secretion and greater than 0.6-fold over baseline for CD25 surface staining were considered significant and a positive response (Table 3). Compounds were ranked into bins according to their readouts as follows:

For IL-2 secretion with anti-CD3 antibody and anti-CD28 antibody co-stimulation the bins are: C indicates ≤15 fold, B indicates 15-20 fold, A indicates >20 fold;

For IL-2 secretion with anti-CD3 antibody stimulation the bins are: C indicates <0.40 fold, B indicates 0.40-0.85 fold, A indicates >0.85 fold;

For CD25 staining with anti-CD3 antibody and anti-CD28 antibody co-stimulation the bins are: C indicates ≤1.24 fold, B indicates 1.24-1.39 fold, A indicates >1.39 fold; and

185

For CD25 staining with anti-CD3 antibody stimulation the bins are: C indicates ≤1.00 fold, B indicates 1.00-1.15 fold, and A indicates >1.15 fold.

TABLE 3

T-cell activation as assessed by IL-2 secretion and CD25 surface staining as a consequence of stimulation with anti-CD3, or anti-CD3 and anti-CD28

| Cmpd No. | IL-2 secretion CD3/CD28 | | IL-2 secretion CD3 | | CD25 staining CD3/CD28 | | CD25 staining CD3 | |
|---|---|---|---|---|---|---|---|---|
| | 1 µM | 0.3 µM | 3 µM | 1 µM | 1 µM | 0.3 µM | 3 µM | 1 µM |
| 1 | C | C | C | C | B | B | B | B |
| 2 | C | C | C | C | C | C | B | B |
| 3 | C | C | C | C | C | C | B | C |
| 4 | B | C | B | B | B | B | A | A |
| 5 | A | A | A | A | A | A | A | A |
| 6 | C | C | B | B | C | C | C | B |
| 7 | C | C | C | C | B | C | C | C |
| 9 | C | C | C | C | B | C | B | C |
| 10 | C | C | C | C | C | C | C | C |
| 11 | A | A | A | A | B | B | C | B |
| 12 | B | B | B | A | B | B | B | B |
| 13 | B | B | B | B | B | B | B | A |
| 14 | B | B | B | B | C | C | C | C |
| 15 | B | C | A | B | B | B | B | B |
| 16 | B | C | A | B | B | B | C | B |
| 17 | A | B | B | B | B | B | C | B |
| 18 | A | A | A | A | B | B | C | B |
| 19 | A | A | A | A | A | A | A | A |
| 20 | A | A | A | A | A | A | A | A |
| 21 | A | A | A | A | A | A | A | A |
| 22 | C | C | B | B | A | A | B | B |
| 23 | B | B | B | B | B | B | B | B |
| 24 | B | C | B | B | B | B | B | A |
| 25 | A | A | A | A | B | B | C | B |
| 26 | C | C | C | C | C | C | C | C |
| 27 | C | C | B | C | C | C | C | C |
| 28 | C | C | C | C | C | C | C | C |
| 29 | C | C | B | C | B | B | B | A |
| 30 | C | C | C | C | C | C | B | C |
| 31 | A | A | A | A | A | A | A | A |
| 32 | A | A | A | A | A | A | A | A |
| 33 | C | C | B | B | C | C | C | C |
| 34 | C | C | B | C | C | C | C | C |
| 35 | B | B | B | B | B | B | B | B |
| 36 | B | C | B | C | A | B | B | B |
| 37 | B | C | B | C | B | B | C | B |
| 38 | B | C | A | B | A | A | A | A |
| 39 | C | C | C | C | C | B | C | C |
| 40 | B | C | A | B | B | B | C | B |
| 41 | C | C | C | C | A | B | B | C |
| 42 | A | B | A | A | C | C | B | B |
| 43 | A | C | B | B | C | C | B | B |
| 44 | C | C | C | C | C | C | B | C |
| 45 | A | C | A | B | B | B | B | B |
| 46 | B | C | A | B | A | A | A | A |
| 47 | A | A | A | A | A | A | A | A |
| 48 | A | C | B | B | A | A | A | A |
| 49 | A | A | A | A | A | A | A | A |
| 50 | A | A | B | A | A | A | A | A |
| 53 | B | B | B | B | C | C | B | B |
| 54 | A | A | A | A | B | B | C | C |
| 55 | A | A | A | A | B | B | C | C |
| 56 | A | B | B | B | C | C | B | B |
| 57 | A | B | A | B | B | B | C | B |

*Conclusions*

Cbl-b inhibitors enhanced IL-2 secretion in T-cells stimulated with anti-CD3 antibody alone or in combination with anti-CD28 antibody. Expression of the surface activation marker, CD25, increased in T-cells stimulated with anti-CD3 antibody alone or in combination with anti-CD28 antibody. These results indicate the identified Cbl-b inhibitors have the ability to activate T-cells and that such activation did not require co-stimulation with anti-CD28 antibody.

186

Biological Example 3: Evaluation of Immunomodulatory Effects of Cbl-b Inhibitors Cbl-b inhibitors identified from screening assays demonstrated the ability to activate total human T-cells in vitro as evidenced by enhanced TL-2 secretion and expression of the CD25 surface activation marker. Further in vitro studies were conducted to assess additional cytokine secretion by T-cells and expression of surface activation markers on T-cells. Additional immunomodulatory effects on T-cells contacted with the Cbl-b inhibitors described herein were assessed, such as the ability of a Cbl-b inhibitor to increase T-cell proliferation, decrease T-cell exhaustion, and decrease T-cell anergy. The ability of Cbl-b inhibitors, such as those described herein, to activate T-cells in vivo was also assessed. Other immunomodulatory effects by the Cbl-b inhibitors were assessed, such as the ability of Cbl-b inhibitors to activate B-cells and NK-cells.

Purification and Assessment of Primary Human Total T-Cell Activation

Peripheral blood mononuclear cells (PBMC) were obtained either: 1) by using Ficoll-Paque™ (GE Healthcare) for separation of peripheral blood hematopoietic cells from buffy coats of healthy human donors; or 2) directly from LeukoPak donations. Total human primary T-cells were isolated from the PMBCs utilizing negative selection with commercial kits following the manufacturer's protocol (Miltenyi Biotec Catalog #130-096-535 (i.e., cocktail of antibodies against surface markers CD14, CD15, CD16, CD19, CD34, CD36, CD56, CD123, and CD235a were incubated with the PBMCs before passing the samples by magnetic beads for removal of cells expressing those surface markers) or Stemcell Technolgies Catalog #17951) to yield >95% CD3+ cells as assessed by flow cytometry. For measurement of cell proliferation, cells were labeled with Cell Trace Violet (Invitrogen) following the manufacturer's protocol prior to activation by stimulation with anti-CD3 antibody alone or in combination with anti-CD28 antibody. The Cbl-b inhibitor was added to $1 \times 10^5$ cells per well at multiple concentrations (e.g., 10 µM, 1.11 µM, or 0.123 µM) with a final DMSO concentration of <0.1%. The plate was incubated for one hour at 37° C. in 5% $CO_2$. Following incubation with the Cbl-b inhibitor, primary human total T-cells were stimulated with either plate bound anti-CD3 antibody (OKT3) alone or plate bound anti-CD3 antibody (OKT3) with soluble anti-CD28 antibody (28.2) (Life Technologies). To prepare plates with plate bound anti-CD3 antibody (OKT3), 96-well round bottom tissue culture plates were coated with 100 µL of anti-CD3 antibody (OKT3) at 10 µg/mL for 4 hours at 37° C. 5% $CO_2$ in phosphate buffered saline (PBS). The plates were washed with PBS prior to adding the cells with or without soluble anti-CD28 antibody (28.2) to each well at a final concentration of 5 µg/mL. Cells were stimulated for 48 hours prior to harvesting the cell free supernatant and staining the cell population for surface marker assessment by flow cytometry. Supernatants were analyzed for cytokine secretion (e.g., GM-CSF, IFNγ, and TNFα) by ELISA (R&D Systems, Peprotech or Life Technologies) or Luminex multiplex kits (Procarta Life Technologies) following the manufacturer's protocol. Cells were stained with anti-CD69 (BD Biosciences) to assess levels of surface markers of activation. Proliferation was measured by flow cytometry and data was analyzed with FlowJo v7.6.5 or v10. Readouts were reported as fold change over baseline. In some embodiments, baseline was the measurement obtained from total human T-cells stimulated with anti-CD3 antibody alone, wherein the cells were not incubated with a Cbl-b inhibitor. In some embodiments, baseline was the measurement obtained from total human T-cells stimulated with anti-CD3 antibody and anti-CD28 antibody, where the cells were not incubated with a Cbl-b inhibitor.

Cbl-b inhibitor effects on primary human T-cells were also evaluated in the context of an allogenic mixed lymphocyte reaction (MLR). Allogenic immature dendritic cells were generated under the following conditions. Peripheral blood mononuclear cells (PBMC) were obtained either: 1) by using Ficoll-Paque™ (GE Healthcare) for separation of peripheral blood hematopoietic cells from buffy coats of healthy human donors; or 2) directly from LeukoPak donations. Monocytes were isolated from the PMBCs utilizing positive selection with a commercial kit following the manufacturer's protocol (Stemcell Technologies Catalog #17858) to yield >95% CD14+ cells as assessed by flow cytometry. Monocytes were cultured with 30 ng/mL of recombinant human GM-CSF and 20 ng/mL of recombinant human IL-4 for seven days to generate immature dendritic cells. Monocytes and T-cells were either isolated fresh from peripheral blood or thawed from frozen stocks. Human T-cells were isolated, labeled with CFSE and incubated with inhibitors as described above. The Cbl-b inhibitor was added to $1 \times 10^5$ T-cells in coculture with $2 \times 10^3$ allogenic immature dendritic cells per well at multiple concentrations (e.g., 10 µM, or 1.11 µM) with a final DMSO concentration of <0.1% and incubated at 37° C. in 5% $CO_2$ for 5 days. Proliferation of the T-cells was evaluated by flow cytometry.

Cbl-b inhibitors were tested to determine their ability to induce or enhance secretion of cytokines from T-cells (e.g., GM-CSF, IFNγ, and TNFα) and/or surface expression of cell surface markers on T-cells (e.g., CD69) that was indicative of T-cell activation. Cbl-b inhibitors were also tested to determine their ability to induce or enhance T-cell proliferation. Cbl-b inhibitors were tested for their effects on T-cell activation in the presence of costimulation and where conditions are suboptimal for priming.

Human T-Cell In Vitro Models of T-Cell Exhaustion

T-cell exhaustion was characterized by cells having a poor effector response and a sustained level of inhibitory receptor expression that results in T-cell dysfunction in response to chronic infections and cancer. In vitro models of T-cell exhaustion include allogenic and autologous models. In an autologous model, myeloid cells and SEB (Staphylococcal enterotoxin B, Millipore) were used to stimulate anti-CD3 stimulated T-cells. Peripheral blood mononuclear cells (PBMC) were obtained either: 1) by using Ficoll-Paque™ (GE Healthcare) for separation of peripheral blood hematopoietic cells from buffy coats of healthy human donors; or 2) directly from LeukoPak donations. Monocytes were isolated with commercial kits using negative selection with Stemcell Technologies EasySep Human Monocyte Enrichment Kit without CD16 Depletion (Catalog #19058) following the manufacturer's protocol. Isolated monocytes were cultured in complete media (e.g., RPMI 1640 with no additives, 10% HI FBS, 1× Glutamine and 1× β-mercaptoethanol) with 50 ng/mL recombinant human M-CSF (R&D System or Peprotech). Cells were plated at $2 \times 10^6$ cells per well (Day 0) and cultured for 5 days and were fed with fresh media and cytokines on Day 2. On Day 5 IFNγ was added at 100 ng/mL and the cells were incubated overnight. Primary human T-cells from the same donor were isolated from PBMCs with a commercial kit using negative selection (with Stemcell Technologies EasySep Human T-cell Isolation Kit (Catalog #17951) following the manufacturer's protocol. Purity was confirmed by surface marker detection by flow cytometry for CD4, CD8, CD45RA, CD45RO, CD19, CD14, CD56, and CD3 (BD Biosciences). $3 \times 10^6$ cells per/mL T-cells were stimulated with 10 µg/mL of plate bound anti-CD3 antibody (Clone UCHT-1) for 5 days. This was done in parallel with myeloid cell generation. On Day 6, $2.5 \times 10^4$ T-cells were added per well, $12.5 \times 10^3$ myeloid cells per well and SEB antigen (0.1 µg/mL) were added to wells of a round bottom 96-well plate. Test agents (e.g., Cbl-b inhibitor compounds) or controls (e.g., checkpoint neutralizing antibodies such as anti-PD1 antibody) were added to the wells at the indicated concentrations (e.g., 10 µM). Cells were cultured for 3 days at which point cell free supernatants were collected and assessed for secreted cytokines (e.g., GM-CSF, IFNγ, and IL-2) by ELISA (R&D Systems, Peprotech or Life Technologies) or Luminex multiplex kits (Procarta Life Technologies). The T-cells were stained for a panel of surface markers including checkpoint inhibitors (e.g., CTLA4) and evaluated by flow cytometry for Cbl-b inhibitor effects.

Cbl-b inhibitors were tested to determine their ability to induce or enhance secretion of cytokines from exhausted T-cells (e.g., GM-CSF, IFNγ, and IL-2) in the presence of myeloid cells, which was indicative of decreased T-cell exhaustion. Cbl-b inhibitors were also tested for their effects on checkpoint modulator expression levels following activation of exhausted T-cells.

Human T-Cell In Vitro Models of T-Cell Anergy

Peripheral blood mononuclear cells (PBMC) were obtained either: 1) by using Ficoll-Paque™ (GE Healthcare) for separation of peripheral blood hematopoietic cells from buffy coats of healthy human donors; or 2) directly from LeukoPak donations. Total human primary T-cells were isolated from the PBMCs utilizing negative selection with commercial kits following the manufacturer's protocol (Miltenyi Biotec Catalog #130-096-535 (i.e., cocktail of antibodies against surface markers CD14, CD15, CD16, CD19, CD34, CD36, CD56, CD123, and CD235a were incubated with the PBMCs before passing the samples by magnetic beads for removal of cells expressing those surface markers) or Stemcell Technologies Catalog #17951) to yield >95% CD3+ cells assessed by flow cytometry. The cells were activated with immobilized anti-CD3 antibody (OKT3) and soluble anti-CD28 antibody (28.2) for two days at which time they were washed and allowed to rest for three days in the absence of stimulation. They were then treated with ionomycin (Sigma) for 18-24 hours to induce anergy. Following two washes to remove the ionomycin from the samples, Cbl-b inhibitor compounds were added to the cells at the indicated concentrations (e.g., 10, 1.11, and 0.37 µM) and incubated for 1 hour. The cells were then re-challenged with anti-CD3 antibody and anti-CD28 antibody for 24 hours at which point cell free supernatants were collected and assessed for cytokines (e.g., IFNγ) by ELISA (R&D Systems or Peprotech) or Luminex multiplex kits (Procarta Life Technologies) following the manufacturer's protocols.

Cbl-b inhibitors were tested to determine their ability to induce or enhance secretion of cytokines from anergic T-cells (e.g., IFNγ), which was indicative of decreased T-cell tolerance.

In Vivo Activity of Cbl-b Inhibitors

A method of determining the pharmacodynamic profile of Cbl-b inhibitors was performed by dosing strains of mice with competent immune systems such as C57BL/6 or BALB/c with a Cbl-b inhibitor. The Cbl-b inhibitor was dissolved in a suitable formulation and administered by one of various routes such as intravenous (IV), intraperitoneal (IP), subcutaneous (SC), or oral (PO), at a suitable dose level and frequency (e.g., twice per day BID or thrice per day TID) as informed by prior pharmacokinetic and tolerability studies. Following administration of the Cbl-b inhibitor, T-cells and indirectly other immune cells (e.g., via cytokine production) were stimulated in vivo by administration of an anti-CD3 antibody or antigen-binding fragment thereof in PBS at defined amounts such as 2 µg or 10 µg per animal by routes such as IV or IP (See Hirsh et al., J. Immunol., 1989; Ferran et al., Eur. J. Immunol., 1990). Additional study control arms included groups of mice treated with a vehicle formulation alone (i.e., formulation without the Cbl-b inhibitor and anti-CD3 antibody), a formulation containing the Cbl-b inhibitor alone, a formulation containing the anti-CD3 antibody alone, PBS alone, or combinations of these agents. The level of immune activation was then assessed by analysis of plasma cytokine levels and/or expression of activation markers on immune cells (e.g., T-cells). Blood or lymphoid organs (e.g. spleen) were collected at defined time points (e.g., 8 hours or 24 hours). Blood samples were processed to collect plasma for determination of cytokine levels using standard methods known in the art. Cytokines measured included IL-2, IFNγ, and TNFα. Additional blood samples and lymphoid tissues were processed for flow cytometric analysis of immune cells (e.g., T-cells) using standard methods to determine expression of cell type-specific markers and activation markers such as CD25 and/or CD69. Augmentation of immune stimulation by Cbl-b inhibitor administration was assessed by comparing the relative concentrations of cytokines in plasma, or the expression levels of activation markers on immune cells between appropriate groups (e.g., mice treated with Cbl-b inhibitor and 2 g anti-CD3 antibody versus mice treated with vehicle and 2 g anti-CD3 antibody).

Cbl-b inhibitors were tested to determine their ability to induce or enhance the level of cytokines (e.g., IL-2, IFNγ, and TNFα) in blood obtained from treated mice stimulated with an anti-CD3 antibody, which was indicative of modulation of the immune response. Cbl-b inhibitors were also tested to determine their ability to induce or enhance the expression of cell surface markers on T-cells (e.g., CD25 and/or CD69) isolated from treated mice stimulated with an anti-CD3 antibody, which was indicative of modulation of the immune response.

B-Cell Activation Assay

Peripheral blood mononuclear cells (PBMC) were obtained either: 1) by using Ficoll-Paque™ (GE Healthcare) for separation of peripheral blood hematopoietic cells from buffy coats of healthy human donors; or 2) directly from LeukoPak donations. Human primary B-cells were isolated from the PBMCs utilizing negative selection with commercial kits following the manufacturer's protocol (Stemcell Technologies Catalog #17954) to yield >95% CD20+ cells assessed by flow cytometry. Primary human B-cells were plated at $0.7-1\times10^5$ per well in a 96-well plate with Cbl-b inhibitors over a dose ranging from 10 µM to 1 nM and incubated at 37° C. 5% $CO_2$, with a final DMSO concentration of <0.5%. Cells were stimulated with anti-IgM for 20 hours at 37° C. 5% $CO_2$. Surface activation markers on mature $CD20^+IgD^+$ B-cells were monitored by FACS using an anti-CD69 antibody (BD Biosciences).

Cbl-b inhibitors were tested to determine their ability to induce or enhance surface expression of cell surface markers on B-cells (e.g., CD69), which was indicative of B-cell activation.

Purification and Activation of Primary Human NK-Cells

Peripheral blood mononuclear cells (PBMC) were obtained either: 1) by using Ficoll-Paque™ (GE Healthcare) for separation of peripheral blood hematopoietic cells from buffy coats of healthy human donors; or 2) directly from LeukoPak donations. Total human primary NK-cells were isolated from the PBMCs utilizing negative selection with commercial kits following the manufacturer's protocol (Miltenyi Biotec Catalog #130-092-657 or Stemcell Technologies Catalog #17955) to yield >92% CD56+, CD3-cells as assessed by flow cytometry. The cells were cultured overnight with IL-2 (60 ng/mL) at 37° C. 5% $CO_2$. Cbl-b inhibitors were added 1 hour prior to stimulation and incubated at 37° C. 5% $CO_2$ at a specific concentration (e.g., 10 µM, 1 µM, or 0.1 µM) with a final DMSO concentration of <0.1%. NK-cells were co-cultured with target cells that were engineered to have a red nucleus (K562 NucRed) measurable by flow cytometry. K562 NucRed cells were produced by transduction of K562 cells with IncuCyte NucLight Red Lentivirus reagent (Catalog #4476) and selected for 5 days. Clonal populations were isolated and expanded using standard tissue culture techniques, and individual clones were validated by comparison to wildtype K562 cells in NK-cell killing assays. The cells were mixed at the indicated ratios (e.g., 5:1, 1:1, or 1:5) of NK (effector cells) to K562 NucRed (target cells) for 6 hours. Cell free supernatants were collected and analyzed for cytokine secretion (e.g., TNFα, IFNγ, or MIP1β) by ELISA or Luminex multiplex kits following the manufacturer's protocol. IFNγ secretion was assessed using an R&D Systems ELISA kit (Catalog #DY285), TNFα secretion was assessed using an R&D Systems ELISA kit (Catalog #DY210), and MIP1β secretion was assessed using an R&D Systems ELISA kit (Catalog #DY271).

Biological Example 4: Evaluation of a Cbl-b Inhibitor in Combination with an Immune Checkpoint Inhibitor for Treating Cancer Tumor microenvironments exploit T-cell inhibitory pathways as a mechanism to evade anti-tumor immune responses. The use of immune checkpoint inhibitors such as inhibitors of PD-1, PD-L1, and CTLA-4 have resulted in strikingly efficacious and durable responses against some tumor types (Marshall and Djamgoz, Front Oncol, 8:315, 2018). However, the response to immune checkpoint inhibitor monotherapy is not universal and therefore benefits only a small subset of cancer patients (Lv et al., Journal for ImmunoTherapy of Cancer, 7:159, 2019). This example describes the evaluation of a combination therapy for treating cancer including an immune checkpoint inhibitor and a Cbl-b inhibitor.

In brief, combination therapies were tested in strains of mice with competent immune systems (e.g., C57BL/6 or BALB/c) in whom syngeneic tumors can be grown. Syngeneic murine tumor cells were injected subcutaneously: CT26 colon cancer cells in BALB/c mice; TC-1 lung cancer cells in C57BL/6 mice; or MC-38 colon cancer cells in C57BL/6 mice. Tumors were allowed to grow to up to 100-200 mm³ at which time the animals were randomized and treatment was initiated. Alternatively, treatment was administered in a prophylactic setting within 1-3 days of tumor cell implant. The Cbl-b inhibitor was dissolved in a suitable formulation and administered at a suitable dose level and frequency as informed by prior pharmacokinetic and tolerability studies. The Cbl-b inhibitor formulation was administered orally (PO) or parenterally (e.g., IV, IP, SC, or intratumorally at one to three injection sites per tumor). The immune checkpoint inhibitor formulation was administered by IP injection every three days (e.g., Days 1, 4, and 7). In addition to the test group of mice who received the combination therapy, the study included control groups of mice who received either the vehicle formulation alone, the Cbl-b inhibitor formulation alone, or the immune checkpoint inhibitor alone.

The level of response was evaluated by measuring tumor growth and comparing tumor growth in the test mice versus the control mice. The level of immune activation was assessed by collecting tumors for analysis of tumor infiltrating lymphocytes (TILs). TILs and lymphoid tissues were processed for flow cytometric analysis using standard methods to determine cell lineage, expression of cell type-specific markers, and expression of activation markers such as granzyme B, PD-1, TIM3, and LAG3. Augmentation of the anti-tumor immune response by the combination therapy was assessed by comparing the relative percentage of immune cell populations in the tumor, and the relative levels of expression of activation markers on immune cells in mice of the test and study groups.

Biological Example 5: Evaluation of a Cbl-b Inhibitor in Combination with an Anti-Neoplastic Agent for Treating Cancer Chemotherapy has been reported to have a positive immunologic effect on tumor infiltrating lymphocytes (Lazzari et al., Ther Adv Med Oncol, 10:1-12, 2018), with the balance of regulatory and effector immune cells influencing prognosis. In addition, chemotherapy is contemplated to increase the intratumoral T-cell repertoire by augmenting tumor antigen presentation. This example describes the evaluation of a combination therapy for treating cancer including an anti-neoplastic agent and a Cbl-b inhibitor.

In brief, combination therapies were tested in strains of mice with competent immune systems (e.g., C57BL/6 or BALB/c) in whom syngeneic tumors were grown. Syngeneic murine tumor cells were injected subcutaneously: CT26 colon cancer cells in BALB/c mice; or TC-1 lung cancer cells in C57BL/6 mice. Tumors were allowed to grow up to about 120 mm$^3$ at which time the animals were randomized and treatment was initiated. The Cbl-b inhibitor was dissolved in a suitable formulation and administered at a suitable dose level and frequency as informed by prior pharmacokinetic and tolerability studies. The Cbl-b inhibitor formulation was administered orally (PO) or parenterally (e.g., IV, IP, SC, or intratumorally at one to three injection sites per tumor). The anti-neoplastic agent (e.g., gemcitabine and/or oxaliplatin) was administered by IP injection once every three or four days. In addition to the test group of mice who received the combination therapy, the study included control groups of mice who received either the vehicle formulation alone, the Cbl-b inhibitor formulation alone, or the anti-neoplastic agent alone.

The level of response was evaluated by measuring tumor growth and comparing tumor growth in the test mice versus the control mice. The level of immune activation was assessed by collecting tumors for analysis of tumor infiltrating lymphocytes (TILs). TILs and lymphoid tissues were processed for flow cytometric analysis using standard methods to determine cell lineage, expression of cell type-specific markers, and expression of activation markers such as granzyme B, PD-1, TIM3, and LAG3. Augmentation of the anti-tumor immune response by the combination therapy was assessed by comparing the relative percentage of immune cell populations in the tumor, and the relative levels of expression of activation markers on immune cells in mice of the test and study groups.

Biological Example 6: Evaluation of a Cbl-b Inhibitor in Combination with Radiation Therapy for Treating Cancer Ablative radiation therapy targeting local tumors limits damage to normal tissue and has the ability to enhance the diversity of the T-cell receptor repertoire by increasing the presence of tumor antigens (Lee et al., Blood, 114: 589-595, 2009). Radiotherapy at one site has been reported to lead to regression of distant site tumors that were not irradiated (Ngwa et al., Nat Rev Cancer, 18: 313-322, 2018). The systemic effect of a localized therapy is termed an "abscopal effect," which in the context of radiation therapy is thought to involve the immune system. This example describes the evaluation of a combination therapy for treating cancer including radiation therapy and a Cbl-b inhibitor.

In brief, combination therapies were tested in strains of mice with competent immune systems (e.g., C57BL/6 or BALB/c) in whom syngeneic tumors were grown. Syngeneic murine tumor cells were injected subcutaneously: CT26 colon cancer cells in BALB/c mice; or B16-F10 melanoma cells in C57BL/6 mice. Tumors were allowed to grow up to about 80 mm$^3$ at which time the animals were randomized and treatment was initiated. In some studies, tumor cells were implanted in both flanks and only one tumor was treated to assess the abscopal effect. The Cbl-b inhibitor was dissolved in a suitable formulation and administered at a suitable dose level and frequency as informed by prior pharmacokinetic and tolerability studies. The Cbl-b inhibitor formulation was administered orally (PO) or parenterally (e.g., IV, IP, SC, or intratumorally at one to three injection sites per tumor). Radiation therapy was administered once at a dose of 20 grays using an X-ray based focal beam irradiator. In addition to the test group of mice who received the combination therapy, the study included control groups of mice who received either the vehicle formulation alone, the Cbl-b inhibitor formulation alone, or radiation therapy alone.

The level of response was evaluated by measuring tumor growth and comparing tumor growth in the test mice versus the control mice. The level of immune activation was assessed by collecting tumors for analysis of tumor infiltrating lymphocytes (TILs). TILs and lymphoid tissues were processed for flow cytometric analysis using standard methods to determine cell lineage, expression of cell type-specific markers, and expression of activation markers such as granzyme B, PD-1, TIM3, and LAG3. Augmentation of the anti-tumor immune response by the combination therapy was assessed by comparing the relative percentage of immune cell populations in the tumor, and the relative levels of expression of activation markers on immune cells in mice of the test and study groups.

Biological Example 7: Evaluation of a Cbl-B Inhibitor in Combination with Adoptive Cell Therapy for Treating Cancer Adoptive cell therapy (ACT) utilizing autologous tumor-specific T-cells leverages the natural function of T-cells to specifically recognize and eliminate target cells (Hinrichs and Rosenberg, Immunol Rev, 257: 56-71, 2014). Specificity of tumor infiltrating lymphocytes (TILs) is due to their ability to recognize tumor-associated antigens, including neoantigens derived from products of mutated genes. This example describes the evaluation of an in vivo lymphoconditioning program with a Cbl-b inhibitor prior to ex vivo expansion of TILs for treating cancer with ACT.

Strains of mice with competent immune systems (e.g., C57BL/6 or BALB/c) in whom syngeneic tumors were grown were utilized. Syngeneic murine tumor cells were injected subcutaneously or intravenously: 4T1 breast cancer cells in BALB/c mice; RENCA kidney cancer cells in BALB/c mice; B16-F10 melanoma cells in C57BL/6 mice; 3LL lung cancer cells in C57BL/6 mice; or MC-38 colon cancer cells in C57BL/6 mice. Tumors were allowed to grow up to about 50-600 mm$^3$ at which time the animals were randomized and treatment was initiated. The Cbl-b inhibitor was dissolved in a suitable formulation and administered at a suitable dose level and frequency as informed by prior pharmacokinetic and tolerability studies. The Cbl-b inhibitor formulation was administered orally (PO) or parenterally (e.g., IV, IP, SC, or intratumorally at one to three injection sites per tumor). In addition to the test group of mice who received the Cbl-b inhibitor prior to tumor harvest, a control group of mice received either the vehicle formulation alone or remained untreated prior to tumor harvest. Tumor tissue was harvested either from the primary tumor or from tissues with metastases (e.g., lung). The tissues were minced and cultured in medium in the presence or absence of one or more exogenous T-cell growth factors (e.g., IL-2, IL-7, IL-15, and/or IL-21) under conditions suitable for expansion of TILs. Expansion of TILs was done in the presence or absence of the Cbl-b inhibitor. Expanded TILs were assessed for phenotype by flow cytometric analysis by measuring expression of markers for memory, effector, and stemness (e.g., CD95, TCF7, CD62L, CD44, etc.). Upon successful expansion of the TILs, tumor bearing mice were infused with TTLs in the presence or absence of the Cbl-b inhibitor to assess the effect of lympho-conditioning and/or subsequent in vivo treatment on TIL engraftment and anti-tumor immune responses.

Anti-tumor efficacy of ACT was assessed through tumor measurements to determine the level of tumor growth inhibition by TTLs.

Biological Example 8: Evaluation of Cbl-b Inhibition by Candidate Inhibitors

Candidate compounds were evaluated for their ability to bind and inhibit Cbl-b, an E3 ubiquitin-protein ligase, as evidenced by their ability to displace a fluorophore-labeled probe bound to Cbl-b.

Materials and Methods

Cbl-b Displacement Assay (Cbl-b Inhibition Assay)

The ability of candidate compounds to displace a known inhibitor and thereby inhibit Cbl-b activity was measured by monitoring the interaction of Cbl-b with a fluorophore-labeled probe in the presence of the candidate compound. A truncated variant of Cbl-b (UniProt number Q13191) containing residues 36-427 and an Avitag at its N-terminus was co-expressed with BirA biotin ligase and purified using a standard protocol (see Dou et al., Nature Structural and Molecular Biology 8: 982-987, 2013; Avidity LLC).

Fluorescently-labeled inhibitor probe was synthesized and tagged with BODIPY FL. Cbl-b displacement assays were performed in a 384-well plate at room temperature in a 10 μL reaction volume by pre-incubating 0.5 nM Cbl-b or 0.125 nM Cbl-b (final concentration, indicated as "High" and "Low," respectively) in an assay buffer containing 20 mM HEPES pH 7.5, 150 mM NaCl, 0.01% Triton X-100, 0.01% BSA, and 0.5 mM TCEP in the presence of a candidate compound in 1% DMSO (final concentration) for 1 hour. After incubation in the presence of the candidate compound, the plate was incubated for an additional one hour in the presence of an approximate EC$_{40}$ binding saturation consisting of 150 nM fluorescently-labeled inhibitor probe and 2 nM Streptavidin-Terbium (Cisbio) (final concentrations). Following the one hour incubation, the plates were read for TR-FRET signal at 520/620 nM using an Envision plate reader (Perkin Elmer). The presence of a TR-FRET signal indicated that the probe was not displaced from Cbl-b by the compound candidate. The absence of a FRET signal indicated that the probe was displaced from Cbl-b by the compound candidate.

Results

The resulting data for the Cbl-b activity assays were analyzed using standard methods to determine the IC$_{50}$ values for the tested compounds. In Table 4, compounds were ranked into bins as follows for IC$_{50}$: A indicates ≤1 nM; B indicates 1 nM-5 nM; and C indicates >5 nM.

TABLE 4

Cbl-b inhibition by tested compounds

| Compound No. | Cbl-b IC$_{50}$ (High) | Cbl-b IC$_{50}$ (Low) |
|---|---|---|
| 1 | B | |
| 4 | | B |
| 11 | | B |
| 19 | | A |
| 20 | | A |
| 21 | | A |
| 56 | | A |
| 60 | | C |

Blank cell indicates data not available.

Biological Example 9: Evaluation of T-Cell Activation by Cbl-b Inhibitors

Cbl-b inhibitors were evaluated for their ability to activate T-cells.

Materials and Methods

Purification and Assessment of Primary Human Total T-Cell Activation

Peripheral blood mononuclear cells (PBMC) were obtained either: 1) by using Ficoll-Paque™ (GE Healthcare) for separation of peripheral blood hematopoietic cells from buffy coats of healthy human donors; or 2) directly from LeukoPak donations. Total human primary T-cells were isolated from the PMBCs utilizing negative selection with commercial kits following the manufacturer's protocol (Miltenyi Biotec Catalog #130-096-535 (i.e., cocktail of antibodies against surface markers CD14, CD15, CD16, CD19, CD34, CD36, CD56, CD123, and CD235a were incubated with the PBMCs before passing the samples by magnetic beads for removal of cells expressing those surface markers) or Stemcell Technologies Catalog #17951) to yield >95% CD3+ cells as assessed by flow cytometry. The cells were rested overnight at 37° C. 5% CO$_2$. The Cbl-inhibitor was added to 1×10$^5$ cells per well and the plate was incubated for one hour at 37° C. in 5% CO$_2$ at the concentrations indicated (Table 5) with a final DMSO concentration of <0.1%. For samples stimulated with anti-CD3 antibody and anti-CD28 antibody (anti-CD3/anti-CD28), the Cbl-b inhibitor concentrations tested were 1 μM, and 0.3 μM. For samples stimulated with anti-CD3 antibody alone (anti-CD3), the Cbl-b inhibitor concentrations tested were 3 μM, and 1 μM. Following incubation with the Cbl-b inhibitor, primary human total T-cells were stimulated with either plate bound anti-CD3 antibody (OKT3) alone or plate bound anti-CD3 antibody (OKT3) with soluble anti-CD28 antibody (28.2) (Life Technologies). To prepare plates with plate bound anti-CD3 antibody (OKT3), 96-well round bottom tissue culture plates were coated with 100 μL of anti-CD3 antibody (OKT3) at 10 μg/mL for 4 hours at 37° C. 5% $CO_2$ in phosphate buffered saline (PBS). The plates were washed with PBS once prior to adding the cells with or without soluble anti-CD28 antibody (28.2) to each well at a final concentration of 5 μg/mL. Cells were stimulated for 48 hours prior to harvesting the cell free supernatant and staining the cell population for surface marker assessment by flow cytometry. Supernatants were analyzed for cytokine secretion, including IL-2 by ELISA (R&D Systems, Peprotech or Life Technologies) or Luminex multiplex kits (Procarta Life Technologies) following the manufacturer's protocol. Cells were stained with anti-CD25 antibody (BD Biosciences) to assess levels of surface marker of activation.

Results

Readouts were reported as fold change over baseline. Baseline for this study was the measurement obtained from total human T-cells stimulated with anti-CD3 antibody and with soluble anti-CD28 antibody, wherein the cells were not incubated with a Cbl-b inhibitor (Table 5). For T-cells stimulated with anti-CD3/anti-CD28, changes greater than 2.5-fold over baseline for IL-2 secretion and greater than 1.3-fold over baseline for CD25 surface staining were considered significant and a positive response. For T-cells stimulated with anti-CD3 alone, changes greater than 0.1-fold over baseline for IL-2 secretion and greater than 0.6-fold over baseline for CD25 surface staining were considered significant and a positive response.

Compounds were ranked into bins according to their readouts as follows: For IL-2 secretion with anti-CD3 antibody and anti-CD28 antibody co-stimulation the bins are: C indicates <10 fold, B indicates 10-15 fold, A indicates >15 fold; For IL-2 secretion with anti-CD3 antibody stimulation the bins are: C indicates ≤0.33 fold, B indicates 0.34-0.66 fold, A indicates >0.66 fold; For CD25 staining with anti-CD3 antibody and anti-CD28 antibody co-stimulation the bins are: C indicates ≤1.24 fold, B indicates 1.25-1.39 fold, A indicates >1.39 fold; and For CD25 staining with anti-CD3 antibody stimulation the bins are: C indicates ≤1.04 fold, B indicates 1.05-1.14 fold, and A indicates >1.14 fold.

TABLE 5

T-cell activation as assessed by IL-2 secretion and CD25 surface staining as a consequence of stimulation with anti-CD3, or anti-CD3 and anti-CD28

| Cmpd No. | IL-2 secretion CD3/CD28 | | IL-2 secretion CD3 | CD25 staining CD3/CD28 | | CD25 staining CD3 | |
|---|---|---|---|---|---|---|---|
| | 1 μM | 0.3 μM | 3 μM | 1 μM | 0.3 μM | 3 μM | 1 μM |
| 1 | B | C | B | B | B | B | A | A |
| 4 | A | A | A | A | A | A | A | A |
| 11 | A | A | A | A | A | A | A | A |
| 19 | A | A | A | A | A | A | A | A |
| 20 | A | A | A | A | A | A | A | A |
| 21 | A | A | A | A | A | A | A | A |
| 56 | A | A | A | A | A | A | A | A |
| 60 | B | C | B | B | A | A | A | A |

Cbl-b inhibitors enhanced IL-2 secretion by T-cells stimulated with an anti-CD3 antibody alone or in combination with an anti-CD28 antibody. Expression of the CD25 activation marker on the surface of T cells increased when stimulated with an anti-CD3 antibody alone or in combination with an anti-CD28 antibody. These results indicate the identified Cbl-b inhibitors have the ability to activate T-cells and that such activation did not require co-stimulation with an anti-CD28 antibody.

Biological Example 10: Evaluation of Immunomodulatory Effects of Cbl-b Inhibitors Cbl-b inhibitors identified from screening assays demonstrated the ability to activate total human T-cells in vitro as evidenced by enhanced IL-2 secretion and expression of the CD25 surface activation marker.

Further in vitro studies were conducted to assess additional cytokine secretion by T-cells and expression of surface activation markers on T-cells. Additional immunomodulatory effects on T-cells contacted with the Cbl-b inhibitors described herein were assessed, such as the ability of a Cbl-b inhibitor to increase T-cell proliferation, decrease T-cell exhaustion, and decrease T-cell anergy. The ability of Cbl-b inhibitors, such as those described herein, to activate T-cells in vivo was also assessed. Other immunomodulatory effects by the Cbl-b inhibitors were assessed, such as the ability of Cbl-b inhibitors to activate B-cells and NK-cells.

Purification and Assessment of Primary Human Total T-Cell Activation

Peripheral blood mononuclear cells (PBMC) were obtained either: 1) by using Ficoll-Paque™ (GE Healthcare) for separation of peripheral blood hematopoietic cells from buffy coats of healthy human donors; or 2) directly from LeukoPak donations. Total human primary T-cells were isolated from the PMBCs utilizing negative selection with commercial kits following the manufacturer's protocol (Miltenyi Biotec Catalog #130-096-535 (i.e., cocktail of antibodies against surface markers CD14, CD15, CD16, CD19, CD34, CD36, CD56, CD123, and CD235a were incubated with the PBMCs before passing the samples by magnetic beads for removal of cells expressing those surface markers) or Stemcell Technologies Catalog #17951) to yield >95% CD3+ cells as assessed by flow cytometry. For measurement of cell proliferation, cells were labeled with Cell Trace Violet (Invitrogen) following the manufacturer's protocol prior to activation by stimulation with anti-CD3 antibody alone or in combination with anti-CD28 antibody. The Cbl-b inhibitor was added to $1 \times 10^5$ cells per well at multiple concentrations (e.g., 10 μM, 1.11 μM, or 0.123 μM) with a final DMSO concentration of <0.1%. The plate was incubated for one hour at 37° C. in 5% $CO_2$. Following incubation with the Cbl-b inhibitor, primary human total T-cells were stimulated with either plate bound anti-CD3 antibody (OKT3) alone or plate bound anti-CD3 antibody (OKT3) with soluble anti-CD28 antibody (28.2) (Life Technologies). To prepare plates with plate bound anti-CD3 antibody (OKT3), 96-well round bottom tissue culture plates were coated with 100 μL of anti-CD3 antibody (OKT3) at 10 μg/mL for 4 hours at 37° C. 5% $CO_2$ in phosphate buffered saline (PBS). The plates were washed with PBS prior to adding the cells with or without soluble anti-CD28 antibody (28.2) to each well at a final concentration of 5 μg/mL. Cells were stimulated for 48 hours prior to harvesting the cell free supernatant and staining the cell population for surface marker assessment by flow cytometry. Supernatants were analyzed for cytokine secretion (e.g., GM-CSF, IFNγ, and TNFα) by ELISA (R&D Systems, Peprotech or Life Technologies) or Luminex multiplex kits (Procarta Life Technologies) following the manufacturer's protocol. Cells were stained with anti-CD69 (BD Biosciences) to assess levels of surface markers of activation. Proliferation was measured by flow cytometry and data was analyzed with FlowJo v7.6.5 or v10. Readouts were reported as fold change over baseline. In some embodiments, baseline was the measurement obtained from total human T-cells stimulated with anti-CD3 antibody alone, wherein the cells were not incubated with a Cbl-b inhibitor. In some embodiments, baseline was the measurement obtained from total human T-cells stimulated with anti-CD3 antibody and anti-CD28 antibody, wherein the cells were not incubated with a Cbl-b inhibitor.

Cbl-b inhibitor effects on primary human T-cells were also evaluated in the context of an allogenic mixed lymphocyte reaction (MLR). Allogenic immature dendritic cells were generated under the following conditions. Peripheral blood mononuclear cells (PBMC) were obtained either: 1) by using Ficoll-Paque™ (GE Healthcare) for separation of peripheral blood hematopoietic cells from buffy coats of healthy human donors; or 2) directly from LeukoPak donations. Monocytes were isolated from the PMBCs utilizing positive selection with a commercial kit following the manufacturer's protocol (StemCells Catalog #17858) to yield >95% CD14+ cells as assessed by flow cytometry. Monocytes were cultured with 30 ng/mL of recombinant human GM-CSF and 20 ng/mL of recombinant human IL-4 for seven days to generate immature dendritic cells. Monocytes and T-cells were either isolated fresh from peripheral blood or thawed from frozen stocks. Human T-cells were isolated, labeled with CFSE, and incubated with inhibitors as described above. The Cbl-b inhibitor was added to $1\times10^5$ T-cells in coculture with $2\times10^3$ allogenic immature dendritic cells per well at multiple concentrations (e.g., 10 µM, or 1.11 µM) with a final DMSO concentration of <0.1% and incubated at 37° C. in 5% $CO_2$ for 5 days. Proliferation of the T-cells was evaluated by flow cytometry.

Cbl-b inhibitors were tested to determine their ability to induce or enhance secretion of cytokines from T-cells (e.g., GM-CSF, IFNγ, and TNFα) and/or surface expression of cell surface markers on T-cells (e.g., CD69) that was indicative of T-cell activation. Cbl-b inhibitors were also tested to determine their ability to induce or enhance T-cell proliferation. Cbl-b inhibitors were tested for their effects on T-cell activation in the presence of costimulation and where conditions were suboptimal for priming.

Human T-Cell In Vitro Models of T-Cell Exhaustion

T-cell exhaustion was characterized by cells having a poor effector response and a sustained level of inhibitory receptor expression that results in T-cell dysfunction in response to chronic infections and cancer. In vitro models of T-cell exhaustion include allogenic and autologous models. In an autologous model, myeloid cells and SEB (Staphylococcal enterotoxin B, Millipore) were used to stimulate anti-CD3 stimulated T-cells. Peripheral blood mononuclear cells (PBMC) were obtained either: 1) by using Ficoll-Paque™ (GE Healthcare) for separation of peripheral blood hematopoietic cells from buffy coats of healthy human donors; or 2) directly from LeukoPak donations. Monocytes were isolated with commercial kits using negative selection with StemCells EasySep Human Monocyte Enrichment Kit without CD16 Depletion (Catalog #19058) following the manufacturer's protocol. Isolated monocytes were cultured in complete media (e.g., RPMI 1640 with no additives, 10% HI FBS, 1× Glutamine and 1× β-mercaptoethanol) with 50 ng/mL recombinant human M-CSF (R&D System or Peprotech). Cells were plated at $2\times10^6$ cells per well (Day 0) and cultured for 5 days and were fed with fresh media and cytokines on Day 2. On Day 5, IFNγ was added at 100 ng/mL and the cells were incubated overnight. Primary human T-cells from the same donor were isolated from PBMCs with a commercial kit using negative selection (with Stemcell Technologies EasySep Human T-cell Isolation Kit (Catalog #17951) following the manufacturer's protocol. Purity was confirmed by surface marker detection by flow cytometry for CD4, CD8, CD45RA, CD45RO, CD19, CD14, CD56, and CD3 (BD Biosciences). $3\times10^6$ cells per/mL T-cells were stimulated with 10 µg/mL of plate bound anti-CD3 antibody (Clone UCHT-1) for 5 days. This was done in parallel with myeloid cell generation. On Day 6, $2.5\times10^4$ T-cells were added per well, $12.5\times10^3$ myeloid cells per well and SEB antigen (0.1 µg/mL) were added to wells of a round-bottom 96-well plate. Test agents (e.g., Cbl-b inhibitor compounds) or controls (e.g., checkpoint neutralizing antibodies such as anti-PD1 antibody) were added to the wells at the indicated concentrations (e.g., 10 µM). Cells were cultured for 3 days at which point cell free supernatants were collected and assessed for secreted cytokines (e.g., GM-CSF, IFNγ, and IL-2) by ELISA (R&D Systems, Peprotech or Life Technologies) or Luminex multiplex kits (Procarta Life Technologies). The T-cells were stained for a panel of surface markers including checkpoint inhibitors (e.g., CTLA4) and evaluated by flow cytometry for Cbl-b inhibitor effects.

Cbl-b inhibitors were tested to determine their ability to induce or enhance secretion of cytokines from exhausted T-cells (e.g., GM-CSF, IFNγ, and IL-2) in the presence of myeloid cells, which was indicative of decreased T-cell exhaustion. Cbl-b inhibitors were also tested for their effects on checkpoint modulator expression levels following activation of exhausted T-cells.

Human T-Cell In Vitro Models of T-Cell Anergy

Peripheral blood mononuclear cells (PBMC) were obtained either: 1) by using Ficoll-Paque™ (GE Healthcare) for separation of peripheral blood hematopoietic cells from buffy coats of healthy human donors; or 2) directly from LeukoPak donations. Total human primary T-cells were isolated from the PBMCs utilizing negative selection with commercial kits following the manufacturer's protocol (Miltenyi Biotec Catalog #130-096-535 (i.e., cocktail of antibodies against surface markers CD14, CD15, CD16, CD19, CD34, CD36, CD56, CD123, and CD235a were incubated with the PBMCs before passing the samples by magnetic beads for removal of cells expressing those surface markers) or Stemcell Technologies Catalog #17951) to yield >95% CD3+ cells assessed by flow cytometry. The cells were activated with immobilized anti-CD3 antibody (OKT3) and soluble anti-CD28 antibody (28.2) for two days at which time they were washed and allowed to rest for three days in the absence of stimulation. They were then treated with ionomycin (Sigma) for 18-24 hours to induce anergy. Following two washes to remove the ionomycin from the samples, Cbl-b inhibitor compounds were added to the cells at the indicated concentrations (e.g., 10, 1.11, and 0.37 µM) and incubated for 1 hour. The cells were then re-challenged with anti-CD3 antibody and anti-CD28 antibody for 24 hours at which point cell free supernatants were collected and assessed for cytokines (e.g., IFNγ) by ELISA (R&D Systems or Peprotech) or Luminex multiplex kits (Procarta Life Technologies) following the manufacturer's protocols.

Cbl-b inhibitors were tested to determine their ability to induce or enhance secretion of cytokines from anergic T-cells (e.g., IFNγ), which was indicative of decreased T-cell tolerance.

In Vivo Activity of Cbl-b Inhibitors

A method of determining the pharmacodynamic profile of Cbl-b inhibitors was performed by dosing strains of mice with competent immune systems such as C57BL/6 or BALB/c with a Cbl-b inhibitor. The Cbl-b inhibitor was dissolved in a suitable formulation and administered by one of various routes such as intravenous (IV), intraperitoneal (IP), subcutaneous (SC), or oral (PO), at a suitable dose level and frequency (e.g., twice per day BID or thrice per day TID) as informed by prior pharmacokinetic and tolerability studies. Following administration of the Cbl-b inhibitor, T-cells and indirectly other immune cells (e.g., via cytokine production) were stimulated in vivo by administration of an anti-CD3 antibody or antigen-binding fragment thereof in PBS at defined amounts such as 2 g or 10 g per animal by routes such as IV or IP (see Hirsh et al., J. Immunol., 1989; Ferran, et al., Eur. J. Immunol., 1990). Additional study control arms included groups of mice treated with a vehicle formulation alone (i.e., formulation without the Cbl-b inhibitor and anti-CD3 antibody), a formulation containing the Cbl-b inhibitor alone, a formulation containing the anti-CD3 antibody alone, PBS alone, or combinations of these agents. The level of immune activation was then assessed by analysis of plasma cytokine levels and/or expression of activation markers on immune cells (e.g., T-cells). Blood or lymphoid organs (e.g., spleen) were collected at defined time points (e.g., 8 hours or 24 hours). Blood samples were processed to collect plasma for determination of cytokine levels using standard methods known in the art. Cytokines measured included IL-2, IFNγ, and TNFα. Additional blood samples and lymphoid tissues were processed for flow cytometric analysis of immune cells (e.g., T-cells) using standard methods to determine expression of cell type-specific markers and activation markers such as CD25 and/or CD69. Augmentation of immune stimulation by Cbl-b inhibitor administration was assessed by comparing the relative concentrations of cytokines in plasma, or the expression levels of activation markers on immune cells between appropriate groups (e.g., mice treated with Cbl-b inhibitor and 2 g anti-CD3 antibody versus mice treated with vehicle and 2 g anti-CD3 antibody).

Cbl-b inhibitors were tested to determine their ability to induce or enhance the level of cytokines (e.g., IL-2, IFNγ, and TNFα) in blood obtained from treated mice stimulated with an anti-CD3 antibody, which was indicative of modulation of the immune response. Cbl-b inhibitors were also tested to determine their ability to induce or enhance the expression of cell surface markers on T-cells (e.g., CD25 and/or CD69) isolated from treated mice stimulated with an anti-CD3 antibody, which was indicative of modulation of the immune response.

B-Cell Activation Assay

Peripheral blood mononuclear cells (PBMC) were obtained either: 1) by using Ficoll-Paque™ (GE Healthcare) for separation of peripheral blood hematopoietic cells from buffy coats of healthy human donors; or 2) directly from LeukoPak donations. Human primary B-cells were isolated from the PBMCs utilizing negative selection with commercial kits following the manufacturer's protocol (Stemcell Technologies Catalog #17954) to yield >95% CD20+ cells as assessed by flow cytometry. Primary human B-cells were plated at $0.7$-$1\times10^5$ per well in a 96-well plate with Cbl-b inhibitors over a dose ranging from 10 μM to 1 nM and incubated at 37° C. 5% $CO_2$, with a final DMSO concentration of <0.5%. Cells were stimulated with anti-IgM for 20 hours at 37° C. 5% $CO_2$. Surface activation markers on mature $CD20^+IgD^+$ B-cells were monitored by FACS using an anti-CD69 antibody (BD Biosciences).

Cbl-b inhibitors were tested to determine their ability to induce or enhance surface expression of cell surface markers on B-cells (e.g., CD69), which was indicative of B-cell activation.

Purification and Activation of Primary Human NK-Cells.

Peripheral blood mononuclear cells (PBMC) were obtained either: 1) by using Ficoll-Paque™ (GE Healthcare) for separation of peripheral blood hematopoietic cells from buffy coats of healthy human donors; or 2) directly from LeukoPak donations. Total human primary NK-cells were isolated from the PBMCs utilizing negative selection with commercial kits following the manufacturer's protocol (Miltenyi Biotec Catalog #130-092-657 or Stemcell Technologies Catalog #17955) to yield >92% CD56+, CD3-cells as assessed by flow cytometry. The cells were cultured overnight with IL-2 (60 ng/mL) at 37° C. 5% $CO_2$. Cbl-b inhibitors were added one hour prior to stimulation and incubated at 37° C. 5% $CO_2$ at a specific concentration (e.g., 10 μM, 1 μM, or 0.1 μM) with a final DMSO concentration of <0.1%. NK-cells were co-cultured with target cells that were engineered to have a red nucleus (K562 NucRed) measurable by flow cytometry. K562 NucRed cells were produced by transduction of K562 cells with IncuCyte NucLight Red Lentivirus reagent (Catalog #4476) and selected for 5 days. Clonal populations were isolated and expanded using standard tissue culture techniques, and individual clones were validated by comparison to wildtype K562 cells in NK-cell killing assays. The cells were mixed at the indicated ratios (e.g., 5:1, 1:1, or 1:5) of NK (effector cells) to K562 NucRed (target cells) for 6 hours. Cell free supernatants were collected and analyzed for cytokine secretion (e.g., TNFα, IFNγ, or MIP1β) by ELISA or Luminex multiplex kits following the manufacturer's protocol. IFNγ secretion was assessed using an R&D Systems ELISA kit (Catalog #DY285), TNFα secretion was assessed using an R&D Systems ELISA kit (Catalog #DY210), and MIP1β secretion was assessed using an R&D Systems ELISA kit (Catalog #DY271).

Biological Example 11: Evaluation of a Cbl-b Inhibitor in Combination with a Cancer Vaccine for Treating Cancer This example describes the evaluation of a combination therapy for treating cancer in mice including a cancer vaccine and a Cbl-b inhibitor.

Materials and Methods

In brief, the combination therapy was tested in C57BL/6 mice bearing a syngeneic TC-1 cell tumor. TC-1 cells were derived from primary murine lung cells, which had been transfected with human papillomavirus strain 16 (HPV16) early proteins 6 and 7 (E6 and E7) and an activated human c-Ha-ras oncogene (Lin et al., Cancer Research, 56: 21-26, 1996). Either $2.5\times10^4$ (first study) or $5.0\times10^4$ (second study) TC-1 cells (obtained from Johns Hopkins University) were injected subcutaneously into the mid flank of each mouse. Tumors were allowed to grow to 50-100 $mm^3$ at which time the animals were randomized and treatment was initiated (Day 0).

The HPV16 E7 cancer vaccine (Shrimali et al., Cancer Immunol Res, 5: 755-766, 2017) included 100 μg of a synthetic peptide with the amino acid sequence of a CTL epitope of residues 49-57 of E7 (RAHYNIVTF set forth as SEQ ID NO:2), mixed with 20 μg of a synthetic peptide with the amino acid sequence of a Th epitope known as PADRE (aK-Cha-VAAWTLKAAa set for as SEQ ID NO:3, where "a" is D-alanine and "Cha" is L-cyclohexylalanine) and 20 μg of a Quil-A® adjuvant marketed by Brenntag Biosector A/S, which contains purified quillaja saponins. The HPV16 E7 vaccine or Dulbecco's phosphate-buffered saline (DPBS) was administered subcutaneously (SC) on Days 2 and 9

(=Day 16 and Day 23 post TC-1 injection). The Cbl-b inhibitor was dissolved in a suitable formulation and administered at a suitable dose level and frequency as informed by prior pharmacokinetic and tolerability studies. In initial studies, the Cbl-b inhibitor (Compound No. 60) in a suitable vehicle, or the vehicle, was administered orally (PO) at a dose of 180 mg/kg twice per day (BID) beginning on Day 0 (=Day 14 post TC-1 injection). In further studies, a Cbl-b inhibitor formulation was administered orally (PO) or parenterally (e.g., IV, IP, SC, or intratumorally at one to three injection sites per tumor). In addition to the test group of mice who received the combination therapy (the Cbl-b inhibitor formulation plus the HPV16 E7 vaccine), the study included control groups of mice who received the vehicle formulation plus DPBS, the Cbl-b inhibitor formulation plus DPBS, or the vehicle formulation plus the HPV16 E7 vaccine.

Tumor size was recorded twice a week starting on Day 0 (Day 14 post TC-1 injection) and continued through duration of dosing until humane endpoints were reached between Day 33 and Day 42 (=between Day 47 and Day 56 post TC-1 injection). The level of response was evaluated by comparing tumor growth in the test mice versus the control mice (10 mice per group). In addition, the level of immune activation was assessed by collecting tumors for analysis of tumor infiltrating lymphocytes (TILs) on Day 10 (=Day 24 post TC-1 injection) in test and control mice (6 mice per group). TILs were processed for flow cytometric analysis using standard methods to determine antigen specificity, expression of cell type-specific markers, and expression of activation markers such as granzyme B, CD25, CD69, PD-1, and LAG3. In further experiments, PBMCs and/or splenocytes were also collected and processed. Augmentation of the anti-tumor immune response by the combination therapy was assessed by comparing the relative percentage of total or E7-specific (tumor antigen-specific) CD8+ T cells, and the relative levels of expression of activation markers on immune cells in mice of the test and study groups.

Results

As shown in Table 6, Cbl-b inhibition in combination with tumor peptide vaccination promoted tumor infiltration by tumor peptide-specific CD8+ T cells. In addition, the combination therapy including a Cbl-b inhibitor and a tumor peptide vaccine resulted in elevated levels in tumors of both tumor peptide-specific (E7+) and other (E7−) activated CD8+ T cells. Moreover, the combination therapy including a Cbl-b inhibitor and a tumor peptide vaccine yielded more partial responders (6/10 mice) than did the respective monotherapies (0/10 partial responders to the Cbl-b inhibitor alone and 3/10 partial responders to the tumor peptide vaccine alone). In this experiment, partial responders were defined by a significant decrease in tumor size (tumor volume) relative to the size of tumors of control mice who did not receive the Cbl-b inhibitor or the tumor peptide vaccine.

TABLE 6

Mean Increase in CD8+ T cells in TILs of Recipients of an HPV16 E7 Vaccine and a Cbl-b Inhibitor^

| TIL Profile | HPV16 E7 Vaccine + Compound No. 60 |
| --- | --- |
| % E7 positive T cells | 33.7 |
| % Granzyme positive (E7 + T cells) | 7.86 |
| % PD1 positive (E7 + T cells) | 14.97 |
| % LAG3 positive (E7 + T cells) | 13.49 |

TABLE 6-continued

Mean Increase in CD8+ T cells in TILs of Recipients of an HPV16 E7 Vaccine and a Cbl-b Inhibitor^

| TIL Profile | HPV16 E7 Vaccine + Compound No. 60 |
| --- | --- |
| % Granzyme positive (E7 − T cells) | 4.12 |
| % PD1 positive (E7 − T cells) | 20.23 |
| % LAG3 positive (E7 − cells) | 0.96 |

^Percent increase is relative to CD8+ T cells in TILs of Recipients of an HPV16 E7 vaccine in the absence of a Cbl-b inhibitor.

Biological Example 12: Evaluation of Cbl-b Inhibition by Candidate Inhibitors

Candidate compounds were evaluated for their ability to bind and inhibit Cbl-b, an E3 ubiquitin-protein ligase, as evidenced by their ability to displace a fluorophore-labeled probe bound to Cbl-b.

Materials and Methods

Cbl-b Displacement Assay (Cbl-b Inhibition Assay)

The ability of candidate compounds to displace a known inhibitor and thereby inhibit Cbl-b activity was measured by monitoring the interaction of Cbl-b with a fluorophore-labeled probe in the presence of the candidate compound. A truncated variant of Cbl-b (UniProt number Q13191) containing residues 36-427 and an Avitag at its N-terminus was co-expressed with BirA biotin ligase and purified using a standard protocol (see Dou et al., Nature Structural and Molecular Biology 8: 982-987, 2013; Avidity LLC).

Fluorescently-labeled inhibitor probe was synthesized and tagged with BODIPY FL. Cbl-b displacement assays were performed in a 384-well plate at room temperature in a 10 µL reaction volume by pre-incubating 0.5 nM Cbl-b or 0.125 nM Cbl-b (final concentration, indicated as "High" and "Low," respectively) in an assay buffer containing 20 mM HEPES pH 7.5, 150 mM NaCl, 0.01% Triton X-100, 0.01% BSA and 0.5 mM TCEP in the presence of a candidate compound in 1% DMSO (final concentration) for one hour. After incubation in the presence of the candidate compound, the plate was incubated for an additional one hour in the presence of an approximate $EC_{40}$ binding saturation consisting of 150 nM fluorescently-labeled inhibitor probe and 2 nM Streptavidin-Terbium (Cisbio) (final concentrations). Following the one hour incubation, the plates were read for TR-FRET signal at 520/620 nM using an Envision plate reader (Perkin Elmer). The presence of a TR-FRET signal indicated that the probe was not displaced from Cbl-b by the compound candidate. The absence of a FRET signal indicated that the probe was displaced from Cbl-b by the compound candidate.

Results

The resulting data for the Cbl-b activity assays were analyzed using standard methods to determine the $IC_{50}$ values for the tested compounds. In Table 7, compounds were ranked into bins as follows for $IC_{50}$: A indicates ≤1 nM; and B indicates 1 nM-5 nM; and C indicates >5 nM.

TABLE 7

Cbl-b inhibition by tested compounds

| Compound No. | Cbl-b $IC_{50}$ (High) | Cbl-b $IC_{50}$ (Low) |
| --- | --- | --- |
| 1 | B | |
| 4 | | B |

TABLE 7-continued

Cbl-b inhibition by tested compounds

| Compound No. | Cbl-b IC$_{50}$ (High) | Cbl-b IC$_{50}$ (Low) |
|---|---|---|
| 11 |  | B |
| 19 |  | A |
| 20 |  | A |
| 21 |  | A |
| 56 |  | A |
| 60 |  | C |

Blank cell indicates data not available.

Biological Example 13: Evaluation of T-cell Activation by Cbl-b Inhibitors

Cbl-b inhibitors were evaluated for their ability to activate T-cells.

Materials and Methods

Purification and Assessment of Primary Human Total T-Cell Activation

Peripheral blood mononuclear cells (PBMC) were obtained either: 1) by using Ficoll-Paque™ (GE Healthcare) for separation of peripheral blood hematopoietic cells from buffy coats of healthy human donors; or 2) directly from LeukoPak donations. Total human primary T-cells were isolated from the PMBCs utilizing negative selection with commercial kits following the manufacturer's protocol (Miltenyi Biotec Catalog #130-096-535 (i.e., cocktail of antibodies against surface markers CD14, CD15, CD16, CD19, CD34, CD36, CD56, CD123, and CD235a were incubated with the PBMCs before passing the samples by magnetic beads for removal of cells expressing those surface markers) or Stemcell Technologies Catalog #17951) to yield >95% CD3+ cells as assessed by flow cytometry. The cells were rested overnight at 37° C. 5% $CO_2$. The Cbl-inhibitor was added to 1×10$^5$ cells per well and the plate was incubated for one hour at 37° C. in 5% $CO_2$ at the concentrations indicated (Table 8) with a final DMSO concentration of <0.1%. For samples stimulated with anti-CD3 antibody and anti-CD28 antibody (anti-CD3/anti-CD28), the Cbl-b inhibitor concentrations tested were 1 µM, and 0.3 µM. For samples stimulated with anti-CD3 antibody alone (anti-CD3), the Cbl-b inhibitor concentrations tested were 3 µM, and 1 µM. Following incubation with the Cbl-b inhibitor, primary human total T-cells were stimulated with either plate bound anti-CD3 antibody (OKT3) alone or plate bound anti-CD3 antibody (OKT3) with soluble anti-CD28 antibody (28.2) (Life Technologies). To prepare plates with plate bound anti-CD3 antibody (OKT3), 96-well round bottom tissue culture plates were coated with 100 µL of anti-CD3 antibody (OKT3) at 10 µg/mL for 4 hours at 37° C. 5% $CO_2$ in phosphate buffered saline (PBS). The plates were washed with PBS once prior to adding the cells with or without soluble anti-CD28 antibody (28.2) to each well at a final concentration of 5 µg/mL. Cells were stimulated for 48 hours prior to harvesting the cell free supernatant and staining the cell population for surface marker assessment by flow cytometry. Supernatants were analyzed for cytokine secretion, including IL-2 by ELISA (R&D Systems, Pepro-tech or Life Technologies) or Luminex multiplex kits (Procarta Life Technologies) following the manufacturer's protocol. Cells were stained with anti-CD25 antibody (BD Biosciences) to assess levels of surface marker of activation.

Results

Readouts were reported as fold change over baseline. Baseline for this study was the measurement obtained from total human T-cells stimulated with anti-CD3 antibody and with soluble anti-CD28 antibody, wherein the cells were not incubated with a Cbl-b inhibitor (Table 8). For T-cells stimulated with anti-CD3/anti-CD28, changes greater than 2.5-fold over baseline for IL-2 secretion and greater than 1.3-fold over baseline for CD25 surface staining were considered significant and a positive response. For T-cells stimulated with anti-CD3 alone, changes greater than 0.1-fold over baseline for IL-2 secretion and greater than 0.6-fold over baseline for CD25 surface staining were considered significant and a positive response.

Compounds were ranked into bins according to their readouts as follows: For IL-2 secretion with anti-CD3 antibody and anti-CD28 antibody co-stimulation the bins are: C indicates ≤10 fold, B indicates 11-15 fold, A indicates >15 fold; For IL-2 secretion with anti-CD3 antibody stimulation the bins are: C indicates ≤0.33 fold, B indicates 0.34-0.66 fold, A indicates >0.66 fold; For CD25 staining with anti-CD3 antibody and anti-CD28 antibody co-stimulation the bins are: C indicates ≤1.24 fold, B indicates 1.25-1.39 fold, A indicates >1.39 fold; and For CD25 staining with anti-CD3 antibody stimulation the bins are: C indicates ≤1.04 fold, B indicates 1.05-1.14 fold, and A indicates >1.14 fold.

TABLE 8

T-cell activation as assessed by IL-2 secretion and CD25 surface staining as a consequence of stimulation with anti-CD3, or anti-CD3 and anti-CD28

| Cmpd No. | IL-2 secretion CD3/CD28 | | IL-2 secretion CD3 | CD25 staining CD3/CD28 | | CD25 staining CD3 |
|---|---|---|---|---|---|---|
|  | 1 µM | 0.3 µM | 3 µM | 1 µM | 1 µM | 0.3 µM | 3 µM | 1 µM |
| 1 | B | C | B | B | B | B | A | A |
| 4 | A | A | A | A | A | A | A | A |
| 11 | A | A | A | A | A | A | A | A |
| 19 | A | A | A | A | A | A | A | A |
| 20 | A | A | A | A | A | A | A | A |
| 21 | A | A | A | A | A | A | A | A |
| 56 | A | A | A | A | A | A | A | A |
| 60 | B | C | B | B | A | A | A | A |

Cbl-b inhibitors enhanced IL-2 secretion by T-cells stimulated with an anti-CD3 antibody alone or in combination with an anti-CD28 antibody. Expression of the CD25 activation marker on the surface of T cells increased when stimulated with an anti-CD3 antibody alone or in combination with an anti-CD28 antibody. These results indicate the identified Cbl-b inhibitors have the ability to activate T-cells and that such activation did not require co-stimulation with an anti-CD28 antibody.

Biological Example 14: Evaluation of Immunomodulatory Effects of Cbl-b Inhibitors Cbl-b inhibitors identified from screening assays demonstrated the ability to activate total human T-cells in vitro as evidenced by enhanced TL-2 secretion and expression of the CD25 surface activation marker.

Further in vitro studies were conducted to assess additional cytokine secretion by T-cells and expression of surface activation markers on T-cells. Additional immuno-modulatory effects on T-cells contacted with the Cbl-b inhibitors described herein were assessed, such as the ability of a Cbl-b inhibitor to increase T-cell proliferation, decrease T-cell exhaustion, and decrease T-cell anergy. The ability of Cbl-b inhibitors, such as those described herein, to activate T-cells in vivo was also assessed. Other immunomodulatory effects by the Cbl-b inhibitors were assessed, such as the ability of Cbl-b inhibitors to activate B-cells and NK-cells.

Purification and Assessment of Primary Human Total T-Cell Activation

Peripheral blood mononuclear cells (PBMC) were obtained either: 1) by using Ficoll-Paque™ (GE Healthcare) for separation of peripheral blood hematopoietic cells from buffy coats of healthy human donors; or 2) directly from LeukoPak donations. Total human primary T-cells were isolated from the PMBCs utilizing negative selection with commercial kits following the manufacturer's protocol (Miltenyi Biotec Catalog #130-096-535 (i.e., cocktail of antibodies against surface markers CD14, CD15, CD16, CD19, CD34, CD36, CD56, CD123, and CD235a were incubated with the PBMCs before passing the samples by magnetic beads for removal of cells expressing those surface markers) or Stemcell Technologies Catalog #17951) to yield >95% CD3+ cells as assessed by flow cytometry. For measurement of cell proliferation, cells were labeled with Cell Trace Violet (Invitrogen) following the manufacturer's protocol prior to activation by stimulation with anti-CD3 antibody alone or in combination with anti-CD28 antibody. The Cbl-b inhibitor was added to $1 \times 10^5$ cells per well at multiple concentrations (e.g., 10 µM, 1.11 µM, or 0.123 µM) with a final DMSO concentration of <0.1%. The plate was incubated for one hour at 37° C. in 5% $CO_2$. Following incubation with the Cbl-b inhibitor, primary human total T-cells were stimulated with either plate bound anti-CD3 antibody (OKT3) alone or plate bound anti-CD3 antibody (OKT3) with soluble anti-CD28 antibody (28.2) (Life Technologies). To prepare plates with plate bound anti-CD3 antibody (OKT3), 96-well round-bottom tissue culture plates were coated with 100 µL of anti-CD3 antibody (OKT3) at 10 µg/mL for 4 hours at 37° C. 5% $CO_2$ in phosphate buffered saline (PBS). The plates were washed with PBS prior to adding the cells with or without soluble anti-CD28 antibody (28.2) to each well at a final concentration of 5 µg/mL. Cells were stimulated for 48 hours prior to harvesting the cell free supernatant and staining the cell population for surface marker assessment by flow cytometry. Supernatants were analyzed for cytokine secretion (e.g., GM-CSF, IFNγ, and TNFα) by ELISA (R&D Systems, Peprotech or Life Technologies) or Luminex multiplex kits (Procarta Life Technologies) following the manufacturer's protocol. Cells were stained with anti-CD69 (BD Biosciences) to assess levels of surface markers of activation. Proliferation was measured by flow cytometry and data was analyzed with FlowJo v7.6.5 or v10. Readouts were reported as fold change over baseline. In some embodiments, baseline was the measurement obtained from total human T-cells stimulated with anti-CD3 antibody alone, wherein the cells were not incubated with a Cbl-b inhibitor. In some embodiments, baseline was the measurement obtained from total human T-cells stimulated with anti-CD3 antibody and anti-CD28 antibody, wherein the cells were not incubated with a Cbl-b inhibitor.

Cbl-b inhibitor effects on primary human T-cells were also evaluated in the context of an allogenic mixed lymphocyte reaction (MLR). Allogenic immature dendritic cells were generated under the following conditions. Peripheral blood mononuclear cells (PBMC) were obtained either: 1) by using Ficoll-Paque™ (GE Healthcare) for separation of peripheral blood hematopoietic cells from buffy coats of healthy human donors; or 2) directly from LeukoPak donations. Monocytes were isolated from the PMBCs utilizing positive selection with a commercial kit following the manufacturer's protocol (StemCells Catalog #17858) to yield >95% CD14+ cells as assessed by flow cytometry. Monocytes were cultured with 30 ng/mL of recombinant human GM-CSF and 20 ng/mL of recombinant human IL-4 for seven days to generate immature dendritic cells. Monocytes and T-cells were either isolated fresh from peripheral blood or thawed from frozen stocks. Human T-cells were isolated, labeled with CFSE, and incubated with inhibitors as described above. The Cbl-b inhibitor was added to $1 \times 10^5$ T-cells in coculture with $2 \times 10^3$ allogenic immature dendritic cells per well at multiple concentrations (e.g., 10 µM, or 1.11 µM) with a final DMSO concentration of <0.1% and incubated at 37° C. in 5% $CO_2$ for 5 days. Proliferation of the T-cells was evaluated by flow cytometry.

Cbl-b inhibitors were tested to determine their ability to induce or enhance secretion of cytokines from T-cells (e.g., GM-CSF, IFNγ, and TNFα) and/or surface expression of cell surface markers on T-cells (e.g., CD69) that was indicative of T-cell activation. Cbl-b inhibitors were also tested to determine their ability to induce or enhance T-cell proliferation. Cbl-b inhibitors were tested for their effects on T-cell activation in the presence of costimulation and where conditions were suboptimal for priming.

Human T-Cell In Vitro Models of T-Cell Exhaustion

T-cell exhaustion was characterized by cells having a poor effector response and a sustained level of inhibitory receptor expression that results in T-cell dysfunction in response to chronic infections and cancer. In vitro models of T-cell exhaustion include allogenic and autologous models. In an autologous model, myeloid cells and SEB (Staphylococcal enterotoxin B, Millipore) were used to stimulate anti-CD3 stimulated T-cells. Peripheral blood mononuclear cells (PBMC) were obtained either: 1) by using Ficoll-Paque™ (GE Healthcare) for separation of peripheral blood hematopoietic cells from buffy coats of healthy human donors; or 2) directly from LeukoPak donations. Monocytes were isolated with commercial kits using negative selection with StemCells EasySep Human Monocyte Enrichment Kit without CD16 Depletion (Catalog #19058) following the manufacturer's protocol. Isolated monocytes were cultured in complete media (e.g., RPMI 1640 with no additives, 10% HI FBS, 1× Glutamine and 1× β-mercaptoethanol) with 50 ng/mL recombinant human M-CSF (R&D System or Peprotech). Cells were plated at $2 \times 10^6$ cells per well (Day 0) and cultured for 5 days and were fed with fresh media and cytokines on Day 2. On Day 5, IFNγ was added at 100 ng/mL and the cells were incubated overnight. Primary human T-cells from the same donor were isolated from PBMCs with a commercial kit using negative selection (with Stemcell Technologies EasySep Human T-cell Isolation Kit (Catalog #17951) following the manufacturer's protocol. Purity was confirmed by surface marker detection by flow cytometry for CD4, CD8, CD45RA, CD45RO, CD19, CD14, CD56, and CD3 (BD Biosciences). $3 \times 10^6$ cells per/mL T-cells were stimulated with 10 µg/mL of plate bound anti-CD3 antibody (Clone UCHT-1) for 5 days. This was done in parallel with myeloid cell generation. On Day 6, $2.5 \times 10^4$ T-cells were added per well, $12.5 \times 10^3$ myeloid cells per well and SEB antigen (0.1 µg/mL) were added to wells of a round-bottom 96-well plate. Test agents (e.g. Cbl-b inhibitor compounds) or controls (e.g., checkpoint neutralizing antibodies such as anti-PD1 antibody) were added to the wells at the indicated concentrations (e.g., 10 µM). Cells were cultured for 3 days at which point cell free supernatants were collected and assessed for secreted cytokines (e.g., GM-CSF, IFNγ, and IL-2) by ELISA (R&D Systems, Peprotech or Life Technologies) or Luminex multiplex kits (Procarta Life Technologies). The T-cells were stained for a panel of surface markers including checkpoint inhibitors (e.g., CTLA4) and evaluated by flow cytometry for Cbl-b inhibitor effects.

Cbl-b inhibitors were tested to determine their ability to induce or enhance secretion of cytokines from exhausted T-cells (e.g., GM-CSF, IFNγ, and IL-2) in the presence of myeloid cells, which was indicative of decreased T-cell exhaustion. Cbl-b inhibitors were also tested for their effects on checkpoint modulator expression levels following activation of exhausted T-cells.

Human T-Cell In Vitro Models of T-Cell Anergy

Peripheral blood mononuclear cells (PBMC) were obtained either: 1) by using Ficoll-Paque™ (GE Healthcare) for separation of peripheral blood hematopoietic cells from buffy coats of healthy human donors; or 2) directly from LeukoPak donations. Total human primary T-cells were isolated from the PBMCs utilizing negative selection with commercial kits following the manufacturer's protocol (Miltenyi Biotec Catalog #130-096-535 (i.e., cocktail of antibodies against surface markers CD14, CD15, CD16, CD19, CD34, CD36, CD56, CD123, and CD235a were incubated with the PBMCs before passing the samples by magnetic beads for removal of cells expressing those surface markers) or Stemcell Technologies Catalog #17951) to yield >95% CD3+ cells as assessed by flow cytometry. The cells were activated with immobilized anti-CD3 antibody (OKT3) and soluble anti-CD28 antibody (28.2) for two days at which time they were washed and allowed to rest for three days in the absence of stimulation. They were then treated with ionomycin (Sigma) for 18-24 hours to induce anergy. Following two washes to remove the ionomycin from the samples, Cbl-b inhibitor compounds were added to the cells at the indicated concentrations (e.g., 10, 1.11, and 0.37 µM) and incubated for one hour. The cells were then re-challenged with anti-CD3 antibody and anti-CD28 antibody for 24 hours at which point cell free supernatants were collected and assessed for cytokines (e.g., IFNγ) by ELISA (R&D Systems or Peprotech) or Luminex multiplex kits (Procarta Life Technologies) following the manufacturer's protocols.

Cbl-b inhibitors were tested to determine their ability to induce or enhance secretion of cytokines from anergic T-cells (e.g., IFNγ), which was indicative of decreased T-cell tolerance.

In Vivo Activity of Cbl-b Inhibitors

A method of determining the pharmacodynamic profile of Cbl-b inhibitors was performed by dosing strains of mice with competent immune systems such as C57BL/6 or BALB/c with a Cbl-b inhibitor. The Cbl-b inhibitor was dissolved in a suitable formulation and administered by one of various routes such as intravenous (IV), intraperitoneal (IP), subcutaneous (SC), or oral (PO), at a suitable dose level and frequency (e.g., twice per day BID or thrice per day TID) as informed by prior pharmacokinetic and tolerability studies. Following administration of the Cbl-b inhibitor, T-cells and indirectly other immune cells (e.g., via cytokine production) were stimulated in vivo by administration of an anti-CD3 antibody or antigen-binding fragment thereof in PBS at defined amounts such as 2 g or 10 g per animal by routes such as IV or IP (see Hirsh et al., J. Immunol., 1989; Ferran, et al., Eur. J. Immunol., 1990). Additional study control arms included groups of mice treated with a vehicle formulation alone (i.e., formulation without the Cbl-b inhibitor and anti-CD3 antibody), a formulation containing the Cbl-b inhibitor alone, a formulation containing the anti-CD3 antibody alone, PBS alone, or combinations of these agents. The level of immune activation was then assessed by analysis of plasma cytokine levels and/or expression of activation markers on immune cells (e.g., T-cells). Blood or lymphoid organs (e.g., spleen) were collected at defined time points (e.g., 8 hours or 24 hours). Blood samples were processed to collect plasma for determination of cytokine levels using standard methods known in the art. Cytokines measured included IL-2, IFNγ, and TNFα. Additional blood samples and lymphoid tissues were processed for flow cytometric analysis of immune cells (e.g., T-cells) using standard methods to determine expression of cell type-specific markers and activation markers such as CD25 and/or CD69. Augmentation of immune stimulation by Cbl-b inhibitor administration was assessed by comparing the relative concentrations of cytokines in plasma, or the expression levels of activation markers on immune cells between appropriate groups (e.g., mice treated with Cbl-b inhibitor and 2 g anti-CD3 antibody versus mice treated with vehicle and 2 g anti-CD3 antibody).

Cbl-b inhibitors were tested to determine their ability to induce or enhance the level of cytokines (e.g., IL-2, IFNγ, and TNFα) in blood obtained from treated mice stimulated with an anti-CD3 antibody, which was indicative of modulation of the immune response. Cbl-b inhibitors were also tested to determine their ability to induce or enhance the expression of cell surface markers on T-cells (e.g., CD25 and/or CD69) isolated from treated mice stimulated with an anti-CD3 antibody, which was indicative of modulation of the immune response.

B-Cell Activation Assay

Peripheral blood mononuclear cells (PBMC) were obtained either: 1) by using Ficoll-Paque™ (GE Healthcare) for separation of peripheral blood hematopoietic cells from buffy coats of healthy human donors; or 2) directly from LeukoPak donations. Human primary B-cells were isolated from the PBMCs utilizing negative selection with commercial kits following the manufacturer's protocol (Stemcell Technologies Catalog #17954) to yield >95% CD20+ cells as assessed by flow cytometry. Primary human B-cells were plated at $0.7-1\times10^5$ per well in a 96-well plate with Cbl-b inhibitors over a dose ranging from 10 µM to 1 nM and incubated at 37° C. 5% $CO_2$, with a final DMSO concentration of <0.5%. Cells were stimulated with anti-IgM for 20 hours at 37° C. 5% $CO_2$. Surface activation markers on mature $CD20^+IgD^+$ B-cells were monitored by FACS using an anti-CD69 antibody (BD Biosciences).

Cbl-b inhibitors were tested to determine their ability to induce or enhance surface expression of cell surface markers on B-cells (e.g., CD69), which was indicative of B-cell activation.

Purification and Activation of Primary Human NK-Cells.

Peripheral blood mononuclear cells (PBMC) were obtained either: 1) by using Ficoll-Paque™ (GE Healthcare) for separation of peripheral blood hematopoietic cells from buffy coats of healthy human donors; or 2) directly from LeukoPak donations. Total human primary NK-cells were isolated from the PBMCs utilizing negative selection with commercial kits following the manufacturer's protocol (Miltenyi Biotec Catalog #130-092-657 or Stemcell Technologies Catalog #17955) to yield >92% CD56+, CD3-cells as assessed by flow cytometry. The cells were cultured overnight with IL-2 (60 ng/mL) at 37° C. 5% $CO_2$. Cbl-b inhibitors were added one hour prior to stimulation and incubated at 37° C. 5% $CO_2$ at a specific concentration (e.g., 10 µM, 1 µM, or 0.1 µM) with a final DMSO concentration of <0.1%. NK-cells were co-cultured with target cells that were engineered to have a red nucleus (K562 NucRed)

measurable by flow cytometry. K562 NucRed cells were produced by transduction of K562 cells with IncuCyte NucLight Red Lentivirus reagent (Catalog #4476) and selected for 5 days. Clonal populations were isolated and expanded using standard tissue culture techniques, and individual clones were validated by comparison to wildtype K562 cells in NK-cell killing assays. The cells were mixed at the indicated ratios (e.g., 5:1, 1:1, or 1:5) of NK (effector cells) to K562 NucRed (target cells) for 6 hours. Cell free supernatants were collected and analyzed for cytokine secretion (e.g., TNFα, IFNγ, or MIP1β) by ELISA or Luminex multiplex kits following the manufacturer's protocol. IFNγ secretion was assessed using an R&D Systems ELISA kit (Catalog #DY285), TNFα secretion was assessed using an R&D Systems ELISA kit (Catalog #DY210), and MIP1β secretion was assessed using an R&D Systems ELISA kit (Catalog #DY271).

Biological Example 15: Evaluation of a Cbl-b Inhibitor in Combination with an Oncolytic Virus for Treating Cancer Oncolytic viruses preferentially infect and kill cancer cells and stimulate host anti-tumor immune responses. This example describes the evaluation of a combination therapy including an oncolytic virus and a Cbl-b inhibitor for treating cancer in mice.
Materials and Methods
In brief, the combination therapy was tested in C57BL/6 mice bearing a syngeneic MC-38 cell tumor. MC-38 cells were derived from a murine adenocarcinoma, which had been induced by subcutaneous injection of dimethylhydrazine (Cameron et al., J Exp Med, 171: 249-263, 1990). MC-38 cells were injected subcutaneously or intraperitoneally. Tumors were allowed to grow for about 5-7 days at which time the animals were randomized and treatment was initiated.

An oncolytic virus, such as vaccinia virus, was administered intraperitoneally at a dose of about $10^8$-$10^9$ plaque forming units (Puhlmann et al., Cancer Gene Therapy, 7: 66-73, 2000). The Cbl-b inhibitor was dissolved in a suitable formulation and administered at a suitable dose level and frequency as informed by prior pharmacokinetic and tolerability studies. In initial studies, a Cbl-b inhibitor in a suitable vehicle, or the vehicle alone, was administered orally (PO) at a dose of 180 mg/kg twice per day (BID) beginning on Day 0 (=Day 5-7 post MC-38 injection). In further studies, a Cbl-b inhibitor formulation was administered orally (PO) or parenterally (e.g., IV, IP, SC, or intratumorally at one to three injection sites per tumor). In addition to the test group of mice who received the combination therapy (the Cbl-b inhibitor formulation plus the oncolytic virus), the study included control groups of mice who received the vehicle formulation plus DPBS, the Cbl-b inhibitor formulation plus DPBS, or the vehicle formulation plus the oncolytic virus.

The level of response was evaluated by measuring tumor growth and comparing tumor growth in the test mice versus the control mice. In addition, the level of immune activation was assessed by collecting tumors for analysis of tumor infiltrating lymphocytes (TILs). In further experiments, PBMCs or splenocytes were also collected. TILs and optionally other lymphocyte samples were processed for flow cytometric analysis using standard methods to determine antigen specificity, expression of cell type-specific markers, and expression of activation markers such as granzyme B, CD25, CD69, PD-1, and LAG3. Augmentation of the anti-tumor immune response by the combination therapy was assessed by comparing the relative percentage of immune cell populations in the tumor, and the relative levels of expression of activation markers on immune cells in mice of the test and study groups.

The disclosures of all publications, patents, patent applications, and published patent applications referred to herein by an identifying citation are hereby incorporated herein by reference in their entirety.

Although aspects of the foregoing disclosure have been described in some detail by way of illustration and example for purposes of clarity of understanding, it is apparent to those skilled in the art that certain changes and modifications will be practiced. Therefore, the description and examples should not be construed as limiting the scope of this disclosure.

What is claimed is:

1. A compound having the following formula

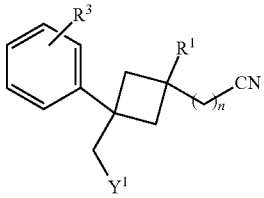

or
a stereoisomer thereof wherein
Y$^1$ is —COOH, —COO—C$_1$-C$_6$ alkyl, or

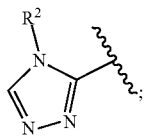

R$^1$ is hydrogen, C$_1$-C$_6$ alkyl, or C$_1$-C$_6$ haloalkyl;
R$^2$ is hydrogen, C$_1$-C$_6$ alkyl, C$_1$-C$_6$ haloalkyl, or C$_3$-C$_6$ cycloalkyl;
R$^3$ is selected from the group consisting of —N(R$^{100}$)$_2$ and halo;
each R$^{100}$ is independently hydrogen or C$_1$-C$_6$ alkyl; and
n is zero or one.

2. The compound of claim 1, or a stereoisomer thereof wherein
Y$^1$ is

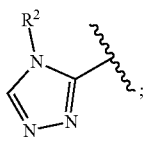

R$^1$ is hydrogen;
R$^2$ is hydrogen, C$_1$-C$_6$ alkyl, C$_1$-C$_6$ haloalkyl, or C$_3$-C$_6$ cycloalkyl;
R$^3$ is selected from the group consisting of —N(R$^{100}$)$_2$ and halo;
each R$^{100}$ is independently hydrogen or C$_1$-C$_6$ alkyl; and
n is zero.

3. The compound of claim 2, selected from the group consisting of

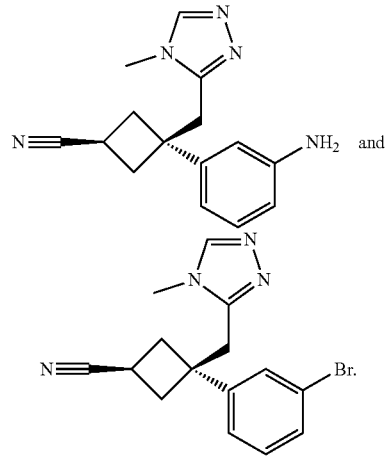

and

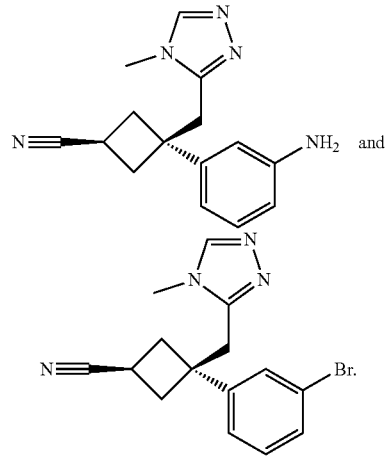

4. A compound having the following formula

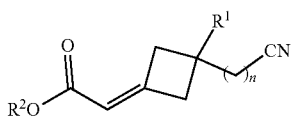

wherein
R$^1$ is hydrogen, C$_1$-C$_6$ alkyl, or C$_1$-C$_6$ haloalkyl;
R$^2$ is methyl, n-propyl, isopropyl, n-butyl, t-butyl, isobutyl, sec-butyl, n-pentyl, 1,1-dimethylpropyl, 2,2-dimethylpropyl, 3-methylbutyl, pentan-2-yl, pentan-3-yl, 3-methylbutan-2-yl, 2-methylbutyl, n-hexyl, 2-hexyl, 3-hexyl, 2-methylpentanyl, 2-methyl-2-pentanyl, 2-methyl-3-pentanyl, 2-methyl-4-pentanyl, 2-methyl-5-pentanyl, 3-methyl-1-pentanyl, 3-methyl-2-pentanyl, 3-methyl-3pentanyl, 2,2-dimethyl-1-butanyl, 2,2-dimethyl-3-butanyl, 2,2-dimethyl-4-butanyl, 2,3-dimethyl-1-butanyl, or 2,3-dimethyl-2-butanyl; and n is zero or one; or
R² is ethyl, and n is one.

5. The compound of claim 4, wherein the compound is

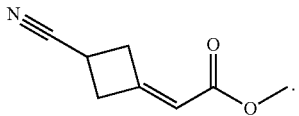

6. A method for making a compound of the following formula

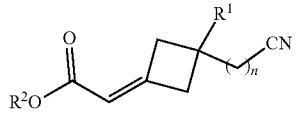

comprising
(a) treating a compound having the following formula

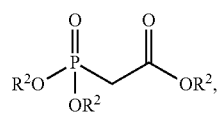

with a base in a polar aprotic solvent at 0° C.; and
(b) treating the mixture of step (a) with a compound having the following formula

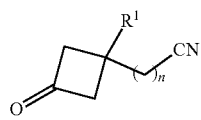

in a polar aprotic solvent at 0° C. to form

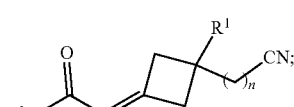

wherein
R¹ is hydrogen, $C_1$-$C_6$ alkyl, or $C_1$-$C_6$ haloalkyl;
R² is methyl, n-propyl, isopropyl, n-butyl, t-butyl, isobutyl, sec-butyl, n-pentyl, 1,1-dimethylpropyl, 2,2-dimethylpropyl, 3-methylbutyl, pentan-2-yl, pentan-3-yl, 3-methylbutan-2-yl, 2-methylbutyl, n-hexyl, 2-hexyl, 3-hexyl, 2-methylpentanyl, 2-methyl-2-pentanyl, 2-methyl-3-pentanyl, 2-methyl-4-pentanyl, 2-methyl-5-pentanyl, 3-methyl-1-pentanyl, 3-methyl-2-pentanyl, 3-methyl-3pentanyl, 2,2-dimethyl-1-butanyl, 2,2-dimethyl-3-butanyl, 2,2-dimethyl-4-butanyl, 2,3-dimethyl-1-butanyl, or 2,3-dimethyl-2-butanyl;
n is zero or one; or
R² is ethyl, and n is one;
base is MH, $MNH_2$, $MN(CH(CH_3)_2)_2$, MOH, or $MOC_1$-$C_6$ alkyl;
M is lithium, sodium, or potassium; and
polar aprotic solvent is THF or sulfolane.

7. The method of claim 6, wherein the base is NaH; and the polar aprotic solvent is THF.

8. A method for making a compound of the following formula

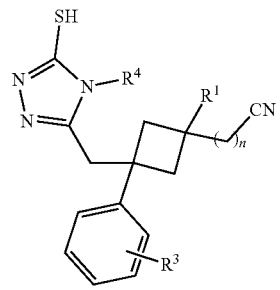

comprising
(a) mixing a compound of the following formula

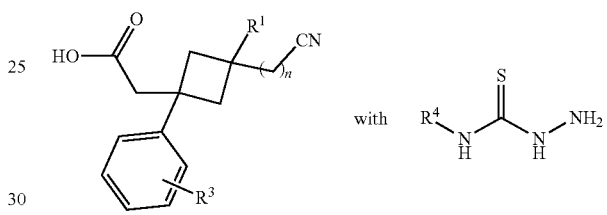

and a first base in a polar aprotic solvent;
(b) treating the mixture of step (a) with an amide coupling agent;
(c) treating the mixture of step (b) with a second base; and
(d) heating the mixture of step (c) to form

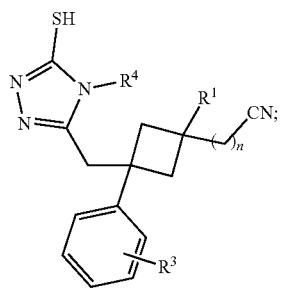

wherein
R¹ is hydrogen, $C_1$-$C_6$ alkyl, or $C_1$-$C_6$ haloalkyl;
R³ is —N(R¹⁰⁰)₂ wherein each R¹⁰⁰ is independently hydrogen, $C_1$-$C_6$ alkyl, or a protecting group;
R⁴ is $C_1$-$C_6$ alkyl;
n is zero or one;
the first base is an amine base;
the polar aprotic solvent is THF, DMF, DMSO, DCM, or sulfolane;
the amide coupling agent is N,N'-dicyclohexylcarbodiimide (DCC), 1-Ethyl-3-(3-dimethylaminopropyl)carbodiimide (EDC), or HATU; and
second base is MOH wherein M is lithium, sodium, or potassium.

9. The method of claim 8, wherein the
first base is DIPEA;
polar aprotic solvent is DMF;
amide coupling agent is HATU; and
second base is NaOH.

10. The method of claim 8, further comprising
(e) mixing the compound of

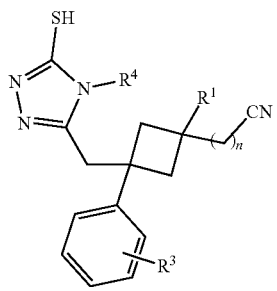

and an acid in a polar aprotic solvent;
(f) treating the mixture of step (e) with an oxidizing agent at 0° C.; and
(g) heating the mixture of step (f) to 30° C. to form a compound of the following formula

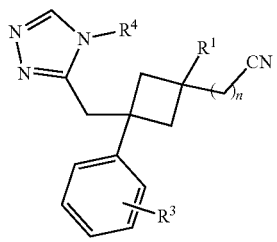

wherein
$R^1$ is hydrogen, $C_1$-$C_6$ alkyl, or $C_1$-$C_6$ haloalkyl;
$R^3$ is —N$(R^{100})_2$ wherein each $R^{100}$ is independently hydrogen, $C_1$-$C_6$ alkyl, or a protecting group;
$R^4$ is $C_1$-$C_6$ alkyl;
n is zero or one;
the acid is a weak acid;
the polar aprotic solvent is THF, DMF, DMSO, DCM, or sulfolane; and
the oxidizing agent is a peroxide.

11. The method of claim 10, wherein the weak acid is acetic acid;
polar aprotic solvent is DCM; and
peroxide is $H_2O_2$.

12. The method of claim 10, further comprising
(h) mixing the compound of

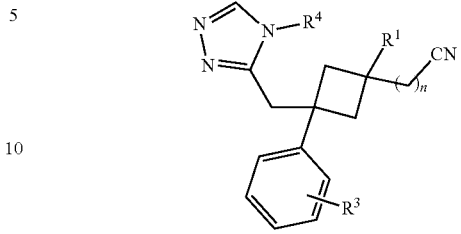

with a strong acid source in a polar aprotic solvent; wherein
$R^1$ is hydrogen, $C_1$-$C_6$ alkyl, or $C_1$-$C_6$ haloalkyl;
$R^3$ is —N$(R^{100})_2$ wherein each $R^{100}$ is independently hydrogen or $C_1$-$C_6$ alkyl;
$R^4$ is $C_1$-$C_6$ alkyl;
n is zero or one;
the strong acid source is HCl, TFA, trialkylsilyl halide, or an acyl halide; and
the polar aprotic solvent is THF, DMF, DMSO, DCM, or sulfolane.

13. The method of claim 12, wherein
strong acid source is trialkylsilyl halide; and
polar aprotic solvent is DCM.

14. The method of claim 13, wherein the trialkylsilyl halide is trimethylsilyl iodide (TMSI).

15. The method of claim 12, further comprising
(i) mixing the compound of

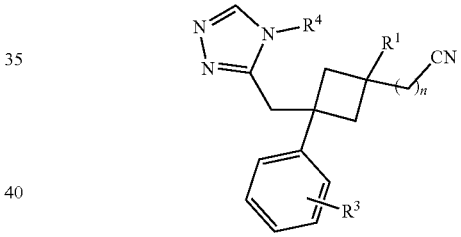

with a Cu(II) halide in a polar aprotic solvent; and
(j) treating the mixture of step (i) with an alkyl nitrite;
wherein
$R^1$ is hydrogen, $C_1$-$C_6$ alkyl, or $C_1$-$C_6$ haloalkyl;
$R^3$ is halogen;
$R^4$ is $C_1$-$C_6$ alkyl;
n is zero or one;
Cu(II) halide is CuBr$_2$, CuCll$_2$, or CuI$_2$; and
polar aprotic solvent is THF, DMF, DMSO, MeCN, or sulfolane.

16. The method of claim 15, wherein
Cu(II) halide is CuBr$_2$; and
polar aprotic solvent is MeCN.

* * * * *

SEQUENCE LISTING

```
Sequence total quantity: 3
SEQ ID NO: 1            moltype = AA  length = 392
FEATURE                 Location/Qualifiers
REGION                  1..392
                        note = misc_feature - Cbl-b amino acid residues 36-427
source                  1..392
                        mol_type = protein
                        organism = Homo sapiens
SEQUENCE: 1
PKQAAADRRT VEKTWKLMDK VVRLCQNPKL QLKNSPPYIL DILPDTYQHL RLILSKYDDN    60
QKLAQLSENE YFKIYIDSLM KKSKRAIRLF KEGKERMYEE QSQDRRNLTK LSLIFSHMLA   120
EIKAIFPNGQ FQGDNFRITK ADAAEFWRKF FGDKTIVPWK VFRQCLHEVH QISSGLEAMA   180
LKSTIDLTCN DYISVFEFDI FTRLFQPWGS ILRNWNFLAV THPGYMAFLT YDEVKARLQK   240
YSTKPGSYIF RLSCTRLGQW AIGYVTGDGN ILQTIPHNKP LFQALIDGSR EGFYLYPDGR   300
SYNPDLTGLC EPTPHDHIKV TQEQYELYCE MGSTFQLCKI CAENDKDVKI EPCGHLMCTS   360
CLTAWQESDG QGCPFCRCEI KGTEPIIVDP FD                                 392

SEQ ID NO: 2            moltype = AA  length = 9
FEATURE                 Location/Qualifiers
REGION                  1..9
                        note = Synthetic: CTL epitope of residues 49-57 of E7
source                  1..9
                        mol_type = protein
                        organism = synthetic construct
SEQUENCE: 2
```

```
RAHYNIVTF                                                                9
SEQ ID NO: 3          moltype = AA  length = 13
FEATURE               Location/Qualifiers
REGION                1..13
                      note = Synthetic: amino acid sequence of a Th epitope known
                       as PADRE
MOD_RES               1
                      note = D-alanine
MOD_RES               3
                      note = Xaa is L-cyclohexylalanine
MOD_RES               13
                      note = D-alanine
source                1..13
                      mol_type = protein
                      organism = synthetic construct
SEQUENCE: 3
AKXVAAWTLK AAA                                                           13
```